US008263607B2

(12) United States Patent
Shishikura et al.

(10) Patent No.: US 8,263,607 B2
(45) Date of Patent: Sep. 11, 2012

(54) 1-SUBSTITUTED TETRAHYDROISOQUINOLINE COMPOUND

(75) Inventors: Jun-ichi Shishikura, Tokyo (JP); Makoto Inoue, Tokyo (JP); Takashi Ogiyama, Tokyo (JP); Koichi Yonezawa, Tokyo (JP); Susumu Yamaki, Tokyo (JP); Kazuhiro Yokoyama, Tokyo (JP); Shuichirou Kakimoto, Tokyo (JP); Hidetsugu Okada, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 292 days.

(21) Appl. No.: 12/600,503

(22) PCT Filed: May 20, 2008

(86) PCT No.: PCT/JP2008/059287
§ 371 (c)(1),
(2), (4) Date: Nov. 17, 2009

(87) PCT Pub. No.: WO2008/143263
PCT Pub. Date: Nov. 27, 2008

(65) Prior Publication Data
US 2010/0168154 A1 Jul. 1, 2010

(30) Foreign Application Priority Data
May 22, 2007 (JP) ................................ 2007-135452

(51) Int. Cl.
*C07D 217/04* (2006.01)
*C07D 491/04* (2006.01)
*A61K 31/472* (2006.01)

(52) U.S. Cl. .......... 514/278; 514/307; 514/308; 546/16; 546/140; 546/146

(58) Field of Classification Search ........................ None
See application file for complete search history.

(56) References Cited

U.S. PATENT DOCUMENTS

| 3,910,915 | A | 10/1975 | Yonan |
| 2004/0044031 | A1 | 3/2004 | Yamada et al. |
| 2004/0167118 | A1 | 8/2004 | Yamamoto et al. |
| 2004/0214833 | A1 | 10/2004 | Hauel et al. |
| 2008/0058311 | A1 | 3/2008 | Yamamoto et al. |

FOREIGN PATENT DOCUMENTS

| EP | 0 696 593 | 2/1996 |
| JP | 50 041874 | 4/1975 |
| JP | 2002 363163 | 12/2002 |
| RU | 2006101053 A | 6/2006 |
| WO | 01 85693 | 11/2001 |
| WO | 02 079189 | 10/2002 |
| WO | 03 018538 | 3/2003 |
| WO | 03 082828 | 10/2003 |
| WO | 2004 089950 | 10/2004 |
| WO | WO 2004/110986 A1 | 12/2004 |
| WO | 2005 005392 | 1/2005 |
| WO | 2005 021523 | 3/2005 |
| WO | 2006 040181 | 4/2006 |

OTHER PUBLICATIONS

Zhang, Yu-an et al., "Inhibitory Effects of Tetrahydroisoquinoline Derivatives on $Ca^{2+}$ and $Na^+$ Channels in Crude Nerve Endings", Biol. Pharm. Bull., vol. 23, No. 3, pp. 375-378, Mar. 2000.
Zhishan, Z. et al., "Syntheses of 1,2-Disubstituted Tetrahydroisoquinoline Derivatives and Their Antiarrhythmic Effects", Fudan University Journal of Medical Science, vol. 14, No. 1, pp. 15-20, (1987), (with English abstract).
Zhishan, Z. et al., "Studies on Antiarrhythmic Agents, II Syntheses of 1-P-Methylphenyl-2-Substituted Tetrahydroisoquinoline Derivatives", Fudan University Journal of Medical Science, vol. 16, No. 1, pp. 71-74, (1989), (with English abstract).
Guoyou, Xu et al., "Studies on Synthesis, Biological Activity and Structure-Activity Relationship of N-Aminoacetyl Benzyltetrahydroisoquinolines and Related Compounds", Journal of China Pharmaceutical University, vol. 24, No. 4, pp. 193-201, May 5, 1993, (with English abstract and partial English translation).
Ichida, Seiji et al., "Structural Specificity for the Inhibitory Effect of Calmodulin on Specific$^{125}$ I-Omega-Conotoxin GVIA Binding", Neurochemical Research, vol. 28, No. 12, pp. 1813-1818, Dec. 2003.
Hirose, Masaaki et al., "N-Acyl 6,7-Dimethoxy-1,2,3,4-tetrahydroisoquinoline:The first Orexin-2 Receptor Selective Nonpeptidic Antagonist", Bioorganic & Medicinal Chemistry Letters, vol. 13, No. 24, pp. 4497-4499, (2003).
Office Action issued Sep. 14, 2010, in Mexican Patent Application No. MX/a/2009/012610 filed May 20, 2008 (with English-language Translation).
Office Action issued Jan. 4, 2012, in Australian Patent Application No. 2008254061.
Extended Search Report issued Dec. 6, 2010, in European Patent Application No. 08764424.1-2101 / 2149560 PCT/JP2008059287.
Office Action issued May 28, 2012, in Russian Patent Application No. 2009147451, filed May 20, 2008 (with English-language Translation).

*Primary Examiner* — Zinna Northington Davis
(74) *Attorney, Agent, or Firm* — Oblon, Spivak, McClelland, Maier & Neustadt, L.L.P.

(57) ABSTRACT

Provided is a compound useful as an N-type $Ca^{2+}$ channel blocker. As a result of intensive studies of compounds having an action of blocking N-type $Ca^{2+}$ channels, the present inventors found that a tetrahydroisoquinoline compound of the present invention having a substituent at the 1-position has an action of blocking the N-type $Ca^{2+}$ channels, an antinociceptive pain action, an antineuropathic pain action, an abdominal pain-inhibitory action and an opioid-induced constipation-improving action, and the present invention has been completed based on these findings. The compound of the present invention can be used as a pharmaceutical composition for preventing and/or treating various pains such as neuropathic pain and nociceptive pain, headaches such as migraine and cluster headache, central nervous system diseases such as anxiety, depression, epilepsy, cerebral stroke and restless legs syndrome, abdominal symptoms such as abdominal pain and abdominal distension, stool abnormalities such as diarrhea and constipation, digestive system diseases such as irritable bowel syndrome, urinary system diseases such as overactive bladder and interstitial cystitis, etc.

22 Claims, No Drawings

1-SUBSTITUTED TETRAHYDROISOQUINOLINE COMPOUND

CONTINUING DATA

This application is a 371 of PCT/JP08/59287 filed May 20, 2008.

TECHNICAL FIELD

The present invention relates to a medicament, and specifically to a 1-substituted tetrahydroisoquinoline compound which is useful as an active ingredient of a pharmaceutical composition for preventing and/or treating pain, abdominal symptoms, spastic constipation, and irritable bowel syndrome.

BACKGROUND ART

Pain is an important biological defense mechanism which reflects the addition of any invasion to organisms. When pain or dysesthesia still lasts even after tissue damage or diseases responsible for the onset of pain have been cured, such a condition is recognized as a disease. Pain is broadly classified into nociceptive pain and neuropathic pain. Nociceptive pain includes pain caused by tissue inflammation, cancer-induced nerve compression, or the like (inflammatory pain, cancer pain, etc.). Non-steroidal anti-inflammatory drugs (NSAIDs) or opioids are therapeutically effective for the treatment of nociceptive pain.

On the other hand, neuropathic pain is chronic pain caused by nerve tissue damage or compression, or the like. Symptoms of neuropathic pain include unpleasant dysesthesia such as continuous or sudden spontaneous pain, numbness, burning sensation, the pain of being cut into small pieces, and stabbing pain; a condition which is a painful response to a usually non-painful weak stimulus (hyperalgesia); pain due to a stimulus that does not normally provoke pain (allodynia), such as caused by contact with clothing or changes in temperatures; and the like. Specific diseases of neuropathic pain include trigeminal neuralgia, complex regional pain syndrome, post spinal surgery syndrome, phantom limb pain, pain after brachial plexus injury, post-spinal cord injury pain, post-stroke pain, painful diabetic neuropathy, postherpetic neuralgia, HIV-induced neuropathy, and further some cases of cancer pain and low back pain on which analgesic effects of opioids are not sufficiently exerted, in addition to anticancer drug- and anti-HIV drug-induced neuropathy.

Neuropathic pain is known as pain on which NSAIDs or opioids which are effective on nociceptive pain exhibit difficulty in being therapeutically effective. In practical medication therapy, alleviation of pain is effected by hemp, capsaicin cream, or intraspinal administration of opioids, as well as by administration of antidepressants (duloxetine, amitriptylin, etc.), antiepileptic drugs (pregabalin, carbamazepine, etc.), or local analgesics (mexiletine, etc.). Unfortunately, effects of these drugs are limited since many neuropathic pains are developed by an overlap of multiple pathogenic causes and individual patients have different disease backgrounds. Further, there are also problems associated with inherent side effects of individual drugs. To this end, there is a strong need for an anti-neuropathic pain agent which has more potent and broader analgesic spectrum and lower side effects.

Irritable bowel syndrome (IBS) is a syndrome which brings about abdominal symptoms such as abdominal pain and abdominal distension and stool abnormalities such as diarrhea or defecation urgency and constipation or difficulty in defecation, due to the dysfunction of the lower digestive tract around the large intestine, despite no occurrence of organic alteration such as inflammation and tumor. Depending on predominant bowel habits, IBS is broadly subclassified into diarrhea type IBS (IBS-D), constipation type IBS (IBS-C), and mix type IBS (IBS-M) with alternating diarrhea and constipation (Gastroenterology 130: 1377-90, 1480-91 (2006)). As a medication therapy for IBS, there may be mentioned anticholinergic drugs for abdominal pain, tricyclic antidepressants (TCAs) for improving decreased pain threshold of the digestive tract, and in the case of bowel movement disturbance, antidiarrheals or intestinal remedies for diarrhea and cathartic salts for constipation, which are merely allopathic therapies and are also uncertain in their effects (Irritable bowel syndrome~Communication between the brain and the intestines (ISBN4-521-67671-5, 2006)).

As drugs which are recently attracting attention, alosetron which is a 5-$HT_3$ receptor antagonist and tegaserod which is a 5-$HT_4$ receptor agonist are used for IBS-D and IBS-C, respectively. However, use of alosetron is limited due to the incidence of constipation in 30% to 35% of patients, in conjunction with serious side effects of ischemic colitis (including death), even though it exhibits a comparatively high improvement rate of 40% to 60% for abdominal symptoms and diarrhea (Drug Today 36: 595-607 (2000), FDA information about lotronex, GlaxoSmithKline press release). In addition, it is said that tegaserod has little effect on abdominal symptoms due to poor constipation-alleviating effects, which may result in the risk of tachyphylaxis (phenomenon of producing resistance to a drug after repeated doses over a short period of time) (Clinical Therapeutics 25: 1952-1974 (2003)). In addition, an application of tegaserod is also strongly limited in terms of side effects, due to having adverse effects on the circulatory system (FDA information about zelnorm, Novartis press release).

Opioids, such as morphine, which have been commonly used as pain-relieving drugs, are known to cause severe dysfunction of the digestive tract including constipation, which is called opioid bowel dysfunction (OBD). Among symptoms of OBD, the onset of constipation is very high without creating drug resistance unlike other opioid-induced central nervous system side-effects, so it is necessary to take appropriate measures to deal with the situation (American J. Surgery 182: 11S-18S (2001), Jpn. Cancer Chemother. 32: 1377-1383 (2005)). For these reasons, in opioid treatment particularly on cancer pain patients, a combined prophylactic treatment with a laxative agent is essential from the beginning of administering an opioid drug, but it is not easy to control defecation by means of the laxative agent (Drugs 63: 649-671 (2003), Pharmacotherapy 22: 240-250 (2002)).

The digestive tract is provided with an independent nerve network, called the enteric nervous system. Various kinds of neurons are present in the enteric nervous system and are responsible for governing respective digestive tract functions. Among those neurons, Intrinsic Primary Afferent Neutrons (IPANs) are neurons that primarily receive changes in the digestive tract lumen. IPANs detect physical or chemical changes in the digestive tract lumen and transmit the information to motor neurons or sensory neurons. Therefore, drugs altering the activity of IPANs bring about changes in the digestive tract function, called peristaltic motion or visceral perception (Progress in Neurobiol. 54: 1-18 (1998)). Further, from the fact that the N-type $Ca^{2+}$ channel is expressed in IPANs and contributes to the activity of IPANs (J. Comp. Neurol. 409: 85-104 (1999)), it can be considered that a compound blocking the N-type $Ca^{2+}$ channel would be useful for functional digestive tract diseases by altering digestive tract functions.

In addition, it is known that abdominal pain signals, like somatic pain, travel to the brain via the dorsal root ganglion (DRG) and the spinal cord (Neurogastroentel. Motil. 16: 113-124 (2004)). This signaling pathway is hypersensitized in IBS patients, suggesting significant occurrences of abdominal symptoms (Gut 53: 1465-1470 (2004)). Therefore, it is anticipated that a blocker of the N-type $Ca^{2+}$ channel involved in this pain-signaling pathway would be an effective therapeutic agent against abdominal symptoms of IBS. In fact, it has been reported that gabapentin or pregabalin, which is a ligand for the $Ca^{2+}$ channel α2δ subunit, exerts analgesic effects in animal models of abdominal pain hypersensitization (J. Pharmacol. Exp. Ther. 295: 162-167 (2000), Anesthesiology 98: 729-733 (2003)).

There are many kinds of $Ca^{2+}$-dependent functional proteins in cells, and changes in the intracellular $Ca^{2+}$ concentration play an important role in the expression or regulation of various physiological functions such as neuronal viability, synaptic plasticity, and gene expression. Among $Ca^{2+}$ channels present on the cell membrane, a channel using a membrane potential as a trigger in the opening of the channel is called a voltage-dependent $Ca^{2+}$ channel (VDCC), which consists mainly of an α1 subunit forming the channel body, a β subunit controlling an expression level of the α1 subunit or functions of the channel, and an α2δ subunit (Trends Neurosci. 21 148-154 (1998)). The $Ca^{2+}$ channels are classified into high-threshold $Ca^{2+}$ channels such as L-type (α1S, C, D, and F), P/Q-type (α1A), N-type (α1B), and R-type (α1E); and low-threshold $Ca^{2+}$ channels such as T-type (α1G, H, I), depending on α1 subunit type and activation threshold potential (Rev. Physiol. Biochem. Pharmacol. 139: 33-87 (1999)).

Among the high-threshold $Ca^{2+}$ channels, the P/Q-, N-, and R-type $Ca^{2+}$ channels are present in neuron synaptic terminals and serve as a trigger of the neurotransmitter release. In particular, the N-type $Ca^{2+}$ channel is highly expressed in the dorsal root ganglion (DRG) (J. Neurosci. 15: 4315-4327 (1995)) which is a collection of cell bodies of the sensory neurons or the spinal dorsal horn (J. Neurosci. 18: 6319-6330 (1998)) which is a synaptic projection region of sensory neurons. Further, the spinal dorsal horn of neuropathic pain model rats exhibited an increased expression of the N-type $Ca^{2+}$ channel in synchronization with the progression of hyperalgesia (Exp. Brain Res. 147: 456-463 (2002)). From these facts, it is believed that the N-type $Ca^{2+}$ channel plays a role as a trigger that transmits an excess of pain signals to the brain.

With recent observations showing that a selective N-type $Ca^{2+}$ channel-blocking peptide, ω-conotoxin (ω-CTx) exhibits broad analgesic effects in animal models of nociceptive, inflammatory and neuropathic pain, respectively (J. Pharmacol. Exp. Ther. 279: 1243-1249 (1996), J. Pharmacol. Exp. Ther. 287: 232-237 (1998), J. Pharmacol. Exp. Ther. 269: 1117-1123 (1994)), and no neuropathic pain occurs in α1B-deficient mice (EMBO J. 20: 2349-2356 (2001)), it has been suggested that the N-type $Ca^{2+}$ channel is deeply implicated in the pathogenesis of neuropathic pain. In fact, it has been reported that chronic spinal administration of ziconotide (ω-conotoxin MVIIA:ω-CTxMVIIA) by means of an implantable pump improves hyperalgesia and allodynia in morphine non-responsive neuropathic pain patients (Clin. J. Pain 13: 256-259 (1997)). Further, it has been demonstrated that gabapentin or pregabalin, frequently used as an anti-neuropathic pain agent, binds with a high affinity to the $Ca^{2+}$ channel α2δ subunit to exert thereby analgesic effects (J. Pharm. Sci. 100: 471-486 (2006)). Based on the above-mentioned findings, the N-type $Ca^{2+}$ channel blocker is expected to be an excellent therapeutic agent for pain, particularly neuropathic pain. Further, from the fact that the N-type $Ca^{2+}$ channel is involved in hyperactivity of neurons, cellular death and the like, the N-type $Ca^{2+}$ channel blocker is consequently expected to be useful for the prevention or treatment of conditions or diseases associated with activation of the N-type $Ca^{2+}$ channel, in addition to the above-mentioned pain. Taken altogether, it is believed that a compound having the N-type $Ca^{2+}$ channel-blocking action would be useful for various pains such as neuropathic pain and nociceptive pain, headaches such as migraine and cluster headache, central nervous system diseases such as anxiety, depression, epilepsy, cerebral stroke and restless legs syndrome, digestive system diseases such as abdominal pain and irritable bowel syndrome, and urinary system diseases such as overactive bladder and interstitial cystitis.

N-type $Ca^{2+}$ channel-blocking compounds have been hitherto reported. For example, it has been described that the following benzazepine derivatives have an action of blocking N-type $Ca^{2+}$ channels and are useful as an agent for preventing and/or treating cerebral infarction, transient cerebral ischemic attack, encephalomyelopathy after cardiac surgery, spinal cord vascular disorders, stress-induced hypertension, neurosis, epilepsy, asthma, frequent micturition, and ophthalmic diseases, or as anti-pain drugs (Patent Document 1).

[Chem. 1]

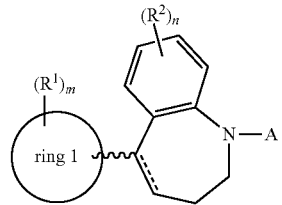

(See the above-referenced document for symbols in the formula)

However, there is no specific disclosure of a 1-substituted tetrahydroisoquinoline compound which pertains to the present invention.

Further, it has been described that the following diarylalkene or diarylalkane derivatives have an action of blocking N-type $Ca^{2+}$ channels and are useful for treating pain, brain infarction, cerebral disorders caused by acute ischemia after the onset of cerebral hemorrhage, Alzheimer's disease, AIDS-associated dementia, Parkinson's disease, progressive degenerative diseases of the brain, neurological disorders caused by head injury, bronchial asthma, unstable angina, irritable colon inflammatory diseases, and withdrawal symptoms of drug addiction (Patent Document 2).

[Chem. 2]

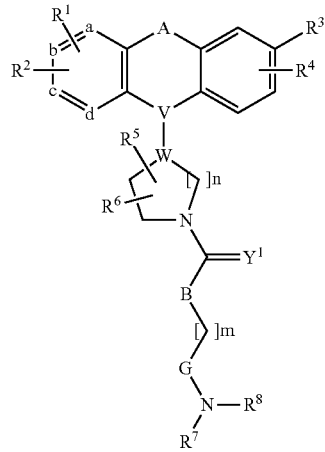

(See the above-referenced document for symbols in the formula)

However, there is no specific disclosure of a 1-substituted tetrahydroisoquinoline compound which pertains to the present invention.

Further, it has been described that the following tricyclic heteroaromatic compounds have an action of blocking N-type Ca$^{2+}$ channels and are useful as a medicament, particularly an analgesic agent (Patent Document 3).

[Chem. 3]

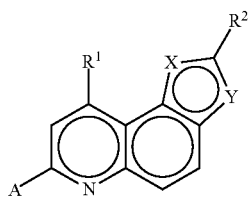

(See the above-referenced document for symbols in the formula)

However, there is no specific disclosure of a 1-substituted tetrahydroisoquinoline compound which pertains to the present invention.

Further, it has been described that the following substituted piperazine compounds have an action of blocking N-type Ca$^{2+}$ channels and are useful for treating cerebral stroke, pain, anxiety, depression, gastrointestinal disorders, genitourinary disturbance, cardiovascular disturbance, epilepsy, diabetes, and cancer (Patent Document 4).

[Chem. 4]

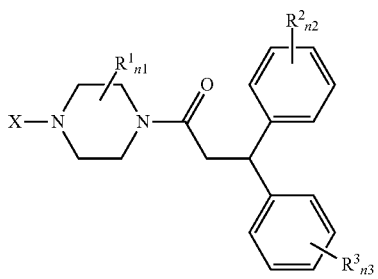

(See the above-referenced document for symbols in the formula)

However, there is no specific disclosure of a 1-substituted tetrahydroisoquinoline compound which pertains to the present invention.

Further, it has been reported that the following azacyclo compounds are useful for treating or preventing diseases associated with a flow of sodium ions of the sensory neuron channel, for example, pain such as chronic and acute pain, hypersensitivity diseases such as bladder diseases and irritable bowel syndrome, and demyelinating diseases (Patent Document 5).

[Chem. 5]

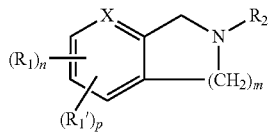

(See the above-referenced document for symbols in the formula)

However, there is no specific disclosure of a 1-substituted tetrahydroisoquinoline compound which pertains to the present invention.

Further, it has been reported that the following compounds have a farnesyl protein transferase inhibitory activity and are useful as an anticancer drug (Patent Document 6).

[Chem. 6]

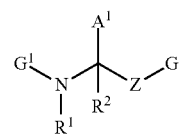

(See the above-referenced document for symbols in the formula)

However, there is no specific disclosure of a 1-substituted tetrahydroisoquinoline compound which pertains to the present invention. In addition, there is no disclosure or suggestion of their effects on N-type Ca$^{2+}$ channel-blocking action, pain including neuropathic pain, and digestive system diseases including irritable bowel syndrome.

Further, it has been reported that the following compounds have an anti-arrhythmic action (Non-Patent Document 1).

[Chem. 7]

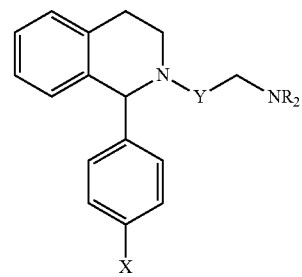

(See the above-referenced document for symbols in the formula)

However, an English Abstract attached to the above-referenced Document contains no specific disclosure of a 1-substituted tetrahydroisoquinoline compound which pertains to the present invention. In addition, there is no disclosure or suggestion of their effects on N-type Ca$^{2+}$ channel-blocking action, pain including neuropathic pain, and digestive system diseases including irritable bowel syndrome.

Further, it has been reported that the following compounds have an anti-arrhythmic action (Non-Patent Document 2).

[Chem. 8]

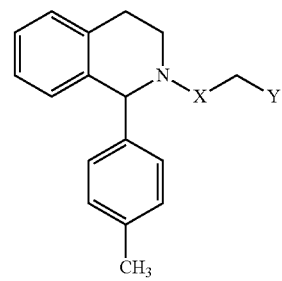

(See the above-referenced document for symbols in the formula)

However, an English Abstract attached to the above-referenced Document contains no specific disclosure of a 1-substituted tetrahydroisoquinoline compound which pertains to the present invention. In addition, there is no disclosure or suggestion of their effects on N-type Ca$^{2+}$ channel-blocking action, pain including neuropathic pain, and digestive system diseases including irritable bowel syndrome.

Further, it has been reported that the following compounds have an action of blocking Ca$^{2+}$ channels and are useful as a hypotensive agent and an anti-arrhythmic agent (Non-Patent Document 3).

[Chem. 9]

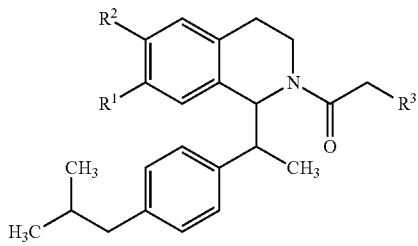

(See the above-referenced document for symbols in the formula)

However, an English Abstract attached to the above-referenced Document contains no specific disclosure of a 1-substituted tetrahydroisoquinoline compound which pertains to the present invention. In addition, there is no disclosure or suggestion of their effects on N-type Ca$^{2+}$ channel-blocking action, pain including neuropathic pain, and digestive system diseases including irritable bowel syndrome.

Further, it has been reported that the following compounds have a Ca$^{2+}$ channel-blocking action, a Na$^+$ channel-blocking action and a calmodulin inhibitory activity and are possibly useful in neuroprotective therapy (Non-Patent Documents 4 and 5).

[Chem. 10]

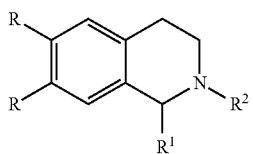

(See the above-referenced document for symbols in the formula)

However, there is no specific disclosure of a 1-substituted tetrahydroisoquinoline compound which pertains to the present invention.

Further, the following compounds have been reported as an Orexin-2 receptor antagonist (Non-Patent Document 6). Additionally, it has also been suggested that an Orexin-2 receptor is involved in the transmission of nociceptive stimuli.

[Chem. 11]

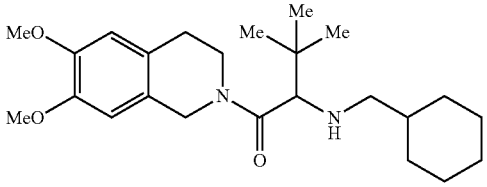

(Me in the formula represents methyl)

However, there is no specific disclosure of a 1-substituted tetrahydroisoquinoline compound which pertains to the present invention.

As other references which disclose compounds having a tetrahydroisoquinoline skeleton, there are Patent Documents 7 to 9. However, these documents contain no specific disclosure of a 1-substituted tetrahydroisoquinoline compound which pertains to the present invention.

[Patent Document 1] JP-A-2002-363163
[Patent Document 2] Pamphlet of International Publication No. WO 03/018538
[Patent Document 3] Pamphlet of International Publication No. WO 2004/089950
[Patent Document 4] Pamphlet of International Publication No. WO 2005/021523
[Patent Document 5] Pamphlet of International Publication No. WO 2005/005392
[Patent Document 6] European Patent Application Laid-open Publication No. EP 0 696 593
[Patent Document 7] Pamphlet of International Publication No. WO 01/85693
[Patent Document 8] Pamphlet of International Publication No. WO 02/079189
[Patent Document 9] Pamphlet of International Publication No. WO 03/082828
[Non-Patent Document 1] Fudan University Journal of Medical Science, 1987, 14 (1), 15-20
[Non-Patent Document 2] Fudan University Journal of Medical Science, 1989, 16 (1), 71-74
[Non-Patent Document 3] Journal of China Pharmaceutical University, 1993, 24 (4), 193-201
[Non-Patent Document 4] Biological & Pharmaceutical Bulletin, 2000, 23 (3), 375-378
[Non-Patent Document 5] Neurochemical Research, 2003, 28 (12), 1813-1818
[Non-Patent Document 6] Bioorganic & Medicinal Chemistry Letters, 2003, 13 (24), 4497-4499

DISCLOSURE OF THE INVENTION

Problem that the Invention is to Solve

It is an object of the present invention to provide a medicament having a selective blocking action on N-type Ca$^{2+}$ channels, and specifically a compound useful as an active ingredient of a pharmaceutical composition for preventing and/or treating pain and irritable bowel syndrome.

The compound of the present invention has a structural characteristic in that in the formula (I), at least one of R$^{1a}$ and R$^{1b}$ is a substituent other than —H, and R$^{22}$ is a hydroxyl-containing substituent. Further, the compound of the present invention has pharmacological properties in that it has an N-type Ca$^{2+}$ channel-blocking action, an antinociceptive pain action, an antineuropathic pain action, an abdominal pain-inhibitory action and an opioid-induced constipation-improving action.

Means for Solving the Problem

As a result of intensive studies on compounds having a selective blocking action on N-type $Ca^{2+}$ channels, the present inventors found that a 1-substituted tetrahydroisoquinoline compound of the present invention has a selective N-type $Ca^{2+}$ channel-blocking action, an antinociceptive pain action, an antineuropathic pain action, an abdominal pain-inhibitory action and an opioid-induced constipation-improving action. The present invention has been completed based on these findings.

That is, the present invention relates to a compound of the formula (I) or a pharmaceutically acceptable salt thereof, and a pharmaceutical composition comprising a compound of the formula (I) or a pharmaceutically acceptable salt thereof and a pharmaceutically acceptable excipient.

[1]
A compound of the formula (I):

[Chem. 12]

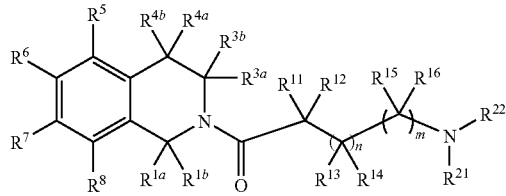

(I)

wherein the symbols in the formula have the following meanings:

$R^{1a}$ and $R^{1b}$: the same or different and —H, $C_{1-6}$ alkyl which may be substituted, cycloalkyl which may be substituted, aryl which may be substituted, or an aromatic hetero ring which may be substituted, provided that both of $R^{1a}$ and $R^{1b}$ cannot be —H, and $R^{1a}$ and $R^{1b}$, taken together with the carbon atom to which they are attached, may represent cycloalkyl which may be substituted, $R^{3a}$, $R^{3b}$, $R^{4a}$ and $R^{4b}$: the same or different and —H, or $C_{1-6}$ alkyl, $R^5$, $R^6$, $R^7$ and $R^8$: the same or different and —H, $C_{1-6}$ alkyl which may be substituted, —O—($C_{1-6}$ alkyl) which may be substituted, cyano, carbamoyl which may be substituted with one or two $C_{1-6}$ alkyl, or halogen, and any two adjacent groups of $R^5$, $R^6$, $R^7$ and $R^8$ taken together may form —O—$CH_2$—O— or —O—$(CH_2)_2$—O—, $R^{11}$, $R^{12}$, $R^{13}$, $R^{14}$, $R^{15}$ and $R^{16}$: the same or different and —H or $C_{1-6}$ alkyl, $R^{21}$: —H, $C_{1-6}$ alkyl which may be substituted, or cycloalkyl which may be substituted, $R^{22}$:

(1) cycloalkyl which is substituted with one or more groups selected from the group consisting of —OH and —$CH_2OH$ and which may be further substituted;

(2) $C_{1-8}$ alkyl substituted with one or two —OH, wherein the $C_{1-8}$ alkyl may further have a substituent, and one or two methylene groups (—$CH_2$—) contained in this alkyl chain may be replaced with —O—; or (3) $C_{1-6}$ alkyl substituted with cycloalkyl which is substituted with one or more groups selected from the group consisting of —OH and —$CH_2OH$ and which may be further substituted, wherein the $C_{1-6}$ alkyl may be substituted with —OH, and one or two methylene groups (—$CH_2$—) contained in this alkyl chain may be replaced with —O—;

n and m: the same or different and are 0 or 1, $R^{12}$ and $R^{21}$ taken together may form methylene, ethylene, or trimethylene, and in this case, $R^{11}$ may represent —OH, or $R^{21}$ and $R^{22}$, taken together with the nitrogen atom to which they are attached, may form azetidine, pyrrolidine, piperidine, azepane, azocane, morpholine, tetrahydroisoquinoline or thiomorpholine which are substituted with —OH or $C_{1-6}$ alkyl substituted with —OH; or a pharmaceutically acceptable salt thereof.

[2]
The compound according to [1], wherein m is 0, n is 0, and $R^{1a}$, $R^{3a}$, $R^{3b}$, $R^{4a}$, $R^{4b}$, $R^{11}$, $R^{12}$ and $R^{21}$ are each —H; or a pharmaceutically acceptable salt thereof.

[3]
The compound according to [2], wherein $R^{1b}$ is isopropyl, methoxymethyl, phenyl, 2-(trifluoromethyl)benzyl, or cyclohexyl; or a pharmaceutically acceptable salt thereof.

[4]
The compound according to [2] or [3], wherein $R^5$, $R^6$, $R^7$ and $R^8$ are the same or different and are independently selected from the group consisting of —H, methyl, ethyl, methoxy, and fluoro; or a pharmaceutically acceptable salt thereof.

[5]
The compound according to [2], [3] or [4], wherein $R^{22}$ is 2-hydroxypropan-1-yl, 2-hydroxy-3-methoxypropan-1-yl, or (1-hydroxycyclohexyl)methyl; or a pharmaceutically acceptable salt thereof.

[6]
The compound according to [1], which is
1-[({2-[(1S)-1-cyclohexyl-3,4-dihydroisoquinolin-2(1H)-yl]-2-oxoethyl}amino)methyl]cyclohexanol,
(2S)-1-({2-[(1S)-1-cyclohexyl-3,4-dihydroisoquinolin-2(1H)-yl]-2-oxoethyl}amino)-3-methoxy propan-2-ol,
1-({[2-(1(1S)-isopropyl-6-methoxy-3,4-dihydroisoquinolin-2(1H)-yl)-2-oxoethyl]amino}methyl)cyclohexanol,
(2R)-1-({2-[(1S)-8-methoxy-1-phenyl-3,4-dihydroisoquinolin-2(1H)-yl]-2-oxoethyl}amino)propan-2-ol,
1-[({2-[(1R)-7-ethyl-1-(methoxymethyl)-3,4-dihydroisoquinolin-2(1H)-yl]-2-oxoethyl}amino)methyl]cyclohexanol,
(2S)-1-methoxy-3-[(2-oxo-2-{1(1S)-[2-(trifluoromethyl)benzyl]-3,4-dihydroisoquinolin-2(1H)-yl}ethyl)amino] propan-2-ol,
1-({[3-(1-cyclohexyl-3,4-dihydroisoquinolin-2(1H)-yl)-3-oxo propyl]amino}methyl)cyclohexanol,
(2R)-1-{[2-(1-cyclohexyl-3,4-dihydroisoquinolin-2(1H)-yl)-2-oxoethyl]amino}propan-2-ol,
(2R)-1-[(2-oxo-2-{1-[2-(trifluoromethyl)phenyl]-3,4-dihydroisoquinolin-2(1H)-yl}ethyl)amino]propan-2-ol,
(2S)-1-{[2-(1-cyclohexyl-7-methyl-3,4-dihydroisoquinolin-2(1H)-yl)-2-oxoethyl]amino}-3-methoxy propan-2-ol,
(2R)-1-({2-oxo-2-[(1S)-1-phenyl-3,4-dihydroisoquinolin-2(1H)-yl]ethyl}amino)propan-2-ol,
1-[({2-[7-fluoro-1-(methoxymethyl)-3,4-dihydroisoquinolin-2(1H)-yl]-2-oxoethyl}amino)methyl]cyclohexanol,
1-[({2-[7-ethyl-1-(methoxymethyl)-3,4-dihydroisoquinolin-2(1H)-yl]-2-oxoethyl}amino)methyl]cyclohexanol,
1-({[2-(1-isopropyl-6-methoxy-3,4-dihydroisoquinolin-2(1H)-yl)-2-oxoethyl]amino}methyl)cyclohexanol,
1-[({2-[5-methoxy-1-(methoxymethyl)-3,4-dihydroisoquinolin-2(1H)-yl]-2-oxoethyl}amino)methyl]cyclohexanol,
1-[({2-[1-(methoxymethyl)-6-methyl-3,4-dihydroisoquinolin-2(1H)-yl]-2-oxoethyl}amino)methyl]cyclohexanol,
(1S,2S)-2-{[2-(1-cyclohexyl-3,4-dihydroisoquinolin-2(1H)-yl)-2-oxoethyl]amino}-1-phenyl propane-1,3-diol, 1-({(2R)-2-[(1-cyclohexyl-3,4-dihydroisoquinolin-2(1H)-yl)carbonyl]pyrrolidin-1-yl}methyl)cyclohexanol,
(2R)-1-{[2-(1-cyclohexyl-1-methyl-3,4-dihydroisoquinolin-2(1H)-yl)-2-oxoethyl]amino}propan-2-ol,
1-({[2-(3',4'-dihydro-2'H-spiro[cyclohexane-1,1'-isoquinolin]-2'-yl)-2-oxoethyl]amino}methyl)cyclohexanol,
(2R)-1-[(2-oxo-2-{1-[2-(trifluoromethoxy)phenyl]-3,4-dihydroisoquinolin-2(1H)-yl}ethyl)amino]propan-2-ol,
(2R)-1-{[2-(1-cyclohexyl-7-ethyl-3,4-dihydroisoquinolin-2(1H)-yl)-2-oxoethyl]amino}propan-2-ol,
1-({[2-(6-fluoro-1-isopropyl-3,4-dihydroisoquinolin-2(1H)-yl)-2-oxoethyl]amino}methyl)cyclohexanol,
1,1-dicyclopropyl-2-({2-[6-fluoro-1-(methoxymethyl)-3,4-dihydroisoquinolin-2(1H)-yl]-2-oxoethyl}amino)ethanol,
1-({[2-(1-tert-butyl-8-methoxy-3,4-dihydroisoquinolin-2(1H)-yl)-2-oxoethyl]amino}methyl)cyclohexanol,
1-({[2-(1-isopropyl-6-methyl-3,4-dihydroisoquinolin-2(1H)-yl)-2-oxoethyl]amino}methyl)cyclohexanol,
1-({[2-(6-fluoro-1-propyl-3,4-dihydroisoquinolin-2(1H)-yl)-2-oxoethyl]amino}methyl)cyclohexanol,
1-[({2-[1-(methoxymethyl)-7-methyl-3,4-dihydroisoquinolin-2(1H)-yl]-2-oxoethyl}amino)methyl]cyclohexanol,
1-({[2-(5-fluoro-1-propyl-3,4-dihydroisoquinolin-2(1H)-yl)-2-oxoethyl]amino}methyl)cyclohexanol,
1-[({2-[5-fluoro-1-(methoxymethyl)-3,4-dihydroisoquinolin-2(1H)-yl]-2-oxoethyl}amino)methyl]cyclohexanol,
1-[({2-[8-methoxy-1-(methoxymethyl)-3,4-dihydroisoquinolin-2(1H)-yl]-2-oxoethyl}amino)methyl]cyclohexanol,
1-[({2-[1-(ethoxymethyl)-7-methyl-3,4-dihydroisoquinolin-2(1H)-yl]-2-oxoethyl}amino)methyl]cyclohexanol, or
(1R,2S)-2-({2-[(1R)-1-(2-methoxyphenyl)-3,4-dihydroisoquinolin-2(1H)-yl]-2-oxoethyl}amino)cyclopentanol; or a pharmaceutically acceptable salt thereof.

[7]
A pharmaceutical composition comprising a compound of [1] or a pharmaceutically acceptable salt thereof and a pharmaceutically acceptable excipient.

[8]
An N-type $Ca^{2+}$ channel blocker comprising a compound of [1] or a pharmaceutically acceptable salt thereof.

[9]
A pharmaceutical composition for preventing or treating pain, neuropathic pain, abdominal symptom, spastic constipation, opioid-induced constipation, irritable bowel syndrome, or constipation-type irritable bowel syndrome, comprising a compound of [1] or a pharmaceutically acceptable salt thereof.

[10]
The pharmaceutical composition according to [9], which is a pharmaceutical composition for preventing or treating pain.

[11]
The pharmaceutical composition according to [10], which is a pharmaceutical composition for preventing or treating neuropathic pain.

[12]
The pharmaceutical composition according to [9], which is a pharmaceutical composition for preventing or treating abdominal symptom.

[13]
The pharmaceutical composition according to [9], which is a pharmaceutical composition for preventing or treating spastic constipation.

[14]
The pharmaceutical composition according to [13], which is a pharmaceutical composition for preventing or treating opioid-induced constipation.

[15]
The pharmaceutical composition according to [9], which is a pharmaceutical composition for preventing or treating irritable bowel syndrome.

[16]
The pharmaceutical composition according to [15], which is a pharmaceutical composition for preventing or treating constipation-type irritable bowel syndrome.

[17]
A pharmaceutical composition comprising a compound of [1] or a pharmaceutically acceptable salt thereof and an opioid as active ingredients.

[18]
A pharmaceutical composition comprising a compound of [1] or a pharmaceutically acceptable salt thereof as an active ingredient, wherein the composition is used in combination with an opioid.

[19]
Use of a compound of [1] or a pharmaceutically acceptable salt thereof for the manufacture of a pharmaceutical composition for preventing or treating pain, neuropathic pain, abdominal symptom, spastic constipation, opioid-induced constipation, irritable bowel syndrome, or constipation-type irritable bowel syndrome.

[20]
A compound of [1] for use as an active ingredient of a pharmaceutical composition for preventing or treating pain, neuropathic pain, abdominal symptom, spastic constipation, opioid-induced constipation, irritable bowel syndrome, or constipation-type irritable bowel syndrome.

[21]
A method for preventing or treating pain, neuropathic pain, abdominal symptom, spastic constipation, opioid-induced constipation, irritable bowel syndrome, or constipation-type irritable bowel syndrome, comprising administering to a patient an effective amount of a compound of [1] or a pharmaceutically acceptable salt thereof.

Further, the present invention relates to a pharmaceutical composition for treating pain, in a certain embodiment neuropathic pain; abdominal symptoms; spastic constipation, in a certain embodiment opioid-induced constipation; or irritable bowel syndrome, in a certain embodiment constipation-type irritable bowel syndrome, comprising a compound of the formula (I) or a pharmaceutically acceptable salt thereof, that is, a pharmaceutical composition for preventing and/or treating pain, in a certain embodiment neuropathic pain; abdominal symptoms; spastic constipation, in a certain embodiment opioid-induced constipation; or irritable bowel syndrome, in a certain embodiment constipation-type irritable bowel syndrome, comprising a compound of the formula (I) or a pharmaceutically acceptable salt thereof.

Further, the present invention relates to use of a compound of the formula (I) or a pharmaceutically acceptable salt thereof for the manufacture of a pharmaceutical composition for treating pain, in a certain embodiment neuropathic pain; abdominal symptoms; spastic constipation, in a certain embodiment opioid-induced constipation; or irritable bowel syndrome, in a certain embodiment constipation-type irritable bowel syndrome, and a method for treating pain, in a certain embodiment neuropathic pain; abdominal symptoms; spastic constipation, in a certain embodiment opioid-induced constipation; or irritable bowel syndrome, in a certain embodiment constipation-type irritable bowel syndrome, comprising administering to a patient an effective amount of a compound of the formula (I) or a pharmaceutically acceptable salt thereof.

Effect of the Invention

The compound of the present invention can be used as a pharmaceutical composition for preventing and/or treating various pains such as neuropathic pain and nociceptive pain, headaches such as migraine and cluster headache, central nervous system diseases such as anxiety, depression, epilepsy, cerebral stroke and restless legs syndrome, abdominal symptoms such as abdominal pain and abdominal distension, stool abnormalities such as diarrhea and constipation, digestive system diseases such as irritable bowel syndrome, urinary system diseases such as overactive bladder and interstitial cystitis, etc.

BEST MODE FOR CARRYING OUT THE INVENTION

Hereinafter, the present invention will be described in detail.

In the definitions of this specification, the "$C_{1-6}$ alkyl" means a linear or branched alkyl having 1 to 6 carbon atoms, and examples thereof include methyl, ethyl, n-propyl, isopropyl, n-butyl, isobutyl, sec-butyl, tert-butyl, n-pentyl, n-hexyl, and the like. The "$C_{1-8}$ alkyl" means a linear or branched alkyl having 1 to 8 carbon atoms, and examples thereof include n-heptyl, n-octyl, diisopropyl ethyl, and the like, in addition to the above-described $C_{1-6}$ alkyls.

The "halogen" means F, Cl, Br, or I.

The "cycloalkyl" is a $C_{3-10}$ saturated hydrocarbon ring group, and examples thereof include cyclopropyl, cyclobutyl, cyclopentyl, cyclohexyl, cycloheptyl, cyclooctyl, adamantyl, and the like. It also includes cyclohexenyl, cyclooctadienyl, and the like, which contain a partially unsaturated bond. Further, it also includes groups wherein one or two methylene groups on the ring are replaced with —O—, for example, tetrahydropyranyl, tetrahydrofuranyl, and the like. Further, its ring may be condensed with a benzene ring, and examples thereof include indenyl, indanyl, dihydronaphthyl, and tetrahydronaphthyl.

The "aryl" is a $C_{6-14}$ monocyclic to tricyclic aromatic hydrocarbon ring group, and examples thereof include phenyl, naphthyl, and the like.

The "aromatic hetero ring" is a 5- to 6-membered monocyclic hetero ring group containing 1 to 3 hetero atoms selected from oxygen, sulfur, and nitrogen, and examples thereof include furyl, thienyl, pyrrolyl, pyrazolyl, imidazolyl, oxazolyl, thiazolyl, isothiazolyl, triazinyl, pyridyl, pyrazyl, pyrimidinyl, pyridazinyl, and the like.

The "which may be substituted" means that it is "not substituted" or "substituted with 1 to 5 substituents which are the same or different". Further, if it has multiple substituents, the substituents may be the same or different from each other.

Examples of the substituent for the "$C_{1-6}$ alkyl which may be substituted" in the definition of $R^{1a}$ and $R^{1b}$ include —OH; —$OR^z$; or phenyl which may be substituted with one or more same or different groups selected from the group consisting of halogen, $R^Y$, and —$OR^Y$. $R^Y$ represents $C_{1-6}$ alkyl which may be substituted with 1 to 5 halogens, and $R^z$ represents $C_{1-6}$ alkyl which may be substituted with one or more same or different groups selected from the group consisting of —O— ($C_{1-6}$ alkyl) and —$OR^Y$ (the same shall apply hereinafter).

Examples of the substituent for the "cycloalkyl which may be substituted" in the definition of $R^{1a}$ and $R^{1b}$ include —OH, halogen, $R^Y$, and —$OR^Y$.

Examples of the substituent for the "aryl which may be substituted" and the "aromatic hetero ring which may be substituted" in the definition of $R^{1a}$ and $R^{1b}$ include —OH, halogen, $R^Y$, —$OR^Y$, —$SR^Y$, cyano, and cycloalkyl.

Examples of the substituent for the "$C_{1-6}$ alkyl which may be substituted" and the "—O—($C_{1-6}$ alkyl) which may be substituted" in the definition of $R^5$, $R^6$, $R^7$ and $R^8$ include —OH, halogen, —$OR^Y$, and —NHCO—($C_{1-6}$ alkyl).

Examples of the substituent for the "$C_{1-6}$ alkyl which may be substituted" in the definition of $R^{21}$ include —OH, halogen, —$OR^Y$, and cycloalkyl.

Examples of the substituent for the "cycloalkyl which may be substituted" in the definition of $R^{21}$ include —OH, halogen, $R^Y$, and —$OR^Y$.

The "cycloalkyl which is substituted by one or more groups selected from the group consisting of —OH and —$CH_2OH$ and which may be further substituted" in the definition of $R^{22}$ means that the cycloalkyl has at least one or more same or different groups selected from the group consisting of —OH and —$CH_2OH$, as substituents, and may be further substituted with other substituents. Examples of the acceptable additional substituents include halogen, $R^Y$, —$OR^Y$, oxo (=O), and oxo protected with ethylene glycol.

The "$C_{1-8}$ alkyl substituted with one or two —OH, wherein the $C_{1-8}$ alkyl may further have a substituent, and one or two methylene groups (—$CH_2$—) contained in this alkyl chain may be replaced with —O—" in the definition of $R^{22}$ means that methylene group(s) on the alkyl chain of the $C_{1-8}$ alkyl may be replaced with —O—, and the $C_{1-8}$ alkyl has at least one or two —OH as substituents and may be further substituted with other substituents. Examples of the acceptable additional substituent include halogen; —$OR^Y$; cycloalkyl; or aryl that may be substituted with one or more same or different groups selected from the group consisting of —OH, halogen, $R^Y$, and —$OR^Y$.

The "$C_{1-6}$ alkyl substituted with cycloalkyl which is substituted with one or more groups selected from the group consisting of —OH and —$CH_2OH$ and which may be further substituted, wherein the $C_{1-6}$ alkyl may be substituted with —OH, and one or two methylene groups (—$CH_2$—) contained in this alkyl chain may be replaced with —O—" in the definition of $R^{22}$ means that the $C_{1-6}$ alkyl may be substituted with —OH, methylene group(s) on the alkyl chain may be replaced with —O—, and the $C_{1-6}$ alkyl has at least cycloalkyl which may be substituted, as a substituent. Cycloalkyl as a substituent of the $C_{1-6}$ alkyl has at least one or more same or different groups selected from the group consisting of —OH and —$CH_2OH$, as substituents, and may be further substituted with other substituents. Examples of the acceptable additional substituents include halogen, $R^Y$, —$OR^Y$, oxo (=O), and oxo protected with ethylene glycol.

The "pain" means a variety of pains including nociceptive pain and neuropathic pain.

The "nociceptive pain" is a pain which is caused by the addition of nociceptive stimuli through nociceptors and examples thereof include pain caused by tissue damage, pain caused by tissue inflammation (inflammatory pain), pain caused by cancer-induced nerve compression (cancer pain).

The "neuropathic pain" is chronic pain which is caused by nerve tissue damage or compression or the like and examples thereof include trigeminal neuralgia, complex regional pain syndrome, post spinal surgery syndrome, phantom limb pain, pain after brachial plexus injury, post-spinal cord injury pain, post-stroke pain, painful diabetic neuropathy, postherpetic neuralgia, HIV-induced neuropathy, and further some cases of cancer pain and low back pain on which analgesic effects of opioids are not sufficiently, in addition to anticancer drug- and anti-HIV drug-induced neuropathy.

The "abdominal symptom" means abdominal discomfort such as abdominal pain and abdominal distension.

The "spastic constipation" is constipation caused by spastic dysmotility of the digestive tract, and examples thereof include opioid-induced constipation, and constipation found in constipation-type irritable bowel syndrome (IBS-C).

The "opioid-induced constipation" means constipation caused by opioids such as morphine.

The "irritable bowel syndrome" is a disease which brings about abdominal symptoms such as abdominal pain and abdominal distension and stool abnormalities such as diarrhea or defecation urgency and constipation or difficulty in defecation, due to the dysfunction of the lower digestive tract around the large intestine, despite no occurrence of organic alterations such as inflammation and tumor and the like, and is a disease which is classified into diarrhea type IBS (IBS-D), constipation type IBS (IBS-C), and mix type IBS (IBS-M) with alternating diarrhea and constipation, depending on bowel conditions.

Hereinafter, some embodiments of the present invention will be described.

(1) In the formula (I), a compound wherein $R^{1a}$ is —H or $C_{1-6}$ alkyl which may be substituted. In another embodiment, a compound wherein $R^{1a}$ is —H or methyl. In yet another embodiment, a compound wherein $R^{1a}$ is —H.

(2) In the formula (I), a compound wherein $R^{1b}$ is $C_{1-6}$ alkyl which may be substituted, cycloalkyl which may be substituted, or aryl which may be substituted. In another embodiment, a compound wherein $R^{1b}$ is n-propyl, isopropyl, tert-butyl, methoxymethyl, ethoxymethyl, phenyl, 2-methoxyphenyl, 2-(trifluoromethyl)phenyl, 2-(trifluoromethoxy)phenyl, 2-(trifluoromethyl)benzyl, or cyclohexyl. In yet another embodiment, a compound wherein $R^{1b}$ is isopropyl, methoxymethyl, phenyl, 2-(trifluoromethyl)benzyl, or cyclohexyl.

(3) In the formula (I), a compound wherein $R^{1a}$ and $R^{1b}$, together with the carbon atom to which they are attached, represent cycloalkyl which may be substituted. In another embodiment, a compound wherein $R^{1a}$ and $R^{1b}$, together with the carbon atom to which they are attached, represent cyclohexyl.

(4) In the formula (I), a compound wherein $R^{3a}$, $R^{3b}$, $R^{4a}$ and $R^{4b}$ are each —H.

(5) In the formula (I), a compound wherein m is 0, and n is 0 or 1. In another embodiment, a compound wherein m is 0, and n is 0.

(6) In the formula (I), a compound wherein $R^5$, $R^6$, $R^7$ and $R^8$ are the same or different and are independently selected from the group consisting of —H, $C_{1-6}$ alkyl, —O—($C_{1-6}$ alkyl), and halogen. In another embodiment, a compound wherein $R^5$, $R^6$, $R^7$ and $R^8$ are the same or different and are selected from the group consisting of —H, methyl, ethyl, methoxy, and fluoro.

(7) In the formula (I), a compound wherein $R^{11}$, $R^{12}$, $R^{13}$, $R^{14}$, $R^{15}$ and $R^{16}$ are each —H.

(8) In the formula (I), a compound wherein m is 0, n is 0, $R^{11}$ is —H, and $R^{12}$ and $R^{21}$ taken together represent methylene, ethylene or trimethylene. In another embodiment, a compound wherein m is 0, n is 0, $R^{11}$ is —H, and $R^{12}$ and $R^{21}$ taken together represent trimethylene.

(9) A compound wherein $R^{21}$ is —H.

(10) In an embodiment, a compound wherein $R^{22}$ is cycloalkyl substituted with one or more groups selected from the group consisting of —OH and —CH$_2$OH. In another embodiment, a compound wherein $R^{22}$ is cyclopentyl or cyclohexyl substituted with one or more groups selected from the group consisting of —OH and —CH$_2$OH. In yet another embodiment, a compound wherein $R^{22}$ is 2-hydroxycyclopentyl.

(11) In an embodiment, a compound wherein $R^{22}$ is $C_{1-8}$ alkyl which is substituted with one or two —OH and is further substituted with one or more the same or different groups selected from the group consisting of —O—($C_{1-6}$ alkyl), cycloalkyl, and aryl. In another embodiment, a compound wherein $R^{22}$ is $C_{1-8}$ alkyl which is substituted with one or two —OH and is further substituted with one or more the same or different groups selected from the group consisting of methoxy, cyclopropyl, and phenyl. In a further embodiment, a compound wherein $R^{22}$ is ethyl or propyl which is substituted with one or two —OH and is further substituted with one or more same or different groups selected from the group consisting of methoxy, cyclopropyl, and phenyl. In a still further embodiment, a compound wherein $R^{22}$ is 2-hydroxypropan-1-yl, 2-hydroxy-3-methoxypropan-1-yl, 1,3-dihydroxy-1-phenylpropan-2-yl, or 2-hydroxy-2,2-dicyclopropylethyl. In yet another embodiment, a compound wherein $R^{22}$ is 2-hydroxypropan-1-yl or 2-hydroxy-3-methoxypropan-1-yl.

(12) In an embodiment, a compound wherein $R^{22}$ is $C_{1-6}$ alkyl substituted with cycloalkyl which is substituted with one or more groups selected from the group consisting of —OH and —CH$_2$OH. In another embodiment, a compound wherein $R^{22}$ is cyclohexylmethyl substituted with —OH. In yet another embodiment, a compound wherein $R^{22}$ is (1-hydroxycyclohexyl)methyl.

(13) In an embodiment, a compound as set forth in (10), (11), or (12). In another embodiment, a compound as set forth in (11) or (12).

(14) A compound which is a combination of any two or more selected from the group consisting of (1), (2), (4), (5), (6), (7), (9), and (13).

(15) A compound which is a combination of any two or more selected from the group consisting of (3), (4), (5), (6), (7), (9), and (13).

(16) A compound which is a combination of any two or more selected from the group consisting of (1), (2), (4), (6), (8), and (13).

(17) A compound which is a combination of any two or more selected from the group consisting of (3), (4), (6), (8), and (13).

(18) In an embodiment, a compound which is any one of (14) to (17). In another embodiment, a compound as set forth in (14).

(19) A compound which is a combination of any two or more of (1) to (12) which are not inconsistent with each other.

Examples of the compounds encompassed by the present invention include the following compounds.

1-[({2-[(1S)-1-cyclohexyl-3,4-dihydroisoquinolin-2(1H)-yl]-2-oxoethyl}amino)methyl]cyclohexanol, (2S)-1-({2-[(1S)-1-cyclohexyl-3,4-dihydroisoquinolin-2(1H)-yl]-2-oxoethyl}amino)-3-methoxy propan-2-ol, 1-({[2-(1(1S)-isopropyl-6-methoxy-3,4-dihydroisoquinolin-2(1H)-yl)-2-oxoethyl]amino}methyl)cyclohexanol, (2R)-1-({2-[(1S)-8-methoxy-1-phenyl-3,4-dihydroisoquinolin-2(1H)-yl]-2-oxoethyl}amino)propan-2-ol, 1-[({2-[(1R)-7-ethyl-1-(methoxymethyl)-3,4-dihydroisoquinolin-2(1H)-yl]-2-oxoethyl}amino)methyl]cyclohexanol, (2S)-1-methoxy-3-[(2-oxo-2-{1(1S)-[2-(trifluoromethyl)benzyl]-3,4-dihydroisoquinolin-2(1H)-yl}ethyl)amino]propan-2-ol.

As another embodiment of compounds that are encompassed in the present invention, the following compounds may be mentioned.

1-({[3-(1-cyclohexyl-3,4-dihydroisoquinolin-2(1H)-yl)-3-oxopropyl]amino}methyl)cyclohexanol,
(2R)-1-{[2-(1-cyclohexyl-3,4-dihydroisoquinolin-2(1H)-yl)-2-oxoethyl]amino}propan-2-ol,
(2R)-1-[(2-oxo-2-{1-[2-(trifluoromethyl)phenyl]-3,4-dihydroisoquinolin-2(1H)-yl}ethyl)amino]propan-2-ol,
(2S)-1-{[2-(1-cyclohexyl-7-methyl-3,4-dihydroisoquinolin-2(1H)-yl)-2-oxoethyl]amino}-3-methoxy propan-2-ol,
(2R)-1-({2-oxo-2-[(1S)-1-phenyl-3,4-dihydroisoquinolin-2(1H)-yl]ethyl}amino)propan-2-ol,
1-[({2-[7-fluoro-1-(methoxymethyl)-3,4-dihydroisoquinolin-2(1H)-yl]-2-oxoethyl}amino)methyl]cyclohexanol,
1-[({2-[7-ethyl-1-(methoxymethyl)-3,4-dihydroisoquinolin-2(1H)-yl]-2-oxoethyl}amino)methyl]cyclohexanol,
1-({[2-(1-isopropyl-6-methoxy-3,4-dihydroisoquinolin-2(1H)-yl)-2-oxoethyl]amino}methyl)cyclohexanol,
1-[({2-[5-methoxy-1-(methoxymethyl)-3,4-dihydroisoquinolin-2(1H)-yl]-2-oxoethyl}amino)methyl]cyclohexanol,
1-[({2-[1-(methoxymethyl)-6-methyl-3,4-dihydroisoquinolin-2(1H)-yl]-2-oxoethyl}amino)methyl]cyclohexanol,
(1S,2S)-2-{[2-(1-cyclohexyl-3,4-dihydroisoquinolin-2(1H)-yl)-2-oxoethyl]amino}-1-phenylpropane-1,3-diol,
1-({(2R)-2-[(1-cyclohexyl-3,4-dihydroisoquinolin-2(1H)-yl)carbonyl]pyrrolidin-1-yl}methyl)cyclohexanol,
(2R)-1-{[2-(1-cyclohexyl-1-methyl-3,4-dihydroisoquinolin-2(1H)-yl)-2-oxoethyl]amino}propan-2-ol,
1-({[2-(3',4'-dihydro-2'H-spiro[cyclohexane-1,1'-isoquinolin]-2'-yl)-2-oxoethyl]amino}methyl)cyclohexanol,
(2R)-1-[(2-oxo-2-{1-[2-(trifluoromethoxy)phenyl]-3,4-dihydroisoquinolin-2(1H)-yl}ethyl)amino]propan-2-ol,
(2R)-1-{[2-(1-cyclohexyl-7-ethyl-3,4-dihydroisoquinolin-2(1H)-yl)-2-oxoethyl]amino}propan-2-ol,
1-({[2-(6-fluoro-1-isopropyl-3,4-dihydroisoquinolin-2(1H)-yl)-2-oxoethyl]amino}methyl)cyclohexanol,
1,1-dicyclopropyl-2-({2-[6-fluoro-1-(methoxymethyl)-3,4-dihydroisoquinolin-2(1H)-yl]-2-oxoethyl}amino)ethanol,
1-({[2-(1-tert-butyl-8-methoxy-3,4-dihydroisoquinolin-2(1H)-yl)-2-oxoethyl]amino}methyl)cyclohexanol,
1-({[2-(1-isopropyl-6-methyl-3,4-dihydroisoquinolin-2(1H)-yl)-2-oxoethyl]amino}methyl)cyclohexanol,
1-({[2-(6-fluoro-1-propyl-3,4-dihydroisoquinolin-2(1H)-yl)-2-oxoethyl]amino}methyl)cyclohexanol,
1-[({2-[1-(methoxymethyl)-7-methyl-3,4-dihydroisoquinolin-2(1H)-yl]-2-oxoethyl}amino)methyl]cyclohexanol,
1-({[2-(5-fluoro-1-propyl-3,4-dihydroisoquinolin-2(1H)-yl)-2-oxoethyl]amino}methyl)cyclohexanol,
1-[({2-[5-fluoro-1-(methoxymethyl)-3,4-dihydroisoquinolin-2(1H)-yl]-2-oxoethyl}amino)methyl]cyclohexanol,
1-[({2-[8-methoxy-1-(methoxymethyl)-3,4-dihydroisoquinolin-2(1H)-yl]-2-oxoethyl}amino)methyl]cyclohexanol,
1-[({2-[1-(ethoxymethyl)-7-methyl-3,4-dihydroisoquinolin-2(1H)-yl]-2-oxoethyl}amino)methyl]cyclohexanol,
(1R,2S)-2-({2-[(1R)-1-(2-methoxyphenyl)-3,4-dihydroisoquinolin-2(1H)-yl]-2-oxoethyl}amino)cyclopentanol.

The compound of the present invention may in some cases exist in the form of other tautomers or geometrical isomers, depending on the kind of the substituents. In the present specification, the compound may be described only in one form of isomers, and the present invention includes these isomers as well as isolated forms or mixtures thereof.

Further, the compound of the formula (I) may have asymmetric carbon atoms or axial asymmetries in some cases, and correspondingly, it may exist in the form of optical isomers such as R- and S-forms. All of the mixtures and isolates of these optical isomers are included in the present invention.

Further, a pharmaceutically acceptable prodrug of the compound of the formula (I) is also included in the present invention. The "pharmaceutically acceptable prodrug" is a compound having a group which can be converted into an amino group, a hydroxyl group, a carboxyl group or the like of the present invention by solvolysis or under a physiological condition. Examples of the group for forming a prodrug include those as described for example in Prog. Med., 5, 2157-2161 (1985) or "Iyakuhin no Kaihatsu (Development of Pharmaceuticals)" (Hirokawa Shoten Ltd., 1990), Vol. 7, "Bunshi Sekkei (Molecular Design)", pp. 163-198.

Further, the compound of the present invention may form an acid addition salt or a salt with a base, depending on the kind of substituents, and this salt is included in the present invention, as long as it is a pharmaceutically acceptable salt. Specifically, examples of such salts include acid addition salts with inorganic acids such as hydrochloric acid, hydrobromic acid, hydroiodic acid, sulfuric acid, nitric acid, and phosphoric acid, or with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methanesulfonic acid, ethanesulfonic acid, benzenesulfonic acid, p-toluenesulfonic acid, aspartic acid, and glutamic acid, salts with inorganic bases such as sodium, potassium, magnesium, calcium, and aluminum, or with organic bases such as methylamine, ethylamine, ethanolamine, lysine, and ornithine, salts with various amino acids and amino acid derivatives such as acetylleucine, ammonium salts, and the like.

In addition, the present invention also includes various hydrates or solvates, and crystalline polymorphs of the compound of the present invention and a pharmaceutically acceptable salt thereof. Further, compounds labeled with various radioactive or non-radioactive isotopes are also included in the present invention.

(Production Methods)

The compound of the present invention and a pharmaceutically acceptable salt thereof can be prepared by applying various known synthetic methods, making use of the characteristics based on its basic skeleton or type of substituents. In that case, depending on the kind of functional groups, there is an effective case from the production technology point of view to replace the functional group with an appropriate protecting group (a group which can be easily converted into the functional group), at the stage of starting materials to intermediates. Examples of such a protecting group include those described for example in "Protective Groups in Organic Synthesis ($3^{rd}$ edition, 1999)", edited by Greene and Wuts, and the like, which may be appropriately selected and used depending on the reaction conditions. According to such a method, a desired compound can be obtained by introducing the protecting group and carrying out the reaction, and then removing the protecting group, if desired.

In addition, the prodrug of the compound (I) can be produced in the same manner as the case of the above-mentioned protecting groups, by carrying out the reaction after introducing a specific group at the stage of starting materials to intermediates or using the obtained compound of the present invention. The reaction can be carried out by employing methods known to those skilled in the art, such as usual esterification, amidation, dehydration and the like.

Hereinafter, the representative production processes for the compound of the present invention will be described. Each of the production processes may also be carried out with reference to References appended to the corresponding description. Further, the production processes of the present invention are not limited to the examples as shown below.

(Production Process 1)

[Chem. 13]

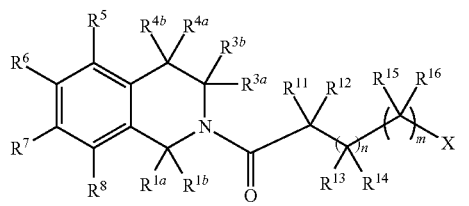

(1a)

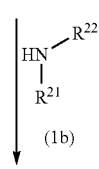

(1b)

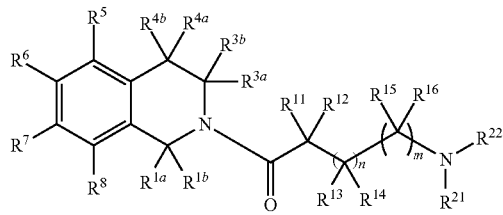

(I)

(In the formula, X represents a leaving group, and other symbols are as defined above. The same shall apply hereinafter)

This production process is a method in which the compound (I) of the present invention is produced by reacting a compound (1a) having a leaving group with an amine derivative (1b).

In this case, examples of the leaving group include halogen, methanesulfonyloxy, and p-toluenesulfonyloxy.

The reaction can be carried out using the compound (1a) and the compound (1b) in equivalent amounts or one of them in an excess amount, from under cooling to under heating, for example, at 0° C. to 80° C. usually stirring for 0.1 hour to 5 days, in a reaction-inert solvent or without a solvent. There is no particular limit to the solvent that can be used herein. Examples of such a solvent include aromatic hydrocarbons such as benzene, toluene, and xylene; ethers such as diethyl ether, tetrahydrofuran (THF), dioxane, and dimethoxyethane (DME); halogenated hydrocarbons such as dichloromethane (DCM), 1,2-dichloroethane (DCE), and chloroform; N,N-dimethylformamide (DMF), dimethylsulfoxide (DMSO), ethyl acetate, acetonitrile, and a mixture thereof. It may be advantageous in some cases for smooth progress of the reaction to carry out the reaction in the presence of an organic base such as triethylamine, N,N-diisopropylethylamine (DIPEA), 1,8-diazabicyclo[5.4.0]-7-undecene, or N-methylmorpholine, or an inorganic base such as potassium carbonate, sodium carbonate, cesium carbonate, or potassium hydroxide, or otherwise in the co-presence of a phase-transfer catalyst such as tetrabutylammonium iodide or 18-crown-6-ether.

REFERENCE LITERATURE

S. R. Sandler and W. Karo, Editors, Organic Functional Group Preparations, $2^{nd}$ edition. Vol. 1, Academic Press Inc., 1991

Courses in Experiment Chemisty, $5^{th}$ edition, edited by The Chemical Society of Japan, Vol. 14 (2005), Maruzen Co., Ltd.

(Production Process 2)

[Chem. 14]

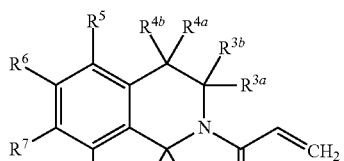

(2a)

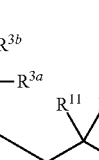

(1b)

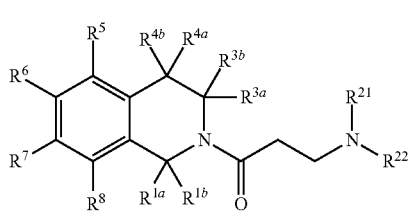

(I-2)

(the symbols in the formula are as defined above)

This production process is a method in which the compound (I-2) of the present invention is produced by reacting an acrylic derivative (2a) with the amine derivative (1b).

The reaction can be carried out using the compound (2a) and the compound (1b) in equivalent amounts or one of them in an excess amount, from under cooling to under heating, for example, at 0° C. to 120° C. usually stirring for 0.1 hour to 5 days, in a reaction-inert solvent or without a solvent. There is no particular limit to the solvent that can be used herein. Examples of such a solvent include aromatic hydrocarbons, ethers, halogenated hydrocarbons, alcohols such as methanol, ethanol, and 2-propanol, N,N-dimethylformamide (DMF), dimethylsulfoxide (DMSO), ethyl acetate, acetonitrile, and a mixture thereof. When the amine derivative is in the form of a salt, it may be advantageous in some cases for smooth progress of the reaction to carry out desalination in the presence of an organic base such as triethylamine, N,N-diisopropylethylamine (DIPEA), 1,8-diazabicyclo[4.5.0]-7-undecene, or N-methylmorpholine, or an inorganic base such as potassium carbonate, sodium carbonate, or potassium hydroxide.

(Production Process 3)

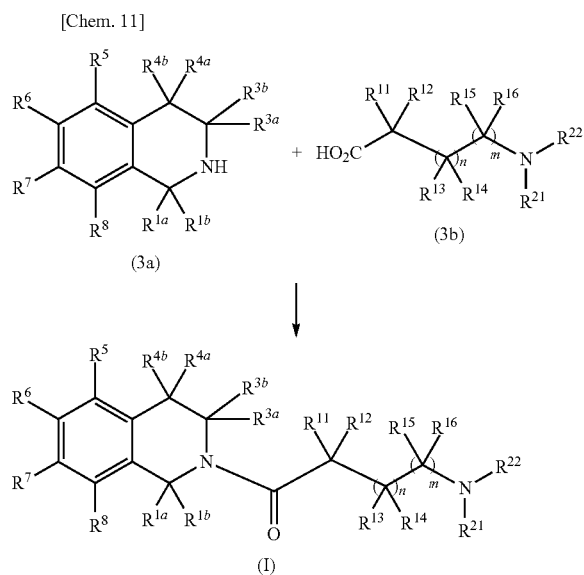

(the symbols in the formula are as defined above)

This production process is a method in which the compound (I) of the present invention is produced by reacting a tetrahydroisoquinoline derivative (3a) with an amino acid derivative (3b).

The reaction can be carried out using the compound (3a) and the compound (3b) in equivalent amounts or one of them in an excess amount in the presence of a condensing agent, from under cooling to under heating, for example, at −20° C. to 60° C. usually stirring for 0.1 hour to 5 days, in a reaction-inert solvent. There is no particular limit to the solvent that can be used herein. Examples of such a solvent include aromatic hydrocarbons, halogenated hydrocarbons, ethers, N,N-dimethylformamide (DMF), N-methylpyrrolidone, ethyl acetate, acetonitrile, water, and a mixture thereof. Examples of the condensing agent include, but are not limited to, 1-(3-dimethylaminopropyl)-3-ethylcarbodiimide (WSC), dicyclohexylcarbodiimide (DCC), 1,1'-carbonyldiimidazole (CDI), diphenylphosphoryl azide, and phosphorus oxychloride. It may be advantageous in some cases for smooth progress of the reaction to carry out the reaction using, for example, an additive such as 1-hydroxybenzotriazole (HOBt).

Further, a method can also be used in which the amino acid derivative (3b) (with respect to a carboxyl group serving as a reaction site) is converted into a reactive derivative thereof, and then the reactive derivative is reacted with the tetrahydroisoquinoline derivative (3a). In this case, examples of the reactive derivative include acid halides obtained by reaction with a halogenating agent such as phosphorus oxychloride or thionyl chloride, mixed acid anhydrides obtained by reaction with isobutyl chloroformate or the like, and active esters obtained by condensation with HOBt or the like. The reaction between the reactive derivative of the compound (3b) and the compound (3a) can be carried out from under cooling to under heating, for example at −20° C. to 60° C., in a reaction-inert solvent such as halogenated hydrocarbons, aromatic hydrocarbons, or ethers.

REFERENCE LITERATURE

S. R. Sandler and W. Karo, Editors, Organic Functional Group Preparations, $2^{nd}$ edition. Vol. 1, Academic Press Inc., 1991

Courses in Experimental Chemistry, $5^{th}$ edition, edited by The Chemical Society of Japan, Vol. 16 (2005), Maruzen Co., Ltd.

(Production Process 4)

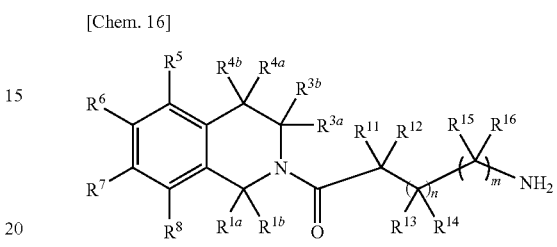

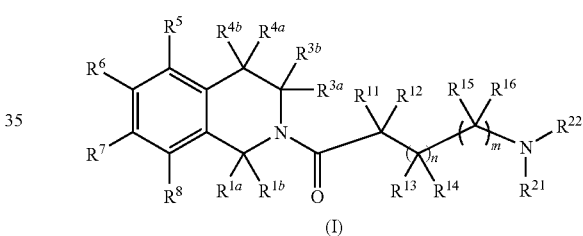

(In the formula, Y represents a leaving group, and other symbols are as defined above. The same shall apply hereinafter).

This production process is a method in which the compound (I) of the present invention is produced by reacting an amine derivative (4a) with a compound (4b) and/or (4c) having a leaving group.

The reaction can be carried out in the same manner as in Production Process 1. When $R^{21}$ represents —H, Step A using the compound (4b) may be omitted. Further, the order of performing Step A using the compound (4b) and Step B using the compound (4c) is not critical.

In addition to N-alkylation using the compound (4b) or (4c) having a leaving group, this production process may also employ N-alkylation using an epoxy derivative corresponding to the compound (4b) or (4c), and reductive amination using an aldehyde derivative corresponding to the compound (4b) or (4c).

The N-alkylation using the epoxy derivative corresponding to the compound (4b) or (4c) can be carried out in the same manner as in Production Process 1.

The reductive amination using the aldehyde derivative corresponding to the compound (4b) or (4c) can be carried out using the compound (4a) and the aldehyde derivative corresponding to the compound (4b) or (4c) in equivalent amounts or one of them in an excess amount, at −45° C. to heating under reflux in the presence of a reducing agent in a reaction-inert solvent, for example, at 0° C. to room temperature, usually stirring for 0.1 hour to 5 days. There is no particular limit to the solvent that can be used herein. Examples of such a solvent include alcohols, ethers, and a mixture thereof. Examples of the reducing agent include sodium cyanoborohydride, triacetoxy sodium borohydride, sodium borohydride, and the like. It may be advantageous in some cases for smooth progress of the reaction to carry out the reaction in the presence of a dehydrating agent such as molecular sieves or an acid such as acetic acid, hydrochloric acid, or titanium (IV) isopropoxide complex. Depending on the reaction, there is a case where an imine compound may be formed by condensation of the compound (4a) with the aldehyde derivative corresponding to the compound (4b) or (4c) and then may be isolated as a stable intermediate. Further, the reaction may be carried out in a solvent such as alcohols or ethyl acetate, in the presence or absence of an acid such as acetic acid or hydrochloric acid, using a reduction catalyst (such as Pd-supported carbon (Pd/C), palladium hydroxide, or Raney nickel), instead of treatment with the reducing agent. In this case, the reaction can be carried out from under cooling to under heating, under a hydrogen atmosphere at normal pressure to 50 atmospheres.

REFERENCE LITERATURE

A. R. Katritzky and R. J. K. Taylor, Editors, Comprehensive Organic Functional Group Transformation II, Vol. 2, Elsevier Pergamon, 2005

Courses in Experimental Chemistry, 5th edition, edited by The Chemical Society of Japan, Vol. 14 (2005), Maruzen Co., Ltd.

Further, the starting compound (4a) of this production process can be prepared by deprotection of the amine through the reaction of the compound (1a) with the protected amine derivative in the same manner as in Production Process 1, or by deprotection of the amino group through the reaction of the compound (3a) with the amino-protected amino acid derivative in the same manner as in Production Process 3.

(Starting Material Synthesis)

(1) Production of Compounds (1a) and (2a)

[Chem. 17]

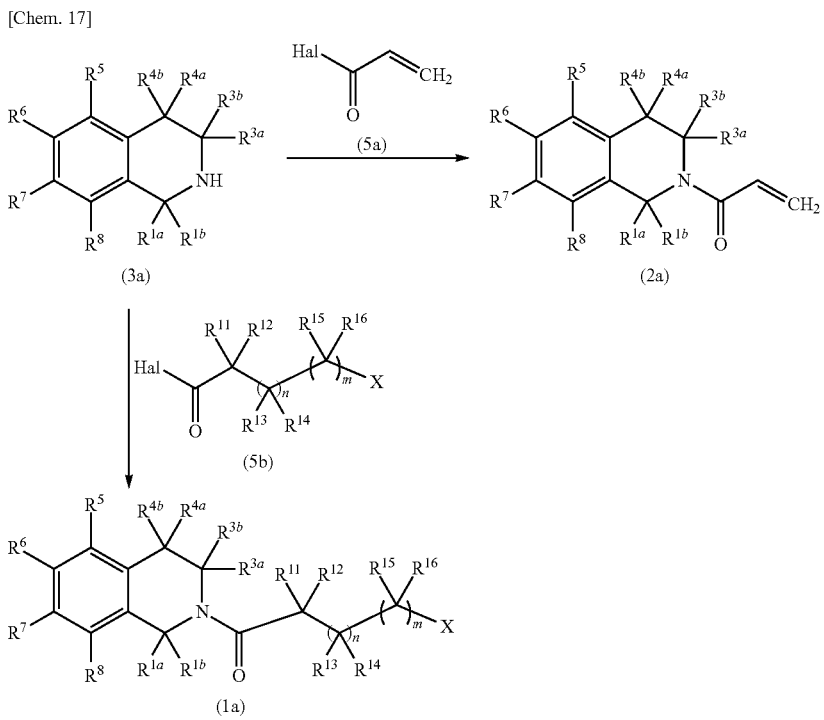

(In the formula, Hal represents halogen, and other symbols are as defined above. The same shall apply hereinafter).

This production process is a method in which the compound (2a) or (1a) is produced by reacting the tetrahydroisoquinoline derivative (3a) with an acid halide (5a) or (5b).

The reaction can be carried out using the compound (3a) and the compound (5a) or (5b) in equivalent amounts or one of them in an excess amount, from under cooling to under heating, for example, at 0° C. to 80° C. usually stirring for 0.1 hour to 5 days, in a reaction-inert solvent or without a solvent. There is no particular limit to the solvent that can be used herein. Examples of such a solvent include aromatic hydrocarbons, ethers, halogenated hydrocarbons, ethyl acetate, acetonitrile, and a mixture thereof. It may be advantageous in some cases for smooth progress of the reaction to carry out the reaction in the presence of an organic base such as triethylamine, N,N-diisopropylethylamine (DIPEA), pyridine, or N-methylmorpholine, or an inorganic base such as potassium carbonate, sodium carbonate, sodium hydrogen carbonate, or potassium hydroxide, or an aqueous solution thereof, or in the presence of 0.01 to 0.2 equivalent amounts, preferably 0.05 to 0.15 equivalent amounts of a catalyst such as N,N-dimethylaminopyridine.

(2) Production of Compound (3a)-1

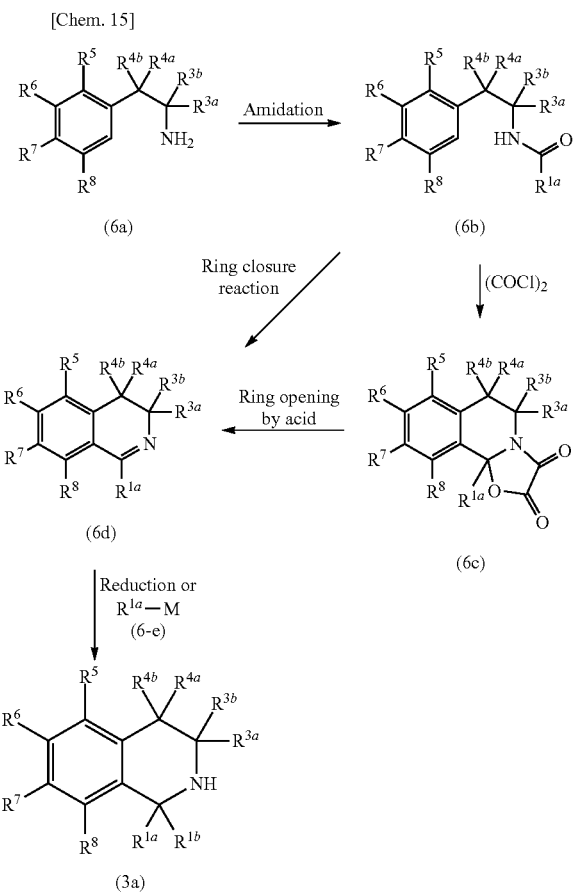

(In the formula, M is an alkali metal or alkaline earth metal and represents an anionic metal salt of $R^{1b}$ showing nucleophilicity in the form of $R^{1b}$-M, and other symbols are as defined above. The same shall apply hereinafter.)

This production process is a method in which the compound (3a) is produced by subjecting a phenethylamide derivative (6b) obtained by amidation of a phenethylamine derivative (6a) to a ring closure reaction using a phosphoric acid derivative, or to a condensation reaction using oxalyl chloride, followed by acid-catalyzed ring cleavage to obtain a dihydroisoquinoline derivative (6d), and reduction of the compound (6d) or addition of a nucleophilic reagent to the compound (6d).

The amidation step of the compound (6a) can be carried out in the same manner as in Production Process 3.

The ring closure step of the compound (6b) can be carried out by stirring the compound (6b) in a reaction-inert solvent or without a solvent, in the presence of a phosphoric acid derivative, usually for 1 hour to 5 days. The reaction is typically carried out from under cooling to under heating, for example, from room temperature to heating under reflux. It may be advantageous in some cases to carry out the reaction in the absence of a solvent. The solvent, if used, is not particularly limited, but examples thereof include high-boiling aromatic hydrocarbons such as toluene, and xylene. Examples of the phosphoric acid derivative include diphosphorus pentoxide, a mixture of diphosphorus pentoxide and phosphorus oxychloride, polyphosphoric acid, ethyl polyphosphate, and the like.

Alternatively, this step can be carried out in such a manner that an oxalyl chloride is reacted with the amide (6b) to construct a 2-chlorooxazolone ring, the resulting product is subjected to ring-closure condensation in the presence of a Lewis acid catalyst such as iron chloride to obtain a 6,10b-dihydro-5H-[1,3]isoxazolo[2,3-a]isoquinoline-2,3-dione derivative (6c), followed by solvolysis of the derivative (6c) in the presence of a strong acid such as sulfuric acid or using an alkali metal alkoxide such as sodium methoxide to result in a compound (6d).

When $R^{1b}$ is hydrogen, the compound (3a) wherein $R^{1b}$ is hydrogen can be obtained by reduction of the compound (6d). The reaction is carried out by treating the compound (6d) with an equivalent or excess amount of a reducing agent, from under cooling to under heating, for example, at −20° C. to 80° C. usually for 0.1 hour to 3 days, in a reaction-inert solvent. There is no particular limit to the solvent that can be used herein. Examples of such a solvent include ethers, alcohols, aromatic hydrocarbons, N,N-dimethylformamide (DMF), dimethylsulfoxide (DMSO), ethyl acetate, and a mixture thereof. Examples of the reducing agent include hydride reducing agents such as sodium borohydride, diisobutylaluminum hydride, and lithium aluminum hydride, metal reducing agents such as sodium, zinc, and iron, and other reducing agents as described in the following literature.

REFERENCE LITERATURE

M. Hulicky, Reductions in Organic Chemistry, $2^{nd}$ ed (ACS Monograph: 188), ACS, 1996

R. C. Larock, Comprehensive Organic Transformations, $2^{nd}$ ed, VCH Publishers, Inc., 1999

T. J. Donohoe, Oxidation and Reduction in Organic Synthesis (Oxford Chemistry Primers 6), Oxford Science Publications, 2000

Courses in Experimental Chemistry, $5^{th}$ edition, edited by The Chemical Society of Japan, Vol. 14 (2005), Maruzen Co., Ltd.

When $R^{1b}$ represents a group other than hydrogen, it is possible to make use of anionic addition by means of a nucleophilic reagent (6e) for the compound (6d). The reaction can be carried out using the compound (6d) and the compound (6e) in equivalent amounts or one of them in an excess amount, from under cooling to under heating, for example, at −78° C. to 0° C. usually stirring for 0.1 hour to 5 days, in a reaction-inert solvent. There is no particular limit to the solvent that can be used herein. Examples of such a solvent include ethers, aromatic hydrocarbons, N,N-dimethylformamide (DMF), dimethylsulfoxide (DMSO), and a mixture thereof. For adjustment of the compound (6e), $R^{1b}$-magnesium halide, $R^{1b}$-lithium produced by the reaction of the corresponding halide with magnesium is appropriately used.

In addition, positions of $R^{1a}$ and $R^{1b}$ in the formula may be changed to each other.

(3) Production of Compound (3a)-2

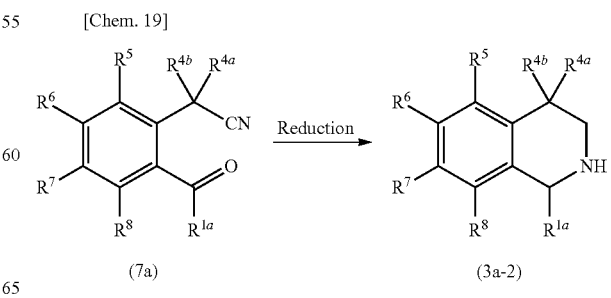

(the symbols in the formula are as defined above)

This production process is a method in which the compound (3a-2) is produced by reducing an acetonitrile derivative (7a).

The reaction can be carried out by stirring the compound (7a) in a reaction-inert solvent under a hydrogen atmosphere, in the presence of a metal catalyst, usually for 1 hour to 5 days. The reaction is typically carried out from under cooling to under heating, for example at room temperature. There is no particular limit to the solvent that can be used herein. Examples of such a solvent include alcohols, ethers, water, ethyl acetate, N,N-dimethylformamide (DMF), dimethylsulfoxide (DMSO) and a mixture thereof. Examples of the metal catalyst that can be preferably used include palladium catalysts such as Pd-supported carbon (Pd/C), palladium black, and palladium hydroxide, platinum catalysts such as platinum oxide, rhodium catalysts such as tetrakis triphenylphosphine chloro rhodium, Raney nickel, iron catalysts such as reduced iron, and the like. Instead of using hydrogen gas, an equivalent or excess amount of formic acid or ammonium formate with regard to the compound (7a) may also be used as a hydrogen source.

REFERENCE LITERATURE

M. Hudlicky, Reductions in Organic Chemistry, 2nd ed (ACS Monograph:188), ACS, 1996
Courses in Experimental Chemistry, 5$^{th}$ edition, edited by The Chemical Society of Japan, Vol. 19 (2005), Maruzen Co., Ltd.
Further, $R^{1a}$ in the formula may also be $R^{1b}$.
(4) Production of Compound (3a)-3

[Chem. 20]

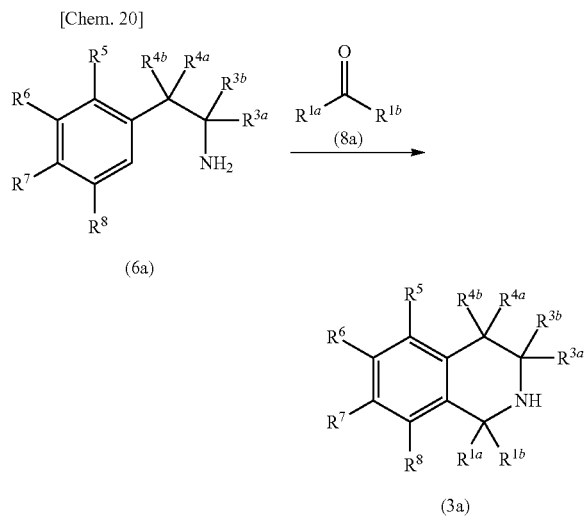

(the symbols in the formula are as defined above)

This production process is a method in which the compound (3a) is produced by condensation of the amine derivative (6a) with a ketone (8a).

The reaction can be carried out using the compound (6a) and the compound (8a) in equivalent amounts or one of them in an excess amount, in a reaction-inert solvent or without a solvent, in the presence of a dehydrating agent or a Lewis acid catalyst, from under cooling to under heating, for example, from room temperature to heating under reflux, usually stirring for 0.1 hour to 5 days. There is no particular limit to the solvent that can be used herein. Examples of such a solvent include halogenated hydrocarbons, ethers, and the like. It may be advantageous in some cases for smooth progress of the reaction to carry out the reaction in the presence of a strong acid such as formic acid-acetic anhydride, and trifluoroacetic acid. Examples of the dehydrating agent include acid anhydrides such as polyphosphoric acid, acetic anhydride, and trifluoroacetic anhydride. Examples of the Lewis acid catalyst include titanium tetraisopropoxide and the like.

The compound of the present invention is isolated and purified as its free compound, or a pharmaceutically acceptable salt, hydrate, solvate or crystalline polymorph thereof. The pharmaceutically acceptable salt of the compound of the formula (I) can also be prepared in accordance with a conventional method for a salt formation reaction.

Isolation and purification are carried out by employing common chemical operations such as extraction, fractional crystallization, and various types of fraction chromatography.

Various isomers can be prepared by selecting an appropriate starting compound, or can be separated by making use of the difference in the physicochemical properties between isomers. For example, the optical isomer can be derived into an optically pure isomer by means of general optical resolution methods (for example, fractional crystallization for inducing diastereomers with optically active bases or acids, chromatography using a chiral column, etc., and the like). In addition, the isomers can also be prepared from an appropriate optically active starting compound.

The pharmacological activity of the compound of the present invention was confirmed by the following tests.

Test Example 1

Test of Compounds on Blockade of N-Type $Ca^{2+}$ Channel

Culture of human fibroblasts (IMR-32 cells), and induction of differentiation were carried out by a modification of the method described in the literature [Carbone et al., Pflugers Arch. Eur. J. Physiol., 416, 170-179 (1990)]. IMR-32 cells were subcultured in a MEM (Invitrogen Corporation, USA) containing 10% fetal bovine serum (FBS), 1% non-essential amino acids, 1% sodium pyruvate, 100 μg/mL streptomycin, and 100 U/mL penicillin. Upon induction of cellular differentiation, 1 mM dibutyryl cyclic adenine monophosphate (dbcAMP) and 2.5 μM 5-bromodeoxyuridine (BrdU) were added to the culture medium, and the cells were cultured for 10 to 11 days to result in expression of the human N-type $Ca^{2+}$ channel.

The 10-11 day differentiation-induced IMR-32 cells were seeded at a density of $6\times10^5$ cells/well in a 96-well plate coated with poly-D-lysine. After the cells were cultured in the culture medium for 3 hours or more, Fluo-3 AM was added thereto, followed by incubation at 37° C. for 60 minutes. The culture was washed in assay buffer (HBSS, 20 mM HEPES, 2.5 mM probenecid, pH 7.4), to which a test compound solution was then added in the presence of 1 μM nitrendipine. After 10 minutes, elevation of an intracellular $Ca^{2+}$ concentration induced by high $K^+$ stimulation with a 50 mM KCl solution was assayed using a FLIPR Calcium Assay Kit (Molecular Devices Corporation, USA). The blocking activity of a test compound on the N-type $Ca^{2+}$ channel was calculated as a relative value, by taking a maximum increase of an intracellular $Ca^{2+}$ concentration in the control group as 100%. Next, a concentration of the compound ($IC_{50}$ value) which is required for 50% inhibition of an increase in the intracellular $Ca^{2+}$ concentration was calculated by nonlinear regression analysis.

As a result, the compounds of the present invention exhibited a blocking action on the N-type $Ca^{2+}$ channel. $IC_{50}$ values for several compounds of the present invention are given in Table 1 below. Abbreviation "Ex" in the table represents Example No.

TABLE 1

| Ex | $IC_{50}(\mu M)$ |
|---|---|
| 1 | 1.0 |
| 2 | 0.75 |
| 117 | 1.4 |
| 121 | 0.87 |
| 134 | 2.0 |
| 157 | 2.1 |
| 174 | 2.1 |
| 199 | 1.1 |
| 202 | 0.78 |
| 236 | 2.0 |
| 274 | 1.5 |
| 292 | 0.89 |
| 296 | 2.4 |
| 316 | 0.89 |
| 319 | 1.3 |
| 330 | 1.4 |
| 379 | 1.2 |
| 386 | 1.9 |
| 409 | 1.3 |
| 415 | 2.1 |
| 429 | 1.1 |
| 433 | 2.0 |
| 435 | 1.4 |
| 436 | 1.4 |
| 449 | 0.85 |
| 461 | 1.2 |
| 473 | 1.9 |
| 474 | 1.6 |
| 476 | 1.0 |
| 478 | 2.0 |
| 480 | 2.0 |
| 490 | 1.0 |
| 504 | 0.62 |

Test Example 2

Effects of Compounds on Nociceptive Pain Model (Formalin Test)

A mouse formalin test was carried out by a modification of the method as described in the literature [Murakami et al., Eur. J. Pharmacol. 419: 175-181 (2001)]. When 20 μL of 2.0% formalin was subcutaneously administered to the paw pads of mice (ddY, male, 5 weeks old), pain behaviors (limb withdrawal and licking behaviors) were induced in the treated animal limbs. From 15 to 25 minutes after the administration of formalin, the time taken for the onset of pain behaviors was measured to thereby evaluate the inhibitory action of the test compound on pain behaviors of animals. The test compound was orally given 30 minutes prior to the administration of formalin. The evaluation of the test compound was made from calculation of an inhibition rate (%) in the test compound-treated group, by taking the time taken for the onset of pain behaviors in the vehicle-treated group as 100%.

Inhibition rate(%)=100−(mean onset time of pain behaviors in test compound-treated group)/(mean onset time of pain behaviors in vehicle-treated group)×100

As a result, the compounds of the present invention exhibited an analgesic action on formalin-induced pain. Inhibition rates (%) of several compounds of the present invention at a dose of 100 mg/kg are given in Table 2 below.

TABLE 2

| Ex | Inhibition rate (%) |
|---|---|
| 1 | 52 |
| 157 | 52 |
| 415 | 95 |
| 433 | 60 |
| 436 | 55 |
| 575 | 77 |

Test Example 3

Effects of Compounds on Neuropathic Pain Model (Antiallodynic Effects in L5/L6 Spinal Nerve-Ligated Rats)

One of the major symptoms in neuropathic pain is a significantly reduced threshold of response to tactile stimulation (allodynia). The antiallodynic effects of the compounds of the present invention were confirmed by assessing the analgesic action in L5/L6 spinal nerve-ligated rats. The assessment was carried out by the method of Kim and Chung (Pain 50, 355-363, 1992) with some modifications.

Under pentobarbital anesthesia, the left L5 and L6 spinal nerves of male SD rats (5-6 weeks old) were tightly ligated with silk thread. For the assessment of analgesic action, the von Frey hair test was adopted. That is, the animal's hind paw pad was pricked with hair and the lowest strength of hair for limb withdrawal response was designated as a response threshold (log gram) to mechanical stimulation. Since it was confirmed in preliminary tests that the response threshold of the animal's hind paw ipsilateral to the side of ligation surgery was significantly low during days 7 to 14 after the surgery (in the state of mechanical allodynia), the antiallodynic effects of the test compound were assessed on any day between days 7 and 14 after the surgery. On the day before the assessment of the test compound, the response threshold before administration of the test compound was measured. The animals were divided into 4 to 5 groups such that mean value differences of response thresholds between groups before administration of the test compound and within-group variation become small. In the assessment of the test compound, the response threshold after administration of the test compound was measured. The test compound was orally administered 30 to 60 minutes before the measurement of the response threshold. The antiallodynic potency of the test compound was assessed as a recovery rate (%) in the test compound-treated group, by taking the response thresholds of ipsilateral and contralateral paws in the vehicle-treated group as 0% and 100%, respectively.

Recovery rate(%)={(mean of response threshold in test compound-treated group)−(mean of response threshold of ipsilateral paw in vehicle-treated group)}/{(mean of response threshold of contralateral paw in the vehicle-treated group)−(mean of response threshold of ipsilateral paw in the vehicle-treated group)}×100

As a result, the compounds of the present invention exhibited an analgesic action on mechanical allodynia in the neuropathic pain model. Recovery rates (%) for groups with administration of several compounds of the present invention are given in Table 3 below.

TABLE 3

| Ex | Recovery rate (%) (dose) |
|---|---|
| 1 | 95 (30 mg/kg) |
| 157 | 97 (30 mg/kg) |
| 415 | 100 (10 mg/kg) |
| 433 | 80 (10 mg/kg) |
| 436 | 156 (10 mg/kg) |
| 575 | 83 (10 mg/kg) |

Test Example 4

Effects of Compounds on Abdominal Pain Model (Assay of CRD-Induced Abdominal Pain in Rats)

In response to pressure stimulation caused by colorectal distension (CRD), IBS patients are known to exhibit a reduction of digestive perception threshold (allodynia) which gives rise to discomfort against weak stimulus that is not perceived by a normal person and hyperalgesia which leads to stronger subjective response to digestive perception than in a normal person (Gastroenterol. 130: 1377-1390 (2006)), and such conditions are believed to be responsible for abdominal symptoms. Improving effects of the compounds of the present invention on digestive tract pain were confirmed by assay of CRD-induced abdominal pain in rats. The rat CRD-induced abdominal pain assay was carried out by a modification of the method described in the literature [Neurogastroenterol. Motil. 15: 363-369 (2003)]. When stimulation of constant internal pressure is applied to the colorectum of an animal by inflation of a 6-cm long balloon inserted into the anus of the rat (Wistar, male, 250-350 g), abdominal flexion reflex behaviors are induced due to abdominal pain. A frequency of reflex behaviors occurring during distension stimulation of 5 minutes was counted to estimate an abdominal pain-inhibitory action of the test compound. The test compound was orally administered 30 minutes before the initiation of distension stimulation. Estimation of the test compound was made by calculating an inhibition rate (%) of abdominal flexion reflex behaviors on the vehicle-treated group.

As a result, the compounds of the present invention exhibited an abdominal pain-inhibitory action. For several compounds of the present invention at a dose of 10 mg/kg, inhibition rates (%) of abdominal flexion reflex behaviors upon distension at an internal pressure of 45 mmHg are given in Table 4 below.

TABLE 4

| Ex | Inhibition rate (%) |
|---|---|
| 157 | 59 |
| 415 | 60 |
| 433 | 43 |
| 435 | 46 |
| 436 | 56 |
| 568 | 61 |

Test Example 5

Effects of Compounds on Spastic Constipation Model (Loperamide-Induced Colon Bead Transport Delay Test)

Generally, it is known that the onset of constipation in IBS-C is caused by spastic dysmotility of the digestive tract and is similar to opioid-induced constipation in terms of pathophysiology of the disease (Eur. J. Pharmacol. 75: 239-245 (1981), American J. Physiol. 96: 667-676 (1931), Nippon Rinsho 64: 1461-1466 (2006)). An improving action of the compounds of the present invention on spastic constipation was confirmed by a loperamide-induced colorectal bead transit delay test in mice. The mouse loperamide-induced colorectal bead transit delay test was carried out by a modification of the method described in the literature [J. Smooth Muscle Res. 29:47-53 (1993)]. A 3-mm diameter glass bead is deeply inserted at a depth of 2 cm into the anus of the mouse (ddY, male, 6 weeks old), and the time taken for excretion of the bead is measured. When 0.3 mg/kg of loperamide is subcutaneously administered 30 minutes before the insertion of the bead, delay of bead excretion is induced. With improving effects on the loperamide-induced bead transit delay, a bowel movement-improving action of the test compound on spastic constipation was evaluated. The test compound was orally administered concurrently with administration of loperamide (30 minutes before the insertion of the bead). The assessment of the test compound was made from calculation of an improvement rate in the bead excretion time of the test compound-treated/loperamide-treated group, by taking the bead excretion time of the non-test compound treated/non-loperamide treated (vehicle-treated/vehicle-treated) group as 100%, and by taking the bead excretion time of the non-test compound treated/loperamide-treated (vehicle-treated/loperamide-treated) group as 0%.

As a result, the compounds of the present invention exhibited an opioid-induced constipation-improving action. For several compounds of the present invention at a dose of 3 mg/kg, improvement rates (%) in the bead excretion time are given in Table 5 below.

TABLE 5

| Ex | Inhibition rate (%) |
|---|---|
| 157 | 40 |
| 415 | 88 |
| 433 | 73 |
| 435 | 67 |
| 436 | 59 |
| 568 | 83 |

Test Example 6

Effects of Compounds in Combined Use with Morphine (1)

Morphine has potent analgesic effects on nociceptive pain through μ opioid receptors. For example, morphine exhibits dose-dependent analgesic effects in a formalin test which is a nociceptive pain model (Pharmacol. Biochem. Behav. 84: 479-486 (2006)). Meanwhile, it is known that a selective N-type $Ca^{2+}$ channel-blocking peptide, ω-conotoxin (ω-CTx) also independently exhibits dose-dependent analgesic effects in the formalin test, and its combined use with morphine enhances analgesic effects over those obtained by single use of morphine (add-on effects) (Pain 84: 271-281 (2000)). Therefore, it can be confirmed that when the compounds of the present invention having an N-type $Ca^{2+}$ channel-blocking action were used in combination with morphine in the formalin test, a potent antinociceptive pain action comparable to or higher than single administration of morphine or single administration of the compound of the present invention is achieved.

Test Example 7

Effects of Compounds in Combined Use with Morphine (2)

It is known that mechanical allodynia observed in L5/L6 spinal nerve-ligated rats exhibits only a partial recovery with treatment of morphine. On the other hand, as described hereinbefore, the compounds of the present invention exhibit almost 100% recovery effects on mechanical allodynia in L5/L6 spinal nerve-ligated rats. Therefore, when the compounds of the present invention were used in combination with morphine, a potent antineuropathic pain action comparable to or higher than single administration of morphine or single administration of the compounds of the present invention can be confirmed by testing their antiallodynic effects in L5/L6 spinal nerve-ligated rats.

Test Example 8

Effects of Compounds in Combined Use with Morphine (3)

Morphine is a μ opioid receptor agonist having the same action mechanism as loperamide, and has a delay action on colon bead transport in mice, similar to loperamide. Upon administering a dose of morphine which exhibits an abdominal pain-inhibitory action in the rat CRD-induced abdominal pain assay and exhibits a transit delay action in the mouse colorectal bead transit test, and a dose of the test compound which improves the bead transit delay caused by the above-defined dose of morphine, it can be confirmed that such combined use exhibits a potent abdominal pain-inhibitory action comparable to or higher than single administration of morphine in the rat CRD-induced abdominal pain assay, and also has an inhibitory action on morphine-induced transit delay in the bead transit test.

Alternatively, upon administering the test compound with a low dose of morphine at which an abdominal pain-inhibitory action is insufficient in the rat CRD-induced abdominal pain assay, but a delay action is not recognized in the mouse colon bead transit test, a sufficient abdominal pain-inhibitory action which was not obtained by a low dose of morphine alone can be confirmed.

From the experimental results as described above, it was confirmed that the compounds of the present invention have an N-type $Ca^{2+}$ channel-blocking action. Therefore, it is clear that the compounds of the present invention are useful as an active ingredient of a pharmaceutical composition for preventing and/or treating various pains such as neuropathic pain and nociceptive pain, headaches such as migraine and cluster headache, central nervous system diseases such as anxiety, depression, epilepsy, cerebral stroke and restless legs syndrome, digestive system diseases such as abdominal pain and irritable bowel syndrome, and urinary system diseases such as overactive bladder and interstitial cystitis.

From the results of the formalin test as described above, it was confirmed that the compounds of the present invention have an antinociceptive pain action. In addition, from the test results of antiallodynic effects in L5/L6 spinal nerve-ligated rats, it was confirmed that the compounds of the present invention have an antineuropathic pain action. Upon considering these facts, it is clear that the compounds of the present invention are useful as an active ingredient of a pharmaceutical composition for preventing and/or treating various pains including neuropathic pain and nociceptive pain. Further, it is clinically demonstrated that pregabalin, which is a $Ca^{2+}$ channel α2δ subunit ligand and is used as an antineuropathic pain agent, exhibits therapeutic effects on fibromyalgia syndrome having a lot in common with neuropathic pain, in terms of clinical condition. Based on this point, it can be considered that the compounds of the present invention are also useful as an active ingredient of a pharmaceutical composition for preventing and/or treating fibromyalgia syndrome.

From the results of the rat CRD-induced abdominal pain assay as described above, it was demonstrated that the compounds of the present invention have an abdominal pain-inhibitory action. Therefore, it is clear that the compounds of the present invention are useful as an active ingredient of a pharmaceutical composition for preventing and/or treating abdominal symptoms, particularly abdominal symptoms of IBS.

From the results of the mouse loperamide-induced colorectal bead transit delay test, it was demonstrated that the compounds of the present invention have an opioid-induced constipation-improving action. Based on this fact, it is clear that the compounds of the present invention are useful as an active ingredient of a pharmaceutical composition for preventing and/or treating spastic constipation, particularly constipation in OBD. In addition, from the fact that constipation in IBS-C is spastic constipation, similar to constipation caused by opioids, it is clear that the compounds of the present invention are also useful as an active ingredient of a pharmaceutical composition for preventing and/or treating constipation in IBS-C.

From the fact demonstrating that the compounds of the present invention are effective in both of the rat CRD-induced abdominal pain assay and the mouse loperamide-induced colorectal bead transit delay test, it is clear that the compounds of the present invention are also useful as an active ingredient of an excellent pharmaceutical composition for preventing and/or treating IBS-C, having a combination of an abdominal symptom-improving action and a constipation-improving action.

It is known that use of a selective N-type $Ca^{2+}$ channel-blocking peptide, ω-conotoxin (ω-CTx) in combination with morphine enhances analgesic effects over those obtained by use of morphine alone (add-on effects) (Pain 84: 271-281 (2000), Life Science 73: 2873-2881 (2003)). Therefore, it can be expected that combined use of the compounds of the present invention and opioids results in an excellent pharmaceutical composition for preventing and/or treating pain, which exerts more potent analgesic effects than single use of opioids.

Opioids are used as a therapeutic agent for severe pain such as cancer pain, but suffer from clinical problems associated with dose-dependent side effects on the digestive system, such as vomiting or constipation (Eur. J. Pharmaceutical Sci. 20: 357-363 (2003)). The compounds of the present invention exhibit excellent improving effects on opioid-induced constipation (OIC). Based on this fact, it can be expected that the compounds of the present invention in combined use with opioids would result in a pharmaceutical composition for preventing and/or treating pain, which inhibits opioid-induced constipation with less side effects. In addition, it can be expected that combined use of the compounds of the present invention and a low dose of opioids would result in an excellent pharmaceutical composition for preventing and/or treating pain, which is capable of exerting sufficient analgesic effects while reducing a dose of opioids and which is also capable of decreasing the onset of constipation through a reduction of the opioid dose.

A preparation containing one or two or more kinds of the compound of the formula (I) or a pharmaceutically acceptable salt thereof as an active ingredient can be prepared in accordance with a generally used method, using a pharmaceutically acceptable carrier, excipient, or the like, that is usually used in the art.

The administration can be carried out by oral administration via tablets, pills, capsules, granules, powders, liquid preparations, or the like, or parenteral administration via injections such as intraarticular injection, intravenous injection, intramuscular injection, or the like, as well as suppositories, eye drops, eye ointments, percutaneous liquid preparations, ointments, percutaneous patches, transmucosal liquid preparations, transmucosal patches, inhalations, and the like.

As solid compositions for oral administration according to the present invention, tablets, powders, granules, or the like are used. In such a solid composition, one or two or more kinds of active ingredients are mixed with at least one inert excipient such as lactose, mannitol, glucose, hydroxypropylcellulose, microcrystalline cellulose, starch, polyvinyl pyrrolidone, and/or magnesium aluminometasilicate. According to a conventional method, the composition may contain inert additives such as a lubricant such as magnesium stearate, a disintegrator such as carboxymethyl starch sodium, a stabilizing agent, and a solubilizing aid. As occasion demands, the tablets or the pills may be coated with a film of a sugar coating, or a gastric or enteric coating agent.

Liquid compositions for oral administration include pharmaceutically acceptable emulsions, solutions, suspensions, syrups, elixirs, or the like, and contain a generally used inert diluent such as purified water or ethanol. In addition to the inert diluent, the liquid composition may contain an adjuvant such as a solubilizing agent, a moistening agent, and a suspending agent, a sweetener, a flavor, an aromatic, and a preservative.

Injections for parenteral administration include sterile aqueous or non-aqueous solutions, suspensions and emulsions. The aqueous solvent includes, for example, distilled water for injection and physiological saline. Examples of the non-aqueous solvent include propylene glycol, polyethylene glycol, vegetable oils such as olive oil, alcohols such as ethanol, Polysorbate 80 (Japanese Pharmacopeia), and the like. Such a composition may further contain a tonicity agent, a preservative, a moistening agent, an emulsifying agent, a dispersing agent, a stabilizing agent, or a solubilizing aid. These are sterilized, for example, by filtration through a bacteria-retaining filter, incorporation of a sterilizing agent, or irradiation. In addition, these can also be used by preparing a sterile solid composition, and dissolving or suspending it in sterile water or a sterile solvent for injection prior to its use.

External preparations include ointments, plasters, creams, jellies, adhesive skin patches, sprays, lotions, eye drops, eye ointments, and the like. The external preparation contains generally used ointment bases, lotion bases, aqueous or non-aqueous liquids, suspensions, emulsions, and the like. Examples of the ointment or lotion bases include polyethylene glycol, propylene glycol, white Vaseline, white beeswax, polyoxyethylene hydrogenated castor oil, glyceryl monostearate, stearyl alcohol, cetyl alcohol, lauromacrogol, sorbitan sesquioleate, and the like.

Transmucosal preparations such as inhalations and transnasal preparations are used in a solid, liquid or semi-solid form and may be prepared in accordance with a conventionally known method. For example, a known excipient, and also a pH-adjusting agent, a preservative, a surfactant, a lubricant, a stabilizing agent, a thickening agent, or the like may be appropriately added thereto. For their administration, an appropriate device for inhalation or blowing may be used. For example, a compound may be administered alone or as a powder of formulated mixture, or as a solution or suspension in combination with a pharmaceutically acceptable carrier, using a conventionally known device or sprayer, such as a measured administration inhalation device. The dry powder inhaler or the like may be for single or multiple administration use, and a dry powder or a powder-containing capsule may be used. Alternatively, it may be in a form such as a pressurized aerosol spray or the like which uses an appropriate propellant, for example, a suitable gas such as chlorofluoroalkane, hydrofluoroalkane, or carbon dioxide.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

The compounds of the present invention can be used in combination with various agents for treating or preventing the diseases for which the compounds of the present invention are considered to be effective. Examples of the drugs that can be used in combination with the compounds of the present invention include opioids such as morphine, antidepressants such as duloxetine and amitriptylin, antiepileptic drugs such as pregabalin and mexiletine, non-steroidal anti-inflammatory drugs such as diclofenac, and the like. For this combined use, the compounds of the present invention are formulated into appropriate dosage forms such as liquid preparations, capsules, granules, pills, powders, tablets, external preparations, jellies, sprays, patches, suppositories, and self-contained implantable pumps, and the combined preparation may be administered simultaneously, or separately and continuously, or at a desired time interval, via an oral, transvenous, percutaneous, transnasal, enteral, spinal epidural, or spinal subarachnoid route. The preparations to be co-administered may be a blend, or may be prepared individually.

EXAMPLES

Hereinafter, production processes of the compound of the present invention will be described in more detail with reference to Examples. The present invention is not limited to the following Examples. In addition, production processes of starting compounds are shown in Production Examples. The production processes of the compound of the present invention are not limited to the production processes of the specific Examples as described below. The compound of the present invention may be produced in accordance with a combination of these production processes or in accordance with a method obvious to a person skilled in the art.

As for Examples, Production Examples and Tables described below, the following abbreviations will be used.

Rex: Production Example number, Ex: Example number, No: compound number, STRUCTURE: structural formula, Data: physicochemical data (FAB: FAB-MS[M+H]$^+$, FAN: FAB-MS[M−H]$^-$, FA1: FAB-MS[M]$^+$, FA2: FAB-MS[M+2H]$^+$, ES: ESI-MS[M+H]$^+$, ES1: ESI-MS[M]$^+$, ES2: ESI-MS[M+2H]$^+$, ESNa: ESI-MS[M+Na]$^+$, AP: APCI-MS[M+H]$^+$, API: APCI-MS[M]$^+$, CI: CI[M+H]$^+$, CIN: CI[M−H]$^-$, CI1: CI[M]$^+$, EI: EI[M+H]$^+$, EIN: EI[M−H]$^-$, EI1: EI[M]$^+$, EIBr: EI[M−Br]$^-$, NMR: δ (ppm) of peak of $^1$H-NMR in DMSO-d$_6$), N/D: not determined, salt: salt (with blank column or no column: it represents that the compound is a free form), CL: hydrochloride, BR: hydrobromate, OX: oxalate, FM: fumarate, MD: D-mandelate, ML: L-mandelic acid, LL: N-acetyl-L-leucine salt, T1: L-tartrate, T2: D-tartrate, TX: dibenzoyl-D-tartrate, TY: dibenzoyl-L-tartrate, TP: diparatoluoyl-D-tartrate, TQ: diparatoluoyl-L-tartrate, MA: L-malic acid, MB: D-malic acid), Me: methyl, Et: ethyl, nPr: normal propyl, iPr: isopropyl, tBu: tert-butyl, cPr: cyclopropyl, cBu: cyclobutyl, cPen: cyclopentyl, cHex: cyclohexyl, Admt: adamantyl, Ph: phenyl, Bn: benzyl, Thp: tetrahydropyranyl, pipe: piperidinyl, pipa: piperadinyl, CN: cyano, boc: tert-butyloxycarbonyl, Ac: acetyl, MOM: methoxymethyl, TMS: trimethylsilyl, di: di, THF: tetrahydrofuran, DMF: N,N-dimethylformamide, DMSO: dimethyl sulfoxide. The numeral before the substituent represents a substitution position, and for example, 6-Cl-2-Py represents 6-chloropyridin-2-yl and 3,3-diF-cHex represents 3,3-difluorocyclohexyl. Rsyn and Syn: Production method (the numerals indicate that the compounds were produced using the corresponding starting materials, with the method similar to the case of compounds respectively having the numerals as the production example numbers or Example numbers). In addition, among the compounds of Production Examples or Examples in Tables, for the compound in which a configuration of a substituent at the 1-position of tetrahydroisoquinoline is not determined but a single configuration is shown in any sides, the configuration in any sides is labeled and then the Production Example number or the Example number is given *. On the other hand, for the compound in which a configuration of a substituent at the 1-position of tetrahydroisoquinoline is determined or the compound in which the configuration is reasonably analogized on the basis of behavior in chiral column chromatography or activity behavior in N-type $Ca^{2+}$-blocking test, the configuration is only labeled.

In addition, the compound in which the same number is given subsequent to * represents that the compound is produced using a compound, to which the same number is given and in which a configuration of a substituent at the 1-position of tetrahydroisoquinoline is not determined but a single configuration is labeled in any sides, as a starting material.

Production Example 1

N-(2-cyclohexa-1-en-1-ylethyl)-2-(1-cyclohexyl-3,4-dihydroisoquinolin-2(1H)-yl)-2-oxoethanamine (431 mg) was dissolved in chloroform (12 mL), and trifluoroacetic anhydride (0.3 mL) was added thereto under ice-cooling, followed by stirring at room temperature for 10 hours and then stirring at 60° C. for 2 hours. The solvent was evaporated, and saturated aqueous sodium bicarbonate was added to the reaction liquid which was then extracted with chloroform. The reaction liquid was washed with saturated brine and dried over magnesium sulfate. The solvent was evaporated and the resulting residue was purified by silica gel column chromatography (chloroform) to obtain N-(2-cyclohexa-1-en-1-ylethyl)-N-[2-(1-cyclohexyl-3,4-dihydroisoquinolin-2(1H)-yl)-2-oxoethyl]-2,2,2-trifluoroacetamide (419 mg).

Production Example 2

N-(2-cyclohexa-1-en-1-ylethyl)-N-[2-(1-cyclohexyl-3,4-dihydroisoquinolin-2(1H)-yl)-2-oxoethyl]-2,2,2-trifluoroacetamide (408 mg) was dissolved in a 3:1 mixture (8 mL) of acetone-water. To the reaction liquid were added 4-methylmorpholine 4-oxide (200 mg) and a solution of 2.5% osmium tetroxide in tert-butyl alcohol (2.68 mL), followed by stirring at room temperature for 18 hours. Then, the reaction solvent was evaporated under reduced pressure, and water was added to the reaction liquid, followed by extraction with chloroform. The extract was washed with saturated brine and dried over magnesium sulfate. The solvent was evaporated and the resulting residue was purified by silica gel column chromatography (chloroform-MeOH) to obtain N-[2-(1-cyclohexyl-3,4-dihydroisoquinolin-2(1H)-yl)-2-oxoethyl]-N-{2-[cis-1,2-dihydroxycyclohexyl]ethyl}-2,2,2-trifluoroacetamide (276 mg).

Production Example 3

2-(chloroacetyl)-1-cyclohexyl-7-methoxy-1,2,3,4-tetrahydroisoquinoline (700 mg) was dissolved in acetonitrile (15 mL), to which potassium carbonate (2.1 g), 2-cyclopenta-1-en-1-lyethanamine hydrochloride (1.6 g), and tetra-n-butylammonium iodide (80 mg) were then added, followed by stirring at 70° C. for 5 hours. Thereafter, the solvent was evaporated, and water was added to the reaction liquid, followed by extraction with EtOAc. The extract was washed with saturated brine and dried over magnesium sulfate. The solvent was evaporated and the resulting residue was purified by silica gel column chromatography (chloroform-MeOH).

The resulting compound was dissolved in chloroform (10 mL) and trifluoroacetic anhydride (0.34 mL) was added thereto, followed by stirring at room temperature for 14 hours. Then, the solvent was evaporated and the resulting residue was purified by silica gel column chromatography (hexane-EtOAc) to obtain N-[2-(1-cyclohexyl-7-methoxy-3,4-dihydroisoquinolin-2(1H)-yl)-2-oxoethyl]-N-(2-cyclopenta-1-en-1-ylethyl)-2,2,2-trifluoroacetamide (450 mg).

Production Example 4

(1R)-1-cyclohexyl-1,2,3,4-tetrahydroisoquinoline (L)-tartrate (520 mg) was dissolved in EtOAc (10 mL) and saturated aqueous sodium bicarbonate (10 mL) was added thereto. Under ice-cooling, a solution of chloroacetyl chloride (0.14 mL) in EtOAc (5 mL) was added dropwise to the reaction liquid over 5 minutes, followed by stirring at room temperature for 1 hour. The reaction liquid was extracted with EtOAc and dried over magnesium sulfate to obtain (1R)-2-(chloroacetyl)-1-cyclohexyl-1,2,3,4-tetrahydroisoquinoline (415 mg).

Production Example 5

7-chloro-1-cyclohexyl-1,2,3,4-tetrahydroisoquinoline hydrochloride (899 mg) was added to saturated aqueous sodium bicarbonate (15 mL), to which EtOAc (10 mL) was then further added. A solution of chloroacetyl chloride (390 mg) in EtOAc (5 mL) was added dropwise to the reaction liquid over 5 minutes. The reaction liquid was stirred for 1 hour, extracted with EtOAc, and dried over magnesium sulfate. The solvent was evaporated and the resulting residue was purified by silica gel column chromatography (hexane-EtOAc) to obtain 7-chloro-2-(chloroacetyl)-1-cyclohexyl-1,2,3,4-tetrahydroisoquinoline (888 mg).

Production Example 6

A mixture of chloroacetyl chloride (1.03 g) and EtOAc (5 mL) was added dropwise with stirring to a mixture of (1S)-1-phenyl-1,2,3,4-tetrahydroquinoline (1.58 g), sodium hydrogen carbonate (960 mg), water (25 mL) and EtOAc (25 mL), followed by stirring at room temperature for 2 hours. The reaction liquid was extracted with EtOAc, and the extract was washed sequentially with saturated aqueous sodium bicarbonate and saturated brine, dried over magnesium sulfate, and concentrated under reduced pressure. The resulting residue was purified by silica gel column chromatography (hexane-AcOEt, 4:1) to obtain (1S)-2-(chloroacetyl)-1-phenyl-1,2,3,4-tetrahydroisoquinoline (2.14 g).

Production Example 7

1-cyclohexyl-1,2,3,4-tetrahydroisoquinoline hydrochloride (800 mg) was dissolved in methylene chloride (12 mL), to which triethylamine (1.1 mL) and acryloyl chloride (0.28 mL) were then added under ice-cooling, followed by stirring under ice-cooling for 30 minutes and then stirring at room temperature for 14 hours. Water was added to the reaction liquid which was then extracted with chloroform. The extract was washed with saturated brine and dried over magnesium sulfate. The solvent was evaporated to obtain 2 acryloyl-1-cyclohexyl-1,2,3,4-tetrahydroisoquinoline (856 mg).

Production Example 8

1-benzyl-4-hydroxypiperidine-4-carboxylic acid (951 mg) was dissolved in DMF (25 mL), and N,N'-carbonyldiimidazole (720 mg) was added thereto, followed by stirring at room temperature for 18 hours. Thereafter, N,N-diisopropylethylamine (784 mg) and 1-cyclohexyl-1,2,3,4-tetrahydroisoquinoline hydrochloride (1.22 g) were added to the reaction liquid, followed by stirring at 60° C. for 18 hours. The solvent was evaporated, and water and EtOAc were added to the reaction liquid. The resulting insoluble materials were separated through celite, extracted with EtOAc and dried over magnesium sulfate, and the solvent was evaporated. The resulting residue was purified by silica gel column chromatography (chloroform-MeOH) and dissolved in 1,4-dioxane (12 mL), and di-tert-butyl dicarbonate (1.3 g) was added thereto, followed by stirring at room temperature for 1 hour. The solvent was evaporated and the resulting residue was purified by silica gel column chromatography (hexane-EtOAc and then chloroform-MeOH) to obtain 1-benzyl-4-[(1-cyclohexyl-3,4-dihydroisoquinolin-2(1H)-yl)carbonyl]piperidin-4-ol (115 mg).

Production Example 9

1-benzyl-4-[(1-cyclohexyl-3,4-dihydroisoquinolin-2 (1H)-yl)carbonyl]piperidin-4-ol (220 mg) was dissolved in MeOH (12 mL), and 20% palladium hydroxide-supported activated carbon (360 mg) was added thereto, followed by stirring under a hydrogen atmosphere, at room temperature and normal pressure, for 15 hours. Thereafter, the catalyst was separated through celite. The solvent was evaporated to obtain 4-[(1-cyclohexyl-3,4-dihydroisoquinolin-2(1H)-yl) carbonyl]piperidin-4-ol (154 mg).

Production Example 10

N-methylmorpholine (0.873 mL) was added to a solution of 1-(tert-butoxycarbonyl)-L-proline (1.28 g) in 1,2-dichloroethane (10 mL) under ice-cooling, followed by further addition of pivaloyl chloride (0.734 mL). The reaction liquid was stirred for 1 hour, and N-methylmorpholine (1.09 mL) and 1-cyclohexyl-1,2,3,4-tetrahydroisoquinoline hydrochloride (1.00 g) were then added thereto. The mixture was stirred at room temperature for 15 hours. To the reaction solution were added EtOAc and an aqueous 1 M HCl solution. The organic layer was washed with water, a saturated aqueous sodium hydrogen carbonate solution, and saturated brine, dried over magnesium sulfate, and filtered. The filtrate was concentrated under reduced pressure to obtain tert-butyl (2S)-2-[(1-cyclohexyl-3,4-dihydroisoquinolin-2(1H)-yl)carbonyl]pyrrolidine-1-carboxylate (1.79 g).

Production Example 11

1-cyclohexyl-1,2,3,4-tetrahydroisoquinoline hydrochloride (1.00 g) was dissolved in methylene chloride (20 mL), and pivaloyl chloride (0.98 mL) and 4-methylmorpholine (2.2 mL) were added thereto under ice-cooling. The reaction liquid was stirred at room temperature for 30 minutes and then ice-cooled, and [(tert-butoxycarbonyl)amino]acetic acid (1.54 g) was added thereto. The reaction liquid was stirred at room temperature for 14 hours and then water was added thereto, followed by extraction with chloroform. The extract was washed with saturated brine, and then dried over magnesium sulfate. The solvent was evaporated and the resulting residue was purified by silica gel column chromatography (chloroform-MeOH) to obtain tert-butyl[2-(1-cyclohexyl-3,4-dihydroisoquinolin-2(1H)-yl)-2-oxoethyl]carbamate (1.49 g).

Production Example 12

4 M HCl/EtOAc (4 mL) was added to a solution of tert-butyl (2S)-2-[(1-cyclohexyl-3,4-dihydroisoquinolin-2(1H)-yl)carbonyl]pyrrolidine-1-carboxylate (1.79 g) in EtOAc (4 mL). The mixture was stirred at room temperature for 5 hours. The solvent was evaporated under reduced pressure, and chloroform and a saturated aqueous sodium hydrogen carbonate solution were added to the residue. The organic layer was washed with saturated brine, dried over magnesium sulfate, filtered, and concentrated to obtain 1-cyclohexyl-2-L-prolyl-1,2,3,4-tetrahydroisoquinoline (1.26 g).

Production Example 13

Tert-butyl[2-(1-cyclohexyl-3,4-dihydroisoquinolin-2 (1H)-yl)-2-oxoethyl]carbamate (1.5 g) was dissolved in EtOAc (20 mL), and 4 M HCl/EtOAc (3 mL) was added thereto under ice-cooling, followed by stirring at 50° C. for 5 hours. Then, the reaction solvent was evaporated. Saturated aqueous sodium bicarbonate was added to the reaction liquid which was then extracted with chloroform. The extract was washed with saturated brine and dried over magnesium sulfate. The solvent was evaporated and the resulting residue was purified by silica gel column chromatography (chloroform-MeOH) to obtain 2-(1-cyclohexyl-3,4-dihydroisoquinolin-2 (1H)-yl)-2-oxoethanamine (1.09 g).

Production Example 14

2-(1-cyclohexyl-3,4-dihydroisoquinolin-2(1H)-yl)-2-oxoethanamine (695 mg) was dissolved in methylene chloride (12 mL), and titanium tetraisopropoxide (1.1 mL) and 1-cyclohexene-1-carboaldehyde (309 mg) were added thereto, followed by stirring at room temperature for 3 hours. Thereafter, the solvent was evaporated, and MeOH (15 mL) and then sodium cyanotrihydroborate (190 mg) were added to the mixture, followed by stirring for 14 hours. The solvent was evaporated, and water and EtOAc were added to the mixture. The mixture was filtered through celite and extracted with EtOAc. The extract was washed with saturated brine and then dried over magnesium sulfate. The solvent was evaporated and the resulting residue was purified by silica gel column chromatography (chloroform-MeOH) to obtain N-(cyclohexa-1-en-1-ylmethyl)-2-(1-cyclohexyl-3,4-dihydroisoquinolin-2(1H)-yl)-2-oxoethanamine (585 mg).

The resulting compound (525 mg) was dissolved in 1,4-dioxane (10 mL), and di-tert-butyl dicarbonate (312 mg) was added thereto, followed by stirring at room temperature for 4 hours. The solvent was evaporated and the resulting residue was purified by silica gel column chromatography (hexane-EtOAc) to obtain tert-butyl N-(cyclohexa-1-en-1-ylmethyl)-N-[2-(1-cyclohexyl-3,4-dihydroisoquinolin-2(1H)-yl)-2-oxoethyl]carbamate (564 mg).

Production Example 15

Chloroacetyl chloride (0.151 mL) was added to a solution of 1,1-diphenyl-1,2,3,4-tetrahydroisoquinoline (339 mg) and p-toluenesulfonate monohydrate (11.3 mg) in toluene (5 mL). The mixture was heated under reflux for 3 hours. The solvent was evaporated under reduced pressure, and EtOAc and an aqueous 1 M HCl solution were added to the residue. The organic layer was washed with water, a saturated aqueous sodium hydrogen carbonate solution, and saturated brine, dried over magnesium sulfate, and filtered. The filtrate was concentrated under reduced pressure to obtain 2-(chloroacetyl)-1,1-diphenyl-1,2,3,4-tetrahydroisoquinoline (452 mg).

Production Example 16

10% Pd-supported carbon (900 mg) was added to a solution of 2-benzyl-1,1-diphenyl-1,2,3,4-tetrahydroisoquinoline (1.81 g) in a 2:1 THF-MeOH mixture (30 mL). The mixture was stirred under a hydrogen atmosphere at room temperature for 16 hours. Further, 10% Pd-supported carbon (900 mg) was added to the mixture, followed by stirring for 8 hours. The reaction mixture was filtered through celite, and the filtrate was concentrated under reduced pressure. The residue was purified by silica gel column chromatography (hexane-EtOAc) to obtain 1,1-diphenyl-1,2,3,4-tetrahydroisoquinoline (339 mg).

Production Example 17

In an ice bath under argon flow, a solution of 1.07 M phenylmagnesium bromide in THF (33.2 mL) was added dropwise to a solution of 2-benzyl-1-phenyl-3,4-dihydroisoquinoline hydrobromate (8.95 g) in THF (80 mL) over 1 hour. The mixture was stirred at room temperature for 1 hour. A saturated aqueous ammonium chloride solution was added to the mixture which was then extracted with EtOAc. The extract was washed with water and saturated brine, dried over magnesium sulfate, and filtered. The filtrate was concentrated under reduced pressure, and the resulting residue was purified by silica gel column chromatography (hexane-EtOAc) to obtain 2-benzyl-1,1-diphenyl-1,2,3,4-tetrahydroisoquinoline (1.81 g).

Production Example 18

Sodium borohydride (450 mg) was added with stirring to a solution of 6,8-dimethoxy-1-phenyl-3,4-dihydroisoquinoline (1.96 g) in EtOH (50 mL) over 5 minutes. The reaction mixture was stirred at room temperature for 2 hours and then further stirred at 60° C. for 1.5 hours. The reaction mixture was cooled to room temperature and concentrated under reduced pressure. An aqueous 3 M HCl solution (60 mL) was added to the resulting residue, followed by heating under reflux for 3 minutes. After cooling, an aqueous 20% NaOH solution was added to the mixture to have strong alkalinity, followed by extraction with chloroform. The organic layer was washed with saturated brine, dried over magnesium sulfate, and concentrated under reduced pressure to obtain 6,8-dimethoxy-1-phenyl-1,2,3,4-tetrahydroisoquinoline (1.88 g).

Production Example 19

1-cyclohexyl-6-methyl-3,4-dihydroisoquinoline (4.84 g) was dissolved in MeOH (100 mL), and then sodium borohydride (966 mg) was added thereto, followed by stirring at room temperature for 3 hours. The solvent was evaporated under reduced pressure. Water was added to the reaction mixture which was then extracted with chloroform. The extract was dried over magnesium sulfate, and the solvent was evaporated under reduced pressure.

The resulting residue was dissolved in EtOAc (100 mL), and a 4 M HCl/EtOAc solution (8 mL) was added thereto under ice-cooling, followed by stirring at room temperature. The resulting insoluble materials were collected and washed with EtOAc to obtain 1-cyclohexyl-6-methyl-1,2,3,4-tetrahydroisoquinoline hydrochloride (3.6 g).

Production Example 20

Potassium carbonate (92 g) and water (500 mL) were added to 1-isopropyl-6-methoxy-1,2,3,4-tetrahydroisoquinoline hydrochloride (86 g). The reaction mixture was extracted with EtOAc and dried over magnesium sulfate, and then the solvent was evaporated. To the resulting residue were added iPrOH (1100 mL) and (+)-mandelic acid (50 g), followed by stirring under heating at 95° C. for dissolution. The mixture was left to cool and stirred at room temperature overnight. The resulting solid was collected and repeatedly recrystallized three times using iPrOH to obtain 1-isopropyl-6-methoxy-1,2,3,4-tetrahydroisoquinoline (+)-mandelate (43 g) as a single enantiomer.

Production Example 21

1-cyclohexyl-1,2,3,4-tetrahydroisoquinoline (31.1 g) was dissolved in EtOH (1.26 L) at 80° C., and (D)-tartaric acid (10.83 g) was then added thereto. The reaction mixture was left to cool and stirred at room temperature overnight. The resulting insoluble materials (16.64 g) were collected and dried.

The solid was mixed with a solid obtained in the same manner as mentioned above, and the mixture (33.26 g) was dissolved in EtOH (1 L), followed by stirring under heating at reflux for 2 hours and then stirring at 80° C. for 5 hours. The mixture was stirred at room temperature overnight and then the insoluble materials were collected to obtain (1S)-1-cyclohexyl-1,2,3,4-tetrahydroisoquinoline (D)-tartrate (30.8 g).

Production Example 22

Under an argon atmosphere, a 1.0 M borane-THF complex solution (110 mL) was added to a mixture of (1R,2S)-1-amino-2-indanol (8.17 g) and diethyl ether (200 mL) under stirring at an internal temperature of 5° C. or lower. The mixture was further stirred at room temperature for 1.5 hours. The mixture was cooled to an internal temperature of 4° C. 1-(2-methoxyphenyl)-3,4-dihydroisoquinoline (10 g) was gradually added to the mixture at an internal temperature of 5° C. or lower, followed by stirring at the same temperature for 30 minutes. The mixture was stirred at room temperature for 3 days. Trifluoroacetic acid (61 mL) was added to the reaction mixture to decompose an excess of reagent, further followed by heating under reflux for 3 hours. After cooling, diethyl ether was evaporated under reduced pressure and the mixture was heated under reflux for 10 minutes. The residue was diluted with chloroform and extracted with concentrated aqueous ammonia to be alkaline. The organic layer was washed with saturated brine, dried over magnesium sulfate, and concentrated under reduced pressure. The resulting residue was purified by silica gel column chromatography (chloroform-EtOH-aqueous ammonia) to obtain 1-(2-methoxyphenyl)-1,2,3,4-tetrahydroisoquinoline (8.23 g).

1-(2-methoxyphenyl)-1,2,3,4-tetrahydroisoquinoline (8.227 g) and (2S,3S)-2,3-bis[(4-methybenzoyl)oxy]succinic acid (13.282 g) were dissolved with stirring in acetonitrile (246 mL) at 70° C. The mixture was slowly cooled with stirring. The resulting crystal was collected by filtration, washed with acetonitrile, and dried under reduced pressure to obtain (1S)-1-(2-methoxyphenyl)-1,2,3,4-tetrahydroisoquinoline (2S,3S)-2,3-bis[(4-methylbenzoyl)oxy]succinate (16.193 g).

Production Example 23

Under cooling in a dry ice-acetone bath, lithium aluminum hydride (1.03 g) was added to THF (30 mL) to make a suspension. A solution of 1-[2-(trifluoromethyl)phenyl]-3,4-dihydroisoquinoline (6.22 g) in THF (30 mL) was added dropwise to the suspension under an argon atmosphere. The reaction solution was stirred at room temperature for 15 hours. The reaction liquid was cooled in ice and then a saturated aqueous Rochelle salt solution (1.5 mL) was added to stop the reaction. The liquid was stirred at room temperature for 1 hour and magnesium sulfate and celite were then added thereto. The mixture was filtered through celite, and the filtrate was concentrated under reduced pressure. The resulting residue was purified by silica gel column chromatography (hexane-EtOAc) to obtain 1-[2-(trifluoromethyl)phenyl]-1,2,3,4-tetrahydroisoquinoline (5.42 g).

Production Example 24

N-[2-(4-chlorophenyl)ethyl]cyclohexanecarboxamide (2.03 g) was dissolved in 1,2-dichloroethane (15 mL), and oxalyl chloride (0.8 mL) was added thereto under ice-cooling. The reaction mixture was stirred at room temperature for 1 hour and then cooled to −20° C. Ferric chloride (1.49 g) was added to the mixture, followed by stirring at room temperature for 16 hours. An aqueous 1 M HCl solution was added to the mixture which was then stirred at room temperature for 30 minutes, followed by extraction with chloroform. The extract was washed with water and saturated brine, and dried over magnesium sulfate. The solvent was evaporated and the resulting residue was dried to obtain 9-chloro-10b-cyclohexyl-6,10b-dihydro-5H-[1,3]oxazolo[2,3-a]isoquinoline-2,3-dione (2.38 g).

Production Example 25

9-chloro-10b-cyclohexyl-6,10b-dihydro-5H-[1,3]oxazolo[2,3-a]isoquinoline-2,3-dione (2.37 g) was dissolved in MeOH (16 mL), and a solution of sulfuric acid (8 mL) in MeOH (24 mL) was added thereto, followed by stirring under heating at reflux for 18 hours. The reaction mixture was left to cool and then the solvent was evaporated. The reaction mixture was neutralized by an aqueous 1 M sodium hydroxide solution, extracted with chloroform, washed with saturated brine, and then dried over magnesium sulfate. The solvent was evaporated and then the resulting residue was dried to obtain 7-chloro-1-cyclohexyl-3,4-dihydroisoquinoline (1.78 g).

Production Example 26

N-[2-(2-chlorophenyl)ethyl]cyclohexanecarboxamide (2.55 g) was dissolved in 1,2-dichloroethane (25 mL), and oxalyl chloride (1.0 mL) was added thereto under ice-cooling. The reaction mixture was stirred at room temperature for 1 hour and then cooled to −20° C. Iron chloride (1.87 g) was added to the mixture, followed by stirring at room temperature for 16 hours. An aqueous 1 M HCl solution was added to the mixture, followed by stirring at room temperature for 30 minutes and extraction with chloroform. The extract was washed with water and saturated brine, and dried over magnesium sulfate. Then, the solvent was evaporated.

The resulting residue (2.55 g) was dissolved in 1,2-dichloroethane (25 mL), and oxalyl chloride (1.0 mL) was added thereto under ice-cooling. The reaction mixture was stirred at room temperature for 1 hour and then cooled to −20° C. To the mixture was added iron chloride (1.87 g), followed by stirring at room temperature for 16 hours. An aqueous 1 M HCl solution was added to the mixture which was then stirred at room temperature for 30 minutes, followed by extraction with chloroform. The extract was washed with water and saturated brine, and dried over magnesium sulfate. The solvent was evaporated and the resulting residue was dissolved in MeOH (16 mL), and a solution of sulfuric acid (8 mL) in MeOH (24 mL) was added thereto, followed by stirring under heating at reflux for 18 hours. The reaction mixture was left to cool and then the solvent was evaporated. The reaction mixture was neutralized by an aqueous 1 M sodium hydroxide solution, extracted with chloroform, washed with saturated brine, and then dried over magnesium sulfate. The solvent was evaporated and the resulting residue was dried to obtain 5-chloro-1-cyclohexyl-3,4-dihydroisoquinoline (2.22 g).

Production Example 27

N-[2-(4-methoxyphenyl)ethyl]cyclohexanecarboxamide (5.56 g) was dissolved in toluene (120 mL), and diphosphorus pentoxide (3.0 g) and phosphorus oxychloride (6.0 mL) were sequentially added thereto, followed by stirring under heating at reflux for 5.5 hours. The reaction mixture was left to cool and then the solvent was evaporated. An aqueous 8 M potassium hydroxide solution, water and chloroform were added to the resulting residue to completely dissolve the insoluble materials to achieve a pH of around pH 8, followed by extraction with chloroform. The extract was washed with saturated brine, and then dried over magnesium sulfate. The solvent was evaporated and the resulting residue was purified by silica gel column chromatography (chloroform-MeOH) to obtain 1-cyclohexyl-7-methoxy-3,4-dihydroisoquinoline (1.87 g).

Production Example 28

Phosphoric acid (11.9 mL) was added to diphosphorus pentoxide (20.0 g) over 5 minutes. The mixture was stirred at 150° C. for 0.5 hours. 3-fluoro-N-(2-phenylethyl)benzamide (5.00 g) was added to the mixture, followed by stirring at 160° C. for 2.5 hours. After cooling, water was added to the reaction solution to which 28% aqueous ammonia was then added to be alkaline. The reaction solution was extracted with EtOAc, washed with saturated brine, and dried over magnesium sulfate. After filtration, the filtrate was concentrated under reduced pressure to obtain 1-(3-fluorophenyl)-3,4-dihydroisoquinoline (4.87 g).

Production Example 29

Ethyl polyphosphoric acid (50 mL) was added to 3,3-difluoro-N-(2-phenylethyl)cyclohexanecarboxamide (6.4 g), followed by stirring under heating at 120° C. for 2 hours. The reaction liquid was added to ice water (150 mL), extracted with chloroform and dried over magnesium sulfate. The solvent was evaporated to obtain 1-(3,3-difluorocyclohexyl)-3,4-dihydroisoquinoline (4.1 g).

Production Example 30

Ethyl polyphosphoric acid (10 mL) was added to trans-4-methyl-N-(2-phenylethyl)cyclohexanecarboxamide (2 g), followed by stirring under heating at 120° C. for 2 hours. Water was added to the reaction liquid which was then extracted with EtOAc. The organic layer was washed with water and saturated brine, and then dried over magnesium sulfate. The solvent was evaporated. To the resulting residue were added EtOH (10 mL) and then sodium borohydride (0.31 g) under ice-cooling, directly followed by stirring for 2 hours. Water was added to the reaction liquid, followed by extraction with EtOAc. The organic layer was washed with water and saturated brine, and then dried over magnesium sulfate. The solvent was evaporated to obtain 1-(trans-4-methylcyclohexyl)-1,2,3,4-tetrahydroisoquinoline (2 g).

Production Example 31

N-[2-(2-methylphenyl)ethyl]butanamide (4.58 g) was dissolved in xylene (30 mL), and then diphosphorus pentoxide (10 g) was added thereto, followed by stirring at 140° C. for 4 hours. The reaction mixture was left to cool and then the solvent was evaporated. An aqueous 8 M potassium hydroxide solution, water, and chloroform were used to dissolve completely the insoluble materials. The reaction mixture was adjusted to a pH of around 8, and extracted with chloroform. The extract was washed with saturated brine, and then dried over magnesium sulfate. The solvent was evaporated under reduced pressure and the resulting residue was purified by silica gel column chromatography (hexane-EtOAc) to obtain 5-methyl-1-propyl-3,4-dihydroisoquinoline (2.14 g).

Production Example 32

N-[2-(2-bromo-5-methoxyphenyl)ethyl]-2-methoxyacetamide (7.8 g) was dissolved in xylene (80 mL), and diphosphorus pentoxide (11 g) was added thereto, followed by stirring at 140° C. for 4 hours. Then, the solvent was evaporated, and an aqueous 6 M sodium hydroxide solution was added to the reaction mixture to be around a pH of 8. The reaction mixture was extracted with chloroform, washed with saturated brine, and then dried over magnesium sulfate. The solvent was evaporated, and the resulting residue was purified by silica gel column chromatography (hexane-EtOAc).

The resulting compound was dissolved in EtOH (30 mL), and N,N-diisopropylethylamine, and 20% palladium hydroxide-supported activated carbon (400 mg) was added thereto, followed by stirring under a hydrogen atmosphere, at normal pressure and room temperature, for 3 hours. Thereafter, the reaction mixture was filtered through celite to separate the catalyst, and the solvent was evaporated.

To the resulting residue were added saturated aqueous sodium bicarbonate (30 mL) and then EtOAc (20 mL). A solution of chloroacetyl chloride (1.17 mL) in EtOAc (10 mL) was added dropwise to the reaction liquid over 5 minutes, followed by stirring for 5 hours. Then, the reaction liquid was extracted with EtOAc and dried over magnesium sulfate. The solvent was evaporated, and the resulting residue was purified by silica gel column chromatography (hexane-EtOAc) to obtain 2-(chloroacetyl)-8-methoxy-1-(methoxymethyl)-1,2,3,4-tetrahydroisoquinoline (367 mg).

Production Example 33

[2-(4-chlorophenyl)ethyl]amine (3.5 g) was dissolved in a 1:2 mixed solution (45 mL) of EtOAc-saturated aqueous sodium bicarbonate. A solution of cyclohexanecarbonyl chloride (3.35 mL) in EtOAc (18 mL) was added dropwise to the reaction liquid over 5 minutes. After stirring for 1.5 hours, the reaction liquid was extracted with EtOAc, washed with an aqueous 1 M sodium hydroxide solution and water, and dried over magnesium sulfate. The solvent was evaporated and the resulting residue was dried to obtain N-[2-(4-chlorophenyl)ethyl]cyclohexanecarboxamide (5.69 g).

Production Example 34

4,4-difluorocyclohexanecarboxylic acid (1.48 g) was dissolved in methylene chloride (20 mL), and 1-(3-dimethylaminopropyl)-3-ethylcarbodiimide (1.68 g), 1-hydroxybenzotriazole (1.21 g), and (2-phenylethyl)amine (1.2 mL) were sequentially added thereto, followed by stirring at room temperature for 18 hours. Then, saturated aqueous sodium bicarbonate was added to the reaction liquid which was then extracted with chloroform. The extract was washed with water and further saturated brine, and then dried over magnesium sulfate. The solvent was evaporated and the resulting residue was purified by silica gel column chromatography (hexane-EtOAc) to obtain 4,4-difluoro-N-(2-phenylethyl)cyclohexanecarboxamide (1.96 g).

Production Example 35

A solution of 1.64 M tert-butyllithium in n-pentane (12 mL) was added to a mixture of 2-(2,2-dimethylpropanoyl)-1,2,3,4-tetrahydroisoquinoline (3.0 g), tetramethylethylenediamine (2.2 ml), and THF (40 mL) at −78° C. The reaction liquid was stirred at −78° C. for 10 minutes. Then, acetone (1.8 mL) was further added to the liquid at −78° C., followed by stirring at −78° C. for 1 hour. Acetic acid (2 mL) was added to the reaction liquid, and the temperature was raised to room temperature. The reaction liquid was evaporated under reduced pressure. EtOAc and water were added thereto, followed by liquid separation. The organic layer was washed sequentially with an aqueous 5% citric acid solution, a saturated aqueous sodium hydrogen carbonate solution, and saturated brine, dried over magnesium sulfate and evaporated under reduced pressure. The residue was purified by silica gel column chromatography (hexane-EtOAc) to obtain 2-[2-(2,2-dimethylpropanoyl)-1,2,3,4-tetrahydroisoquinolin-1-yl]propan-2-ol (2.62 g).

Production Example 36

Trifluoroacetic acid (27 mL) was added to 2-[2-(2,2-dimethylpropanoyl)-1,2,3,4-tetrahydroisoquinolin-1-yl]propan-2-ol (2.79 g), followed by stirring at room temperature for 4 hours. Thereafter, the solvent was evaporated and saturated aqueous sodium bicarbonate was added to the resulting residue, followed by extraction with EtOAc. The extract was washed with water, and then dried over magnesium sulfate. The solvent was evaporated to obtain 1-methyl-1-(1,2,3,4-tetrahydroisoquinolin-1-yl)ethyl pivalate.

1-methyl-1-(1,2,3,4-tetrahydroisoquinolin-1-yl)ethyl pivalate (2.79 g) was dissolved in a 1:4 mixed solvent (30 mL) of EtOAc-saturated aqueous sodium bicarbonate. A solution of chloroacetyl chloride (0.9 mL) in EtOAc (6 mL) was added dropwise to the reaction liquid under ice-cooling, followed by stirring at room temperature for 2 hours and extraction with EtOAc. The extract was washed with saturated brine, and then dried over magnesium sulfate. The solvent was evaporated and the resulting residue was purified by silica gel column chromatography (hexane-EtOAc) to obtain 1-[2 (chloroacetyl)-1,2,3,4-tetrahydroisoquinolin-1-yl]-1-methylethyl pivalate (3.01 g).

Production Example 37

Water (5 mL) and potassium carbonate (1.04 g) were added to a solution of 6-bromo-1-cyclohexyl-1,2,3,4-tetrahydroisoquinoline hydrochloride (1.00 g) in 1,2-dichloroethane (5 mL). To the reaction mixture were added di-tert-butyl dicarbonate (726 mg) and further dimethylaminopyridine (36.9 mg). The mixture was stirred at room temperature for 4 hours and extracted with chloroform. The extract was washed with a saturated aqueous sodium hydrogen carbonate solution and saturated brine, dried over magnesium sulfate, filtered, and then concentrated under reduced pressure to obtain tert-butyl 6-bromo-1-cyclohexyl-3,4-dihydroisoquinoline-2(1H)-carboxylate (1.11 g).

Production Example 38

DMF (20 mL) was added to a mixture of tert-butyl 6-bromo-1-cyclohexyl-3,4-dihydroisoquinoline-2(1H)-carboxylate (1.41 g), zinc cyanide (848 mg), and [1,1'-bis(diphenylphosphino)ferrocene]palladium chloride (535 mg), which was then purged with argon gas. Subsequently, tris(dibenzylideneacetone)dipalladium (458 mg) was added to the mixture which was then stirred at 120° C. under an argon atmosphere for 10 hours. Further, tris(dibenzylideneacetone) dipalladium (200 mg) was added thereto, followed by stirring for 10 hours. The reaction material was filtered through celite, and EtOAc and water were added to the filtrate. The organic layer was collected, washed with water and saturated brine, dried over magnesium sulfate, and filtered. The filtrate was concentrated under reduced pressure. The resulting residue was purified by silica gel column chromatography (hexane-EtOAc) to obtain tert-butyl 6-cyano-1-cyclohexyl-3,4-dihydroisoquinoline-2(1H)-carboxylate (361 mg).

Production Example 39

4 M HCl/EtOAc (2 mL) was added to a solution of tert-butyl 6-cyano-1-cyclohexyl-3,4-dihydroisoquinoline-2(1H)-carboxylate (361 mg) in EtOAc (1 mL). The mixture was stirred at room temperature for 1 hour. The reaction mixture together with the precipitated crystal was diluted with diethyl ether (5 mL). The crystal was collected by filtration, washed with diethyl ether, and dried in air to obtain 1-cyclohexyl-1,2,3,4-tetrahydroisoquinoline-6-carbonitrile hydrochloride (259 mg).

Production Example 40

Tert-butyl 7-(acetamidemethyl)-1-cyclohexyl-3,4-dihydroisoquinoline-2(1H)-carboxylate (861 mg) was dissolved in a 1:1 mixed solution (8 mL) of EtOAc-MeOH, to which 4 M HCl/EtOAc (2.8 mL) was then added. The reaction mixture was stirred at 50° C. for 6 hours and then the solvent was evaporated.

To the resulting residue were added saturated aqueous sodium bicarbonate (15 mL) and then EtOAc (10 mL). A solution of chloroacetyl chloride (0.2 mL) in EtOAc (5 mL) was added dropwise to the reaction liquid over 5 minutes, followed by stirring for 1 hour. The reaction liquid was extracted with EtOAc and dried over magnesium sulfate. The solvent was evaporated and the resulting residue was dried to obtain N-{[2-(chloroacetyl)-1-cyclohexyl-1,2,3,4-tetrahydroisoquinolin-7-yl]methyl}acetamide (655 mg).

Production Example 41

7-bromo-1-cyclohexyl-3,4-dihydroisoquinoline (9.47 g) was dissolved in N-methyl-2-pyrrolidone (150 mL) to which tris(dibenzylideneacetone)dipalladium (2.97 g), 1,1'-bis(diphenylphosphino)ferrocene (7.19 g), and zinc cyanide (11.5 g) were then added, followed by stirring at 120° C. for 18 hours. Then, water was added to the reaction liquid which was then filtered through celite to separate the insoluble materials. The insoluble materials were extracted with EtOAc, washed with saturated brine, and then dried over magnesium sulfate. The solvent was evaporated and the resulting residue was purified by silica gel column chromatography (hexane-EtOAc) to obtain 1-cyclohexyl-3,4-dihydroisoquinoline-7-carbonitrile (7.19 g).

Production Example 42

7-bromo-1-cyclohexyl-3,4-dihydroisoquinoline (4.01 g) was dissolved in 1,4-dioxane (100 mL), to which tributyl(1-ethoxyvinyl)tin (7.43 g), potassium fluoride (2.39 g), and tetrakis(triphenylphosphine)palladium (1.58 g) were then added, followed by stirring at 80° C. for 5 hours. Thereafter, to the reaction liquid were further added tributyl(1-ethoxyvinyl)tin (2.47 g) and tetrakis(triphenylphosphine)palladium (1.58 g), followed by stirring for 14 hours. Then, the reaction liquid was filtered through celite and the insoluble materials were separated. 4 M HCl/dioxane (20 mL) was added to the insoluble materials, followed by stirring at 60° C. for 30 minutes. The solvent was evaporated and water was added to the mixture which was then extracted with EtOAc. The extract was washed with saturated brine, and then dried over magnesium sulfate. The solvent was evaporated and the resulting residue was purified by silica gel column chromatography (chloroform-MeOH) to obtain 1-(1-cyclohexyl-3,4-dihydroisoquinolin-7-yl)ethanone (2.24 g).

Production Example 43

1-(1-cyclohexyl-3,4-dihydroisoquinolin-7-yl)ethanone (600 mg) was dissolved in THF (6 mL). A solution of 0.5 M Tebbe reagent in toluene (4.7 mL) was added to the reaction liquid under ice-cooling, followed by stirring at room temperature for 45 minutes. Then, diethyl ether and 10 drops of an aqueous 1 M NaOH solution were sequentially added to the reaction liquid. The reaction liquid was dried over sodium sulfate and filtered through celite.

To the resulting solution were added EtOH (8 mL) and 20% palladium hydroxide-supported activated carbon (900 mg). The solution was stirred under a hydrogen atmosphere, at room temperature and normal pressure, for 13 hours. Then, the catalyst was separated by filtration through celite and then the solvent was evaporated.

To the resulting residue were added saturated aqueous sodium bicarbonate (15 mL) and then EtOAc (10 mL). A solution of chloroacetyl chloride (265 mg) in EtOAc (5 mL) was added dropwise to the reaction liquid over 5 minutes, followed by stirring for 1 hour. The reaction liquid was extracted with EtOAc and dried over magnesium sulfate. The solvent was evaporated and the resulting residue was purified by silica gel column chromatography (hexane-EtOAc) to obtain 2-(chloroacetyl)-1-cyclohexyl-7-isopropyl-1,2,3,4-tetrahydroisoquinoline (186 mg).

Production Example 44

6-bromo-1-cyclohexyl-1,2,3,4-tetrahydroisoquinoline hydrochloride (1.0 g) was dissolved in THF (20 mL). A solution of 1.6 M n-butyllithium in n-hexane (6 mL) was added to the reaction liquid at −78° C., followed by stirring at −78° C. for 0.5 hours. Thereafter, acetone (20 mL) was added to the reaction liquid, followed by further stirring for 2 hours. The solvent was evaporated and water was added to the reaction liquid, followed by extraction with chloroform. The extract was washed with a saturated aqueous sodium chloride solution, and then dried over magnesium sulfate. The solvent was evaporated.

To the resulting residue were added saturated aqueous sodium bicarbonate (15 mL) and then EtOAc (10 mL). A solution of chloroacetyl chloride (0.24 mL) in EtOAc (5 mL) was added dropwise to the reaction liquid over 5 minutes, followed by stirring for 18 hours. The reaction liquid was extracted with EtOAc and dried over magnesium sulfate. The solvent was evaporated and the resulting residue was purified by silica gel column chromatography (hexane-EtOAc) to obtain 2-[2-(chloroacetyl)-1-cyclohexyl-1,2,3,4-tetrahydroisoquinolin-6-yl]propan-2-ol (646 mg).

Production Example 45

To 5-bromo-1-isopropyl-8-methoxy-1,2,3,4-tetrahydroisoquinoline hydrochloride (3.0 g) were added EtOH (30 mL), triethylamine (1.3 mL), and 10% palladium-supported carbon (0.30 g), followed by stirring under a hydrogen atmosphere for 2 hours. The reaction liquid was filtered through celite and the solvent was evaporated. An aqueous 1 M NaOH solution was added to the reaction liquid, followed by extraction with EtOAc. The extract was washed with saturated brine, and then dried over magnesium sulfate. The solvent was evaporated and the resulting residue was dissolved in EtOAc (30 mL). 4 M HCl/EtOAc (5 mL) was added to the mixture, and the precipitated solid was collected to obtain 1-isopropyl-8-methoxy-1,2,3,4-tetrahydroisoquinoline hydrochloride (2.2 g).

Production Example 46

(2-bromo-5-methylphenyl)acetonitrile (8.2 g) was dissolved in THF (60 mL) to which a borane-dimethyl sulfide complex (5 mL) was then added, followed by stirring at 80° C. for 4 hours. The reaction liquid was cooled in ice, and MeOH (15 mL) was added thereto, followed by stirring for a while. Then, the solvent was evaporated. 4 M HCl/dioxane (30 mL) was added to the residue which was then stirred under heating at 50° C. for 1 hour. After being left to cool, toluene (100 mL) was added to the mixture and the precipitated solid was collected to obtain 2-(2-bromo-5-methylphenyl)ethaneamine hydrochloride (5.5 g).

Production Example 47

Methanesulfonyl chloride (3.9 mL) was added to a mixture of (2-bromo-5-methylphenyl)methanol (9.2 g), dichloromethane (100 mL), and triethylamine (8 mL) under ice-cooling, followed by stirring at room temperature for 5 hours. An aqueous 1 M HCl solution was added to the reaction liquid which was then extracted with chloroform. The organic layer was dried over magnesium sulfate and filtered. Thereafter, the solvent was evaporated.

To the resulting residue (11 g) were added EtOH (60 mL), water (40 mL), and sodium cyanide (2.1 g), followed by stirring at 80° C. for 5 hours. Water was added to the reaction liquid, followed by extraction with EtOAc. The organic layer was dried over magnesium sulfate. The solvent was evaporated to obtain (2-bromo-5-methylphenyl)acetonitrile (8.3 g).

Production Example 48

Aluminum chloride (30 g) was added to benzene (60 mL). 2,6-dimethylbenzoic acid (10 g) was gradually added to the mixture with stirring under ice-cooling, followed by stirring for 30 minutes. The temperature was returned to room temperature, and the mixture was further stirred for 1 hour, followed by stirring under heating at reflux for 4 hours. The reaction liquid was poured into ice water (300 mL), filtered through celite, and extracted with chloroform. The extract was washed with an aqueous 1 M NaOH solution, and then dried over magnesium sulfate. The solvent was evaporated.

The resulting residue (13 g) was dissolved in carbon tetrachloride (150 mL). With stirring under heating at reflux, N-bromosuccinimide (10 g) and 2,2'-azobis(isobutylonitrile) (0.20 g) were added thereto, followed by stirring under heating at reflux for 7 hours. The reaction liquid was left to cool and filtered. The resulting liquid was washed with a saturated aqueous sodium hydrogen carbonate solution and an aqueous sodium thiosulfate solution, and dried over magnesium sulfate. The solvent was evaporated.

To the resulting residue (15 g) were added EtOH (60 mL), water (40 mL), and sodium cyanide (1.5 g), followed by stirring under heating at 80° C. for 5 hours. Water (200 mL) was added to the reaction liquid which was then extracted with EtOAc and dried over magnesium sulfate. The solvent was evaporated and the resulting residue was purified by silica gel column chromatography (hexane:chloroform) to obtain (2-benzoyl-3-methylphenyl)acetonitrile (4.7 g).

Production Example 49

To (2-benzoyl-3-methylphenyl)acetonitrile (3.3 g) were added EtOH (40 mL), 4 M HCl/EtOAc (5 mL), and platinum oxide (IV) (0.53 g), followed by stirring under a hydrogen atmosphere for 5 hours. The reaction liquid was filtered through celite and then concentrated. Toluene was added to the concentrate, followed by extraction with an aqueous 1 M HCl solution. A 28% aqueous ammonia solution was added to the aqueous layer, which was then extracted with toluene and dried over magnesium sulfate. The solvent was evaporated and the residue was dissolved in toluene to which 4 M HCl/EtOAc (5 mL) was then added, followed by concentration. iPrOH and diisopropyl ether were added to the resulting residue, and the precipitated solid was collected to obtain 8-methyl-1-phenyl-3,4-dihydroisoquinoline hydrochloride (1.5 g).

Production Example 50

To (2-benzoyl-3-methylphenyl)acetonitrile (4.6 g) were added EtOH (70 mL), 4 M HCl/EtOAc (15 mL), and platinum oxide (IV) (0.40 g), followed by stirring under a hydrogen atmosphere for 3 days. The reaction liquid was filtered through celite and then concentrated. Toluene was added to the concentrate, followed by extraction with an aqueous 1 M HCl solution. A 28% aqueous ammonia solution was added to the aqueous layer, which was then extracted with toluene and dried over magnesium sulfate. The solvent was evaporated and the residue was dissolved in toluene. 4 M HCl/EtOAc (7 mL) was added to the mixture, followed by concentration under reduced pressure. iPrOH and diisopropyl ether were added to the resulting residue, and the precipitated solid was collected to obtain 1-cyclohexyl-8-methyl-3,4-dihydroisoquinoline hydrochloride (2.2 g).

Production Example 51

A mixture of tetralone (1.50 g), 3-methoxyphenethylamine (1.86 g), and titanium tetraisopropoxide (4.55 mL) was stirred under an argon atmosphere at 80° C. for 1 hour. The reaction mixture was cooled in an ice-MeOH bath. A mixture of formic acid (39 mL) and acetic anhydride (97 mL) was added to the reaction mixture under stirring at an internal temperature of 0° C. or lower. After the addition was complete, the reaction mixture was stirred at 80° C. for 2 hours, and trifluoroacetic acid (158 mL) was added thereto, followed by stirring at an internal temperature of 70° C. for 3 hours. After the reaction was complete, the mixture was cooled to room temperature and concentrated under reduced pressure. The residue was made weak alkaline by using a saturated aqueous sodium hydrogen carbonate solution and was extracted with EtOAc. The organic layer was washed with saturated brine, dried over magnesium sulfate, and concentrated under reduced pressure. The residue was purified by silica gel column chromatography (hexane-EtOAc) to obtain 6 methoxy-3,3',4,4'-tetrahydro-2H,2'H-spiro[isoquinoline-1,1'-naphthalene]-2-carbaldehyde (1.86 g).

A mixture of the resulting compound (1.86 g), dioxane (15 mL), and concentrated hydrochloric acid (3 mL) was refluxed for 2 hours. After being cooled, the reaction liquid was concentrated under reduced pressure, and the resulting residue was made alkaline by addition of saturated aqueous sodium bicarbonate and extracted with chloroform. The organic layer was washed with water and saturated brine, dried over magnesium sulfate, and concentrated under reduced pressure. The resulting residue was dissolved in EtOAc (40 mL), and saturated aqueous sodium bicarbonate (40 mL) was added thereto. A solution of chloroacetyl chloride (700 mg) in EtOAc (10 mL) was added dropwise with stirring to the mixture, followed by stirring for 1 hour at room temperature. The reaction mixture was diluted with EtOAc, and the organic layer was washed with saturated aqueous sodium bicarbonate and saturated brine, dried over magnesium sulfate, and concentrated under reduced pressure. The resulting residue was purified by silica gel column chromatography (hexane-EtOAc) to obtain 2-(chloroacetyl)-6-methoxy-3,3',4,4'-tetrahydro-2H,2'H-spiro[isoquinoline-1,1'-naphthalene] (1.28 g).

Production Example 52

To polyphosphoric acid produced from 80% phosphoric acid (25 g) and diphosphorus pentoxide (25 g) was added a mixture of 3-methoxyphenethylamine (5.2 g) and tetrahydro-4H-4-pyrone (4.13 g) at an internal temperature of 90° C. over 5 minutes. Further, the reaction mixture was stirred for 40 minutes, cooled to room temperature, and poured into ice water (500 mL). Concentrated aqueous ammonia was added to the reaction mixture to be strongly alkaline, followed by extraction with EtOAc. The extract was washed with water and saturated brine, dried over magnesium sulfate, and concentrated under reduced pressure. The resulting residue was purified by silica gel column chromatography (chloroform-EtOH-aqueous ammonia) to obtain 6-methoxy-2',3,3',4,5',6'-hexahydro-2H-spiro[isoquinolone-1,4'-pyrane] (2.36 g).

Production Example 53

Under cooling in an ice-MeOH bath, THF (80 mL) was added to lithium aluminum hydride (3.03 g) to make a suspension. Dicyclopropyl[(trimethylsilyl)oxy]acetonitrile (8.36 g) was added to the suspension. The mixture was stirred at room temperature for 20 hours and cooled in an ice bath. To the mixture were added sodium fluoride (3.35 g) and further water (4.23 mL), followed by stirring at room temperature for 1 hour. Thereafter, the mixture was filtered through celite. The filtrate was concentrated under reduced pressure to obtain an oily material (4.38 g). EtOAc (80 mL) was added to the oily material which was then cooled in ice. 4 M HCl/EtOAc (8 mL) was added to the mixture, which was then stirred together with the precipitated solid at room temperature for 1 hour. Thereafter, the solid was collected by filtration, washed with EtOAc, and dried under reduced pressure at 90° C. to obtain 2-amino-1,1-dicyclopropylethanol hydrochloride (3.68 g).

Production Example 54

In an ice bath under an argon atmosphere, zinc iodide (290 mg) was added to a solution of dicyclopropylmethanone (5.00 g) in 1,2-dichloroethane (50 mL). Subsequently, trimethylsilyl cyanide (6.84 mL) was added dropwise to the mixture over 10 minutes. The mixture was stirred at room temperature for 4 hours and trimethylsilyl cyanide (1.71 mL) was further added thereto, followed by stirring at room temperature for 20 hours. The reaction mixture was poured into a saturated aqueous sodium hydrogen carbonate solution and extracted with EtOAc. The extract was washed with a saturated aqueous sodium hydrogen carbonate solution and saturated brine, and dried over magnesium sulfate. Activated carbon was added to the mixture which was then filtered through celite. The filtrate was concentrated under reduced pressure to obtain dicyclopropyl[(trimethylsilyl)oxy]acetonitrile (8.36 g).

Production Example 55

10% palladium-supported carbon (300 mg) was added to a solution of 2-benzyl-1-(1-methoxy-1-methylethyl)-1,2,3,4-tetrahydroisoquinoline (1.17 g) in MeOH (12 mL). The reaction material was stirred under a hydrogen atmosphere at room temperature for 8 hours. The reaction liquid was filtered through celite and the filtrate was concentrated under reduced pressure to obtain 1-(1-methoxy-1-methylethyl)-1,2,3,4-tetrahydroisoquinoline (770 mg).

Production Example 56

With cooling in an ice-MeOH bath under an argon atmosphere, a solution of 2-(2-benzyl-1,2,3,4-tetrahydroisoquinolin-1-yl)propan-2-ol (1.27 g) in THF (7 mL) was added dropwise to a solution of sodium hydride (60%, 199 mg) in THF (5 mL), followed by stirring at room temperature for 0.5 hours. Then, the reaction liquid was cooled in ice and methyl iodide (0.42 mL) was added thereto. The mixture was stirred at room temperature for 8 hours. To the mixture were added sodium hydride (60%, 199 mg) and methyl iodide (0.42 mL), followed by stirring at room temperature for 12 hours. Water was added to the reaction solution, followed by extraction with EtOAc. The extract was washed with saturated brine, dried over magnesium sulfate, filtered, and then concentrated under reduced pressure. The resulting residue was purified by silica gel column chromatography (hexane-EtOAc) to obtain 2-benzyl-1-(1-methoxy-1-methylethyl)-1,2,3,4-tetrahydroisoquinoline (1.17 g).

Production Example 57

In a dry ice-acetone bath under an argon atmosphere, a solution of 1.0 M methyllithium in diethyl ether (16.2 mL) was added dropwise to a solution of ethyl 2-benzyl-1,2,3,4-tetrahydroisoquinoline-1-carboxylate (1.99 g) in THF (20 mL) over 15 minutes. The reaction liquid was stirred in a dry ice-acetone bath for 0.5 hours and then further stirred in an ice bath for 1 hour. The reaction liquid was cooled again in the dry ice-acetone bath, and a solution of 1.04 M methyllithium in diethyl ether (3.24 mL) was added thereto. The reaction liquid was stirred in the dry ice-acetone bath for 0.5 hours and then stirred in the ice bath for 1 hour. Water was added to the reaction liquid, followed by extraction with EtOAc. The extract was washed with saturated brine, dried over magnesium sulfate, filtered, and concentrated under reduced pressure. The resulting residue was purified by silica gel column chromatography (hexane-EtOAc) to obtain 2-(2-benzyl-1,2,3,4-tetrahydroisoquinolin-1-yl)propan-2-ol (1.27 g).

Production Example 58

In an ice bath, sodium triacetoxyborohydride (6.11 g) was added to a solution of ethyl 1,2,3,4-tetrahydroisoquinoline-1-carboxylate hydrochloride (4.98 g) and benzaldehyde (2.72 g) in acetic acid (50 mL). The mixture was stirred at room temperature for 15 hours. A 1 M aqueous NaOH solution was added to the reaction liquid which was then extracted with chloroform. The extract was washed with water and saturated brine, dried over magnesium sulfate, filtered, and concentrated under reduced pressure. The resulting residue was purified by silica gel column chromatography (hexane-EtOAc) to obtain ethyl 2-benzyl-1,2,3,4-tetrahydroisoquinoline-1-carboxylate (1.99 g).

Production Example 59

A solution of 5-bromo-7,8-dimethoxy-1-phenyl-3,4-dihydroisoquinoline (450 mg), EtOH (30 mL), 10% palladium-supported carbon (80 mg) and 28% sodium methoxide in MeOH (0.1 mL) was stirred under a hydrogen atmosphere at room temperature overnight. The insoluble materials were subjected to filtration and the filtrate was concentrated to obtain 7,8-dimethoxy-1-phenyl-1,2,3,4-tetrahydroisoquinoline (350 mg).

A solution of chloroacetyl chloride (177 mg) in EtOAc (12 mL) was added dropwise to a mixture of 7,8-dimethoxy-1-phenyl-1,2,3,4-tetrahydroisoquinoline (350 mg), a saturated aqueous sodium hydrogen carbonate solution (50 mL), and EtOAc (50 mL) under stirring. After the dropwise addition was complete, the mixture was stirred for 2 hours and extracted with EtOAc. The extract was washed sequentially with a saturated aqueous sodium hydrogen carbonate solution and saturated brine, dried over magnesium sulfate, and concentrated under reduced pressure. The resulting residue was purified by silica gel column chromatography (chloroform-EtOH) to obtain 2-(chloroacetyl)-7,8-dimethoxy-1-phenyl-1,2,3,4-tetrahydroisoquinoline (349 mg).

Production Example 60

1-cyclohexyl-N-isobutyl-3,4-dihydroisoquinoline-7-carboxamide (689 mg) was dissolved in MeOH (12 mL). Sodium borohydride (100 mg) was added to the reaction mixture, followed by stirring at room temperature for 5 hours. The solvent was evaporated. To the resulting residue were added water and chloroform. The residue was extracted with chloroform and dried over magnesium sulfate. Then, the solvent was evaporated under reduced pressure to obtain 1-cyclohexyl-N-isobutyl-1,2,3,4-tetrahydroisoquinoline-7-carboxamide.

To the resulting residue were added saturated aqueous sodium bicarbonate (10 mL) and then EtOAc (5 mL). A solution of chloroacetyl chloride (0.19 mL) in EtOAc (5 mL) was added dropwise to the reaction liquid over 5 minutes, followed by stifling for 1 hour. Then, the reaction liquid was extracted with EtOAc and dried over magnesium sulfate. The solvent was evaporated to obtain 2-(chloroacetyl)-1-cyclohexyl-N-isobutyl-1,2,3,4-tetrahydroisoquinoline-7-carboxamide (410 mg).

Production Example 61

5-methoxy-1-(methoxymethyl)-3,4-dihydroisoquinoline (1.7 g) was dissolved in MeOH (15 mL) to which sodium borohydride (376 mg) was then added, followed by stifling at room temperature for 5 hours. The solvent was evaporated under reduced pressure, and water and chloroform were added to the mixture. The mixture was extracted with chloroform and dried over magnesium sulfate. The solvent was evaporated.

To the resulting residue were added saturated aqueous sodium bicarbonate (20 mL) and then EtOAc (15 mL). A solution of chloroacetyl chloride (0.66 mL) in EtOAc (5 mL) was added dropwise to the reaction liquid over 5 minutes, followed by stirring for 1 hour. The reaction liquid was extracted with EtOAc and dried over magnesium sulfate. The solvent was evaporated and the resulting residue was purified by silica gel column chromatography (hexane-EtOAc) to obtain 2-(chloroacetyl)-5-methoxy-1-(methoxymethyl)-1,2,3,4-tetrahydroisoquinoline (550 mg).

Production Example 62

5-bromo-8-methoxy-1-propyl-1,2,3,4-dihydroisoquinoline (5.5 g) was dissolved in EtOH (30 mL). To the reaction mixture were added DMF (3.4 mL) and 10% palladium-supported carbon (500 mg), followed by stirring under a hydrogen atmosphere, at normal pressure and room temperature, for 3 hours. Thereafter, the catalyst was separated by filtration through celite and sodium borohydride (740 mg) was added to the reaction mixture, followed by stirring at room temperature for 2 hours. The solvent was evaporated under reduced pressure, and water and chloroform were added to the resulting residue. The mixture was extracted with chloroform and dried over magnesium sulfate. The solvent was evaporated under reduced pressure.

The resulting residue was dissolved in EtOAc (10 mL), to which 4 M HCl/EtOAc (15 mL) was then added under ice-cooling, followed by stirring at room temperature. The resulting insoluble materials were collected and washed with EtOAc to obtain 8-methoxy-1-propyl-1,2,3,4-tetrahydroisoquinoline (3.67 g).

Production Example 63

7-bromo-1-cyclohexyl-3,4-dihydroisoquinoline (24.45 g) was dissolved in MeOH (400 mL). The solution was cooled to 0° C. and sodium borohydride (4.8 g) was added thereto, followed by stirring at room temperature for 2 hours. Then, the solvent was evaporated under reduced pressure. Water was added to the residue, followed by extraction with chloroform. The organic layer was dried over magnesium sulfate and then the solvent was evaporated under reduced pressure. The resulting residue was dissolved in EtOAc (200 mL), to which 4 M HCl/EtOAc (21 mL) was then added. The resulting solid was collected.

The resulting residue (1 g) was dissolved in THF (30 mL), followed by cooling at −78° C. To the reaction mixture was added a solution of 2.6 M n-butyllithium in n-hexane (3.7 mL), followed by stirring for 30 minutes. Acetone (30 mL) was added to the mixture at −78° C., and the temperature was raised to room temperature, followed by stirring for 1 hour. Then, the solvent was evaporated under reduced pressure. To the resulting residue was added water, and the mixture was extracted with chloroform. The organic layer was dried over magnesium sulfate and then the solvent was evaporated under reduced pressure.

The resulting residue was dissolved in a mixed solution of EtOAc (10 mL) and saturated aqueous sodium bicarbonate (15 mL). A solution of chloroacetyl chloride (683 mg) in EtOAc (5 mL) was added dropwise to the reaction mixture, followed by stirring at room temperature for two days. Then, water was added to the mixture, followed by extraction with EtOAc. The organic layer was washed with saturated brine and dried over magnesium sulfate. Thereafter, the solvent was evaporated under reduced pressure. The resulting residue was purified by silica gel column chromatography (hexane-EtOAc) to obtain 2-[2-(chloroacetyl)-1-cyclohexyl-1,2,3,4-tetrahydroisoquinolin-7-yl]propan-2-ol (606 mg).

Production Example 64

1-cyclohexyl-3,4-dihydroisoquinoline-7-carbonitrile (1.01 g) was dissolved in EtOH (15 mL), to which a 6 M aqueous NaOH solution (7.0 mL) was then added, followed by stirring under heating at reflux for 6 hours. Water was added to the mixture which was then washed with EtOAc. A 1 M aqueous HCl solution was added to the mixture to have a pH of about 3 and then a saturated aqueous sodium sulfate solution was added thereto. The mixture was extracted with a 4:1 mixed solution of chloroform-iPrOH, washed with saturated brine, and then dried over magnesium sulfate. The solvent was evaporated to obtain 1-cyclohexyl-3,4-dihydroisoquinoline-7-carboxylic acid (1.09 g).

Production Example 65

1-cyclohexyl-3,4-dihydroisoquinoline-7-carboxylic acid (1.15 g) was dissolved in methylene chloride (15 mL). O-(benzotriazol-1-yl)-N,N,N',N'-tetramethyluronium hexafluorophosphate (2.03 g), N,N-diisopropylethylamine (1.55 mL), and 2-methyl-1-propanamine (0.87 mL) were added thereto, followed by stirring at room temperature for 18 hours. Then, water was added to the mixture, followed by extraction with chloroform. The extract was washed with saturated brine, and dried over magnesium sulfate. The solvent was evaporated and the resulting residue was purified by silica gel column chromatography (chloroform-MeOH) to obtain 1-cyclohexyl-N-isobutyl-3,4-dihydroisoquinoline-7-carboxamide (700 mg).

Production Example 66

Sodium methoxide (9.46 g) was added to a suspension of 10b-(chloromethyl)-9-ethyl-6,10b-dihydro-5H-[1,3]oxazolo[2,3-a]isoquinoline-2,3-dione (14.0 mL) in MeOH (140 mL) under ice-cooling. The mixture was stirred at room temperature for 0.5 hours and then heated under reflux for 3 hours. EtOAc and water were added to the mixture, followed by filtration. The organic layer of the filtrate was collected, washed with saturated brine, and dried over magnesium sulfate. Activated carbon and silica gel were added thereto, followed by filtration. The filtrate was concentrated under reduced pressure to obtain 7-ethyl-1-(methoxymethyl)-3,4-dihydroisoquinoline (4.75 g).

Production Example 67

Sodium borohydride (900 mg) was added to a mixed solution of a solution of 5,8-dimethoxy-1-phenyl-2-trifluoroacetyl-1,2,3,4-tetrahydroisoquinoline (4.21 g) in THF (30 mL), and EtOH (100 mL) at room temperature under stirring. The reaction mixture was stirred at room temperature for 3 hours and then stirred at 40° C. for 30 minutes, and concentrated under reduced pressure. To the resulting residue was added a 3 M aqueous HCl solution (30 mL), followed by refluxing for 5 minutes. After cooling, the mixture was made strong alkaline by using a 20% aqueous NaOH solution and extracted with chloroform. The organic layer was washed with saturated brine, dried over magnesium sulfate, and concentrated under reduced pressure to obtain 5,8-dimethoxy-1-phenyl-1,2,3,4-tetrahydroisoquinoline (3.05 g).

Production Example 68

Under an argon atmosphere, a solution of 2,5-dimethoxyphenethylamine (3.175 g) in benzene (4 mL) was added with stirring to a suspension of benzaldehyde (1.86 g) and magnesium sulfate (3.89 g) in benzene (10 mL). An exothermic reaction took place, followed by further stirring overnight. After the reaction was complete, the reaction liquid was filtered and the filtrate was concentrated under reduced pressure to obtain 2-(2,5-dimethoxyphenyl)-N-[(1E)-phenylmethylene]ethanamine (4.72 g).

Production Example 69

2-(2,5-dimethoxyphenyl)-N-[(1E)-phenylmethylene]ethanamine (4.719 g) was dissolved in trifluoroacetic acid (140 mL), followed by refluxing for 2 days. The reaction mixture was cooled to room temperature and trifluoroacetic anhydride (55 mL) was gradually added thereto. The mixture was refluxed for 3 days, cooled to room temperature, and concentrated under reduced pressure. The resulting residue was extracted with a saturated aqueous sodium hydrogen carbonate solution and chloroform. The organic layer was washed with a saturated aqueous sodium hydrogen carbonate solution and saturated brine, dried over magnesium sulfate, and concentrated under reduced pressure. The resulting residue was purified by silica gel column chromatography (hexane-EtOAc) to obtain 5,8-dimethoxy-1-phenyl-2-(trifluoroacetyl)-1,2,3,4-tetrahydroisoquinoline (4.168 g).

Production Example 70

Tert-butyl 7-cyano-1-cyclohexyl-3,4-dihydroisoquinoline-2(1H)-carboxylate (2.38 g) was dissolved in methylene chloride (40 mL). A solution of 0.99 M isobutylaluminum hydride in n-hexane (7.8 mL) was added thereto, followed by stirring at −78° C. for 4 hours. Then, a solution of 0.99 M isobutylaluminium hydride in n-hexane (28 mL) was further added to the reaction mixture. A saturated aqueous Rochelle salt solution was added to stop the reaction, followed by stirring overnight. The mixture was extracted with EtOAc. The extract was washed with saturated brine, and then dried over magnesium sulfate. The solvent was evaporated and the resulting residue was purified by silica gel column chromatography (benzene-EtOAc).

The resulting residue was dissolved in an 8:1 mixed solvent (90 mL) of EtOH-water. Hydroxylamine hydrochloride (812 mg) and sodium acetate (930 mg) were added thereto, followed by stirring at room temperature for 28 hours. Then, the solvent was evaporated. Water was added to the mixture, which was then extracted with chloroform, washed with saturated brine, and then dried over magnesium sulfate. The solvent was evaporated to obtain tert-butyl 1-cyclohexyl-7-[(hydroxyimino)methyl]-3,4-dihydroisoquinoline-2(1H)-carboxylate (2.03 g).

Production Example 71

Tert-butyl 1-cyclohexyl-7-[(hydroxyimino)methyl]-3,4-dihydroisoquinoline-2(1H)-carboxylate (1.04 g) was dissolved in an 8:1:1 mixed solvent (20 mL) of EtOH-acetic acid-water. 10% palladium-supported activated carbon (500 mg) was added thereto, followed by stirring under a hydrogen atmosphere, at room temperature and normal pressure, for 4 hours. Then, the reaction mixture was filtered through celite and the solvent was evaporated.

The resulting residue was dissolved in methylene chloride (12 mL), to which triethylamine (880 mg), acetic anhydride (385 mg), and 4-dimethylaminopyridine (70 mg) were then added, followed by stirring at room temperature for 16 hours. Then, water was added to the mixture which was then extracted with chloroform. The extract was washed with saturated brine, and dried over magnesium sulfate. The solvent was evaporated and the resulting residue was purified by silica gel column chromatography (chloroform) to obtain tert-butyl 7-(acetamidemethyl)-1-cyclohexyl-3,4-dihydroisoquinoline-2(1H)-carboxylate (875 mg).

Production Example 72

Tert-butyl 1-cyclohexyl-7-[(hydroxyimino)methyl]-3,4-dihydroisoquinoline-2(1H)-carboxylate (995 mg) was dissolved in EtOH-acetic acid-water (8:1:1, 20 mL). To the reaction mixture was added 10% palladium-supported carbon (480 mg), followed by stirring under a hydrogen atmosphere, at room temperature and normal pressure, for 4 hours. Then, the reaction mixture was filtered through celite and the solvent was evaporated to obtain tert-butyl 7-(aminomethyl)-1-cyclohexyl-3,4-dihydroisoquinoline-2(1H)-carboxylate (956 mg).

Production Example 73

Tert-butyl 7-(aminomethyl)-1-cyclohexyl-3,4-dihydroisoquinoline-2(1H)-carboxylate (999 mg) was dissolved in methylene chloride. Isobutyric acid (0.33 mL), triethylamine (1.2 mL), and O-(benzotriazol-1-yl)-N,N,N',N'-tetramethyluronium hexafluorophosphate (1.32 g) were added thereto, followed by stirring at room temperature for 18 hours. Water was added to the mixture which was then extracted with chloroform. The extract was washed with a 1 M aqueous NaOH solution and saturated brine, and dried over magnesium sulfate. The solvent was evaporated and the resulting residue was purified by silica gel column chromatography to obtain tert-butyl-1-cyclohexyl-7-[(isobutylamino)methyl]-3,4-dihydroisoquinoline-2(1H)-carboxylate (468 mg).

Production Example 74

1-cyclohexyl-3,4-dihydroisoquinolin-7-ol (2 g) was dissolved in MeOH (40 mL), to which sodium borohydride (396 mg) was then added, followed by stirring at room temperature for 4 hours. Then, the solvent was evaporated. Water was added to the mixture which was then extracted with chloroform. The extract was washed with saturated brine, and then dried over magnesium sulfate. The solvent was evaporated.

The resulting residue was dissolved in dioxane (40 mL). Di-tert-butyl dicarbonate (2.28 g) was added thereto, followed by stirring at room temperature for 2 days. Then, the solvent was evaporated and the resulting residue was purified by silica gel column chromatography (hexane-EtOAc) to obtain tert-butyl 1-cyclohexyl-7-hydroxy-3,4-dihydroisoquinoline-2(1H)-carboxylate (2.66 g).

Production Example 75

Tert-butyl 1-cyclohexyl-7-hydroxy-3,4-dihydroisoquinoline-2(1H)-carboxylate (700 mg) was dissolved in acetonitrile (12 mL). 1-chloroacetone (0.2 mL), potassium carbonate (438 mg), and tetra-n-butylammonium iodide (78 mg) were added thereto, followed by stirring at 60° C. for 16 hours. Then, water was added to the mixture which was then extracted with EtOAc. The extract was washed with saturated brine, and then dried over magnesium sulfate. The solvent was evaporated and the resulting residue was purified by silica gel column chromatography (hexane-EtOAc) to obtain tert-butyl 1-cyclohexyl-7-(2-oxopropoxy)-3,4-dihydroisoquinoline-2(1H)-carboxylate (818 mg).

Production Example 76

Tert-butyl 1-cyclohexyl-7-(2-oxopropoxy)-3,4-dihydroisoquinoline-2(1H)-carboxylate (808 mg) was dissolved in methylene chloride (15 mL). At −78° C., a solution of bis(2-methoxyethyl)aminosulfur trifluoride (0.65 mL) in methylene chloride (5 mL) was added dropwise to the reaction mixture, followed by stirring at room temperature for 14 hours. Saturated aqueous sodium bicarbonate was added to the reaction mixture which was then extracted with chloroform. The extract was washed with saturated brine, and then dried over magnesium sulfate. The solvent was evaporated and the resulting residue was purified by silica gel column chromatography (hexane-EtOAc) to obtain tert-butyl 1-cyclohexyl-7-(2,2-difluoropropoxy)-3,4-dihydroisoquinoline-2(1H)-carboxylate (747 mg).

Production Example 77

A 1 M aqueous NaOH solution was added to (1S)-1-isopropyl-8-methoxy-1,2,3,4-tetrahydroisoquinoline hydrochloride (808 mg). The reaction mixture was extracted with chloroform and the organic layer was dried over magnesium sulfate. The solvent was evaporated under reduced pressure. A mixed solution of a solution of 1 M boron tribromide in dichloromethane (13.4 mL), and dichloromethane (10 mL) was cooled to −78° C. and a solution of the extraction residue in dichloromethane (10 mL) was added dropwise thereto. The temperature was gradually raised and the reaction mixture was stirred at room temperature for 24 hours. Then, saturated aqueous sodium bicarbonate and chloroform were added to the reaction mixture. After liquid separation was complete, the aqueous layer was used in subsequent reaction.

Di-tert-butyl dicarbonate was added to the resulting aqueous layer, followed by stirring at room temperature for 5 hours. The mixture was neutralized by a 1 M aqueous HCl solution and extracted with chloroform. The organic layer was washed with water and dried over magnesium sulfate. Thereafter, the solvent was evaporated under reduced pressure to obtain tert-butyl-(1S)-8-hydroxy-1-isopropyl-3,4-dihydroisoquinoline-2(1H)-carboxylate (973 mg).

Production Example 78

Tert-butyl (1S)-8-hydroxy-1-isopropyl-3,4-dihydroisoquinoline-2(1H)-carboxylate (973 mg) was dissolved in a mixed solution of iPrOH (6 mL) and a 30% aqueous potassium hydroxide solution (3 mL). To the reaction mixture was added chlorodifluoromethane by ventilation, followed by stirring at 70° C. for 20 hours. Water was added to the mixture which was then extracted with chloroform. The organic layer was dried over magnesium sulfate. The solvent was evaporated under reduced pressure and then the residue was purified by silica gel column chromatography (hexane-EtOAc).

The resulting residue (790 mg) was dissolved in EtOAc. 4 M HCl/EtOAc (5.8 mL) was added thereto, followed by stirring at 60° C. for 18 hours. Then, the solvent was evaporated under reduced pressure to obtain (1S)-8-(difluoromethoxy)-1-isopropyl-1,2,3,4-tetrahydroisoquinoline hydrochloride (642 mg).

Production Example 79

A 1 M aqueous NaOH solution was added to (1S)-8-methoxy-1-phenyl-1,2,3,4-tetrahydroisoquinoline hydrochloride (1.81 g). The reaction mixture was extracted with chloroform. The organic layer was dried over magnesium sulfate and the solvent was evaporated under reduced pressure. A mixed solution of a solution of 1 M boron tribromide in dichloromethane (26.3 mL) and dichloromethane (30 mL) was cooled to −78° C. and a solution of the extraction residue in dichloromethane (10 mL) was added dropwise thereto. The temperature was gradually raised and the reaction mixture was stirred at room temperature for 24 hours. Then, saturated aqueous sodium bicarbonate and chloroform were added to the reaction mixture. After liquid separation was complete, the organic layer was dried over magnesium sulfate. The solvent was evaporated under reduced pressure.

The resulting residue (1.48 g) was dissolved in THF (50 mL). A 1 M aqueous NaOH solution (8 mL) and di-tert-butyl dicarbonate (2.87 g) were added thereto, followed by stirring at room temperature for 5 hours. Then, the solvent was evaporated under reduced pressure. To the resulting residue were added water and a 1 M aqueous HCl solution, and the mixture was extracted with chloroform. The organic layer was washed with water and dried over magnesium sulfate. Then, the solvent was evaporated under reduced pressure and the resulting residue was purified by silica gel column chromatography (hexane-EtOAc).

The resulting residue (1.24 g) was dissolved in a mixed solution of iPrOH (20 mL) and a 50% aqueous potassium hydroxide solution (10 mL). To the reaction mixture was added chlorodifluoromethane by ventilation, followed by stirring at 70° C. for 14 hours. Water was added to the mixture which was then extracted with chloroform. The organic layer was dried over magnesium sulfate. The solvent was evaporated under reduced pressure and then the resulting residue was purified by silica gel column chromatography (hexane-EtOAc).

The resulting residue (927 mg) was dissolved in EtOAc (25 mL), to which 4 M HCl/EtOAc (6.2 mL) was then added, followed by stirring at 60° C. for 18 hours. Then, the solvent was evaporated under reduced pressure to obtain (1S)-8-(difluoromethoxy)-1-phenyl-1,2,3,4-tetrahydroisoquinoline hydrochloride (770 mg).

Production Example 80

28% aqueous ammonia was added to 1-oxiran-2-ylcyclohexanol, followed by stirring for 11 hours. The solvent was evaporated under reduced pressure and then water was removed azeotropically with toluene.

The resulting residue was dissolved in a mixed solution of EtOH-diethyl ether. Oxalic acid was added thereto, followed by stirring for a while. The resulting insoluble materials were collected to obtain 1-(2-amino-1-hydroxyethyl)cyclohexanol oxalate (853 mg).

Production Example 81

(1R,2S)-1-amino-2-indanol (511 mg) was dissolved in toluene (60 mL). Under ice-cooling, a solution of a 1 M borane-THF complex in THF (8.16 mL) was added thereto, followed by stirring at room temperature for 1 hour. Then, 7-bromo-1-cyclohexyl-3,4-dihydroisoquinoline (1 g) was added to the mixture, followed by stirring at room temperature for 3 days. The reaction was stopped by addition of trifluoroacetic acid, followed by further stirring at 60° C. for 1 hour. The solvent was evaporated. A 1 M aqueous sodium hydroxide solution was added to the mixture which was then extracted with chloroform. The extract was washed with saturated brine, and then dried over magnesium sulfate. The solvent was evaporated and the resulting residue was purified by silica gel column chromatography (chloroform-MeOH) to obtain crude (1S)-7-bromo-1-cyclohexyl-3,4-tetrahydroisoquinoline (1.06 g). The resulting crude product (203 mg) was dissolved in EtOH (9 mL). To the mixture was added D-(−)-tartaric acid (104 mg) at 80° C. The mixture was gradually cooled to room temperature, followed by stirring for 12 hours. The resulting insoluble materials were collected to obtain (1S)-7-bromo-1-cyclohexyl-3,4-tetrahydroisoquinoline (72 mg).

Production Example 82

Under an argon atmosphere, a 1.09 M borane-THF solution (18.7 mL) was added to a suspension of (1R,2S)-1-aminoindan-2-ol (3.04 g) in toluene (60 mL) under ice-cooling, followed by stirring at room temperature for 1 hour. Then, a solution of 1-[2[(trifluoromethyl)benzyl]-3,4-dihydroisoquinoline (4.00 g) in toluene (20 mL) was added to the reaction mixture under ice-cooling. The mixture was stirred at 4° C. for 45 hours. Trifluoroacetic acid (20 mL) was added to stop the reaction. The mixture was heated under reflux for 1 hour and then cooled. 28% aqueous ammonia (30 mL) was added to the mixture to be alkaline. The mixture was extracted with EtOAc. The extract was washed 3 times and further washed with saturated brine, dried over magnesium sulfate, and then filtered. The filtrate was concentrated to obtain a yellow oily material (4.11 g). The oily material was dissolved in acetonitrile (80 mL). To the mixture was added N-acetyl-L-leucine (2.39 g) at 80° C. The mixture was gradually cooled, followed by stirring at 60° C. for 2 hours and at room temperature for 12 hours. When the crystal was precipitated, the crystal was collected by filtration, cooled in ice, washed with acetonitrile, and dried in air to obtain a crystal (2.48 g). The crystal was recrystallized from acetonitrile (50 mL) to obtain 1-[2-(trifluoromethyl)benzyl]-1,2,3,4-tetrahydroisoquinoline N-acetyl-L-leucine salt (1.72 g).

Production Example 83

Under an argon atmosphere, a 1.09 M borane-THF solution (48.8 mL) was added to a suspension of (1R,2S)-1-aminoindan-2-ol (3.79 g) in toluene (60 mL) under ice-cooling, followed by stirring at room temperature for 1 hour. Then, a solution of 7-ethyl-1-(methoxymethyl)-3,4-dihydroisoquinoline (4.70 g) in THF (40 mL) was added to the reaction mixture under ice-cooling. The mixture was stirred at 4° C. for 8 hours. Trifluoroacetic acid (15 mL) was added to stop the reaction. The mixture was heated under reflux for 1 hour. To the mixture were added chloroform and 28% aqueous ammonia. The organic layer was washed 3 times with water and extracted with a 5% aqueous acetic acid solution. The extract was adjusted to have alkalinity by addition of 28% aqueous ammonia and extracted with EtOAc. The extract was washed two times with water and further washed with saturated brine, dried over magnesium sulfate, and then filtered. The filtrate was concentrated under reduced pressure to obtain a yellow oily material (3.15 g). The oily material was dissolved in iPrOH (63 mL), to which (2S,3S)-2,3-bis(benzoyloxy)succinic acid (4.14 g) was gradually added at 90° C. The mixture was heated under reflux for 1 hour and was gradually cooled to room temperature, followed by stirring at room temperature for 3 hours. When the crystal was precipitated, the crystal was collected by filtration, washed with iPrOH and ether, and dried under reduced pressure to obtain (7-ethyl-1-(methoxymethyl)-1,2,3,4-tetrahydroisoquinoline (2S,3S)-2,3-bis(benzoyloxy)succinate (5.54 g).

Production Example 84

Phosphorus pentoxide (15.85 g) was added to a solution of 2-chloro-N-[2-(4-ethylphenyl)ethyl]acetamide (7.87 g) in xylene (140 mL) under stirring at 90° C. over 5 minutes. The reaction mixture was heated at 120° C. and stirred for 2 hours. The reaction mixture was cooled to room temperature. The supernatant was removed and the residue was washed sequentially with toluene and ether. Crushed ice (150 g) was added to the residue, followed by stirring. A 20% aqueous sodium hydroxide solution was further added to the mixture to be a pH of 10 or higher, and the mixture was extracted with chloroform. The organic layer was collected, washed with water and saturated brine, and dried over anhydrous magnesium sulfate. To the organic layer was added a 4 M HCl/EtOAc solution (15 mL), and the mixture was concentrated under reduced pressure to obtain 1-(chloromethyl)-7-ethyl-3,4-dihydroisoquinoline hydrochloride (8.5 g).

Production Example 85

Tert-butyl (1S)-8-hydroxy-1-phenyl-3,4-dihydroisoquinoline-2(1H)-carboxylate (1.53 g) was dissolved in dichloromethane (20 mL). 2,6-lutidine (1.1 mL) and trifluoromethanesulfonic anhydride (0.9 mL) were added thereto at −78° C., followed by stirring at room temperature for 16 hours. Then, saturated aqueous sodium bicarbonate was added to the mixture which was then extracted with chloroform. The extract was washed with a saturated aqueous sodium chloride solution, and then dried over magnesium sulfate. The solvent was evaporated and the resulting residue was purified by silica gel column chromatography (ethyl acetate:hexane) to obtain tert-butyl (1S)-1-phenyl-8-{[(trifluoromethyl)sulfonyl]oxy}-3,4-dihydroisoquinoline-2(1H)-carboxylate (2.08 g).

Production Example 86

To N-[2-(2-bromo-5-methylphenyl)ethyl]-2-methoxyacetamide (3.9 g) was added xylene (50 mL), followed by stirring under heating at 60° C. Diphosphorus pentoxide (7.0 g) was added with stirring to the reaction mixture, followed by stirring at 140° C. for 3 hours. After the reaction mixture being left to cool, the supernatant of the reaction mixture was discarded. The mixture was dissolved in water, toluene, and an aqueous sodium hydroxide solution, and extracted with toluene. The extract was further extracted with a 1 M aqueous HCl solution. The recovered aqueous layer was neutralized, extracted with toluene, and dried over magnesium sulfate. After filtration was complete, a 4 M HCl/EtOAc solution (5 mL) was added to the layer, and the solvent was evaporated under reduced pressure. To the resulting residue were added EtOH (50 mL), toluene (10 mL), and sodium borohydride (1.0 g), followed by stirring for 4 days. To the reaction mixture was added a 1 M aqueous HCl solution, followed by stirring for 5 hours. Thereafter, an aqueous sodium hydroxide solution was added to the mixture which was then extracted with chloroform. The solvent was evaporated. Sodium carbonate (1.0 g), water (30 mL), toluene (30 mL), and chloroacetyl chloride (0.3 mL) were added to the resulting residue under ice-cooling, followed by stirring at room temperature for 17 hours. Water was added to the reaction liquid, which was then extracted with chloroform. The extract was washed with a 1 M aqueous HCl solution, and then dried over magnesium sulfate. The solvent was evaporated and the resulting residue was purified by silica gel chromatography to obtain 5-bromo-2-(chloroacetyl)-1-(methoxymethyl)-8-methyl-1,2,3,4-tetrahydroisoquinoline (0.323 g).

Production Example 87

8-ethyl-5-methoxy-1-phenyl-1,2,3,4-tetrahydroisoquinoline hydrochloride (2.06 g) was dissolved in methylene chloride (40 mL). To the reaction mixture was added a solution of boron tribromide in dichloromethane (13.6 mL) at −78° C., followed by stirring at room temperature for 16 hours. Thereafter, a saturated aqueous sodium hydrogen carbonate solution was added to the reaction mixture to make it alkaline. Then, di-tert-butyl dicarbonate (2.96 g) was added to the reaction solution, followed by stirring at room temperature for 3 hours. The reaction liquid was extracted with chloroform, washed with a saturated aqueous sodium chloride solution, and dried over magnesium sulfate. The solvent was evaporated and the resulting residue was dissolved in dichloromethane (20 mL). To the mixture were added 2,6-lutidine (1.8 mL) and trifluoromethanesulfonic anhydride (1.55 mL), followed by stirring at room temperature for 18 hours. Thereafter, water was added to the mixture which was then extracted with chloroform. The extract was washed with a saturated aqueous sodium chloride solution, and then dried over magnesium sulfate. The solvent was evaporated and the resulting residue was purified by silica gel column chromatography (EtOAc:hexane). The resulting residue was dissolved in DMF (30 mL). To the mixture were added palladium (II) acetate (305 mg), triethylsilane (5.4 mL), and 1,1'-bis(diphenylphosphino)ferrocene (750 mg), followed by stirring at 70° C. for 20 hours. Then, water was added to the mixture which was then filtered through celite and extracted with diethyl ether. The extract was washed with a saturated aqueous sodium chloride solution, and dried over magnesium sulfate. The solvent was evaporated and the resulting residue was purified by silica gel column chromatography (EtOAc: hexane) to obtain tert-butyl 8-ethyl-1-phenyl-3,4-dihydroisoquinoline-2(1H)-carboxylate (2.29 g).

Production Example 88

Under cooling in an ice bath, a mixture of sodium hydride (suspension of 8 g of sodium hydride in mineral oil (60%) washed with hexane) in THF (10 mL) was added to methoxyethanol (100 mL) under stirring over 20 minutes to produce sodium 2-methoxyethoxide, followed by further stirring for 2 hours. A solution of sodium 2-methoxyethoxide in 2-methoxyethanol (55 mL) was added with stirring to a solution of 1-(chloromethyl)-7-ethyl-3,4-dihydroisoquinoline hydrochloride (8.5 g) in methoxyethanol (50 mL) under cooling in an ice bath, for 5 minutes. The reaction mixture was heated at 60° C., followed by stirring for 3 hours under an argon atmosphere. The reaction mixture was cooled to room temperature and diluted with THF (150 mL), followed by filtration. The filtrate was concentrated under reduced pressure. To the resulting residue was added a saturated aqueous ammonium chloride solution and the residue was extracted with EtOAc. The organic layer was washed with water and a saturated aqueous sodium chloride solution, dried over magnesium sulfate, and concentrated under reduced pressure. The resulting residue was purified by silica gel column chromatography (hexane:EtOAc) to obtain 7-ethyl-1-[(2-methoxyethyl)methyl]-3,4-dihydroisoquinoline (2.13 g).

Production Example 89

Tert-butyl (1S)-1-phenyl-8-{[(trifluoromethyl)sulfonyl]oxy}-3,4-dihydroisoquinoline-2(1H)-carboxylate (3.75 g) was dissolved in N,N-dimethylacetamide (40 mL). To the reaction mixture were added zinc (537 mg), zinc cyanide (1.15 g), trifluoroacetic palladium (II) (682 mg), and biphenyl-2-yl(di-tert-butyl)phosphine (1.22 g). The temperature was increased from room temperature to 95° C. over 45 minutes and then the mixture was stirred at 95° C. for 18 hours. Water was added to the mixture which was then filtered through celite. Thereafter, the mixture was extracted with diethyl ether. The extract was washed with a saturated aqueous sodium chloride solution, and then dried over magnesium sulfate. The solvent was evaporated and the resulting residue was purified by silica gel column chromatography (EtOAc: hexane) to obtain tert-butyl (1S)-8-cyano-1-phenyl-3,4-dihydroisoquinoline-2(1H)-carboxylate (796 mg).

Production Example 90

A solution of 1.55 M n-butyllithium in hexane (10.94 mL) was added with stirring to a solution of 1-(methoxymethyl)-5-methyl-1,2,3,4-tetrahydroisoquinoline (3.07 g) in THF (60 mL) under an argon atmosphere, over about 8 minutes, at −70° C. or below, followed by further stirring for 30 minutes. To the reaction mixture was added with stirring a solution of (1R,2S,5R)-2-isopropyl-5-methylcyclohexyl 4-methylbenzenesulfinate (3.375 g) in THF (25 ml) over 5 minutes at −70° C. or below, followed by further stirring for 1 hour. Thereafter, saturated disodium phosphate was added to the mixture at the same temperature and the temperature was increased to room temperature. The mixture was extracted with ether. The organic layer was washed with a saturated aqueous sodium chloride solution and dried over magnesium sulfate and then the solvent was evaporated. The resulting residue was purified by silica gel column chromatography (hexane:EtOAc) to obtain (1R)-1-(methoxymethy)-5-methyl-2-[(R)-(4-methylphenyl)sulfinyl]-1,2,3,4-tetrahydroisoquinoline (2.144 g) (Rf value=0.14).

Production Example 91

To a mixed solution of (1R)-1-(methoxymethyl)-5-methyl-2-[(R)-(4-methylphenyl)sulfinyl]-1,2,3,4-tetrahydroisoquinoline (2.47 g) in EtOH (45 mL) and THF (10 mL) was added concentrated hydrochloric acid (3.1 mL) under stirring at 0° C., followed by further stirring for 10 minutes. To the mixture was added saturated sodium carbonate water (50 mL), followed by extraction with EtOAc. The organic layer was washed with a 1 M aqueous sodium hydroxide solution and a saturated aqueous sodium chloride solution, dried over magnesium sulfate, and then concentrated under reduced pressure. The resulting residue was purified by silica gel column chromatography (chloroform:EtOH:aqueous ammonia) to obtain (1R)-1-(methoxymethyl)-5-methyl-1,2,3,4-tetrahydroisoquinoline (1.276 g).

Chemical structures of the compounds produced by the above-mentioned Production Examples are shown in Tables 6 to 12. In addition, in the same manner as in the methods in the above-mentioned Production Examples, the compounds of Production Examples shown in Tables 13 to 35 are produced using respective corresponding starting materials. The data from instrumental analysis of these compounds of Production Examples is shown in Tables 36 to 42.

Example 1

(1S)-2-(chloroacetyl)-1-cyclohexyl-1,2,3,4-tetrahydroisoquinoline (4.496 g) was dissolved in acetonitrile (100 mL). To the mixture were added potassium carbonate (6.25 g), tetra-n-butylammoniumiodide (679 mg), and 1-(aminomethyl)cyclohexanol hydrochloride (4.50 g), followed by stirring at 60° C. for 6 hours. Thereafter, the solvent was evaporated and water was added to the reaction mixture, followed by extraction with chloroform. The extract was washed with saturated brine, and then dried over magnesium sulfate. The solvent was evaporated and the resulting residue was purified by silica gel column chromatography to obtain 1-[({2-[(1S)-1-cyclohexyl-3,4-dihydroisoquinolin-2(1H)-yl]-2-oxoethyl}amino)methyl]cyclohexanol (3.02 g).

The resulting compound (3.02 g) was dissolved in EtOH, to which oxalic acid (777 mg) was added. After complete dissolution was achieved, the mixture was stirred for a while and the resulting insoluble materials were collected to obtain 1-[({2-(1S)-1-cyclohexyl-3,4-dihydroisoquinolin-2(1H)-yl]-2-oxoethyl}amino)methyl]cyclohexanol oxalate (2.985 g).

Example 2

2-acryloyl-1-cyclohexyl-1,2,3,4-tetrahydroisoquinoline (516 mg) was dissolved in iPrOH (15 mL). To the reaction mixture were added 1-(aminomethyl)cyclohexanol hydrochloride (635 mg) and triethylamine (0.59 mL), followed by stirring under heating at reflux for 16 hours. Thereafter, the solvent was evaporated and water was added to the mixture, followed by extraction with chloroform. The extract was washed with saturated brine, and then dried over magnesium sulfate. The solvent was evaporated and the resulting residue was purified by silica gel column chromatography (chloroform-MeOH) and then further purified by alkaline silica gel column chromatography (chloroform) to obtain 1-({[3-(1-cyclohexyl-3,4-dihydroisoquinolin-2(1H)-yl)-3-oxopropyl]amino}methyl)cyclohexanol (214 mg).

The resulting compound (214 mg) was dissolved in EtOH (8 mL). Oxalic acid (51 mg) was added to the reaction mixture to obtain 1-({[3-(1-cyclohexyl-3,4-dihydroisoquinolin-2(1H)-yl)-3-oxopropyl]amino}methyl)cyclohexanol oxalate (229 mg).

Example 3

1-cyclohexyl-7-isopropoxide-3,4-dihydroisoquinoline (245 mg) was dissolved in MeOH (6 mL). Thereafter, sodium borohydride (40 mg) was added to the reaction liquid, followed by stirring at room temperature for 4 hours. The solvent was evaporated under reduced pressure, and water and chloroform were added to the mixture. The reaction liquid was extracted with chloroform and dried over magnesium sulfate. Thereafter, the solvent was evaporated under reduced pressure.

Saturated aqueous sodium bicarbonate (6 mL) was added to the resulting residue, to which EtOAc (3 mL) was added. A solution of chloroacetyl chloride (102 mg) in EtOAc (3 mL) was added dropwise to the reaction liquid over 5 minutes, followed by stirring for 1 hour. Thereafter, the reaction liquid was extracted with EtOAc and dried over magnesium sulfate, and then the solvent was evaporated.

The resulting residue was dissolved in 1,4-dioxane (8 mL). (2R)-1-amino-2-propanol (180 mg) and 1,8-diazabicyclo[5.4.0]undeca-7-en (146 mg) were added thereto, followed by stirring at 50° C. for 3 hours. Thereafter, the solvent was evaporated and water was added to the reaction liquid, followed by extraction with EtOAc. The extract was washed with saturated brine, and then dried over magnesium sulfate. The solvent was evaporated and the resulting residue was purified by silica gel column chromatography (chloroform-MeOH).

The resulting residue (211 mg) was dissolved in a 1:4 mixed solution of iPrOH-diethyl ether. Oxalic acid (49 mg) was added to the reaction liquid to obtain (2R)-1-{[2-(1-cyclohexyl-7-isopropoxide-3,4-dihydroisoquinolin-2(1H)-yl)-2-oxoethyl]amino}propan-2-ol oxalate (223 mg).

Example 4

N-(2-cyclohexa-1-en-1-ylethyl)-N-[2-(1-cyclohexyl-3,4-dihydroisoquinolin-2(1H)-yl)-2-oxoethyl]-2,2,2-trifluoroacetamide (210 mg) was dissolved in methylene chloride (5 mL). 75% 3-chloroperbenzoic acid (152 mg) was added thereto, followed by stirring at room temperature for 18 hours. Thereafter, a saturated aqueous sodium sulfite solution was added to the reaction liquid, followed by stirring for a while. The reaction liquid was extracted with chloroform, and the extract was washed with a 1 M aqueous NaOH solution and saturated brine, and then dried over magnesium sulfate.

The solvent was evaporated and the resulting residue was dissolved in a 4:1 mixed solvent (7.5 mL) of THF-1.5% sulfuric acid aqueous solution, followed by stirring under heating at reflux for 5 hours. Water was added to the reaction liquid which was then extracted with EtOAc. The extract was washed with saturated brine, and then dried over magnesium sulfate.

The solvent was evaporated and the resulting residue was dissolved in MeOH (6 mL). To the reaction liquid was added potassium carbonate (304 mg), followed by stirring at 60° C. for 5 hours. Thereafter, the solvent was evaporated and water was added to the reaction liquid which was then extracted with chloroform. The extract was washed with saturated brine, and then dried over magnesium sulfate. The solvent was evaporated and the resulting residue was purified by silica gel column chromatography (chloroform-MeOH) to obtain trans-1-(2-{[2-(1-cyclohexyl-3,4-dihydroisoquinolin-2(1H)-yl)-2-oxoethyl]amino}ethyl)cyclohexane-1,2-diol (93 mg).

The resulting compound (93 mg) was dissolved in a mixed solvent of chloroform-EtOH. Oxalic acid (22 mg) was added to the reaction liquid to obtain trans-1-(2-{[2-(1-cyclohexyl-3,4-dihydroisoquinolin-2(1H)-yl)-2-oxoethyl]amino}ethyl)cyclohexane-1,2-diol oxalate (66 mg).

Example 5

2-(1-cyclohexyl-3,4-dihydroisoquinolin-2(1H)-yl)-N-(cyclohexylmethyl)-2-oxoethanamine (296 mg) was dissolved in acetonitrile (10 mL). To the reaction liquid were added 2-bromoethanol (400 mg), potassium carbonate (555 mg), and potassium iodide (133 mg), followed by stirring under heating at reflux for 16 hours. Thereafter, the solvent was evaporated and water was added to the reaction liquid, followed by extraction with chloroform. The extract was washed with saturated brine, and then dried over magnesium sulfate. The solvent was evaporated and the resulting residue was purified by silica gel column chromatography (chloroform-MeOH) to obtain 2-{[2-(1-cyclohexyl-3,4-dihydroisoquinolin-2(1H)-yl)-2-oxoethyl](cyclohexylmethyl)amino}ethanol (155 mg).

The resulting compound (155 mg) was dissolved in EtOH. Oxalic acid (36 mg) was added to the reaction liquid to obtain 2-{[2-(1-cyclohexyl-3,4-dihydroisoquinolin-2(1H)-yl)-2-oxoethyl](cyclohexylmethyl)amino}ethanol oxalate (159 mg).

Example 6

A mixture of 1-({[2-(5-bromo-1-isopropyl-8-methyl-3,4-dihydroisoquinolin-2(1H)-yl)-2-oxoethyl]amino}methyl)cyclohexanol (0.14 g), EtOH (10 mL), triethylamine (0.05 mL), and 10% palladium-supported carbon (10 mg) was stirred under a hydrogen atmosphere for 6 hours. The reaction liquid was filtered and the solvent was evaporated. A 1 M NaOH aqueous solution was added to the resulting residue, followed by extraction with chloroform. The organic layer was dried over magnesium sulfate and then the solvent was evaporated. The resulting residue was purified by silica gel column chromatography (chloroform-MeOH). The resulting residue was dissolved in 2-propanol (0.8 mL). To the reaction liquid were added oxalic acid (23 mg) and diethyl ether (5 mL) and the precipitated solid was collected by filtration and dried to obtain 1-({[2-(1-isopropyl-8-methyl-3,4-dihydroisoquinolin-2(1H)-yl)-2-oxoethyl]amino}methyl)cyclohexanol oxalate (0.066 g).

Example 7

2 (1 cyclohexyl-3,4-dihydroisoquinolin-2(1H)-yl)-2-oxoethanamine (400 mg) was dissolved in EtOH (10 mL). To the reaction liquid were added 2-methyl-1-oxaspiro[2.5]octane (555 mg) and water (5 mL), followed by stirring under heating at reflux for 2 days. The solvent was evaporated and water was added to the reaction liquid, followed by extraction with chloroform. The extract was washed with saturated brine, and then dried over magnesium sulfate. The solvent was evaporated and the resulting residue was purified by silica gel column chromatography (chloroform-MeOH) to obtain 1-(1-{[2-(1-cyclohexyl-3,4-dihydroisoquinolin-2(1H)-yl)-2-oxoethyl]amino}ethyl)cyclohexanol (585 mg).

The resulting compound (325 mg) was dissolved in a mixed solution of EtOH-acetonitrile. Oxalic acid (80 mg) was added to the reaction liquid to obtain 1-(1-{[2-(1-cyclohexyl-3,4-dihydroisoquinolin-2(1H)-yl)-2-oxoethyl]amino}ethyl)cyclohexanol oxalate (292 mg).

Example 8

2-{[2-(1-cyclohexyl-3,4-dihydroisoquinolin-2(1H)-yl)-2-oxoethyl]amino}ethanol (342 mg) was dissolved in EtOH (5 mL). 1-oxaspiro[2.5]octane (363 mg) and water (5 mL) were added thereto, followed by stirring under heating at reflux for 2 days. The solvent was evaporated and water was added to the reaction liquid, followed by extraction with chloroform. The extract was washed with saturated brine, and then dried over magnesium sulfate. The solvent was evaporated and the resulting residue was purified by silica gel column chromatography (chloroform-MeOH) to obtain 1-({[2-(1-cyclohexyl-3,4-dihydroisoquinolin-2(1H)-yl)-2-oxoethyl](2-hydroxyethyl)amino}methyl)cyclohexanol (346 mg).

The resulting compound (346 mg) was dissolved in EtOH (10 mL). Oxalic acid (76 mg) was added to the reaction liquid to obtain 1-({[2-(1-cyclohexyl-3,4-dihydroisoquinolin-2(1H)-yl)-2-oxoethyl](2-hydroxyethyl)amino}methyl)cyclohexanol oxalate (210 mg).

Example 9

N-[2-(1-cyclohexyl-3,4-dihydroisoquinolin-2(1H)-yl)-2-oxoethyl]-N-{2-[cis-1,2-dihydroxycyclohexyl]ethyl}-2,2,2-trifluoroacetamide (255 mg) was dissolved in MeOH (10 mL). Potassium carbonate (345 mg) was added thereto, followed by stirring at 60° C. for 4 hours. The solvent was evaporated and water was added to the reaction liquid, followed by extraction with chloroform. The extract was washed with saturated brine, and then dried over magnesium sulfate. The solvent was evaporated and the resulting residue was purified by silica gel column chromatography (chloroform-MeOH) to obtain cis-1-(2-{[2-(1-cyclohexyl-3,4-dihydroisoquinolin-2(1H)-yl)-2-oxoethyl]amino}ethyl)cyclohexane-1,2-diol (212 mg).

The resulting compound (212 mg) was dissolved in EtOH. Oxalic acid (46 mg) was added to the reaction liquid to obtain cis-1-(2-{[2-(1-cyclohexyl-3,4-dihydroisoquinolin-2(1H)-yl)-2-oxoethyl]amino}ethyl)cyclohexane-1,2-diol oxalate (170 mg).

Example 10

Tert-butyl[2-(1-cyclohexyl-3,4-dihydroisoquinolin-2(1H)-yl)-2-oxoethyl]{[cis-1,2-dihydroxycyclohexyl]methyl}carbamate (92 mg) was dissolved in EtOAc (4 mL). 4 M HCl/EtOAc (0.45 mL) was added thereto, followed by stirring at room temperature for 14 hours. The solvent was evaporated and a 1 M NaOH aqueous solution was added to the resulting residue, followed by extraction with chloroform. The extract was washed with saturated brine, and then dried over magnesium sulfate. The solvent was evaporated and the resulting residue was purified by silica gel column chromatography (chloroform) to obtain cis-1-({[2-(1-cyclohexyl-3,4-dihydroisoquinolin-2(1H)-yl)-2-oxoethyl]amino}methyl)cyclohexane-1,2-diol (174 mg).

The resulting compound (174 mg) was dissolved in iPrOH. Oxalic acid (43 mg) was added to the reaction liquid to obtain cis-1-({[2-(1-cyclohexyl-3,4-dihydroisoquinolin-2(1H)-yl)-2-oxoethyl]amino}methyl)cyclohexane-1,2-diol oxalate (88 mg).

Example 11

Tert-butyl[2-(6-carbamoyl-1-cyclohexyl-3,4-dihydroisoquinolin-2(1H)-yl)-2-oxoethyl][(1-hydroxycyclohexyl)methyl]carbamate (357 mg) was dissolved in EtOAc (8 mL). 4 M HCl/EtOAc (0.85 mL) was added to the reaction liquid under ice-cooling, followed by stirring at 60° C. for 5 hours. The solvent was evaporated and water was added to the resulting residue, followed by washing with chloroform. Saturated aqueous sodium bicarbonate was added to the aqueous layer which was then adjusted to a pH of around 8, followed by extraction with chloroform. The extract was washed with saturated brine, and then dried over magnesium sulfate to obtain 1-cyclohexyl-2-{N-[(1-hydroxycyclohexyl)methyl]glycyl}-1,2,3,4-tetrahydroisoquinoline-6-carboxamide (116 mg).

The resulting compound (116 mg) was dissolved in a mixed solution of iPrOH-diethyl ether. Oxalic acid (24 mg) was added to the reaction liquid to obtain 1-cyclohexyl-2-{N-[(1-hydroxycyclohexyl)methyl]glycyl}-1,2,3,4-tetrahydroisoquinoline-6-carboxamide oxalate (70 mg).

Example 12

1-[2-(chloroacetyl)-1,2,3,4-tetrahydroisoquinolin-1-yl]-1-methylethyl pivalate (1.2 g) was dissolved in acetonitrile (20 mL). Potassium carbonate (2.36 g), 1-(aminomethyl)cyclohexanol hydrochloride (2.26 g), and tetra-n-butylammoniumiodide (126 mg) were added thereto, followed by stirring at 60° C. for 5 hours. Water was added to the reaction liquid, followed by extraction with EtOAc. The extract was washed with saturated brine, and then dried over magnesium sulfate. The solvent was evaporated and the resulting residue was purified by silica gel column chromatography (chloroform-MeOH).

The resulting residue (1.43 g) was dissolved in methylene chloride (20 mL). To the reaction liquid was added a solution of 1.01 M diisobutylaluminium hydride/n-hexane (9.55 mL) at −78° C., followed by stirring at −78° C. for 5 hours. Thereafter, the temperature was increased to 0° C. over 2 hours. To the reaction liquid was added a saturated aqueous Rochelle salt solution, followed by stirring for 20 minutes. Then, celite was added to the reaction liquid which was then subjected to separation by filtration, followed by extraction with chloroform. The extract was washed with saturated brine, and then dried over magnesium sulfate. The solvent was evaporated and the resulting residue was purified by silica gel column chromatography (chloroform-MeOH) to obtain 1-[({2-[1-(1-hydroxy-1-methylethyl)-3,4-dihydroisoquinolin-2(1H)-yl]-2-oxoethyl}amino)methyl]cyclohexanol (118 mg).

The resulting compound (150 mg) was dissolved in acetonitrile. Oxalic acid (41 mg) was added to the reaction liquid to obtain 1-[({2-[1-(1-hydroxy-1-methylethyl)-3,4-dihydroisoquinolin-2(1H)-yl]-2-oxoethyl}amino)methyl]cyclohexanol oxalate (151 mg).

Example 13

2-(1-cyclohexyl-7-methoxy-3,4-dihydroisoquinolin-2(1H)-yl)-N-(2-{[cis-2-(methoxymethoxy)cyclopentyl]oxy}ethyl)-2-oxoethanamine (500 mg) was dissolved in MeOH (8 mL). To the reaction liquid was added 4 M HCl/EtOAc (0.8 mL) under ice-cooling, followed by stirring at 60°

C. for 5 hours. The solvent was evaporated and saturated aqueous sodium bicarbonate was added to the resulting residue, followed by extraction with chloroform. The extract was washed with saturated brine, and then dried over magnesium sulfate. The solvent was evaporated and the resulting residue was purified by silica gel column chromatography (chloroform-MeOH) to obtain cis-2-(2-{[2-(1-cyclohexyl-7-methoxy-3,4-dihydroisoquinolin-2(1H)-yl)-2-oxoethyl]amino}ethoxy)cyclopentanol (380 mg).

The resulting compound (380 mg) was dissolved in iPrOH. Oxalic acid (80 mg) was added to the reaction liquid to obtain cis-2-(2-{[2-(1-cyclohexyl-7-methoxy-3,4-dihydroisoquinolin-2(1H)-yl)-2-oxoethyl]amino}ethoxy)cyclopentanol oxalate (384 mg).

Example 14

1-(4-chloropyridin-2-yl)-1,2,3,4-tetrahydroisoquinoline hydrochloride (200 mg) and potassium carbonate (344 mg) were dissolved in EtOAc-water (1:1, 4 mL) under ice-cooling. Chloroacetyl chloride (0.85 mL) and benzyltriethylamine hydroboromate (9.2 mg) were added thereto, followed by stirring at room temperature for 1 hour. To the mixture were added 2-amino-1,1-dicyclopropylethanol hydrochloride (190 mg) and potassium carbonate (246 mg). The mixture was stirred at 50° C. for 8 hours. The organic layer was collected, washed with saturate brine, dried over magnesium sulfate, filtered, and then concentrated under reduced pressure. The resulting residue was purified by silica gel column chromatography (chloroform-MeOH) to obtain 2-({2-[1-(4-chloropyridin-2-yl)-3,4-dihydroisoquinolin-2(1H)-yl-2-oxoethyl]amino}-1,1-dicyclopropylethanol (143 mg) as a yellow oily material. The oily material was dissolved in a 3:1 mixed liquid (4 mL) of diethyl ether-iPrOH. Oxalic acid (30.2 mg) was added to the reaction mixture to obtain 2-({2-[1-(4-chloropyridin-2-yl)-3,4-dihydroisoquinolin-2(1H)-yl-2-oxoethyl]amino}-1,1-dicyclopropylethanol oxalate (128 mg).

Example 15

To a solution of 8-({[2-(1-cyclohexyl-3,4-dihydro-2(1H)-isoquinolinyl)-2-oxoethyl]amino}methyl)-1,4-dioxaspiro[4.5]decan-8-ol (324 mg) in THF (2 mL) were added water (1 mL) and concentrated hydrochloric acid (1 mL). The reaction mixture was refluxed for 5 hours. The temperature was cooled to room temperature and sodium hydrogen carbonate was added to the mixture to make it alkaline, followed by extraction with chloroform. The extract was purified by silica gel column chromatography (chloroform-MeOH) to obtain a targeted amine (176 mg).

The amine was dissolved in iPrOH (3 mL), to which oxalic acid (41.7 mg) was added, followed by stirring at room temperature for 2 hours. The resulting crystal was collected by filtration, washed with ether, and dried at 90° C. under reduced pressure to obtain 4-({[2-(1-cyclohexyl-3,4-dihydroisoquinolin-2(1H)-yl)-2-oxoethyl]amino}methyl)-4-hydroxycyclohexanone oxalate (139 mg).

Example 16

To a solution of 2-(chloroacetyl)-1-cyclohexyl-1,2,3,4-tetrahydroisoquinoline (12 mg) in acetonitrile (0.5 mL) were added potassium carbonate (3 mg) and (S)-(+)-2-amino-3-cyclohexyl-1-propanol hydrochloride (15 mg), followed by stirring at 80° C. for 4 hours. Thereafter, a saturated aqueous ammonium chloride solution was added to the reaction liquid, followed by extraction with chloroform. The solvent was evaporated and the resulting residue was purified by preparative HPLC to obtain (2S)-3-cyclohexyl-2-{[2-(1-cyclohexyl-3,4-dihydroisoquinolin-2(1H)-yl)-2-oxoethyl]amino}propan-1-ol (4.1 mg).

Example 17

2-(isopentylamino)-ethanol (26 mg) was added to a solution of 2-acryloyl-1-cyclohexyl-1,2,3,4-tetrahydroisoquinoline (7 mg) in iPrOH (0.1 mL), followed by stirring at 90° C. for 10 hours. Thereafter, the reaction liquid was purified by preparative HPLC to obtain 2-[[3-(1-cyclohexyl-3,4-dihydroisoquinolin-2(1H)-yl)-3-oxopropyl](3-methylbutyl)amino]ethanol (3 mg).

Chemical structures of the compounds produced by the above-mentioned Examples are shown in Tables 43 and 44. In addition, in the same manner as in the methods in the above-mentioned Examples, compounds of Examples shown in Tables 45 to 110 were produced using respective corresponding starting materials. The data from instrumental analysis of these compounds of Examples is shown in Tables 111 to 125.

TABLE 6

| Rex/salt | STRUCTURE |
|---|---|
| 1 | 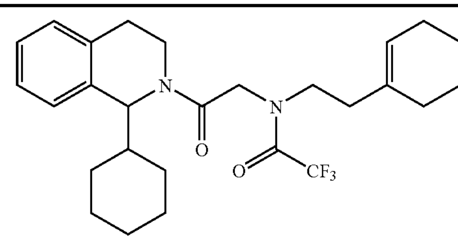 |
| 2 | 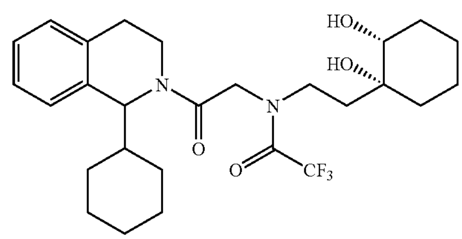 |
| 3 | 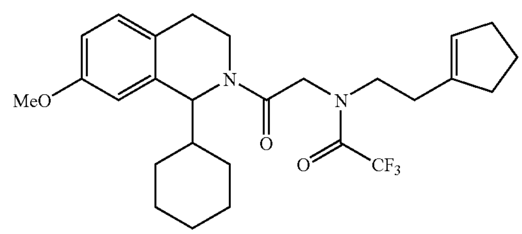 |
| 4* | 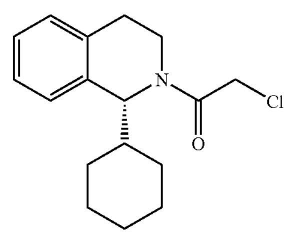 |

TABLE 6-continued

| Rex/salt | STRUCTURE |
|---|---|
| 5 | 7-chloro-1-cyclohexyl-2-(2-chloroacetyl)-1,2,3,4-tetrahydroisoquinoline |
| 6 | 1-phenyl-2-(2-chloroacetyl)-1,2,3,4-tetrahydroisoquinoline (stereochem at C1) |
| 7 | 1-cyclohexyl-2-acryloyl-1,2,3,4-tetrahydroisoquinoline |
| 8 | 1-cyclohexyl-2-(1-benzyl-4-hydroxypiperidine-4-carbonyl)-1,2,3,4-tetrahydroisoquinoline |
| 9 | 1-cyclohexyl-2-(4-hydroxypiperidine-4-carbonyl)-1,2,3,4-tetrahydroisoquinoline |
| 10 | 1-cyclohexyl-2-(N-Boc-prolyl)-1,2,3,4-tetrahydroisoquinoline |
| 11 | 1-cyclohexyl-2-(N-Boc-glycyl)-1,2,3,4-tetrahydroisoquinoline |
| 12 | 1-cyclohexyl-2-prolyl-1,2,3,4-tetrahydroisoquinoline |
| 13 | 1-cyclohexyl-2-glycyl-1,2,3,4-tetrahydroisoquinoline |
| 14 | 1-cyclohexyl-2-[N-Boc-N-(cyclohexenylmethyl)glycyl]-1,2,3,4-tetrahydroisoquinoline |

TABLE 7

| Rex/salt | STRUCTURE |
|---|---|
| 15 | 1,1-diphenyl-2-(2-chloroacetyl)-1,2,3,4-tetrahydroisoquinoline |
| 16 | 1,1-diphenyl-1,2,3,4-tetrahydroisoquinoline |

TABLE 7-continued

| Rex/salt | STRUCTURE |
|---|---|
| 17 | 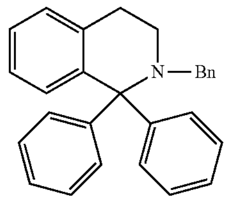 |
| 18 | 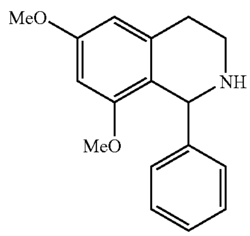 |
| 19/CL | 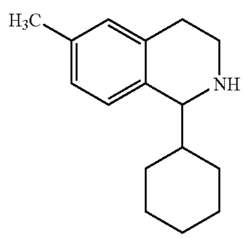 |
| 20*/MD | 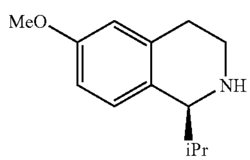 |
| 21*/T2 | 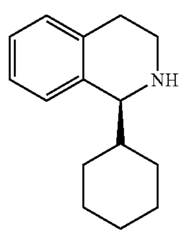 |
| 22/TP | 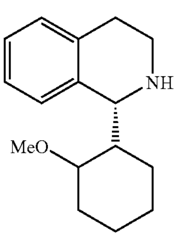 |
| 23 | 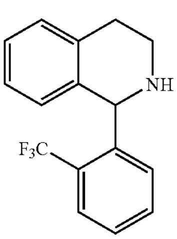 |
| 24 | |
| 25 | |
| 26 | |
| 27 | |
| 28 | |

TABLE 8

| Rex/salt | STRUCTURE |
|---|---|
| 29 | 1-(4,4-difluorocyclohexyl)-3,4-dihydroisoquinoline |
| 30 | 1-(trans-4-methylcyclohexyl)-1,2,3,4-tetrahydroisoquinoline |
| 31 | 5-methyl-1-propyl-3,4-dihydroisoquinoline |
| 32 | 2-(2-chloroacetyl)-8-methoxy-1-(methoxymethyl)-1,2,3,4-tetrahydroisoquinoline |
| 33 | N-[2-(4-chlorophenyl)ethyl]cyclohexanecarboxamide |
| 34 | 4,4-difluoro-N-(2-phenylethyl)cyclohexanecarboxamide |
| 35 | tert-butyl 1-(2-hydroxypropan-2-yl)-3,4-dihydroisoquinoline-2(1H)-carboxylate |

TABLE 8-continued

| Rex/salt | STRUCTURE |
|---|---|
| 36 | 2-(2-chloroacetyl)-1-[2-(Boc-oxy)propan-2-yl]-1,2,3,4-tetrahydroisoquinoline |
| 37 | tert-butyl 6-bromo-1-cyclohexyl-3,4-dihydroisoquinoline-2(1H)-carboxylate |
| 38 | tert-butyl 6-cyano-1-cyclohexyl-3,4-dihydroisoquinoline-2(1H)-carboxylate |
| 39/CL | 1-cyclohexyl-1,2,3,4-tetrahydroisoquinoline-6-carbonitrile |
| 40 | N-{[2-(2-chloroacetyl)-1-cyclohexyl-1,2,3,4-tetrahydroisoquinolin-7-yl]methyl}acetamide |
| 41 | 1-cyclohexyl-3,4-dihydroisoquinoline-7-carbonitrile |

TABLE 8-continued
| Rex/salt | STRUCTURE |
|---|---|
| 42 | 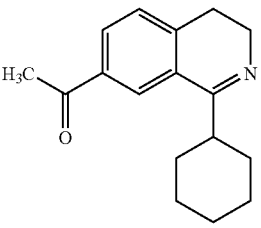 |
TABLE 9
| Rex/salt | STRUCTURE |
|---|---|
| 43 | 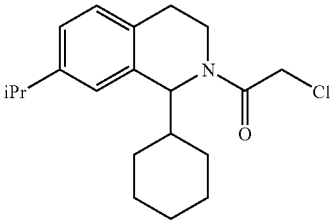 |
| 44 | 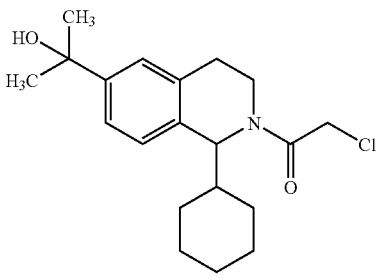 |
| 45/CL | 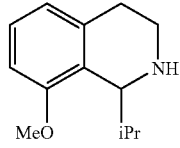 |
| 46/CL | 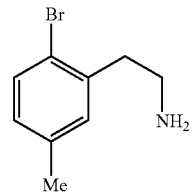 |
| 47 | 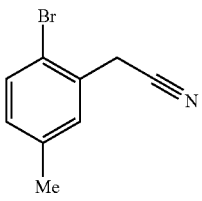 |
TABLE 9-continued
| Rex/salt | STRUCTURE |
|---|---|
| 48 | 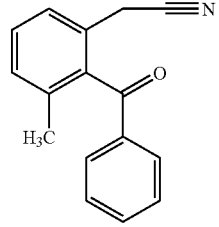 |
| 49/CL | 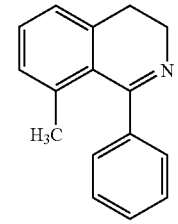 |
| 50/CL | 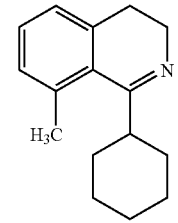 |
| 51 | 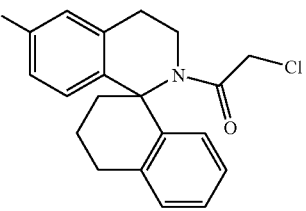 |
| 52 | 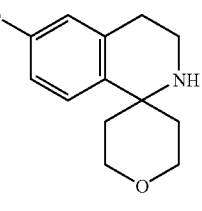 |
| 53/CL | 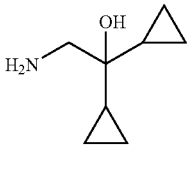 |
| 54 | 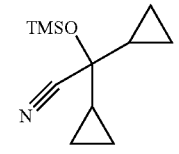 |

TABLE 9-continued

| Rex/salt | STRUCTURE |
|---|---|
| 55 | 1-(2-methoxypropan-2-yl)-1,2,3,4-tetrahydroisoquinoline |
| 56 | 2-benzyl-1-(2-methoxypropan-2-yl)-1,2,3,4-tetrahydroisoquinoline |

TABLE 10

| Rex/salt | STRUCTURE |
|---|---|
| 57 | 2-(2-benzyl-1,2,3,4-tetrahydroisoquinolin-1-yl)propan-2-ol |
| 58 | ethyl 2-benzyl-1,2,3,4-tetrahydroisoquinoline-1-carboxylate |
| 59 | 1-(1-(7,8-dimethoxy-1-phenyl-3,4-dihydroisoquinolin-2(1H)-yl))-2-chloroethanone |
| 60 | N-isopropyl-2-(2-chloroacetyl)-1-cyclohexyl-1,2,3,4-tetrahydroisoquinoline-7-carboxamide |

TABLE 10-continued

| Rex/salt | STRUCTURE |
|---|---|
| 61 | 2-chloro-1-(5-methoxy-1-(methoxymethyl)-3,4-dihydroisoquinolin-2(1H)-yl)ethanone |
| 62/CL | 5,8-dimethoxy-1-propyl-1,2,3,4-tetrahydroisoquinoline |
| 63 | 1-(2-chloroacetyl)-1-cyclohexyl-7-(2-hydroxypropan-2-yl)-1,2,3,4-tetrahydroisoquinoline |
| 64 | 1-cyclohexyl-3,4-dihydroisoquinoline-7-carboxylic acid |
| 65 | 1-cyclohexyl-N-isopropyl-3,4-dihydroisoquinoline-7-carboxamide |
| 66 | 7-ethyl-1-(methoxymethyl)-3,4-dihydroisoquinoline |
| 67 | 5,8-dimethoxy-1-phenyl-1,2,3,4-tetrahydroisoquinoline |

TABLE 10-continued
| Rex/salt | STRUCTURE |
|---|---|
| 68 | 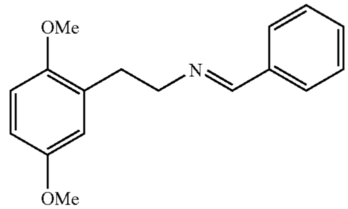 |
| 69 | 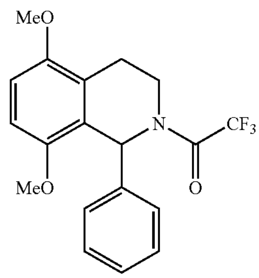 |
| 70 | 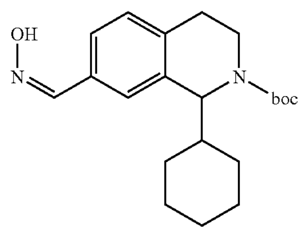 |
TABLE 11
| Rex/salt | STRUCTURE |
|---|---|
| 71 | 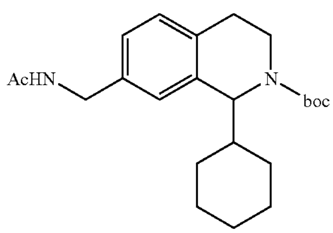 |
| 72 | 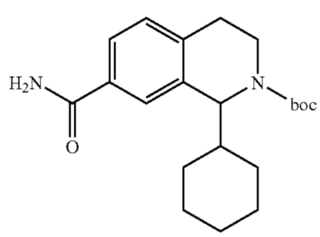 |
| 73 | 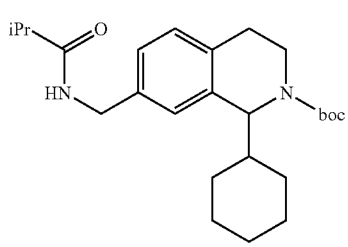 |
TABLE 11-continued
| Rex/salt | STRUCTURE |
|---|---|
| 74 | 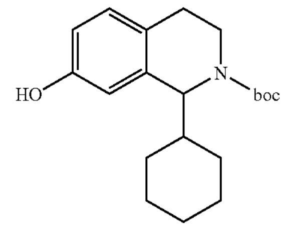 |
| 75 | 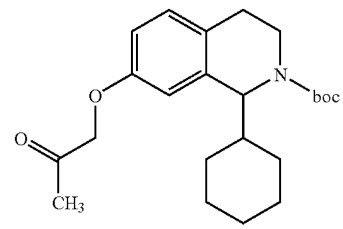 |
| 76 | 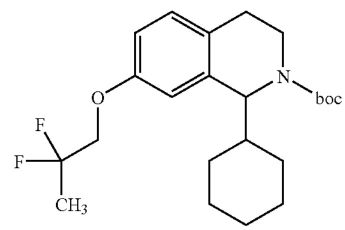 |
| 77* | 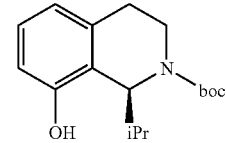 |
| 78*/CL | 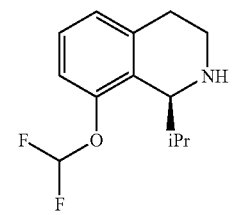 |
| 79*/CL | 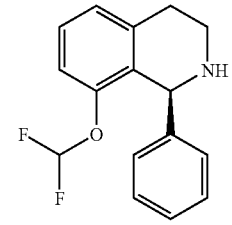 |
| 80/OX | 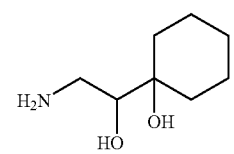 |

TABLE 11-continued

| Rex/salt | STRUCTURE |
|---|---|
| 81*/T2 | 7-bromo-1-cyclohexyl-1,2,3,4-tetrahydroisoquinoline |
| 82*/LL | 1-(2-(trifluoromethyl)benzyl)-1,2,3,4-tetrahydroisoquinoline |
| 83/TX | 7-ethyl-1-(methoxymethyl)-1,2,3,4-tetrahydroisoquinoline |
| 84/CL | 1-(chloromethyl)-7-ethyl-3,4-dihydroisoquinoline |

TABLE 12

| Rex/salt | STRUCTURE |
|---|---|
| 85* | 8-(trifluoromethylsulfonyloxy)-1-phenyl-2-boc-1,2,3,4-tetrahydroisoquinoline |
| 86 | 5-bromo-8-methyl-1-(methoxymethyl)-2-(chloroacetyl)-1,2,3,4-tetrahydroisoquinoline |
| 87 | 8-ethyl-1-phenyl-2-boc-1,2,3,4-tetrahydroisoquinoline |
| 88 | 7-ethyl-1-((2-methoxyethoxy)methyl)-3,4-dihydroisoquinoline |
| 89* | 8-cyano-1-phenyl-2-boc-1,2,3,4-tetrahydroisoquinoline |
| 90*[1] | 5-methyl-1-(methoxymethyl)-2-(p-toluenesulfinyl)-1,2,3,4-tetrahydroisoquinoline |
| 91*[1] | 5-methyl-1-(methoxymethyl)-1,2,3,4-tetrahydroisoquinoline |

TABLE 13

$R^A$-substituted phenethyl-NH-C(=O)-$R^B$

| Rex | $R^A$ | $R^B$ |
|---|---|---|
| 101 | —H | 2-OMe—Bn |
| 102 | —H | 4-Thp |
| 103 | 3-Br | cHex |
| 104 | 2-OMe | cHex |
| 105 | 3-Cl | cHex |

TABLE 13-continued

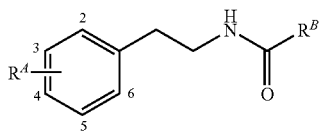

| Rex | R$^A$ | R$^B$ |
|---|---|---|
| 106 | 3-F | cHex |
| 107 | —H | 2-CF$_3$—Ph |
| 108 | —H | 3-F—Ph |
| 109 | —H | 3-CF$_3$—Ph |
| 110 | —H | cyclohexen-4-yl |
| 111 | —H | 2-F—Ph |
| 112 | 4-OMe | cHex |
| 113 | 2-Cl | cHex |
| 114 | 2-Me | cHex |
| 115 | 4-F | cHex |
| 116 | 2-F | cHex |
| 117 | —H | 2-CF$_3$-5-F—Ph |
| 118 | —H | 2-OCF$_3$—Ph |
| 119 | —H | 2-Et—Ph |
| 120 | —H | 2-Cl-3-Py |
| 121 | —H | 3-CF$_3$—Bn |
| 122 | 4-Me | cHex |
| 123 | 4-CF$_3$ | cHex |
| 124 | 4-F | iPr |
| 125 | —H | —(CH$_2$)$_2$—OMe |
| 126 | 3-F | —CH$_2$—OMe |
| 127 | 4-F | —CH$_2$—OMe |
| 128 | 4-Et | —CH$_2$—OMe |
| 129 | —H | 2-Me—Bn |
| 130 | 4-Et | —CH$_2$—Cl |
| 131 | 2-Me | nPr |
| 132 | 3-F | nPr |
| 133 | 2-F | —CH$_2$—OMe |
| 134 | 2-Me | —CH$_2$—OMe |
| 135 | 4-Me | —CH$_2$—OMe |
| 136 | 2-F | nPr |
| 137 | 4-Me | nPr |
| 138 | 2-Me | iPr |
| 139 | 2-F | Ph |
| 140 | 4-Me | Ph |
| 141 | 4-Me | iPr |
| 142 | 3-Me | cHex |
| 143 | 3-Me | iPr |
| 144 | 3-Me | nPr |
| 145 | 3-Me | —CH$_2$—OMe |
| 146 | —H | 3,3-diF-cHex |
| 147 | —H | 6-Me-2-Py |
| 148 | —H | 6-Br-2-Py |
| 149 | —H | 6-Cl-2-Py |
| 150 | —H | 4-Cl-2-Py |
| 151 | —H | 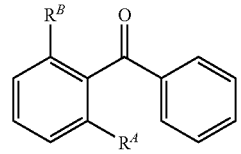 |
| 152 | 4-Me | —CH$_2$—OEt |
| 153 | 4-Me | —CH$_2$—O—(CH$_2$)$_2$—OMe |
| 153A | 3-F | iPr |
| 609 | 4-Et | —CH$_2$—Cl |
| 624 | 4-Et | nPr |
| 641 | 4-Et | Me |
| 661 | —H | 2-OMe-5-F—Ph |
| 662 | —H | 4-CF$_3$—Bn |

TABLE 14

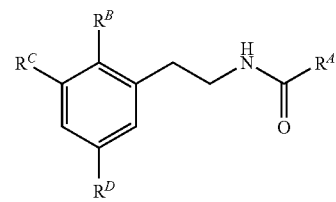

| Rex | R$^A$ | R$^B$ | R$^C$ | R$^D$ |
|---|---|---|---|---|
| 154 | iPr | —Br | —H | —OMe |
| 155 | cHex | —Br | —H | —OMe |
| 156 | tBu | —Br | —H | —OMe |
| 157 | Ph | —Br | —H | —OMe |
| 158 | Ph | —H | —OMe | —OMe |
| 159 | cHex | —Br | —H | —F |
| 160 | nPr | —Br | —H | —OMe |
| 161 | iPr | —Br | —H | Me |
| 162 | —CH$_2$-iPr | —Br | —H | —OMe |
| 610 | iPr | —Br | —H | —F |
| 615 | nPr | —Br | —H | Me |
| 616 | nPr | —Br | —H | —F |
| 619 | —CH$_2$—OMe | —Br | —H | Me |
| 639 | —CH$_2$Cl | —Br | —H | —F |

TABLE 15

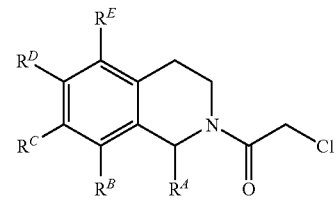

| Rex | R$^A$ | R$^B$ |
|---|---|---|
| 163 | Me | —F |
| 164 | —F | —CH$_2$—Br |
| 165 | —F | —CH$_2$—CN |

TABLE 16

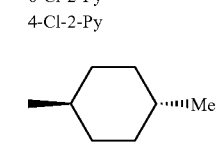

| Rex | R$^A$ | R$^B$ | R$^C$ | R$^D$ | R$^E$ |
|---|---|---|---|---|---|
| 166 | cPen | —H | —H | —H | —H |
| 167 | cHex | —H | —Br | —H | —H |
| 168 | cHex | —H | —H | —H | —Br |
| 169 | cHex | —H | —H | —H | —H |
| 170 | —CHEt$_2$ | —H | —H | —H | —H |
| 171 | cHex | —H | —H | —Br | —H |
| 172 | cHex | —H | —H | CN | —H |
| 173 | cHex | —H | —H | —H | —OMe |
| 174 | cHex | —H | —H | —F | —H |
| 175 | cHex | —H | —H | —Cl | —H |
| 176 | iPr | —H | —F | —H | —H |
| 177 | 4-F—Ph | —H | —H | —H | —H |
| 178 | 4-CN—Ph | —H | —H | —H | —H |

TABLE 16-continued

| Rex | R$^A$ | R$^B$ | R$^C$ | R$^D$ | R$^E$ |
|---|---|---|---|---|---|
| 179 | cyclohexen-4-yl | —H | —H | —H | —H |
| 180 | 3-CF$_3$—Ph | —H | —H | —H | —H |
| 181 | 2-CF$_3$—Ph | —H | —H | —H | —H |
| 182 | 2-F—Ph | —H | —H | —H | —H |
| 183 | cHex | —H | —H | —H | —Cl |
| 184 | cHex | —H | —OMe | —OMe | —H |
| 185 | cHex | —H | —OMe | —H | —H |
| 186 | cHex | —H | —H | —OMe | —H |
| 187 | 2-Cl—Ph | —H | —H | —H | —H |
| 188 | 3-F—Ph | —H | —H | —H | —H |
| 189 | 3-Cl—Ph | —H | —H | —H | —H |
| 190 | cHex | —H | —H | —H | —F |
| 191 | cHex | —H | —F | —H | —H |
| 192 | 1-OH-cHex | —H | —H | —H | —H |
| 193 | 2-OMe-Ph | —H | —H | —H | —H |
| 194 | 2-OCF$_3$-Ph | —H | —H | —H | —H |
| 195 | cHex | —H | —H | —CONH$_2$ | —H |
| 196 | 2-CF$_3$-5-F—Ph | —H | —H | —H | —H |
| 197 | 2-OEt—Ph | —H | —H | —H | —H |
| 198 | tBu | —H | —H | —H | —H |

TABLE 17

| Rex | R$^A$ | R$^B$ | R$^C$ | R$^D$ | R$^E$ |
|---|---|---|---|---|---|
| 199 | iPr | —H | —H | —H | —H |
| 200 | 2-Et—Ph | —H | —H | —H | —H |
| 201 | 2-SMe—Ph | —H | —H | —H | —H |
| 202 | 2-OMe-5-F—Ph | —H | —H | —H | —H |
| 203 | cHex | —H | —O—CH$_2$—O— | | —H |
| 204 | 4-CF$_3$—Bn | —H | —H | —H | —H |
| 205 | 2-Cl—Ph | —H | —Cl | —H | —H |
| 206 | 2-Cl—Ph | —H | —F | —H | —H |
| 207 | cHex | —H | Me | —H | —H |
| 208 | 3-CF$_3$—Bn | —H | —H | —H | —H |
| 209 | cHex | —H | —CF$_3$ | —H | —H |
| 210 | 4-Me—Ph | —H | —H | —H | —H |
| 211 | cHex | —H | Et | —H | —H |
| 212 | cHex | —H | —CH$_2$NHCO-Pr | —H | —H |
| 213 | iPr | —H | —H | —OMe | —H |
| 214 | cBu | —H | —H | —H | —H |
| 215 | —CH$_2$—OMe | —H | —H | —H | —H |
| 216 | —CH(Et)Me | —H | —H | —H | —H |
| 217 | cHex | —H | —OCH$_2$CHF$_2$ | —H | —H |
| 218 | cHex | —H | —OCH$_2$CF$_2$—Me | —H | —H |
| 219 | —(CH$_2$)$_2$—OMe | —H | —H | —H | —H |
| 220 | iPr | —H | —OMe | —OMe | —H |
| 221 | iPr | —H | —OMe | —H | —H |
| 222 | tBu | —H | —OMe | —H | —H |
| 223 | iPr | —H | —F | —H | —H |
| 224 | —CH$_2$—OMe | —H | —F | —H | —H |
| 225 | —CMe$_2$—OMe | —H | —H | —H | —H |
| 226 | —CH$_2$—OMe | —H | Et | —H | —H |
| 227 | 2-F-Bn | —H | —H | —H | —H |
| 228 | cHex | —OMe | —H | —H | —H |

TABLE 17-continued

| Rex | R$^A$ | R$^B$ | R$^C$ | R$^D$ | R$^E$ |
|---|---|---|---|---|---|
| 229 | cHex | —OMe | —H | —H | —Br |

TABLE 18

| Rex | R$^A$ | R$^B$ | R$^C$ | R$^D$ | R$^E$ |
|---|---|---|---|---|---|
| 232 | 2-OMe—Bn | —H | —H | —H | —H |
| 233 | 2-Me—Bn | —H | —H | —H | —H |
| 234 | iPr | —OMe | —H | —H | —H |
| 235 | tBu | —OMe | —H | —H | —H |
| 236A | 2-CF$_3$—Bn | —H | —H | —H | —H |
| 237 | Ph | —OMe | —H | —H | —OMe |
| 238 | Ph | —H | —OMe | —H | —H |
| 241 | Ph | —H | —H | Me | —H |
| 242 | iPr | —H | —H | Me | —H |
| 243 | cHex | —H | —H | Me | —H |
| 244 | iPr | —H | Me | —H | —H |
| 245 | —CH$_2$—OMe | —H | —H | —OMe | —H |
| 246 | Ph | —H | —H | —H | Me |
| 247 | iPr | —H | —H | —H | Me |
| 248 | cHex | —H | —H | —H | Me |
| 249 | nPr | —H | —H | —F | —H |
| 250 | Ph | —H | —H | —F | —H |
| 251 | nPr | —H | —H | —H | Me |
| 252 | nPr | —H | —H | —H | —OMe |
| 253 | nPr | —H | —F | —H | —H |
| 254 | nPr | —H | —H | —H | —F |
| 255 | —CH$_2$—OMe | —H | Me | —H | —H |
| 256 | —CH$_2$—OMe | —H | —OMe | —H | —H |
| 257 | nPr | —H | Me | —H | —H |
| 258 | Ph | —OMe | —H | —OMe | —H |
| 259 | —CH$_2$—OMe | —H | —H | —H | Me |
| 260 | —CH$_2$—OMe | —H | —H | —H | —F |
| 261 | nPr | —OMe | —H | —H | —H |
| 262 | —CH$_2$—OMe | —H | —H | Me | —H |
| 263 | nPr | —H | —H | Me | —H |
| 264 | cHex | Me | —H | —H | —H |
| 265 | cHex | —F | —H | —H | —H |

TABLE 19

| Rex | R$^A$ | R$^B$ | R$^C$ | R$^D$ | R$^E$ |
|---|---|---|---|---|---|
| 266 | Ph | Me | —H | —H | —H |
| 267 | Ph | —F | —H | —H | —H |
| 268 | nPr | —H | —H | —OMe | —H |
| 269 | Ph | —H | —H | —OMe | —H |
| 270 | 4,4-diF-cHex | —H | —H | —H | —H |
| 271 | 3,3-diF-cHex | —H | —H | —H | —H |
| 272 | 4-Thp | —H | —H | —H | —H |
| 273 | 2-Cl-3-Py | —H | —H | —H | —H |
| 274 | 6-Cl-2-Py | —H | —H | —H | —H |
| 275 | 6-Br-2-Py | —H | —H | —H | —H |
| 276 | 6-Me-2-Py | —H | —H | —H | —H |
| 277 | 4-Cl-2-Py | —H | —H | —H | —H |
| 278 | 2-Py | —H | —H | —H | —H |
| 279 | 2-Me—Ph | —H | —H | —H | —H |
| 280 | iPr | Me | —H | —H | —Br |
| 281 | —CH$_2$—OEt | —H | Me | —H | —H |
| 282 | —CH$_2$-iPr | —H | —OMe | —H | —H |
| 283 | —CH$_2$-iPr | —OMe | —H | —H | —H |
| 284 | —CH$_2$—O—(CH$_2$)$_2$—OMe | —H | Me | —H | —H |
| 285 | trans-4-Me-cHex | —H | —H | —H | —H |
| 286 | 1-Admt | —H | —H | —H | —H |
| 614 | iPr | —F | —H | —H | —Br |
| 628 | Ph | Et | —H | —H | —H |
| 629 | Me | —H | Et | —H | —H |
| 633 | Me | —H | Me | —H | —H |
| 635 | nPr | Me | —H | —H | —Br |

TABLE 19-continued

| Rex | R$^A$ | R$^B$ | R$^C$ | R$^D$ | R$^E$ |
|---|---|---|---|---|---|
| 638 | nPr | —F | —H | —H | —Br |
| 655 | —CH$_2$—O—(CH$_2$)$_3$—OMe | —H | Et | —H | —H |
| 648 | —CH$_2$—O—(CH$_2$)$_2$—OMe | —H | Et | —H | —H |
| 656 | —CH$_2$—OMe | —F | —H | —H | —Br |

TABLE 20

| Rex | R$^A$ | R$^B$ | R$^C$ | R$^D$ | R$^E$ |
|---|---|---|---|---|---|
| 230* | iPr | —H | —H | —OMe | —H |
| 240 | —CH$_2$—OMe | —H | Et | —H | —H |
| 287 | 2-OMe—Ph | —H | —H | —H | —H |
| 288 | Ph | —H | —H | —H | —H |
| 289* | cHex | —H | —CMe$_2$—OH | —H | —H |
| 290* | Ph | —OMe | —H | —H | —H |
| 653* | Ph | —H | —H | —F | —H |
| 660*$^2$ | —CH$_2$—OMe | —H | —H | —H | Me |

TABLE 21

| Rex | R$^A$ | R$^B$ | R$^C$ | R$^D$ | R$^E$ |
|---|---|---|---|---|---|
| 231* | iPr | —H | —H | —OMe | —H |
| 236* | 2-CF$_3$—Bn | —H | —H | —H | —H |
| 239 | —CH$_2$—OMe | —H | Et | —H | —H |
| 291 | 2-OMe—Ph | —H | —H | —H | —H |
| 292* | cHex | —H | —CMe$_2$—OH | —H | —H |
| 293* | cHex | —H | —OMe | —H | —H |
| 294* | Ph | —H | —OMe | —H | —H |
| 295* | Ph | —OMe | —H | —H | —H |
| 296* | iPr | —O—CHF$_2$ | —H | —H | —H |
| 297* | Ph | —O—CHF$_2$ | —H | —H | —H |
| 644* | Ph | —CN | —H | —H | —H |
| 651* | Ph | —H | —H | —F | —H |
| 659*$^1$ | —CH$_2$—OMe | —H | —H | —H | Me |

TABLE 22

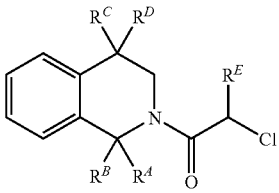

| Rex | R^A | R^B | R^C | R^D | R^E |
|---|---|---|---|---|---|
| 298 | cHex | —H | —H | —H | Me |
| 299 | cHex | —H | Me | Me | —H |
| 300 | cHex | Me | —H | —H | —H |
| 301 | —(CH₂)₂—O—(CH₂)₂— | | —H | —H | —H |
| 302 | Me | Me | —H | —H | —H |

TABLE 23

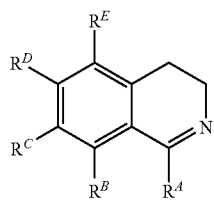

| Rex | salt | R^A | R^B | R^C | R^D | R^E |
|---|---|---|---|---|---|---|
| 303 | | Ph | —H | Me | —H | —H |
| 304 | | —CHEt₂ | —H | —H | —H | —H |
| 305 | | cHex | —H | —H | —Br | —H |
| 306 | | iPr | —OMe | —H | —H | —Br |
| 307 | | iPr | —H | —OMe | —H | —H |
| 308 | | cHex | —H | —OH | —H | —H |
| 309 | | cHex | —H | —H | —H | —OMe |
| 310 | | cHex | —H | —H | —F | —H |
| 311 | | cHex | —H | —H | —Cl | —H |
| 312 | | 2-CF₃—Ph | —H | —H | —H | —H |
| 313 | | cyclohexen-4-yl | —H | —H | —H | —H |
| 314 | | 3-CF₃—Ph | —H | —H | —H | —H |
| 315 | | 2-F—Ph | —H | —H | —H | —H |
| 316 | | 4,4-diF-cHex | —H | —H | —H | —H |
| 317 | | cHex | —H | —H | —H | —F |
| 318 | | cHex | —H | —F | —H | —H |
| 319 | | 2-CF₃-5-F—Ph | —H | —H | —H | —H |
| 320 | | 2-COCF₃—Ph | —H | —H | —H | —H |
| 321 | | 2-OEt—Ph | —H | —H | —H | —H |
| 322 | | 2-Et—Ph | —H | —H | —H | —H |
| 323 | | 2-SMe—Ph | —H | —H | —H | —H |
| 324 | | 2-Cl—Ph | —H | —H | —Cl | —H |
| 325 | CL | 2-Cl—Ph | —H | —H | —F | —H |
| 326 | | 2-OMe-5-F—Ph | —H | —H | —H | —H |
| 327 | | 4-CF₃—Bn | —H | —H | —H | —H |
| 328 | | 3-CF₃—Bn | —H | —H | —H | —H |
| 329 | | cHex | —H | —CF₃ | —H | —H |
| 330 | | cHex | —H | Et | —H | —H |
| 331 | | —CH(Et)—Me | —H | —H | —H | —H |
| 332 | | cHex | —H | —OiPr | —H | —H |
| 333 | | iPr | —H | —F | —H | —H |
| 334 | | —(CH₂)₂—OMe | —H | —H | —H | —H |
| 335 | | —CH₂—OMe | —H | —F | —H | —H |

TABLE 24

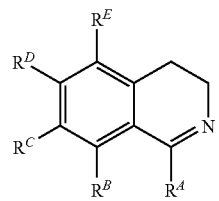

| Rex | salt | R^A | R^B | R^C | R^D | R^E |
|---|---|---|---|---|---|---|
| 336 | | cHex | —OMe | —H | —H | —Br |
| 337 | | 2-F—Bn | —H | —H | —H | —H |
| 338 | | 2-OMe—Bn | —H | —H | —H | —H |
| 339 | | 2-Me—Bn | —H | —H | —H | —H |
| 340 | | Ph | —OMe | —H | —H | Br |
| 341 | | iPr | —H | —H | —OMe | —H |
| 342 | | —CH₂—OMe | —H | Me | —H | —H |
| 343 | | Ph | —OMe | —H | —OMe | —H |
| 344 | | Ph | —H | —H | —H | —F |
| 345 | | —CH₂—OMe | —H | —H | —OMe | —H |
| 346 | | iPr | —H | —H | —H | Me |
| 347 | | cHex | —H | —H | —H | Me |
| 348 | | iPr | —H | Me | —H | —H |
| 349 | | cHex | —H | —H | Me | —H |
| 350 | | iPr | —H | —H | Me | —H |
| 351 | | Ph | —H | —F | —H | —H |
| 352 | | nPr | —H | —H | —H | —OMe |
| 353 | | nPr | —H | Me | —H | —H |
| 354 | | nPr | —H | —H | —H | —F |
| 355 | | nPr | —H | —OMe | —H | —H |
| 356 | | —CH₂—OMe | —H | —OMe | —H | —H |
| 357 | | —CH₂—OMe | —H | —H | —H | Me |
| 358 | | nPr | —H | —H | Me | —H |
| 359 | | nPr | —OMe | —H | —H | —Br |
| 360 | | cHex | —F | —H | —H | —Br |
| 361 | | —CH₂—OMe | —H | —H | —H | —OMe |
| 362 | CL | Ph | —F | —H | —H | —H |
| 363 | | —CH₂—OMe | —H | —H | —H | —F |
| 364 | | 4-Thp | —H | —H | —H | —H |
| 365 | | 2-Cl-3Py | —H | —H | —H | —H |
| 366 | | 6-Me-2-Py | —H | —H | —H | —H |
| 367 | | 6-Br-2-Py | —H | —H | —H | —H |
| 368 | | 6-Cl-2-P | —H | —H | —H | —H |
| 369 | | 4-Cl-2-P | —H | —H | —H | —H |

TABLE 25

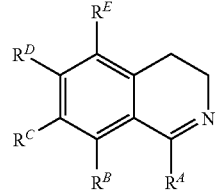

| Rex | R^A | R^B | R^C | R^D | R^E |
|---|---|---|---|---|---|
| 370 | tBu | —OMe | —H | —H | —Br |
| 371 | iPr | Me | —H | —H | —Br |
| 372 | —CH₂—OEt | —H | Me | —H | —H |
| 373 | —CH₂-iPr | —H | —OMe | —H | —H |
| 374 | —CH₂-iPr | —OMe | —H | —H | —Br |
| 375 | —CH₂—O—(CH₂)₂—OMe | —H | Me | —H | —H |
| 375A | iPr | —H | —H | —F | —H |
| 612 | iPr | —F | —H | —H | —Br |
| 620 | nPr | Me | —H | —H | —Br |
| 621 | nPr | —F | —H | —H | —Br |
| 625 | Ph | Et | —H | —H | —OMe |
| 626 | nPr | —H | Et | —H | —H |
| 637 | —CH₂—OMe | —F | —H | —H | —Br |
| 643 | Me | —H | Et | —H | —H |

TABLE 26

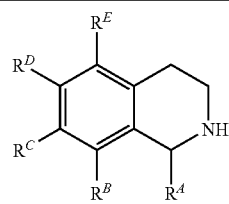

| Rex | salt | R$^A$ | R$^B$ | R$^C$ | R$^D$ | R$^E$ |
|---|---|---|---|---|---|---|
| 376 | CL | iPr | —H | —H | —OMe | —H |
| 377 | | cHex | —H | —H | —H | —H |
| 378 | CL | cHex | —H | —H | —H | —Br |
| 379 | | —CHEt$_2$ | —H | —H | —H | —H |
| 380 | CL | cHex | —H | —H | —Br | —H |
| 381 | CL | iPr | —OMe | —H | —H | —Br |
| 382 | CL | cHex | —H | —H | —F | —H |
| 383 | CL | cHex | —H | —H | —Cl | —H |
| 384 | | cyclohexen-4-yl | —H | —H | —H | —H |
| 385 | | 3-CF$_3$—Ph | —H | —H | —H | —H |
| 386 | | 2-F——Ph | —H | —H | —H | —H |
| 387 | CL | cHex | —H | —H | —H | —OMe |
| 388 | CL | 4,4-diF-cHex | —H | —H | —H | —H |
| 389 | CL | cHex | —H | —H | —H | —Cl |
| 390 | CL | cHex | —H | —OMe | —H | —H |
| 391 | CL | cHex | —H | —H | —OMe | —H |
| 392 | | 3-F—Ph | —H | —H | —H | —H |
| 393 | CL | cHex | —H | —H | —H | —F |
| 394 | CL | 2-OCF$_3$—Ph | —H | —H | —H | —H |
| 395 | | 2-CF$_3$-5-F—Ph | —H | —H | —H | —H |
| 396 | CL | 2-OEt—Ph | —H | —H | —H | —H |
| 397 | CL | 2-Et—Ph | —H | —H | —H | —H |
| 398 | | 2-SMe—Ph | —H | —H | —H | —H |
| 399 | CL | 2-OMe-5-F-Ph | —H | —H | —H | —H |
| 400 | | 4-Thp | —H | —H | —H | —H |
| 401 | CL | 2-Cl-Ph | —H | —Cl | —H | —H |
| 402 | CL | 2-Cl-Ph | —H | —F | —H | —H |
| 403 | | 4-CF$_3$—Bn | —H | —H | —H | —H |
| 404 | CL | cHex | —H | CN | —H | —H |
| 405 | | 3-CF$_3$—Bn | —H | —H | —H | —H |
| 406 | CL | cHex | —H | —CF$_3$ | —H | —H |
| 407 | CL | cHex | —H | —CH$_2$NHCO-iPr | —H | —H |
| 408 | CL | —CH(Et)—Me | —H | —H | —H | —H |

TABLE 27

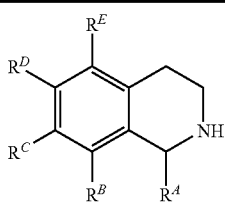

| Rex | salt | R$^A$ | R$^B$ | R$^C$ | R$^D$ | R$^E$ |
|---|---|---|---|---|---|---|
| 409 | CL | iPr | —H | —OMe | —H | —H |
| 500 | CL | iPr | —H | —F | —H | —H |
| 501 | | —(CH$_2$)$_2$—OMe | —H | —H | —H | —H |
| 502 | | —CH$_2$—OMe | —H | —F | —H | —H |
| 503 | CL | cHex | —OMe | —H | —H | —Br |
| 504 | CL | cHex | —OMe | —H | —H | —H |
| 505 | | —CH$_2$—OMe | —H | Et | —H | —H |
| 506 | CL | 2-F—Bn | —H | —H | —H | —H |
| 507 | | 2-OMe—Bn | —H | —H | —H | —H |
| 508 | | 2-Me—Bn | —H | —H | —H | —H |
| 509 | CL | tBu | —OMe | —H | —H | —Br |
| 510 | CL | tBu | —OMe | —H | —H | —H |
| 514 | CL | Ph | —H | —H | —H | —F |
| 515 | CL | Ph | —H | —H | —H | Me |
| 516 | CL | iPr | —H | —H | —H | Me |
| 517 | CL | cHex | —H | —H | —H | Me |
| 518 | | —CH$_2$—OMe | —H | —H | —OMe | —H |

TABLE 27-continued

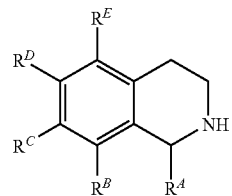

| Rex | salt | R$^A$ | R$^B$ | R$^C$ | R$^D$ | R$^E$ |
| --- | --- | --- | --- | --- | --- | --- |
| 519 |    | nPr        | —H | —H   | —F | —H |
| 520 | CL | iPr        | —H | Me   | —H | —H |
| 521 | CL | Ph         | —H | Me   | —H | —H |
| 522 | CL | iPr        | —H | —H   | Me | —H |
| 523 | CL | Ph         | —H | —F   | —H | —H |
| 524 | CL | nPr        | —H | —H   | —H | Me |
| 525 | CL | nPr        | —H | Me   | —H | —H |
| 526 | CL | nPr        | —H | —H   | —H | —F |
| 527 | CL | nPr        | —H | —OMe | —H | —H |
| 528 | CL | —CH$_2$—OMe | —H | Me  | —H | —H |
| 529 |    | nPr        | —H | —H   | Me | —H |
| 530 | CL | cHex       | —F | —H   | —H | —Br |

TABLE 28

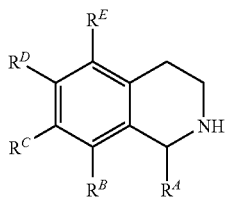

| Rex | salt | R$^A$ | R$^B$ | R$^C$ | R$^D$ | R$^E$ |
| --- | --- | --- | --- | --- | --- | --- |
| 531  | BR | cHex       | —F   | —H | —H | —H |
| 532  | CL | cHex       | Me   | —H | —H | —H |
| 533  | CL | —CH$_2$—OMe | —H  | —H | —H | Me |
| 534  | CL | Ph         | Me   | —H | —H | —H |
| 535  | CL | Ph         | —F   | —H | —H | —H |
| 536  | CL | 3,3-diF-cHex | —H | —H | —H | —H |
| 537  | CL | 2-Cl-3-Py  | —H   | —H | —H | —H |
| 538  |    | 6-Me-2-Py  | —H   | —H | —H | —H |
| 539  |    | 6-Br-2-Py  | —H   | —H | —H | —H |
| 540  |    | 6-Cl-2-Py  | —H   | —H | —H | —H |
| 541  | CL | 4-Cl-2-Py  | —H   | —H | —H | —H |
| 542  |    | iPr        | Me   | —H | —H | —Br |
| 543  |    | —CH$_2$—OEt | —H  | Me | —H | —H |
| 544  |    | —CH$_2$-iPr | —H  | —OMe | —H | —H |
| 545  |    | —CH$_2$-iPr | —OMe | —H | —H | —Br |
| 545A | OX | cPen       | —H   | —H | —H | —H |
| 546  |    | —CH$_2$-iPr | —OMe | —H | —H | —H |
| 546A | CL | iPr        | —H   | —H | —F | —H |
| 547  |    | —CH$_2$—O—(CH$_2$)$_2$—OMe | —H | Me | —H | —H |
| 613  | CL | iPr        | —F   | —H | —H | —Br |
| 622  | CL | nPr        | Me   | —H | —H | —Br |
| 627  |    | nPr        | —H   | Et | —H | —H |
| 631  | CL | Me         | —H   | Et | —H | —H |
| 634  |    | Ph         | Et   | —H | —H | —H |
| 640  | CL | —CH$_2$—O—(CH$_2$)$_3$—OMe | —H | Et | —H | —H |
| 647  |    | —CH$_2$—O—(CH$_2$)$_2$—OMe | —H | Et | —H | —H |
| 649  | CL | Ph         | Et   | —H | —H | —OMe |
| 654  |    | —CH$_2$—OMe | —F  | —H | —H | —Br |

TABLE 29

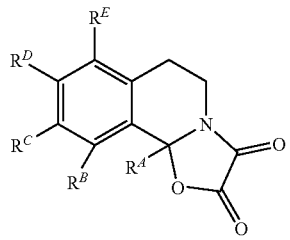

| Rex | R^A | R^B | R^C | R^D | R^E |
|---|---|---|---|---|---|
| 548 | cHex | —H | —H | —Br | —H |
| 549 | cHex | —H | —H | —F | —H |
| 550 | cHex | —H | —H | —Cl | —H |
| 551 | cHex | —H | —H | —H | —F |
| 552 | cHex | —H | —F | —H | —H |
| 553 | cHex | —H | —CF$_3$ | —H | —H |
| 554 | cHex | —H | Et | —H | —H |
| 555 | —(CH$_2$)$_2$—OMe | —H | —H | —H | —H |
| 556 | —CH$_2$—OMe | —H | —F | —H | —H |
| 557 | 2-F—Bn | —H | —H | —H | —H |
| 558 | 2-OMe—Bn | —H | —H | —H | —H |
| 559 | 2-Me-Bn | —H | —H | —H | —H |
| 560 | —CH$_2$—Cl | —H | Et | —H | —H |
| 561 | iPr | —H | —H | —H | Me |
| 562 | cHex | —H | —H | —H | Me |
| 563 | Ph | —H | —H | —H | —F |
| 564 | cHex | —F | —H | —H | —Br |
| 565 | —CH$_2$-iPr | —H | —OMe | —H | H |
| 611 | iPr | —F | —H | —H | —Br |
| 617 | nPr | Me | —H | —H | —Br |
| 618 | nPr | —F | —H | —H | —Br |
| 623 | Ph | Et | —H | —H | —OMe |
| 636 | —CH$_2$—Cl | —F | —H | —H | —Br |
| 642 | Me | —H | Et | —H | —H |

TABLE 30

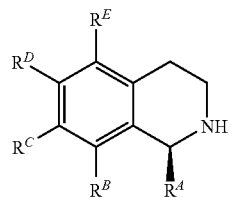

| Rex | salt | R^A | R^B | R^C | R^D | R^E |
|---|---|---|---|---|---|---|
| 566 | TQ | -2-OMe—Ph | —H | —H | —H | —H |
| 567* | T2 | Ph | —OMe | —H | —H | —Br |
| 568* | CL | Ph | —OMe | —H | —H | —H |
| 570* | T2 | iPr | —OMe | —H | —H | —Br |
| 571* | CL | iPr | —OMe | —H | —H | —H |
| 645* | CL | Ph | —CN | —H | —H | —H |
| 650* | T2 | Ph | —H | —H | —F | —H |

TABLE 31

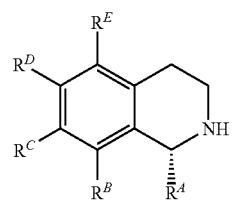

| Rex | salt | R^A | R^B | R^C | R^D | R^E |
|---|---|---|---|---|---|---|
| 513 | TY | —CH$_2$—OMe | —H | Et | —H | —H |
| 547A* | ML | iPr | —H | —H | —OMe | —H |
| 572* | T1 | cHex | —H | —H | —H | —H |
| 575* | T1 | cHex | —H | —Br | —H | —H |
| 576* | T1 | Ph | —OMe | —H | —H | —Br |
| 577* | CL | Ph | —OMe | —H | —H | —H |
| 652* | T1 | Ph | —H | —H | —F | —H |
| 658*² | | —CH$_2$—OMe | —H | —H | —H | Me |

TABLE 32

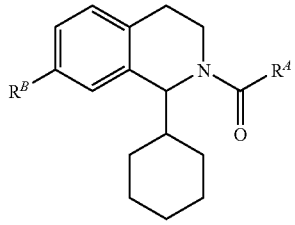

| Rex | R^A | R^B |
|---|---|---|
| 578 | 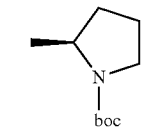 | —H |
| 579 | (2-pyrrolidinyl, NH) | —H |
| 580 | 1-boc-4-pipe | —H |
| 581 | —CH$_2$-(1-boc-4-pipa) | —H |
| 582 | 4-pipe | —H |
| 583 | —CH$_2$-1-pipa | —H |
| 584 | boc | CN |
| 585 | boc | —O—CH$_2$—CHF$_2$ |

TABLE 33
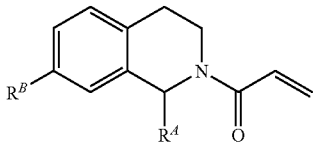
| Rex | R$^A$ | R$^B$ |
|---|---|---|
| 586 | 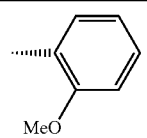 | —H |
| 587 | 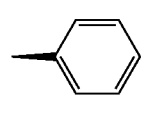 | —H |
| 588 | 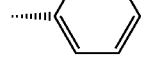 | —H |
| 630 | Me | Et |
| 632 | Me | Me |
| 646 |  | Et |
TABLE 34
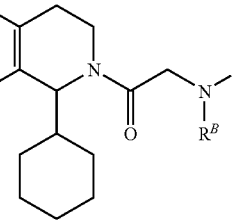
| Rex | R$^A$ | R$^b$ | R$^C$ | R$^D$ |
|---|---|---|---|---|
| 589 | —(CH$_2$)$_2$—OMe | —H | —H | —H |
| 590 | 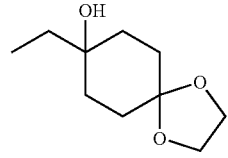 | —H | —H | —H |
| 591 | cPr | —H | —H | —H |
| 592 | —CH$_2$-cHex | —H | —H | —H |
| 593 | —(CH$_2$)$_2$—OH | —H | —H | —H |
| 594 | 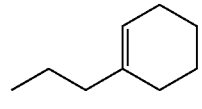 | —H | —H | —H |
| 595 | 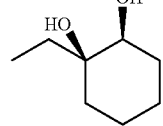 | boc | —H | —H |
TABLE 34-continued
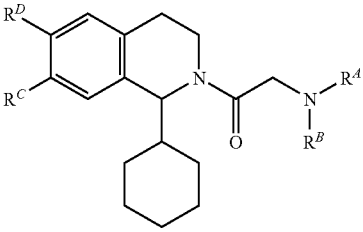
| Rex | R$^A$ | R$^b$ | R$^C$ | R$^D$ |
|---|---|---|---|---|
| 596 | —CH$_2$-(1-OH-cHex) | boc | —H | —CONH$_2$ |
| 597 | 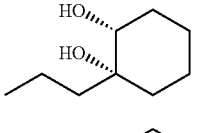 | —COCF$_3$ | —OMe | —H |
| 598 | 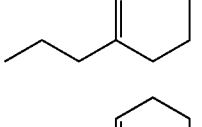 | —COCF$_3$ | —OMe | —H |
| 599 | 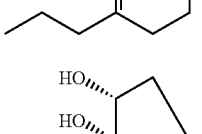 | —H | —OMe | —H |
| 600 | 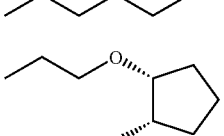 | —COCF$_3$ | —OMe | —H |
| 601 | 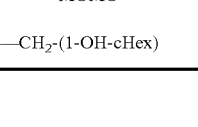 | —H | —OMe | —H |
| 602 | —CH$_2$-(1-OH-cHex) | —H | —H | —CONH$_2$ |
TABLE 35
| Rex | STRUCTURE |
|---|---|
| 603 | 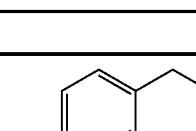 |
| 604 | 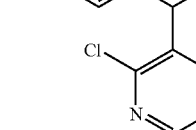 |

TABLE 35-continued

| Rex | STRUCTURE |
|---|---|
| 605 | 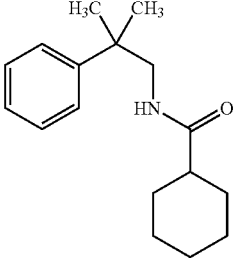 |
| 606 | 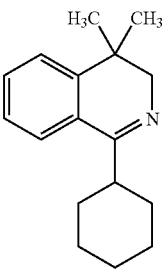 |
| 607 | 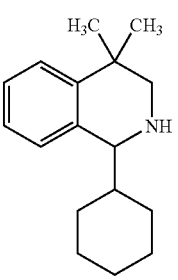 |
| 608 | 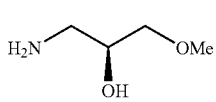 |
| 657*2 | 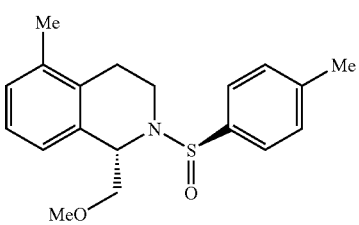 |

TABLE 36

| Rex | Data |
|---|---|
| 1 | FAB: 477 |
| 2 | FAB: 511 |
| 3 | ES: 493 |
| 4 | CI: 292 |
| 5 | FAB: 326 |
| 6 | AP1: 285.87 |
| 7 | FAB: 270 |
| 8 | FAB: 433 |
| 9 | FAB: 343 |
| 10 | APN: 411 |
| 11 | FAB: 373 |
| 12 | ES: 313 |
| 13 | ES: 273 |
| 14 | FAB: 467 |
| 15 | ES: 362 |

TABLE 36-continued

| Rex | Data |
|---|---|
| 16 | ES: 286 |
| 17 | ES: 376 |
| 18 | AP1: 269.96 |
| 19 | CI: 230 |
| 20 | FAB: 206 |
| 21 | ES: 216 |
| 22 | ES: 240 |
| 23 | AP: 278 |
| 24 | FAB: 320 |
| 25 | FAB: 248 |
| 26 | FAB: 248 |
| 27 | FAB: 244 |
| 28 | ES: 226 |
| 29 | FAB: 250 |
| 30 | AP: 230 |
| 31 | FAB: 188 |
| 32 | CI: 284 |
| 33 | FAB: 266 |
| 34 | FAB: 268 |
| 35 | FAB: 276 |
| 36 | ESNa: 374 |
| 37 | ES: 418 |
| 38 | ES: 285 |
| 39 | ES: 241 |
| 40 | FAB: 363 |
| 41 | EI: 238 |
| 42 | FAB: 256 |
| 43 | ES: 334 |
| 44 | FAB: 350 |
| 45 | FAB: 206 |
| 46 | FAB: 214 |
| 47 | EI1: 209 |
| 48 | CI: 236 |
| 49 | FAB: 222 |
| 50 | FAB: 228 |
| 51 | FA1: 355.98 |
| 52 | FAB: 234.13 |
| 53 | ES: 142 |
| 54 | ES: 183 |
| 55 | ES: 206 |
| 56 | ES: 297 |
| 57 | ES: 283 |
| 58 | NMR (CDCl$_3$): 1.28 (3 H, t, J = 7 Hz), 2.73-2.95 (3H, m), 3.45 (1H, m), 3.80 (1H, d, J = 13.4 Hz), 3.87 (1H, d, J = 13.4 Hz), 4.16-4.24 (2H, m), 4.52 (1H, s), 7.11-7.39 (9H, s). |
| 59 | ES: 346.05 |
| 60 | FAB: 391 |
| 61 | ES: 284 |
| 62 | CI: 206 |
| 63 | ESNa: 372 |
| 64 | ES: 258 |
| 65 | FAB: 313 |
| 66 | ES: 205 |
| 67 | FAB: 270.98 |
| 68 | N/D |
| 69 | ES: 366.4 |
| 70 | FAB: 359 |
| 71 | FAN: 385 |
| 72 | N/D |
| 73 | FAB: 413 |
| 74 | FA1: 331 |
| 75 | FAB: 388 |
| 76 | FAB: 410 |
| 77 | ESNa: 314 |
| 78 | ES: 242 |
| 79 | ES2: 277 |
| 80 | ES: 160 |
| 81 | ES1: 294 |
| 82 | ES: 292 |
| 83 | ES: 207 |
| 84 | N/D |
| 85 | FAB: 458 |
| 86 | CI: 348 |
| 87 | FAB: 338 |

TABLE 36-continued

| Rex | Data |
| --- | --- |
| 88 | AP: 248.00 |
| 89 | ES: 357 |
| 90 | ES: 330.13 |
| 91 | ES: 192.18 |

TABLE 37

| Rex | Rsyn | Data |
| --- | --- | --- |
| 101 | 34 | ES: 270 |
| 102 | 34 | AP: 234 |
| 103 | 34 | ES: 310, 312 |
| 104 | 33 | FAB: 262 |
| 105 | 34 | ES: 266, 268 |
| 106 | 34 | ES: 250 |
| 107 | 33 | ES: 294 |
| 108 | 33 | ES: 244 |
| 109 | 33 | ES: 294 |
| 110 | 33 | FAB: 230.16 |
| 111 | 33 | ES: 244 |
| 112 | 33 | FAB: 262 |
| 113 | 33 | FAB: 266 |
| 114 | 33 | FAB: 246 |
| 115 | 33 | FAB: 250 |
| 116 | 33 | FAB: 250 |
| 117 | 33 | ES: 312 |
| 118 | 34 | ES: 310 |
| 119 | 34 | ES: 254 |
| 120 | 34 | ES: 261 |
| 121 | 34 | ES: 308 |
| 122 | 33 | FAB: 246 |
| 123 | 33 | FAB: 300 |
| 124 | 33 | FAB: 210 |
| 125 | 34 | ES: 208 |
| 126 | 33 | ES: 212.0 |
| 127 | 33 | ES: 212 |
| 128 | 33 | ES: 222.18 |
| 129 | 34 | ES: 254 |
| 130 | 33 | ES: 226 |
| 131 | 33 | ES: 206.19 |
| 132 | 33 | ES: 210.08 |
| 133 | 33 | ES: 212.11 |
| 134 | 33 | AP: 208.00 |
| 135 | 33 | ES: 208.1 |
| 136 | 33 | AP: 210.06 |
| 137 | 33 | ES: 206.18 |
| 138 | 33 | EI1: 204 |
| 139 | 33 | ES: 244 |
| 140 | 33 | FAB: 240 |
| 141 | 33 | FAB: 206 |
| 142 | 33 | FAB: 246 |
| 143 | 33 | FAB: 206 |
| 144 | 33 | ES: 206.97 |
| 145 | 33 | ES: 208.17 |
| 146 | 34 | FAB: 268 |
| 147 | 34 | ES: 241 |
| 148 | 34 | ES: 305 |
| 149 | 34 | ES: 261 |
| 150 | 34 | ES: 261 |
| 151 | 34 | AP: 246 |
| 152 | 34 | ES: 222 |
| 153 | 34 | CI: 252 |
| 153A | 33 | FAB: 210 |
| 154 | 33 | FAB: 302 |
| 155 | 33 | FAB: 340 |
| 156 | 33 | FAB: 314 |
| 157 | 33 | FAB: 334 |
| 158 | 33 | ES: 286.79 |
| 159 | 33 | FAB: 328 |
| 160 | 33 | CI1: 300 |
| 161 | 33 | CI: 284 |
| 162 | 34 | CI1: 314 |
| 163 | 48 | EIN: 213 |
| 164 | 48 | EIBr: 213 |
| 165 | 48 | EI1: 239 |

TABLE 37-continued

| Rex | Rsyn | Data |
| --- | --- | --- |
| 166 | 4 | FAB: 278 |
| 167 | 4 | ES: 372 |
| 168 | 4 | ES: 371 |
| 169 | 4 | FAB: 292.1 |
| 170 | 4 | ES: 280 |
| 171 | 4 | ES: 370, 372 |
| 172 | 4 | ES: 317 |
| 173 | 4 | FAB: 322 |
| 174 | 4 | ES: 310 |
| 175 | 4 | AP: 326, 328 |
| 176 | 4 | FAB: 270 |
| 177 | 4 | ES: 304 |
| 178 | 4 | ES: 311 |
| 179 | 4 | FA2: 291.93 |
| 180 | 4 | ES: 354 |

TABLE 38

| Rex | Rsyn | Data |
| --- | --- | --- |
| 181 | 4 | ES: 354 |
| 182 | 4 | ES: 304 |
| 183 | 4 | ES1: 326 |
| 184 | 4 | FAB: 352.07 |
| 185 | 4 | FAB: 322 |
| 186 | 4 | FA1: 322 |
| 187 | 4 | ES: 322 |
| 188 | 4 | ES: 304 |
| 189 | 4 | ES: 320 |
| 190 | 4 | FAB: 310 |
| 191 | 4 | ES: 310 |
| 192 | 4 | FAB: 308 |
| 193 | 4 | ES: 316 |
| 194 | 4 | ES: 370 |
| 195 | Syn: 14 | N/D |
| 196 | 4 | ES: 372 |
| 197 | 4 | ES: 330 |
| 198 | 4 | FAB: 266 |
| 199 | 4 | FAB: 252 |
| 200 | 4 | ES: 314 |
| 201 | 4 | ES: 332 |
| 202 | 4 | ES: 334 |
| 203 | 4 | FAB: 336.07 |
| 204 | 4 | ES: 368 |
| 205 | 4 | FAB: 354 |
| 206 | 4 | FAB: 338 |
| 207 | 4 | FAB: 306 |
| 208 | 4 | ES: 368 |
| 209 | 4 | FAB: 360 |
| 210 | 4 | FAB: 300.02 |
| 211 | 60 | FAB: 320 |
| 212 | 4 | FAB: 391 |
| 213 | 4 | FAB: 282 |
| 214 | 4 | FAB: 264 |
| 215 | 4 | ES: 276 |
| 216 | 4 | FAB: 266 |
| 217 | 40 | FAB: 372 |
| 218 | 40 | FAB: 386 |
| 219 | 4 | ES: 268 |
| 220 | 4 | EI1: 311 |
| 221 | 4 | CI: 282 |
| 222 | 4 | FAB: 296 |
| 223 | 4 | FAB: 270 |
| 224 | 4 | ES: 272 |
| 225 | 4 | ES: 282 |
| 226 | 4 | ES: 282 |
| 227 | 4 | ES: 318 |
| 228 | 4 | FAB: 322 |
| 229 | 4 | FAB: 402 |
| 230 | 4 | FAB: 282 |
| 231 | 4 | CI: 282 |
| 232 | 4 | ES: 330 |
| 233 | 4 | ES: 314 |
| 234 | 4 | FAB: 282 |
| 235 | 4 | FAB: 296 |

TABLE 38-continued

| Rex | Rsyn | Data |
|---|---|---|
| 236 | 4 | ES: 368 |
| 236A | 4 | ES: 368.08 |
| 237 | 4 | FAB: 346.11 |
| 238 | 4 | FAB: 316.02 |
| 239 | 4 | ES: 282 |
| 240 | 4 | ES: 282 |
| 241 | 4 | FAB: 300 |
| 242 | 4 | FAB: 266 |
| 243 | 4 | ES: 306 |
| 244 | 4 | FAB: 266 |
| 245 | 4 | ES: 284.08 |
| 246 | 4 | FAB: 300 |
| 247 | 4 | FAB: 266 |
| 248 | 4 | FAB: 306 |
| 249 | 4 | ES: 270.03 |
| 250 | 4 | ES: 304 |
| 251 | 4 | FAB: 266 |
| 252 | 4 | FAB: 282 |
| 253 | 60 | ES2: 271.70 |
| 254 | 4 | CI: 270 |
| 255 | 4 | FAB: 268 |
| 256 | 60 | FAB: 284 |
| 257 | 4 | FAB: 266 |
| 258 | 4 | ES2: 347.82 |
| 259 | 4 | CI: 268 |

TABLE 39

| Rex | Rsyn | Data |
|---|---|---|
| 260 | 60 | ESNa: 294 |
| 261 | 4 | CI: 282 |
| 262 | 4 | ES2: 269.73 |
| 263 | 4 | ES1: 265.98 |
| 264 | 4 | CI: 306 |
| 265 | 4 | CI: 310 |
| 266 | 4 | CI: 300 |
| 267 | 4 | CI: 304 |
| 268 | 4 | ES: 282.07 |
| 269 | 4 | ES: 316 |
| 270 | 4 | FAB: 328 |
| 271 | 4 | FAB: 328 |
| 272 | 4 | FAB: 294 |
| 273 | 4 | ES: 321 |
| 274 | 4 | ES: 321 |
| 275 | 4 | ES: 365 |
| 276 | 4 | ES: 301 |
| 277 | 4 | ES: 321 |
| 278 | 4 | ES: 287 |
| 279 | 4 | FAB: 00 |
| 280 | 4 | FAB: 346 |
| 281 | 4 | CI: 282 |
| 282 | 4 | ES: 296 |
| 283 | 4 | CI: 296 |
| 284 | 60 | CI: 312 |
| 285 | 4 | AP: 306 |
| 286 | 4 | FAB: 344 |
| 287 | 4 | ES: 316 |
| 288 | 4 | FAB: 286.35 |
| 289 | 44 | ESNa: 372 |
| 290 | 4 | EI1: 315 |
| 291 | 4 | ES: 316 |
| 292 | 44 | CI: 350 |
| 293 | 4 | EI: 321 |
| 294 | 4 | FAB: 316 |
| 295 | 4 | FAB: 316 |
| 296 | 4 | ES: 318 |
| 297 | 4 | ES: 352 |
| 298 | 4 | FAB: 306 |
| 299 | 4 | FAB: 320.0 |
| 300 | 4 | FAB: 306.06 |
| 301 | 4 | FAB: 310.12 |
| 302 | 4 | FAB: 238 |
| 303 | 27 | CI: 222 |
| 304 | 28 | ES: 202 |

TABLE 39-continued

| Rex | Rsyn | Data |
|---|---|---|
| 305 | 25 | ES: 292, 294 |
| 306 | 27 | FAB: 282 |
| 307 | 26 | EIN: 202 |
| 308 | 26 | FAB: 230 |
| 309 | 27 | FAB: 244 |
| 310 | 25 | ES: 232 |
| 311 | 25 | ES: 248 |
| 312 | 27 | ES: 276 |
| 313 | 27 | FA2: 213.28 |
| 314 | 27 | ES: 276 |
| 315 | 27 | ES: 226 |
| 316 | 27 | FAB: 250 |
| 317 | 25 | ES: 232 |
| 318 | 25 | FAB: 232 |
| 319 | 28 | ES: 294 |
| 320 | 27 | ES: 292 |
| 321 | 27 | ES: 252 |
| 322 | 27 | ES: 236 |
| 323 | 27 | ES: 254 |
| 324 | 26 | FAB: 276 |
| 325 | 26 | ES: 260 |
| 326 | 27 | ES: 256 |
| 327 | 29 | ES: 290 |
| 328 | 29 | ES: 291 |
| 329 | 25 | FAB: 282 |
| 330 | 25 | FAB: 242 |
| 331 | 28 | EIN: 186 |
| 332 | 27 | FAB: 272 |
| 333 | 27 | FAB: 192 |
| 334 | 25 | ES: 190 |
| 335 | 25 | ES: 194.22 (M + H) |
| 336 | 27 | FAB: 322 |
| 337 | 25 | ES: 241 |
| 338 | 25 | ES: 252 |
| 339 | 25 | ES: 236 |

TABLE 40

| Rex | Rsyn | Data |
|---|---|---|
| 340 | 27 | FAB: 318 |
| 341 | 27 | EIN: 202 |
| 342 | 31 | CI: 190 |
| 343 | 31 | ES2: 269.20 |
| 344 | 25 | ES: 226 |
| 345 | 31 | ES: 206.23 |
| 346 | 25 | FAB: 188 |
| 347 | 25 | FAB: 228 |
| 348 | 27 | CI: 188 |
| 349 | 26 | CI: 228 |
| 350 | 27 | CI: 188 |
| 351 | 26 | ES: 226 |
| 352 | 31 | FAB: 204 |
| 353 | 31 | FAB: 188 |
| 354 | 31 | FAB: 192 |
| 355 | 29 | FAB: 204 |
| 356 | 29 | CI: 206 |
| 357 | 31 | CI: 190 |
| 358 | 31 | AP: 188.15 |
| 359 | 31 | CI1: 282 |
| 360 | 25 | EI1: 311 |
| 361 | 29 | ES: 206 |
| 362 | 49 | EIN: 224 |
| 363 | 31 | CIN: 192 |
| 364 | 29 | AP: 216 |
| 365 | 28 | ES: 245 |
| 366 | 28 | ES: 223 |
| 367 | 28 | ES: 287 |
| 368 | 28 | ES: 243 |
| 369 | 28 | ES: 243 |
| 370 | 27 | FAB: 296 |
| 371 | 27 | EI1: 265 |
| 372 | 31 | ES: 204 |
| 373 | 26 | ES: 218 |
| 374 | 31 | CI1: 296 |

TABLE 40-continued

| Rex | Rsyn | Data |
|---|---|---|
| 375 | 31 | CI: 234 |
| 375A | 27 | FAB: 192 |
| 376 | 18 | FAB: 206 |
| 377 | 18 | FA2: 217.3 |
| 378 | 18 | ES: 294, 296 |
| 379 | 18 | ES: 204 |
| 380 | 18 | ES: 296 |
| 381 | 18 | FAB: 284 |
| 382 | 18 | ES: 234 |
| 383 | 18 | ES: 250 |
| 384 | 18 | AP: 214.08 |
| 385 | 18 | ES: 278 |
| 386 | 18 | ES: 228 |
| 387 | 18 | FAB: 246 |
| 388 | 18 | FAB: 252 |
| 389 | 18 | ES: 250 |
| 390 | 18 | FAB: 246 |
| 391 | 18 | FAB: 246 |
| 392 | 18 | ES: 228 |
| 393 | 18 | FAB: 243 |
| 394 | 18 | AP: 294 |
| 395 | 23 | ES: 296 |
| 396 | 18 | ES: 254 |
| 397 | 18 | ES: 238 |
| 398 | 18 | ES: 256 |
| 399 | 18 | ES: 258 |
| 400 | 18 | AP: 218 |
| 401 | 18 | FAB: 278 |
| 402 | 18 | FAB: 262 |
| 403 | 18 | ES: 292 |
| 404 | 18 | FAB: 241 |
| 405 | 18 | ES: 292 |
| 406 | 18 | FAB: 284 |
| 407 | 39 | FAB: 315 |
| 408 | 18 | ES: 190 |
| 409 | 18 | FAB: 206 |
| 500 | 18 | FAB: 194 |
| 501 | 18 | ES: 192 |
| 502 | 18 | ES: 197 |
| 503 | 18 | FAB: 324 |
| 504 | 45 | FAB: 246 |
| 505 | 18 | ES: 206 |
| 506 | 18 | ES: 242 |
| 507 | 18 | ES: 254 |
| 508 | 18 | ES: 238 |
| 509 | 18 | FAB: 298 |

TABLE 41

| Rex | Rsyn | Data |
|---|---|---|
| 510 | 45 | FAB: 220 |
| 513 | 83 | ES: 206 |
| 514 | 18 | ES: 228 |
| 515 | 18 | FAB: 224 |
| 516 | 18 | FAB: 190 |
| 517 | 18 | FAB: 230 |
| 518 | 18 | ES: 208.15 |
| 519 | 18 | ES2: 195.05 |
| 520 | 18 | CI: 190 |
| 521 | 18 | CI: 224 |
| 522 | 18 | CI: 190 |
| 523 | 18 | ES: 228 |
| 524 | 18 | FAB: 190 |
| 525 | 18 | FAB: 190 |
| 526 | 18 | FAB: 194 |
| 527 | 18 | FAB: 206 |
| 528 | 18 | CI: 192 |
| 529 | 18 | AP: 190.19 |
| 530 | 18 | FAB: 312 |
| 531 | 45 | FAB: 234 |
| 532 | 18 | FAB: 230 |
| 533 | 18 | ES: 192 |
| 534 | 18 | ES: 224 |
| 535 | 18 | CI: 228 |

TABLE 41-continued

| Rex | Rsyn | Data |
|---|---|---|
| 536 | 18 | FAB: 252 |
| 537 | 18 | ES: 245 |
| 538 | 18 | ES: 225 |
| 539 | 18 | ES: 289 |
| 540 | 18 | ES: 245 |
| 541 | 18 | ES: 245 |
| 542 | 18 | CI: 268 |
| 543 | 18 | ES: 206 |
| 544 | 18 | ES: 220 |
| 545 | 18 | CI1: 298 |
| 546 | 45 | ES: 220 |
| 547 | 60 | CI: 312 |
| 548 | 24 | ES: 364, 366 |
| 549 | 24 | ES: 304 |
| 550 | 24 | ES: 320 |
| 551 | 24 | FAB: 304 |
| 552 | 24 | FAB: 304 |
| 553 | 24 | FAB: 354 |
| 554 | 24 | FAB: 314 |
| 555 | 25 | ESNa: 284 |
| 556 | 24 | ES: 266 |
| 557 | 24 | ES: 312 |
| 558 | 24 | ES: 324 |
| 559 | 24 | ES: 308 |
| 560 | 24 | ES: 280 |
| 561 | 24 | FAB: 260 |
| 562 | 24 | FAB: 300 |
| 563 | 24 | ES: 298 |
| 564 | 24 | FAB: 382 |
| 565 | 26 | N/D |
| 566 | 22 | ES: 240 |
| 567 | 81 | EI1: 317 |
| 568 | 45 | CI: 240 |
| 570 | 81 | ES: 286 |
| 571 | 45 | ES: 206 |
| 572 | 21 | ES: 216 |
| 575 | 81 | FAB: 294 |
| 576 | 81 | EI1: 317 |
| 577 | 45 | CI: 240 |
| 578 | 10 | ES: 413 |
| 579 | 12 | ES: 313 |
| 580 | 10 | ES: 427 |
| 581 | Syn: 1 | ES: 442 |
| 582 | 12 | ES: 327 |
| 583 | Syn: 10 | ES: 342 |
| 584 | 37 | FAB: 341 |
| 585 | 75 | FAB: 396 |
| 586 | 7 | FAB: 294.01 |
| 587 | 7 | FAB: 264.01 |
| 588 | 7 | FAB: 264.03 |
| 589 | Syn: 1 | ES: 331 |
| 590 | Syn: 1 | N/D |
| 591 | Syn: 1 | ES: 313 |
| 592 | Syn: 1 | FAB: 369 |
| 593 | Syn: 1 | FAB: 317 |
| 594 | Syn: 1 | ES: 381 |

TABLE 42

| Rex | Rsyn | Data |
|---|---|---|
| 595 | 2 | ES: 501 |
| 596 | 14 | FAB: 528 |
| 597 | 2 | FAN: 541 |
| 598 | 1 | FAB: 507 |
| 599 | Syn: 1 | FAB: 411 |
| 600 | 2 | ES: 526 |
| 601 | Syn: 1 | FAB: 475 |
| 602 | Syn: 10 | N/D |
| 603 | Syn: 1 | FAB: 360 |
| 604 | Syn: 1 | FAB: 437 |
| 605 | 33 | FA2: 261.2 |
| 606 | 27 | FA2: 243.5 |
| 607 | 18 | FA2: 245.4 |
| 608 | 80 | AP: 106.0 |

TABLE 42-continued

| Rex | Rsyn | Data |
|---|---|---|
| 609 | 33 | ES: 255.99 |
| 610 | 33 | CI: 288 |
| 611 | 24 | CI: 344 |
| 612 | 25 | ES: 270 |
| 613 | 18 | ES: 272 |
| 614 | 4 | CI: 350 |
| 615 | 33 | CI: 284 |
| 616 | 33 | CI: 288 |
| 617 | 24 | FAB: 338 |
| 618 | 24 | FAB: 342 |
| 619 | 33 | CI: 286 |
| 620 | 25 | EIN: 264 |
| 621 | 25 | EIN: 268 |
| 622 | 18 | ES: 268 |
| 623 | 24 | ES: 338 |
| 624 | 33 | AP: 220.03 |
| 625 | 25 | CI: 266 |
| 626 | 84 | AP: 202.06 |
| 627 | 18 | AP: 204.00 |
| 628 | 40 | EI1: 313 |
| 629 | 4 | CI: 252 |
| 630 | 7 | CI: 230 |
| 631 | 18 | ES: 176 |
| 632 | 7 | EI1: 215 |
| 633 | 4 | CI: 238 |
| 634 | 40 | EI1: 237 |
| 635 | 4 | CI: 344 |
| 636 | 24 | FAB: 350 |
| 637 | 66 | N/D |
| 638 | 4 | CI: 350 |
| 639 | 33 | ES: 296 |
| 640 | 88 | CI: 264 |
| 641 | 33 | EI: 192 |
| 642 | 24 | ES: 246 |
| 643 | 25 | EI1: 173 |
| 644 | 40 | FAB: 311 |
| 645 | 40 | ES: 235 |
| 646 | 7 | CI: 260 |
| 647 | 18 | ES: 250.25 |
| 648 | 4 | ES: 326 |
| 649 | 18 | ES: 268 |
| 650 | 21 | FAB: 228 |
| 651 | 4 | CI: 304 |
| 652 | 21 | FAB: 228 |
| 653 | 4 | FAB: 304 |
| 654 | 18 | CI: 274 |
| 655 | 4 | CI: 340 |
| 656 | 4 | CI: 352 |
| 657 | 90 | ES: 330.14 |
| 658 | 91 | ES: 192.13 |
| 659 | 4 | ES: 268.09 |
| 660 | 4 | ES: 268.09 |
| 661 | 34 | ES: 274 |
| 662 | 34 | ES: 308 |

TABLE 43

| Ex/salt | STRUCTURE |
|---|---|
| 1/OX | |
| 2/OX | 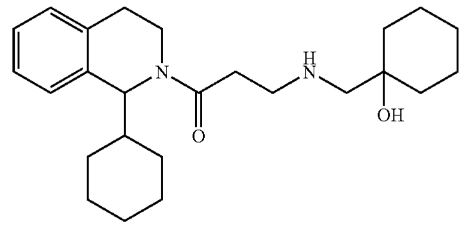 |
| 3/OX | 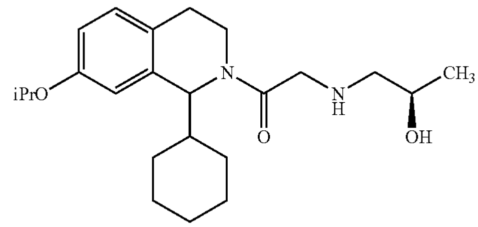 |
| 4/OX | 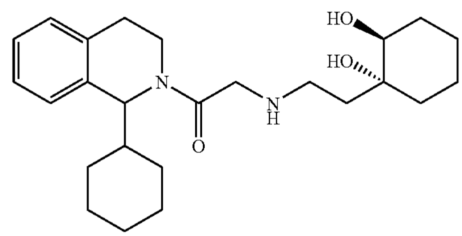 |
| 5/OX | 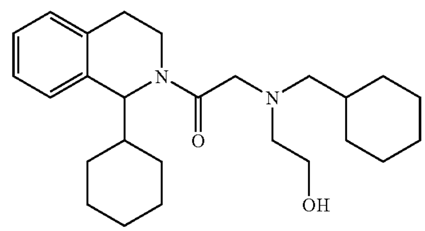 |
| 6/OX | 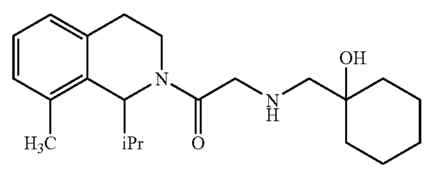 |
| 7/OX | 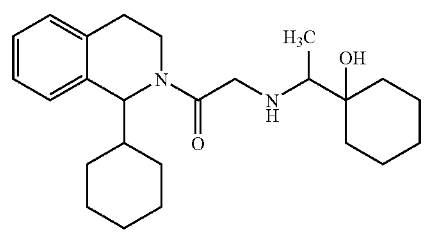 |
| 8/OX | 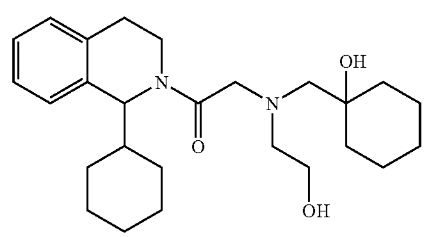 |

TABLE 43-continued

| Ex/salt | STRUCTURE |
|---|---|
| 9/OX | (structure) |
| 10/OX | (structure) |
| 11/OX | (structure) |
| 12/OX | (structure) |

TABLE 44

| Ex/salt | STRUCTURE |
|---|---|
| 13/OX | (structure) |
| 14/OX | (structure) |

TABLE 44-continued

| Ex/salt | STRUCTURE |
|---|---|
| 15/OX | (structure) |
| 16 | (structure) |
| 17 | (structure) |

TABLE 45

| Ex | salt | STRUCTURE |
|---|---|---|
| 101 | OX | (structure) |
| 102 | OX | (structure) |

TABLE 45-continued

| Ex | salt | STRUCTURE |
|----|------|-----------|
| 103 | OX | 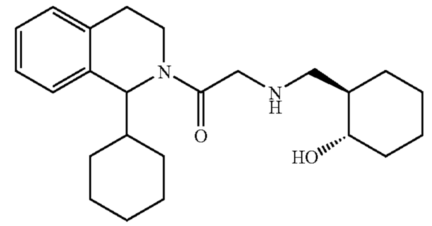 |
| 104 | OX | 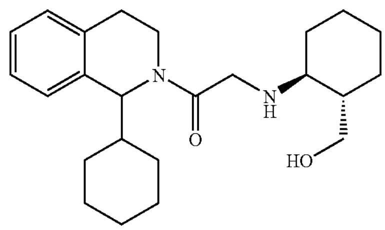 |
| 105 | OX | 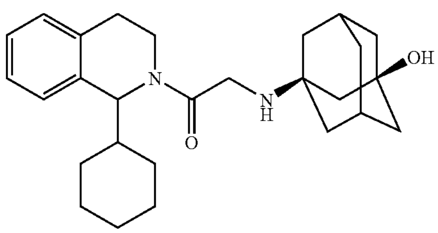 |
| 106 | OX | 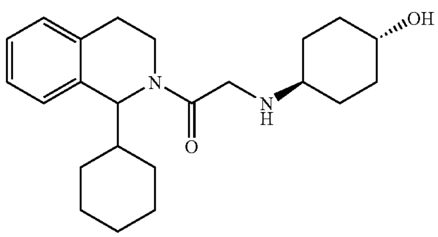 |
| 107 | OX | 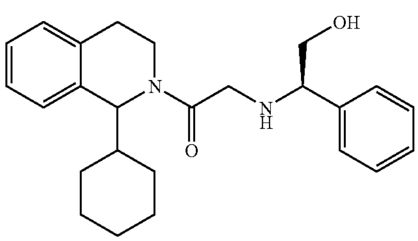 |

TABLE 46

| Ex | salt | STRUCTURE |
|----|------|-----------|
| 108 | OX | 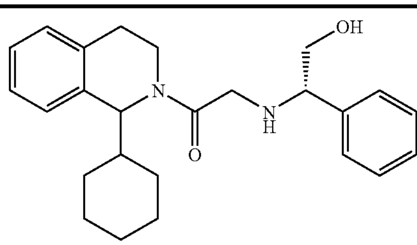 |

TABLE 46-continued

| Ex | salt | STRUCTURE |
|----|------|-----------|
| 109 | OX | 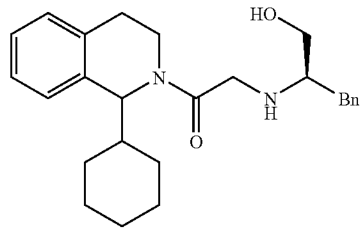 |
| 110 | OX | 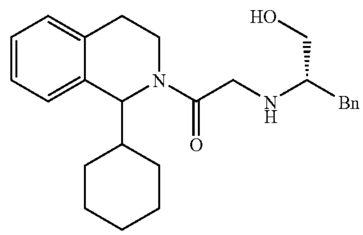 |
| 111 | OX | 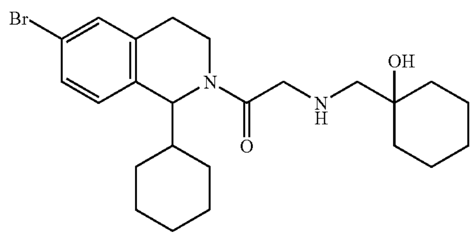 |
| 112 | OX | 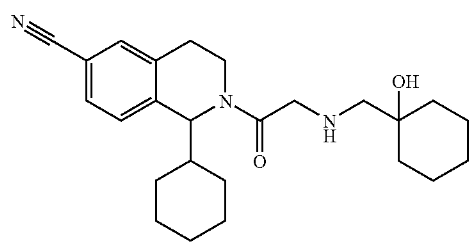 |
| 113 | OX | 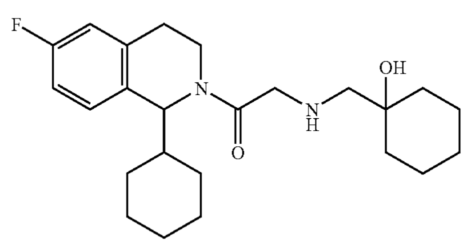 |
| 114 | | 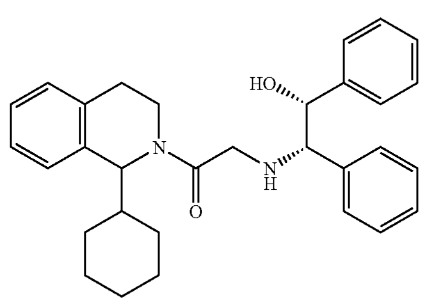 |

TABLE 47

| Ex | salt | STRUCTURE |
|---|---|---|
| 115 | | 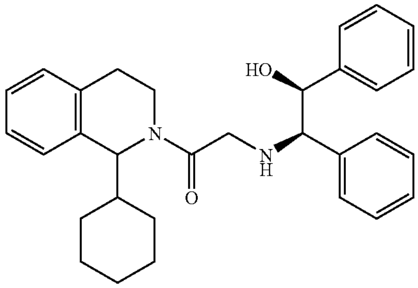 |
| 116 | OX | 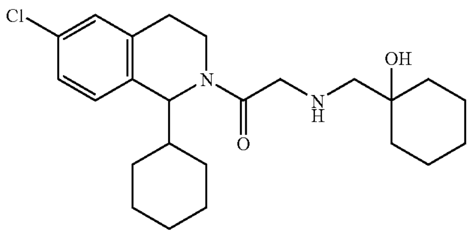 |
| 117 | OX | 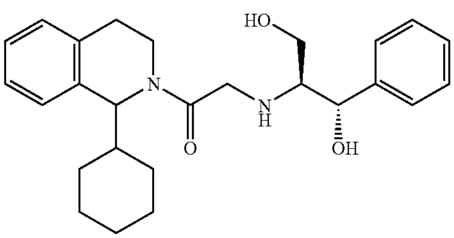 |
| 118 | OX | 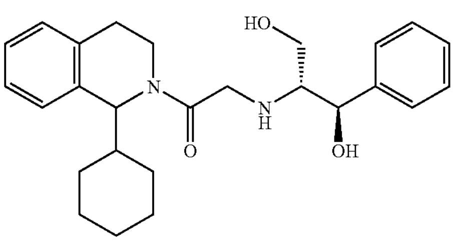 |
| 119 | OX | 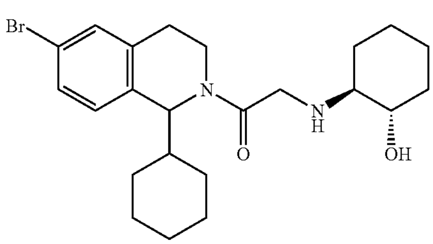 |
| 120 | OX | 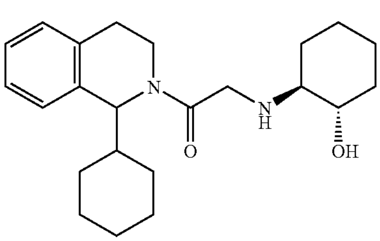 |

TABLE 47-continued

| Ex | salt | STRUCTURE |
|---|---|---|
| 121 | OX | |

TABLE 48

| Ex | salt | STRUCTURE |
|---|---|---|
| 122 | OX | 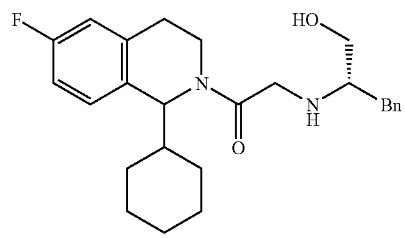 |
| 123 | OX | 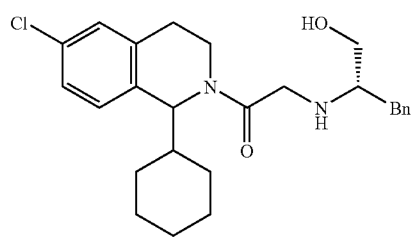 |
| 124 | OX | 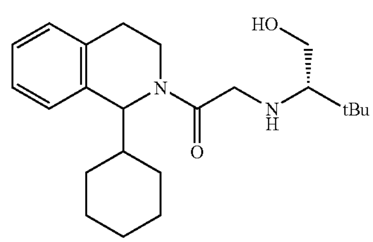 |
| 125 | OX | 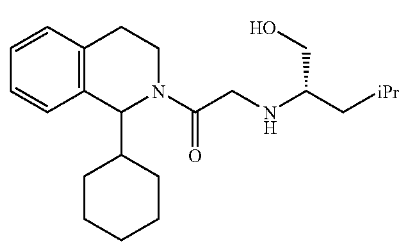 |

TABLE 48-continued
| Ex | salt | STRUCTURE |
|---|---|---|
| 126 | OX | 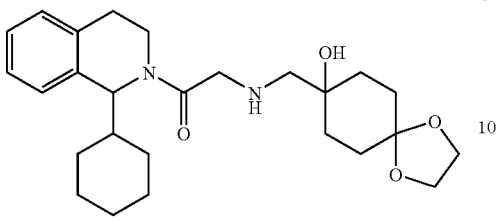 |
| 127 | OX | 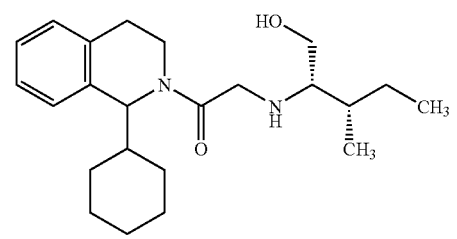 |
| 128 | OX | 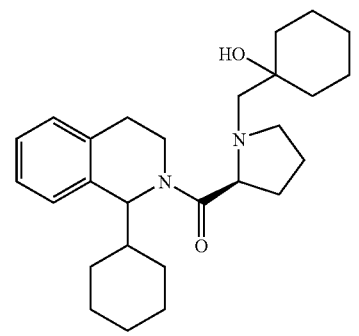 |
TABLE 49
| Ex | salt | STRUCTURE |
|---|---|---|
| 129 | OX | 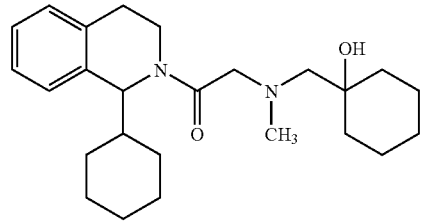 |
| 130 | OX | 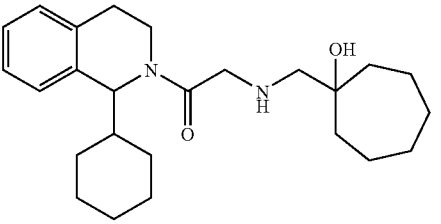 |
| 131 | OX | 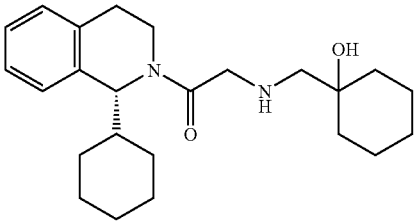 |
| 132 | OX | 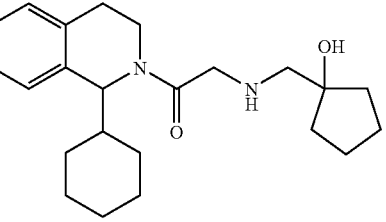 |
| 133 | OX | 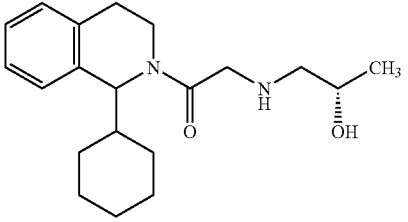 |
| 134 | OX | 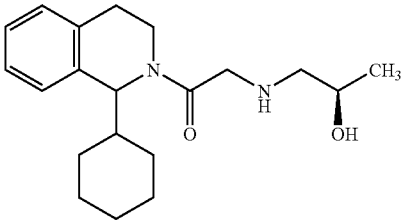 |
| 135 | OX | 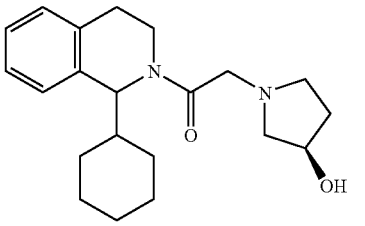 |
TABLE 50
| Ex | salt | STRUCTURE |
|---|---|---|
| 136 | OX | 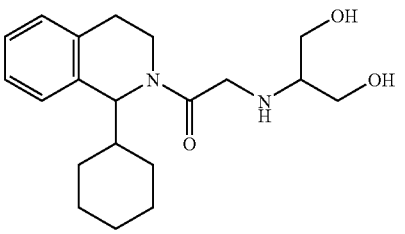 |

TABLE 50-continued

| Ex | salt | STRUCTURE |
|---|---|---|
| 137 | OX | 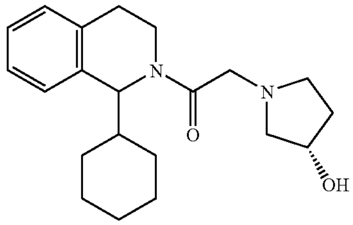 |
| 138 | OX | 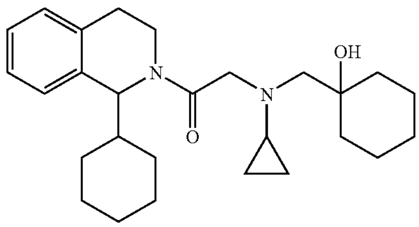 |
| 139 | OX | 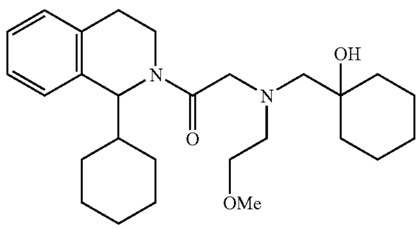 |
| 140 | OX | 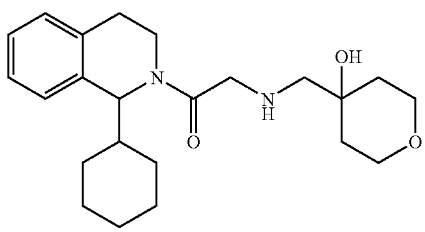 |
| 141 | OX | 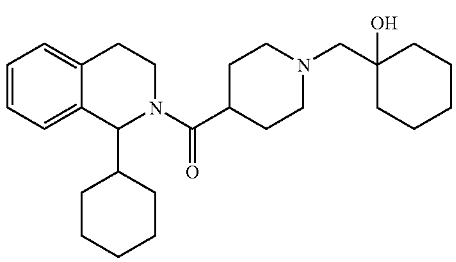 |

TABLE 51

| Ex | salt | STRUCTURE |
|---|---|---|
| 143 | FM | |
| 144 | OX | 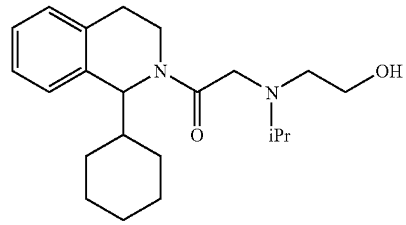 |
| 145 | FM | 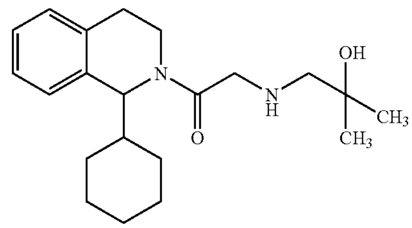 |
| 146 | OX | 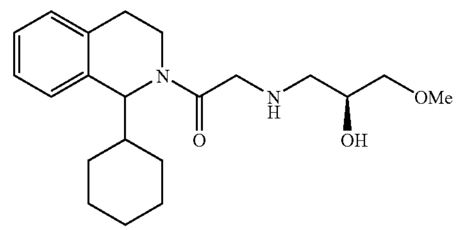 |
| 147 | OX | 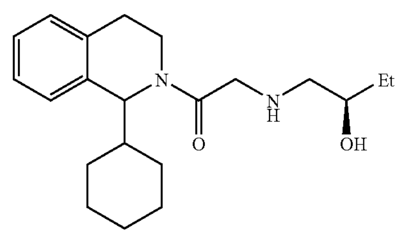 |
| 148 | OX | 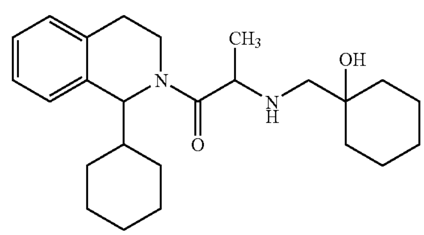 |
| 149 | OX | 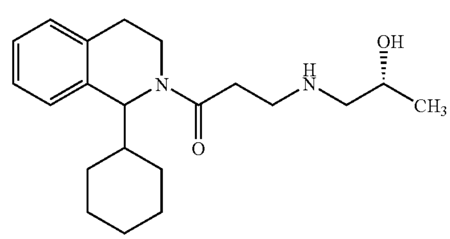 |

TABLE 52

| Ex | salt | STRUCTURE |
|---|---|---|
| 150 | OX | (structure) |
| 151 | OX | (structure) |
| 152 | OX | (structure) |
| 153 | FM | (structure) |
| 154 | OX | (structure) |
| 155 | OX | (structure) |

TABLE 53

| Ex | salt | STRUCTURE |
|---|---|---|
| 156 | OX | (structure) |
| 157 | CL | (structure) |
| 158 | OX | (structure) |
| 159 | OX | (structure) |
| 160 | OX | (structure) |
| 161 | OX | (structure) |

TABLE 54

| Ex | salt | STRUCTURE |
|---|---|---|
| 162 | OX | (structure) |
| 163 | OX | (structure) |
| 164 | OX | (structure) |
| 165 | OX | (structure) |
| 166 | OX | (structure) |

TABLE 54-continued

| Ex | salt | STRUCTURE |
|---|---|---|
| 167 | OX | (structure) |

TABLE 55

| Ex | salt | STRUCTURE |
|---|---|---|
| 168 | FM | (structure) |
| 169 | FM | (structure) |
| 170 | OX | (structure) |
| 171 | OX | (structure) |
| 172 | OX | (structure) |

TABLE 55-continued
| Ex | salt | STRUCTURE |
|----|------|-----------|
| 173 | OX | 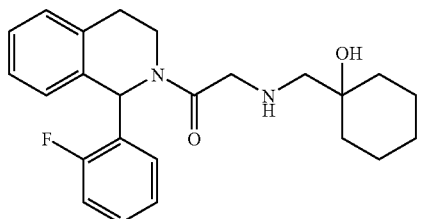 |
| 174 | OX | 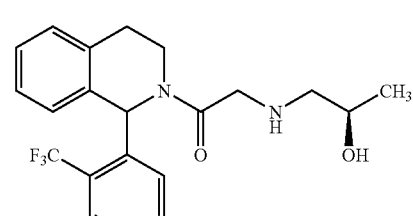 |
TABLE 56
| Ex | salt | STRUCTURE |
|----|------|-----------|
| 175 | OX | 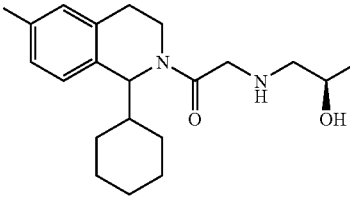 |
| 176 | OX | 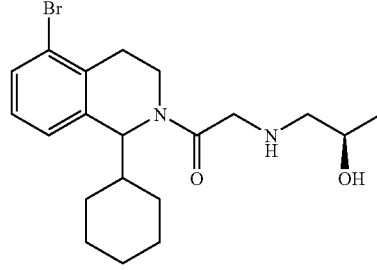 |
| 177 | OX | 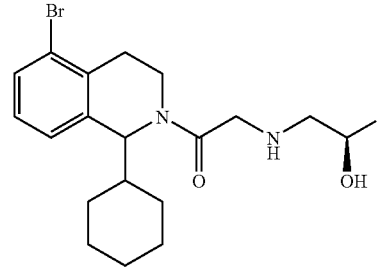 |
| 178 | OX | 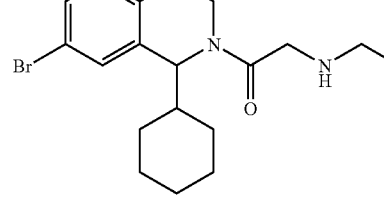 |
TABLE 56-continued
| Ex | salt | STRUCTURE |
|----|------|-----------|
| 179 | OX | 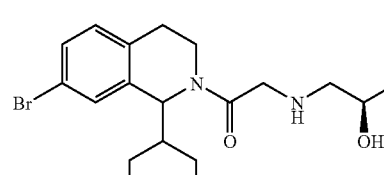 |
| 180 | OX | 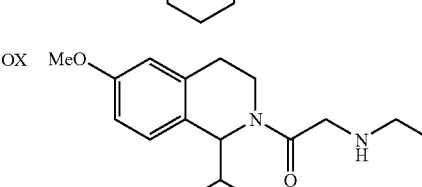 |
| 181 | OX | 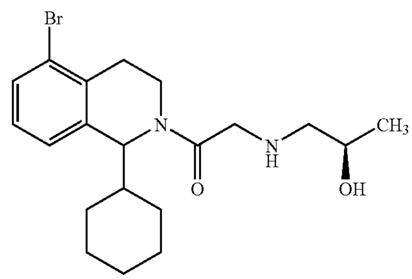 |
TABLE 57
| Ex | salt | STRUCTURE |
|----|------|-----------|
| 182 | OX | 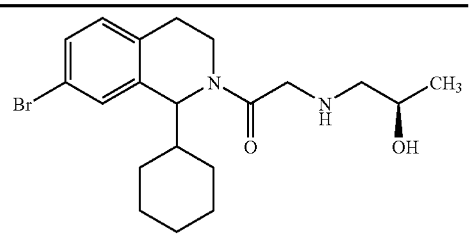 |
| 183 | OX | 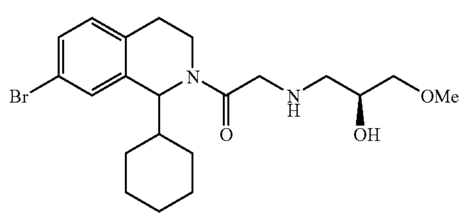 |
| 184 | OX | 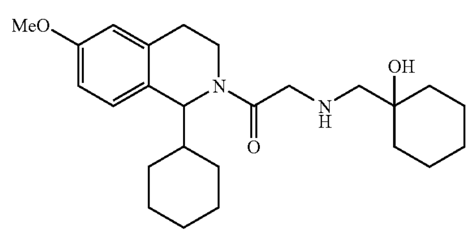 |

TABLE 57-continued
| Ex | salt | STRUCTURE |
|---|---|---|
| 185 | OX | 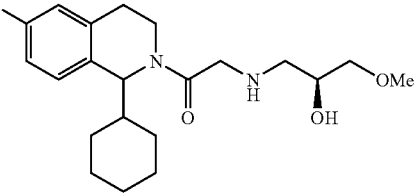 |
| 186 | OX | 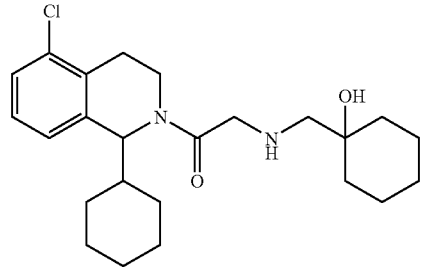 |
| 187 | OX | 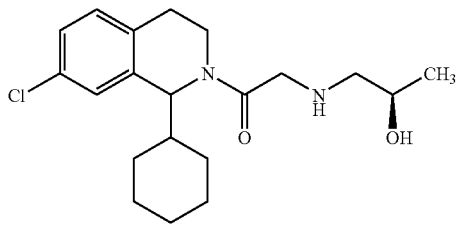 |
| 188 | OX | 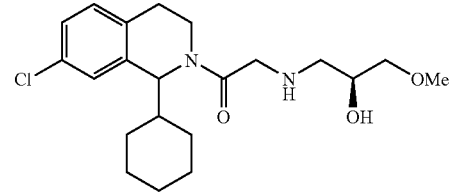 |
TABLE 58
| Ex | salt | STRUCTURE |
|---|---|---|
| 189 | OX | 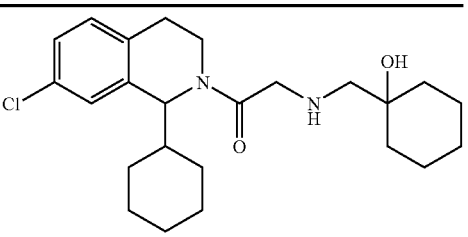 |
| 190 | OX | 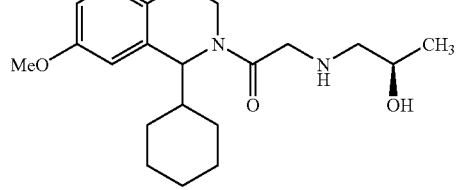 |
TABLE 58-continued
| Ex | salt | STRUCTURE |
|---|---|---|
| 191 | OX | 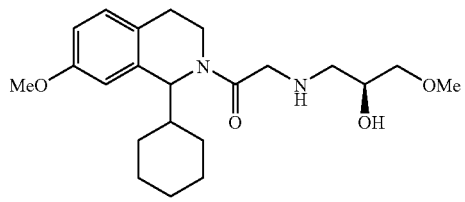 |
| 192 | OX | 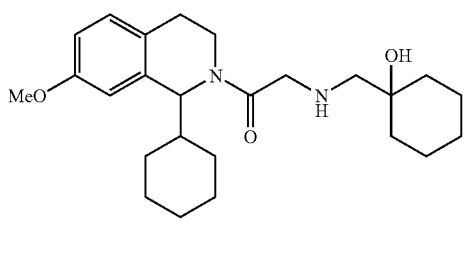 |
| 193 | OX | 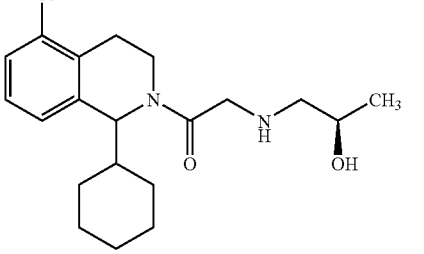 |
| 194 | OX | 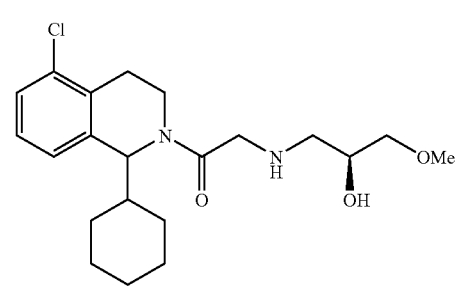 |
TABLE 59
| Ex | salt | STRUCTURE |
|---|---|---|
| 195 | OX | 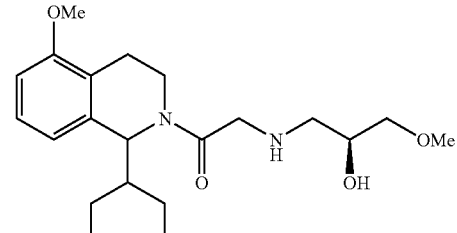 |

TABLE 59-continued

| Ex | salt | STRUCTURE |
|---|---|---|
| 196 | OX | 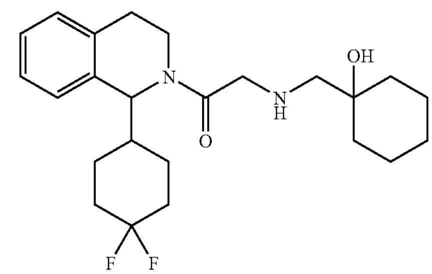 |
| 197 | OX | 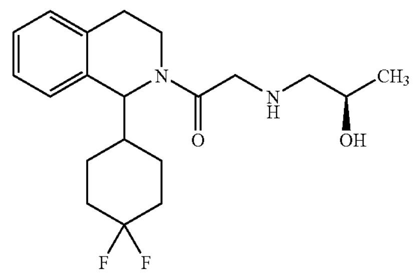 |
| 198 | OX | 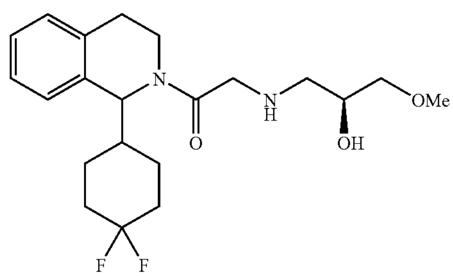 |
| 199 | FM | 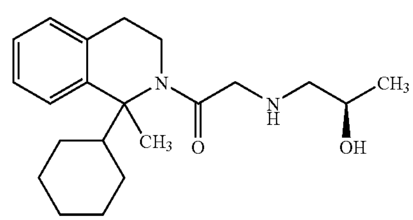 |
| 200 | FM | 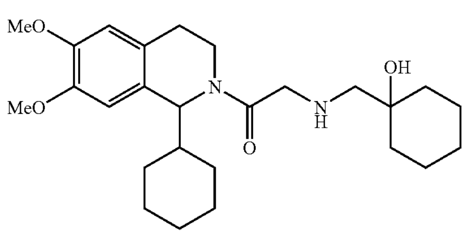 |
| 201 | FM | 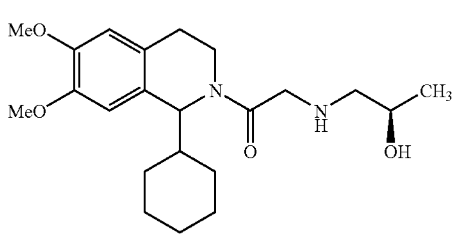 |

TABLE 60

| Ex | salt | STRUCTURE |
|---|---|---|
| 202 | FM | 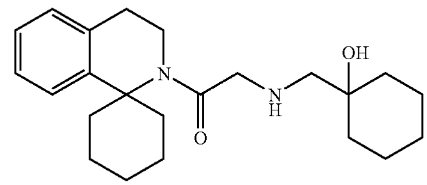 |
| 203 | OX | 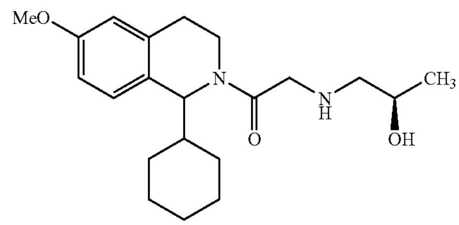 |
| 204 | FM | 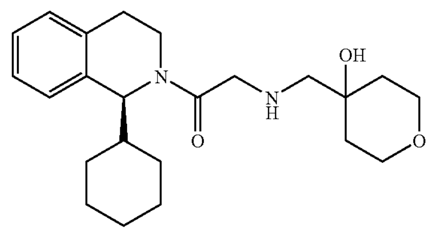 |
| 205 | OX | 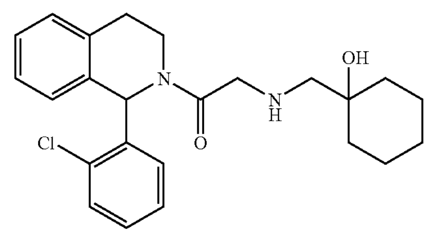 |
| 206 | OX | 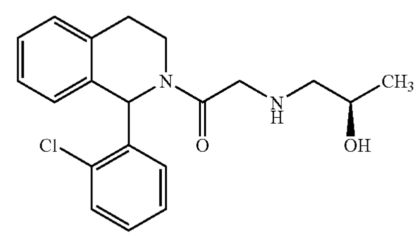 |
| 207 | OX | 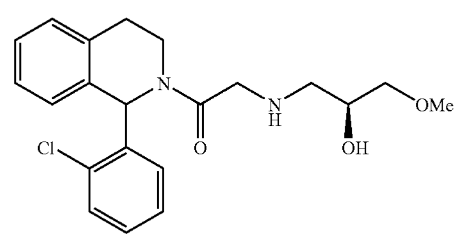 |
| 208 | OX | 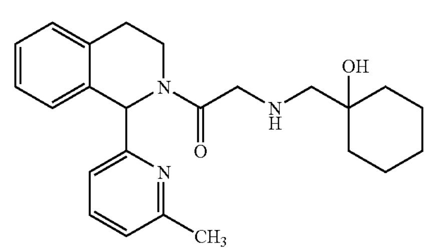 |

TABLE 61

| Ex | salt | STRUCTURE |
|---|---|---|
| 209 | FM | 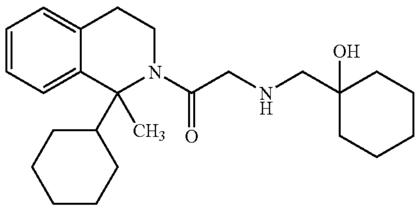 |
| 210 | FM | 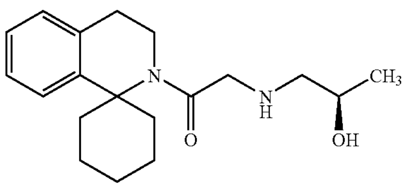 |
| 211 | OX | 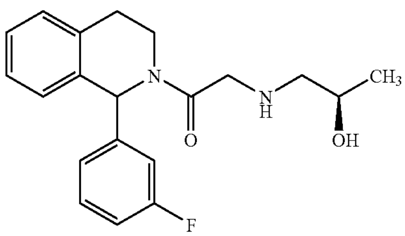 |
| 212 | OX | 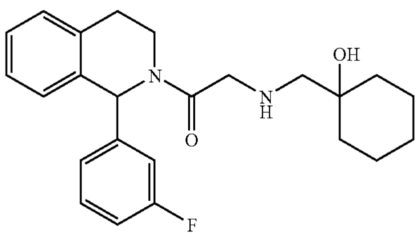 |
| 213 | OX | 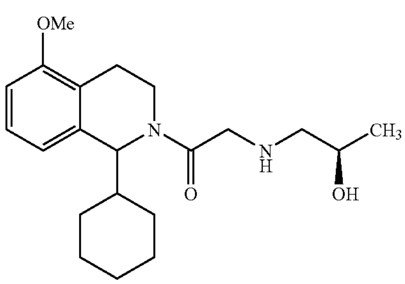 |
| 214 | OX | 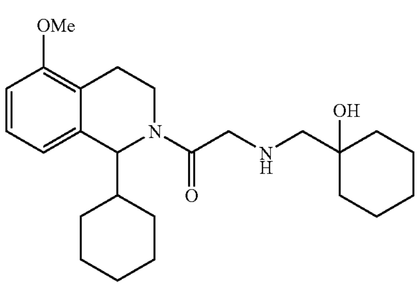 |

TABLE 61-continued

| Ex | salt | STRUCTURE |
|---|---|---|
| 215 | OX | 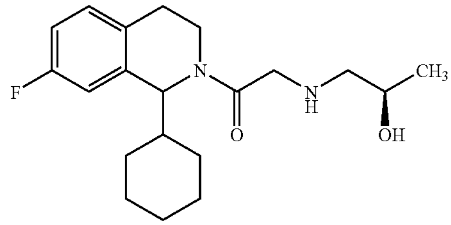 |

TABLE 62

| Ex | salt | STRUCTURE |
|---|---|---|
| 216 | OX | 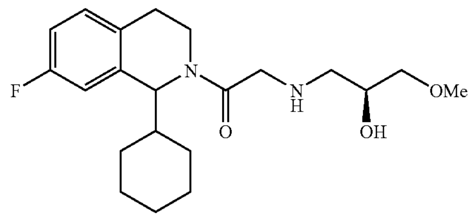 |
| 217 | OX | 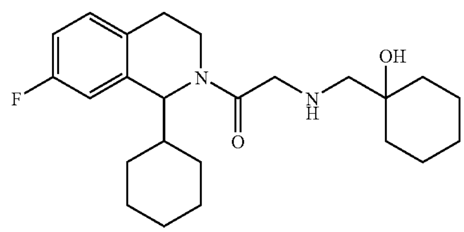 |
| 218 | OX | 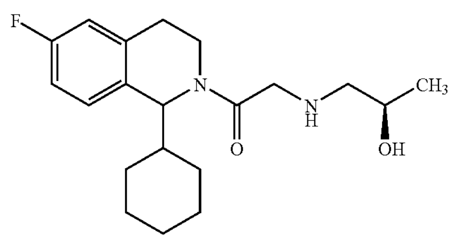 |
| 219 | OX | 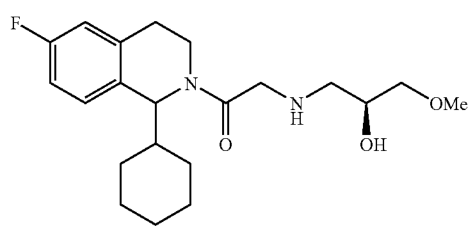 |
| 220 | OX | 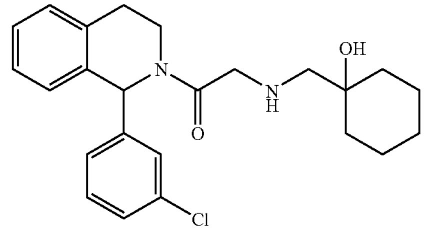 |

TABLE 62-continued

| Ex | salt | STRUCTURE |
|---|---|---|
| 221 | OX | 1-(3-chlorophenyl)-1,2,3,4-tetrahydroisoquinoline with N-C(O)-CH2-NH-CH2-CH(OH)-CH3 |
| 222 | OX | 1-(3-fluorophenyl)-1,2,3,4-tetrahydroisoquinoline with N-C(O)-CH2-NH-CH2-CH(OH)-CH2-OMe |

TABLE 63

| Ex | salt | STRUCTURE |
|---|---|---|
| 223 | OX | 1-(3-chlorophenyl)-1,2,3,4-tetrahydroisoquinoline with N-C(O)-CH2-NH-CH2-CH(OH)-CH2-OMe |
| 224 | OX | 1-(CHEt2)-1,2,3,4-tetrahydroisoquinoline with N-C(O)-CH2-NH-CH2-C(OH)(cyclohexyl) |
| 225 | OX | 1-(1-hydroxycyclohexyl)-1,2,3,4-tetrahydroisoquinoline with N-C(O)-CH2-NH-CH2-CH(OH)-CH3 |
| 226 | OX | 1-(CHEt2)-1,2,3,4-tetrahydroisoquinoline with N-C(O)-CH2-NH-CH2-CH(OH)-CH3 |
| 227 | OX | 1-(CHEt2)-1,2,3,4-tetrahydroisoquinoline with N-C(O)-CH2-NH-CH2-CH(OH)-CH2-OMe |

TABLE 63-continued

| Ex | salt | STRUCTURE |
|---|---|---|
| 228 | OX | 5-fluoro-1-cyclohexyl-1,2,3,4-tetrahydroisoquinoline with N-C(O)-CH2-NH-CH2-CH(OH)-CH3 |
| 229 | OX | 5-fluoro-1-cyclohexyl-1,2,3,4-tetrahydroisoquinoline with N-C(O)-CH2-NH-CH2-CH(OH)-CH2-OMe |

TABLE 64

| Ex | salt | STRUCTURE |
|---|---|---|
| 230 | OX | 5-fluoro-1-cyclohexyl-1,2,3,4-tetrahydroisoquinoline with N-C(O)-CH2-NH-CH2-C(OH)(cyclohexyl) |
| 231 | OX | 1-(pyridin-2-yl)-1,2,3,4-tetrahydroisoquinoline with N-C(O)-CH2-NH-CH2-C(OH)(cyclohexyl) |
| 232 | OX | 1-(6-bromopyridin-2-yl)-1,2,3,4-tetrahydroisoquinoline with N-C(O)-CH2-NH-CH2-CH(OH)-CH3 |

TABLE 64-continued
| Ex | salt | STRUCTURE |
|---|---|---|
| 233 | OX | 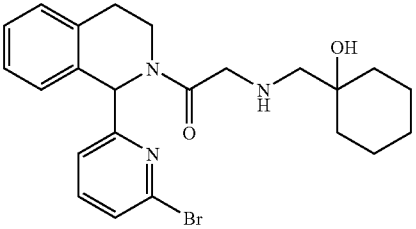 |
| 234 | OX | 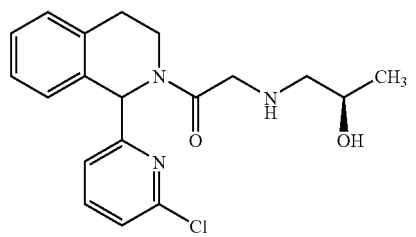 |
| 235 | OX | 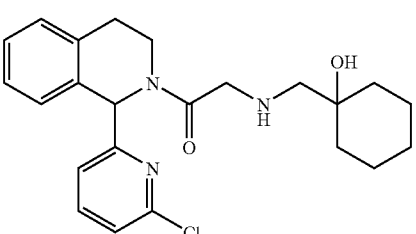 |
| 236 | OX | 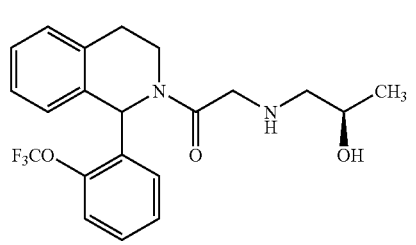 |
TABLE 65
| Ex | salt | STRUCTURE |
|---|---|---|
| 237 | OX | 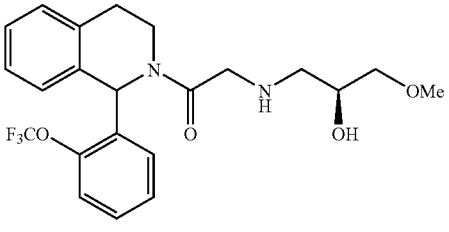 |
| 238 | OX | 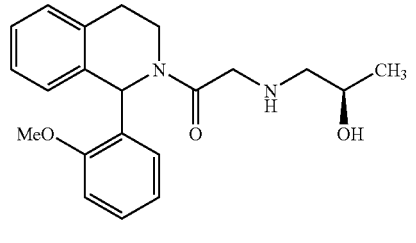 |
TABLE 65-continued
| Ex | salt | STRUCTURE |
|---|---|---|
| 239 | OX | 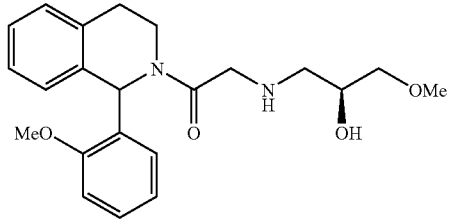 |
| 240 | OX | 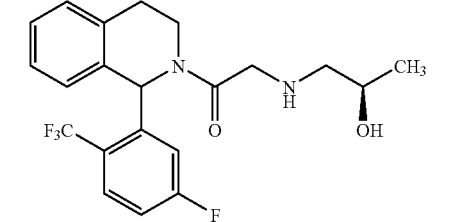 |
| 241 | OX | 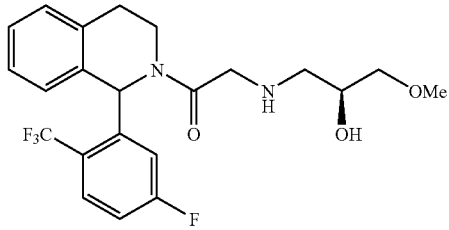 |
| 242 | OX | 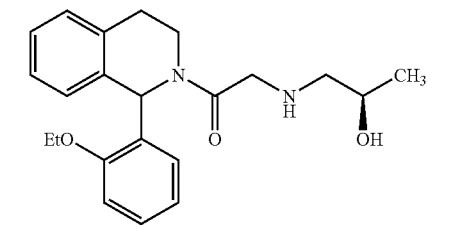 |
| 243 | OX | 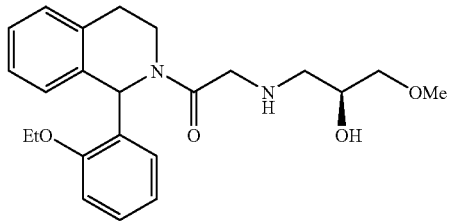 |
TABLE 66
| Ex | salt | STRUCTURE |
|---|---|---|
| 244 | OX | 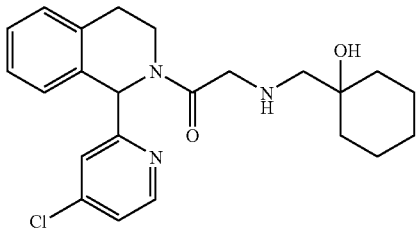 |

TABLE 66-continued

| Ex | salt | STRUCTURE |
|---|---|---|
| 245 | OX | 1-(5-chloropyridin-2-yl)-1,2,3,4-tetrahydroisoquinoline coupled via N-C(O)-CH2-NH-CH(CH3)-CH2OH |
| 246 | OX | 1-(2-ethylphenyl)-1,2,3,4-tetrahydroisoquinoline coupled via N-C(O)-CH2-NH-CH2-CH(OH)-CH3 |
| 247 | OX | 1-(2-ethylphenyl)-1,2,3,4-tetrahydroisoquinoline coupled via N-C(O)-CH2-NH-CH2-CH(OH)-CH2-OMe |
| 249 | OX | 6-cyano-1-cyclohexyl-1,2,3,4-tetrahydroisoquinoline coupled via N-C(O)-CH2-NH-CH2-CH(OH)-CH2-OMe |
| 250 | OX | 6-cyano-1-cyclohexyl-1,2,3,4-tetrahydroisoquinoline coupled via N-C(O)-CH2-NH-CH(CH3)-CH2OH |

TABLE 67

| Ex | salt | STRUCTURE |
|---|---|---|
| 252 | OX | 1-(2-(methylthio)phenyl)-1,2,3,4-tetrahydroisoquinoline coupled via N-C(O)-CH2-NH-CH2-CH(OH)-CH3 |
| 253 | OX | 1-(2-(methylthio)phenyl)-1,2,3,4-tetrahydroisoquinoline coupled via N-C(O)-CH2-NH-CH2-CH(OH)-CH2-OMe |
| 254 | OX | 1-(2-methoxy-5-fluorophenyl)-1,2,3,4-tetrahydroisoquinoline coupled via N-C(O)-CH2-NH-CH2-CH(OH)-CH3 |
| 255 | OX | 1-(2-methoxy-5-fluorophenyl)-1,2,3,4-tetrahydroisoquinoline coupled via N-C(O)-CH2-NH-CH2-CH(OH)-CH2-OMe |
| 256 | OX | 1-tert-butyl-1,2,3,4-tetrahydroisoquinoline coupled via N-C(O)-CH2-NH-CH2-(1-hydroxycyclohexyl) |
| 257 | OX | 1-tert-butyl-1,2,3,4-tetrahydroisoquinoline coupled via N-C(O)-CH2-NH-CH2-CH(OH)-CH3 |
| 258 | OX | 1-tert-butyl-1,2,3,4-tetrahydroisoquinoline coupled via N-C(O)-CH2-NH-CH2-CH(OH)-CH2-OMe |
| 259 | OX | 1-isopropyl-1,2,3,4-tetrahydroisoquinoline coupled via N-C(O)-CH2-NH-CH2-(1-hydroxycyclohexyl) |

TABLE 68

| Ex | salt | STRUCTURE |
|---|---|---|
| 260 | OX | (tetrahydroisoquinoline with iPr substituent)-C(=O)-CH2-NH-CH2-CH(OH)-CH3 |
| 261 | OX | (tetrahydroisoquinoline with iPr substituent)-C(=O)-CH2-NH-CH2-CH(OH)-CH2-OMe |
| 262 | FM | (6-MeO-tetrahydroisoquinoline spiro tetrahydropyran)-C(=O)-CH2-NH-CH2-(1-hydroxycyclohexyl) |
| 263 | FM | (methylenedioxy-tetrahydroisoquinoline with cyclohexyl)-C(=O)-CH2-NH-CH2-CH(OH)-CH3 |
| 264 | OX | (tetrahydroisoquinoline with tetrahydropyran-4-yl)-C(=O)-CH2-NH-CH2-(1-hydroxycyclohexyl) |
| 265 | OX | (tetrahydroisoquinoline with tetrahydropyran-4-yl)-C(=O)-CH2-NH-CH2-CH(OH)-CH3 |
| 266 | OX | (tetrahydroisoquinoline with tetrahydropyran-4-yl)-C(=O)-CH2-NH-CH2-CH(OH)-CH2-OMe |

TABLE 69
| Ex | salt | STRUCTURE |
|---|---|---|
| 267 | OX | 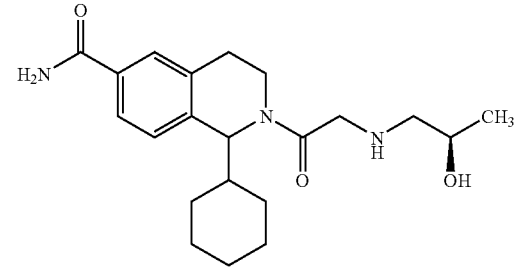 |
| 268 |  | 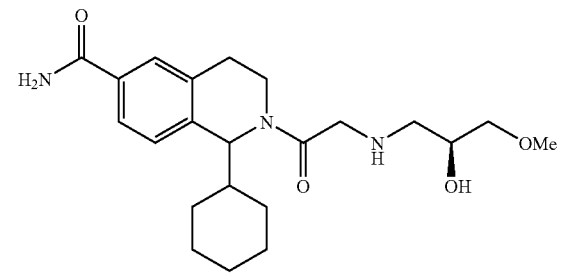 |
| 269 | OX | 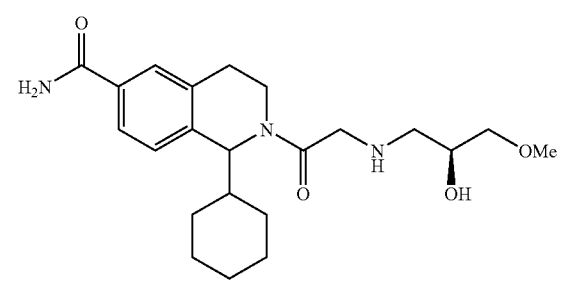 |
| 270 | OX | 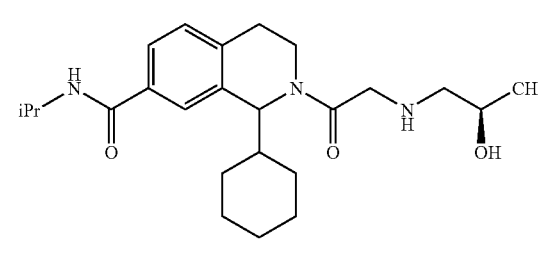 |
| 271 | OX | 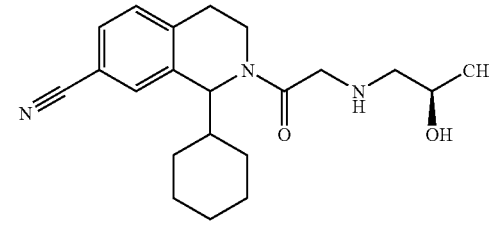 |
| 272 | OX | 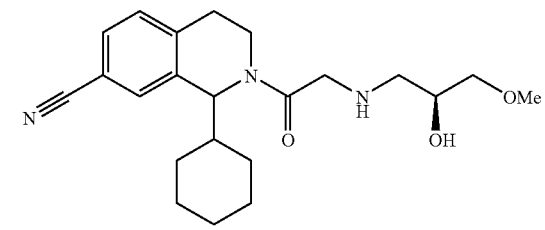 |

TABLE 70

| Ex | salt | STRUCTURE |
|---|---|---|
| 273 | OX | 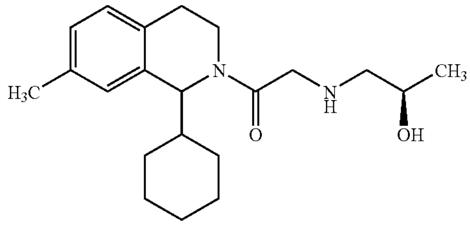 |
| 274 | OX | 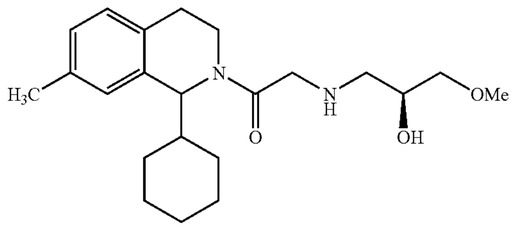 |
| 275 | OX | 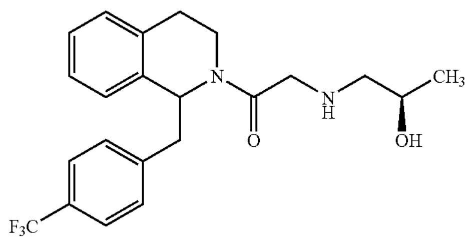 |
| 276 | OX | 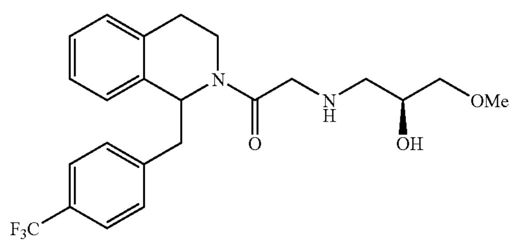 |
| 277 | OX | 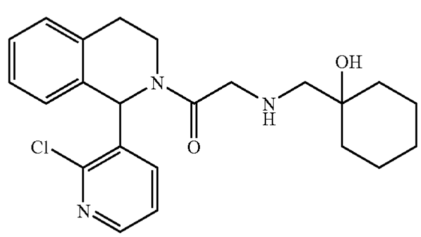 |
| 278 | FM | 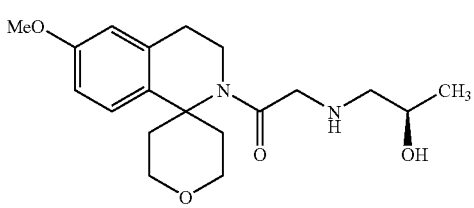 |

TABLE 70-continued

| Ex | salt | STRUCTURE |
|---|---|---|
| 279 | OX | 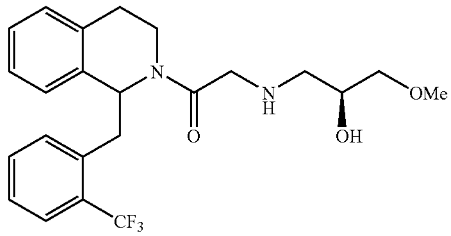 |

TABLE 71

| Ex | salt | STRUCTURE |
|---|---|---|
| 280 | FM | 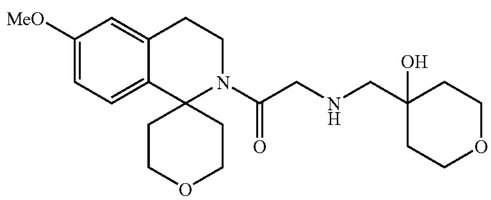 |
| 281 | OX | 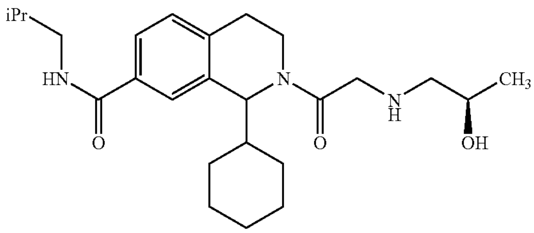 |
| 282 | OX | 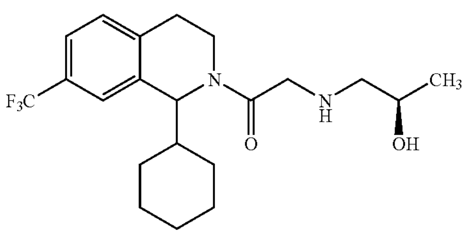 |
| 283 | OX | 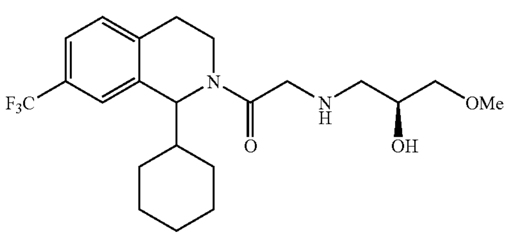 |
| 284 | OX | 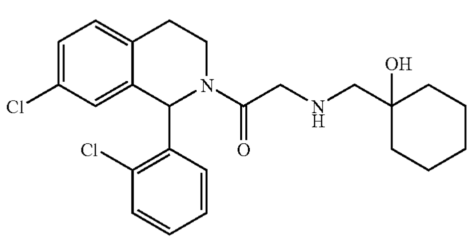 |

147
148
TABLE 71-continued
| Ex | salt | STRUCTURE |
|----|------|-----------|
| 285 | OX | 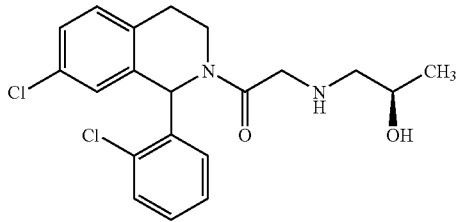 |
| 286 | OX | 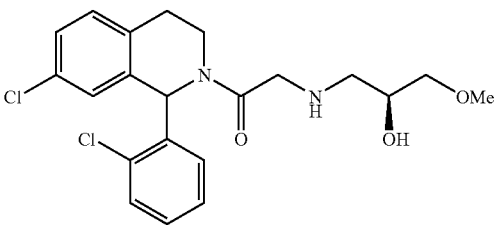 |
| 287 | OX | 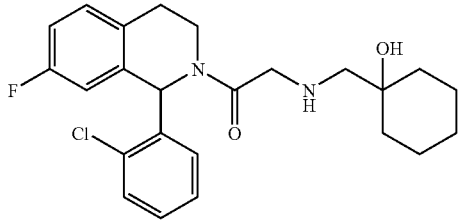 |
TABLE 72
| Ex | salt | STRUCTURE |
|----|------|-----------|
| 288 | OX | 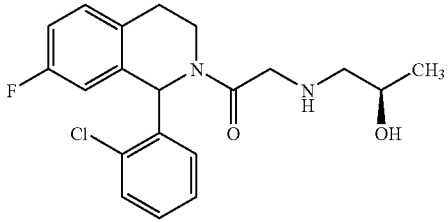 |
| 289 | OX | 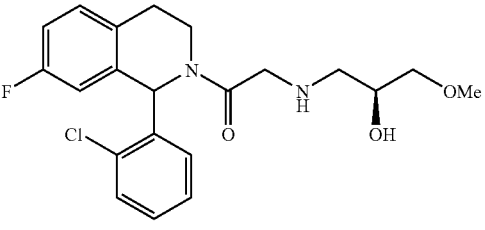 |
| 290 | FM | 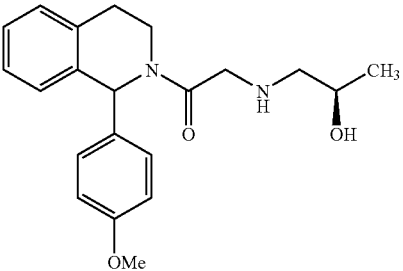 |

TABLE 72-continued
| Ex | salt | STRUCTURE |
|---|---|---|
| 291 | FM | 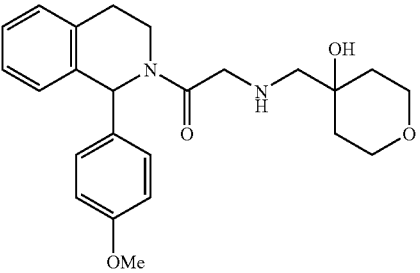 |
| 292 | OX | 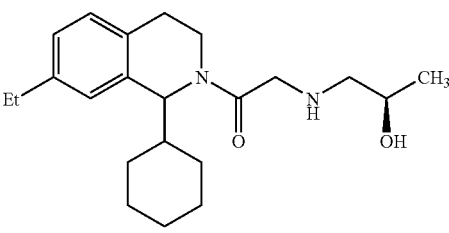 |
| 293 | OX | 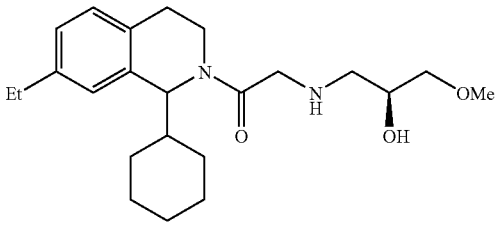 |
| 294 | OX | 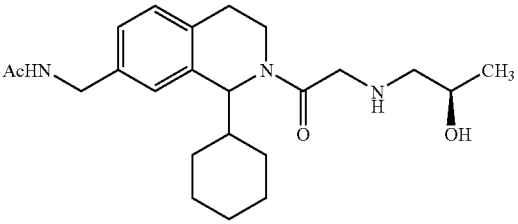 |
| 295 | OX | 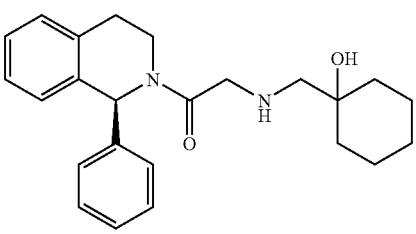 |
TABLE 73
| Ex | salt | STRUCTURE |
|---|---|---|
| 296 | OX | 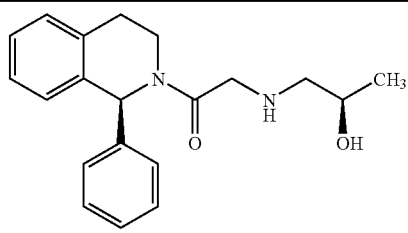 |

TABLE 73-continued

| Ex | salt | STRUCTURE |
|---|---|---|
| 297 | OX | 1-phenyl-tetrahydroisoquinoline-N-C(O)-CH₂-NH-CH₂-CH(OH)-CH₂-OMe (S-config at OH) |
| 298 | OX | 1-cyclopentyl-tetrahydroisoquinoline-N-C(O)-CH₂-NH-CH₂-C(OH)(cyclohexyl) |
| 299 | OX | 1-cyclopentyl-tetrahydroisoquinoline-N-C(O)-CH₂-NH-CH₂-CH(OH)-CH₃ (S) |
| 300 | OX | 1-cyclopentyl-tetrahydroisoquinoline-N-C(O)-CH₂-NH-CH₂-CH(OH)-CH₂-OMe (S) |
| 301 | OX | 1-adamantyl-tetrahydroisoquinoline-N-C(O)-CH₂-NH-CH₂-CH(OH)-CH₃ (S) |
| 302 | OX | 7-AcNHCH₂-1-cyclohexyl-tetrahydroisoquinoline-N-C(O)-CH₂-NH-CH₂-C(OH)(cyclohexyl) |

TABLE 73-continued

| Ex | salt | STRUCTURE |
|---|---|---|
| 303 | OX | (iPr-C(O)-NH-CH2- attached to tetrahydroisoquinoline with cyclohexyl at 1-position, N-C(O)-CH2-NH-CH2-CH(OH)-CH3 (S)) |

TABLE 74

| Ex | salt | STRUCTURE |
|---|---|---|
| 304 | OX | 1-(3-(trifluoromethyl)benzyl)-tetrahydroisoquinoline-N-C(O)-CH2-NH-CH2-CH(OH)-CH3 (S) |
| 305 | OX | 1-(3-(trifluoromethyl)benzyl)-tetrahydroisoquinoline-N-C(O)-CH2-NH-CH2-CH(OH)-CH2-OMe (S) |
| 306 | T2 | 1-(2-methoxyphenyl)-tetrahydroisoquinoline-N-C(O)-CH2-NH-CH2-CH(OH)-CH2-OMe (with stereochem) |
| 307 | T1 | 1-(2-methoxyphenyl)-tetrahydroisoquinoline-N-C(O)-CH2-NH-CH2-CH(OH)-CH2-OMe (with stereochem) |
| 308 | OX | 7-(2-hydroxypropan-2-yl)-1-cyclohexyl-tetrahydroisoquinoline-N-C(O)-CH2-NH-CH2-CH(OH)-CH3 (S) |

TABLE 74-continued

| Ex | salt | STRUCTURE |
|---|---|---|
| 309 | OX | 7-iPr-1-cyclohexyl-tetrahydroisoquinoline-N-C(O)-CH₂-NH-CH₂-CH(OH)-CH₃ (2S) |
| 310 | FM | 1-(4-methylphenyl)-tetrahydroisoquinoline-N-C(O)-CH₂-NH-CH₂-CH(OH)-CH₃ (2S) |

TABLE 75

| Ex | salt | STRUCTURE |
|---|---|---|
| 311 | OX | 1-(2-methoxyphenyl)-tetrahydroisoquinoline-N-C(O)-CH₂-NH-CH₂-CH(OH)-CH₃ |
| 312 | OX | 1-(2-methoxyphenyl)-tetrahydroisoquinoline-N-C(O)-CH₂-NH-CH₂-CH(OH)-Ph |
| 313 | OX | 1-(4-methylcyclohexyl)-tetrahydroisoquinoline-N-C(O)-CH₂-NH-CH₂-C(OH)(cyclohexyl) |

TABLE 75-continued

| Ex | salt | STRUCTURE |
|---|---|---|
| 314 | OX | 1-(trans-4-methylcyclohexyl)-3,4-dihydroisoquinolin-2(1H)-yl with -C(O)-CH2-NH-CH2-CH(OH)-CH3 |
| 315 | OX | 1-(trans-4-methylcyclohexyl)-3,4-dihydroisoquinolin-2(1H)-yl with -C(O)-CH2-NH-CH2-CH(OH)-CH2-OMe |
| 316 | OX | 6-fluoro-1-iPr-3,4-dihydroisoquinolin-2(1H)-yl with -C(O)-CH2-NH-CH2-C(OH)(cyclohexyl) |
| 317 | OX | 6-fluoro-1-iPr-3,4-dihydroisoquinolin-2(1H)-yl with -C(O)-CH2-NH-CH2-CH(OH)-CH3 |
| 318 | OX | 6-fluoro-1-iPr-3,4-dihydroisoquinolin-2(1H)-yl with -C(O)-CH2-NH-CH2-CH(OH)-CH2-OMe |

TABLE 76

| Ex | salt | STRUCTURE |
|---|---|---|
| 319 | OX | 6-MeO-1-iPr-3,4-dihydroisoquinolin-2(1H)-yl with -C(O)-CH2-NH-CH2-C(OH)(cyclohexyl) |
| 320 | OX | 6-MeO-1-iPr-3,4-dihydroisoquinolin-2(1H)-yl with -C(O)-CH2-NH-CH2-CH(OH)-CH3 |

TABLE 76-continued
| Ex | salt | STRUCTURE |
|---|---|---|
| 321 | OX | 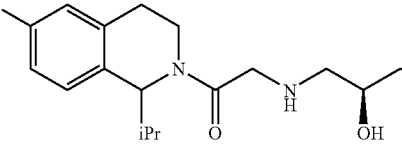 |
| 322 | OX | 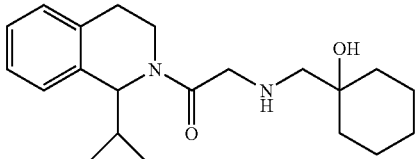 |
| 323 | OX | 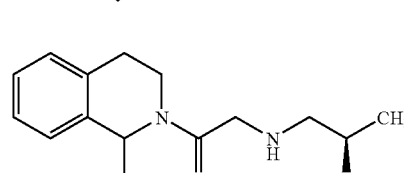 |
| 324 | OX | 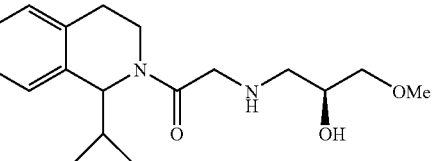 |
| 325 | OX | 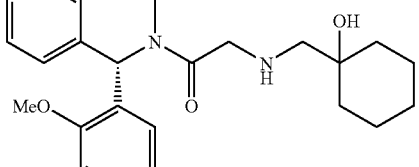 |
| 326 | OX | 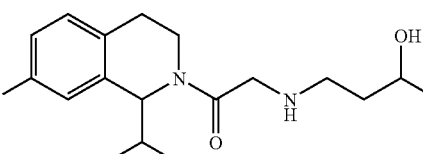 |

TABLE 77

| Ex | salt | STRUCTURE |
|---|---|---|
| 327 | OX | (1-(2-methoxyphenyl)-3,4-dihydroisoquinolin-2(1H)-yl)-CO-CH2CH2-NH-CH2-CH(OH)CH3 |
| 328 | OX | (1-(2-methoxyphenyl)-3,4-dihydroisoquinolin-2(1H)-yl)-CO-CH2-NH-CH2-CH(OH)-Ph |
| 329 | OX | (1-(2-methoxyphenyl)-3,4-dihydroisoquinolin-2(1H)-yl)-CO-CH2-NH-CH2-CH(OH)CH3 |
| 330 | OX | (1-(2-methoxyphenyl)-3,4-dihydroisoquinolin-2(1H)-yl)-CO-CH2-NH-(2-hydroxycyclopentyl) |

TABLE 77-continued

| Ex | salt | STRUCTURE |
|---|---|---|
| 331 | OX | (1-(2-methoxyphenyl)-3,4-dihydroisoquinolin-2(1H)-yl)-CO-CH2-NH-(2-hydroxycyclopentyl) |
| 332 | BR | (1-(2-methoxyphenyl)-3,4-dihydroisoquinolin-2(1H)-yl)-CO-CH2CH2-NH-CH2CH2OH |
| 333 | FM | (1-(2-methoxyphenyl)-3,4-dihydroisoquinolin-2(1H)-yl)-CO-CH2CH2-NH-CH(CH2iPr)-CH2OH |

TABLE 78

| Ex | salt | STRUCTURE |
|---|---|---|
| 334 | OX | (1-phenyl-3,4-dihydroisoquinolin-2(1H)-yl)-CO-CH2CH2-NH-CH(CH2iPr)-CH2OH |
| 335 | OX | (1-phenyl-3,4-dihydroisoquinolin-2(1H)-yl)-CO-CH2CH2-NH-CH(CH2iPr)-CH2OH |

TABLE 78-continued
| Ex | salt | STRUCTURE |
|---|---|---|
| 336 | OX | 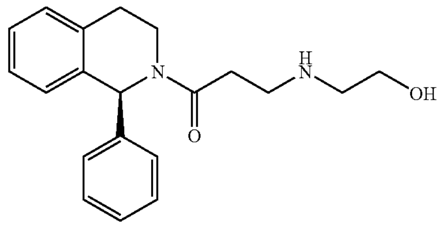 |
| 337 | OX | 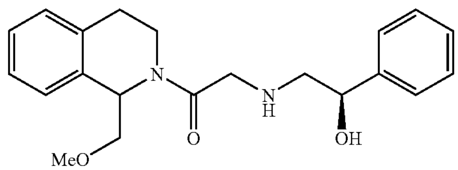 |
| 338 | OX | 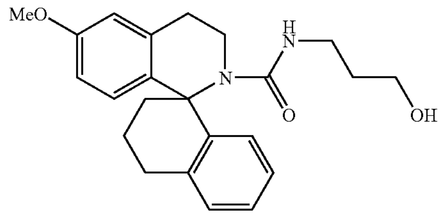 |
| 339 | OX | 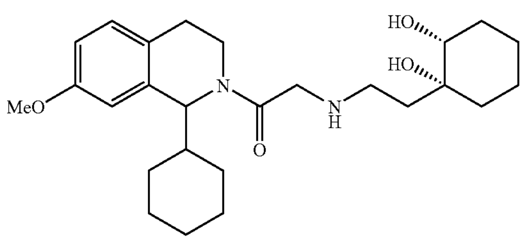 |
| 340 | OX | 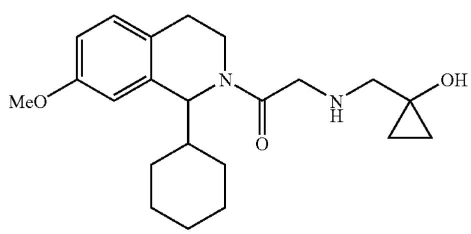 |
| 341 | OX | 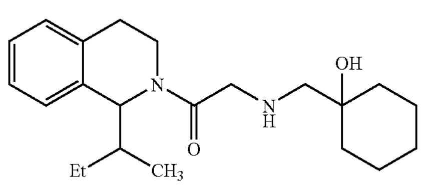 |
TABLE 79
| Ex | salt | STRUCTURE |
|---|---|---|
| 342 | OX | 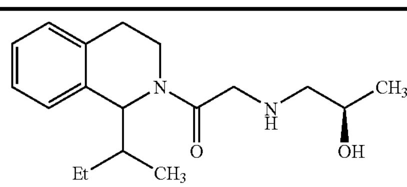 |

TABLE 79-continued
| Ex | salt | STRUCTURE |
|---|---|---|
| 343 | OX | 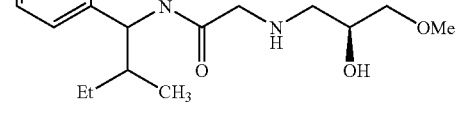 |
| 344 | OX | 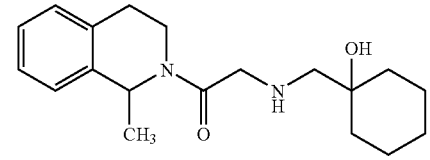 |
| 345 | OX | 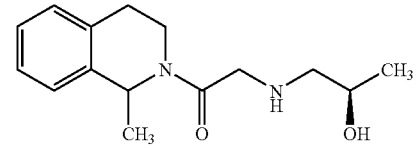 |
| 346 | OX | 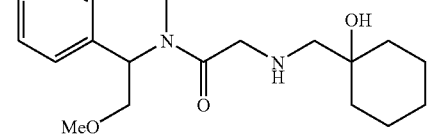 |
| 347 | OX | 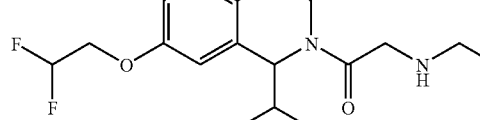 |
| 348 | OX | 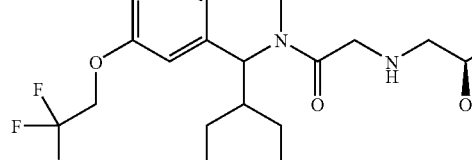 |
| 349 | OX | 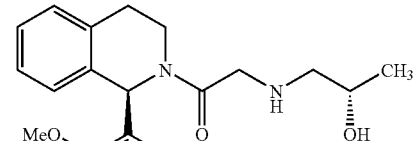 |

TABLE 80

| Ex | salt | STRUCTURE |
|---|---|---|
| 350 | OX | 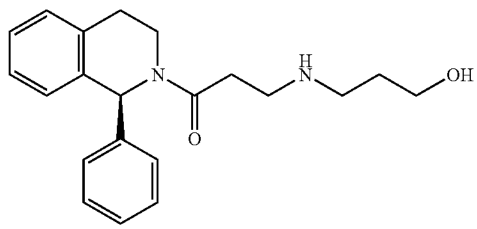 |
| 351 | OX | 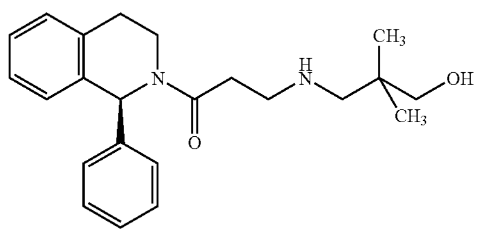 |
| 352 | OX | 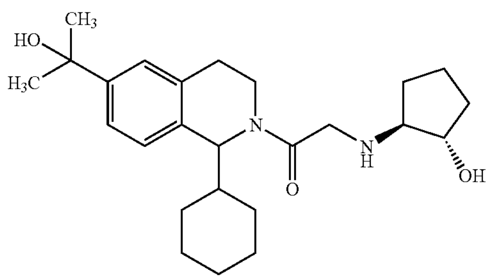 |
| 353 | OX | 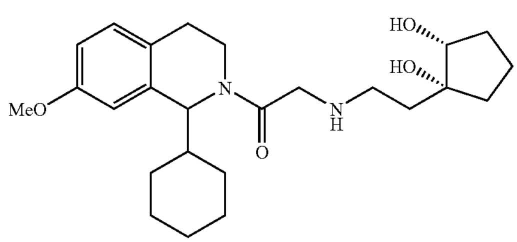 |
| 354 | OX | 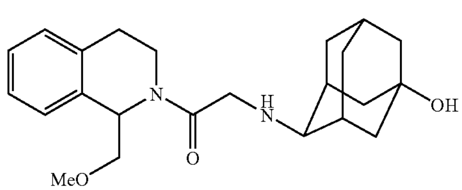 |
| 355 | OX | 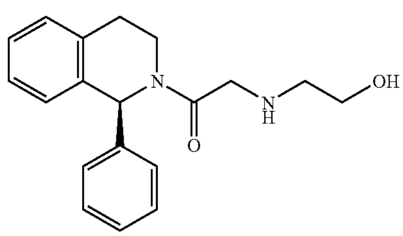 |

TABLE 80-continued

| Ex | salt | STRUCTURE |
|---|---|---|
| 356 | OX | (1S)-1-phenyl-3,4-dihydroisoquinolin-2(1H)-yl-C(=O)-CH2-NH-CH2CH2CH2-OH |

TABLE 81

| Ex | salt | STRUCTURE |
|---|---|---|
| 357 | OX | (1S)-1-phenyl-3,4-dihydroisoquinolin-2(1H)-yl-C(=O)-CH2-NH-CH(CH2iPr)-CH2OH |
| 358 | OX | 1-(MeOCH2)-3,4-dihydroisoquinolin-2(1H)-yl-C(=O)-CH2-NH-CH2-C(OH)(adamantyl) |
| 359 | OX | 1-(MeOCH2)-3,4-dihydroisoquinolin-2(1H)-yl-C(=O)-CH2-NH-CH2-C(OH)(cyclopropyl)2 |
| 360 | OX | 1-(MeOCH2CH2)-3,4-dihydroisoquinolin-2(1H)-yl-C(=O)-CH2-NH-CH2-C(OH)(adamantyl) |
| 361 | OX | 1-(MeOCH2CH2)-3,4-dihydroisoquinolin-2(1H)-yl-C(=O)-CH2-NH-CH2-C(OH)(cyclopropyl)2 |

TABLE 81-continued
| Ex | salt | STRUCTURE |
|---|---|---|
| 362 | OX | 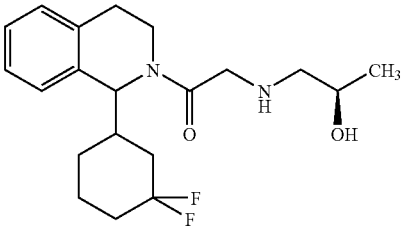 |
| 363 | OX | 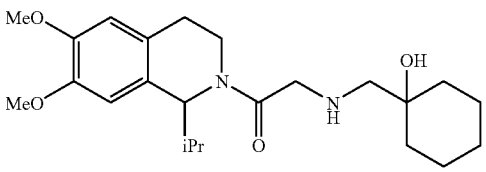 |
| 364 | OX | 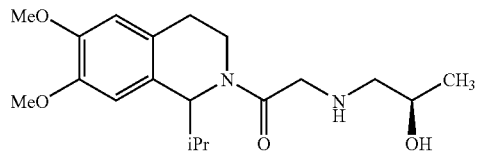 |
TABLE 82
| Ex | salt | STRUCTURE |
|---|---|---|
| 365 | OX | 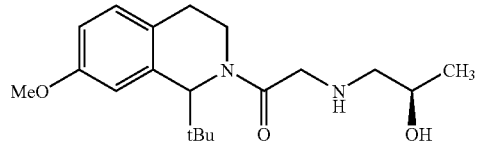 |
| 366 | OX | 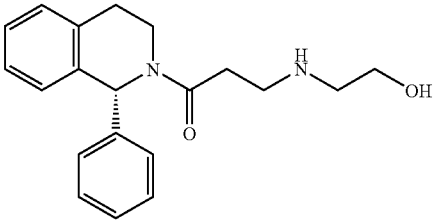 |
| 367 | OX | 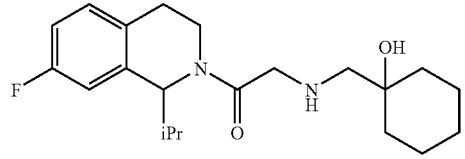 |
| 368 | OX | 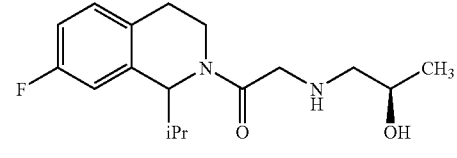 |
| 369 | OX | 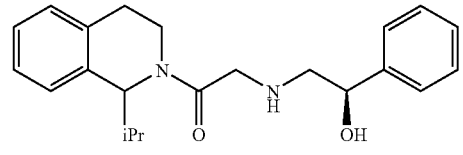 |

TABLE 82-continued

| Ex | salt | STRUCTURE |
|---|---|---|
| 370 | OX | 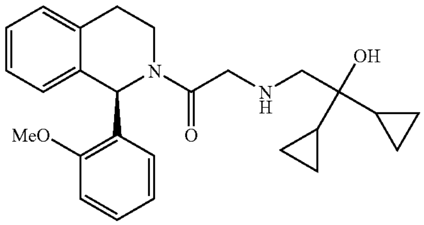 |
| 371 | OX | 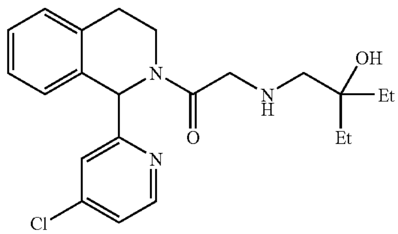 |
| 372 | OX | 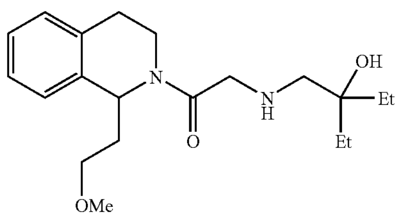 |

TABLE 83

| Ex | salt | STRUCTURE |
|---|---|---|
| 373 | OX | 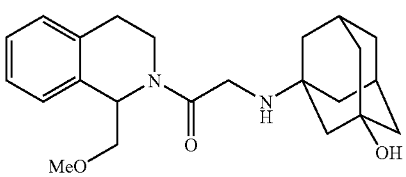 |
| 374 | OX | 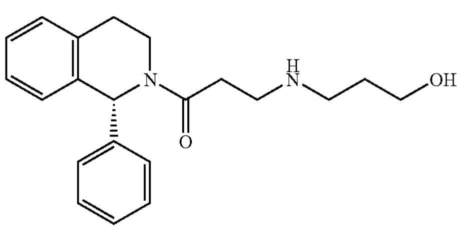 |
| 375 | OX | 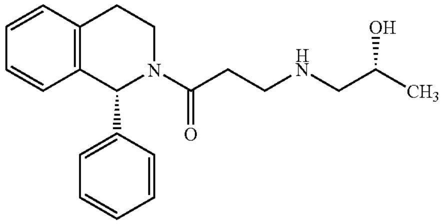 |

TABLE 83-continued

| Ex | salt | STRUCTURE |
|---|---|---|
| 376 | OX | 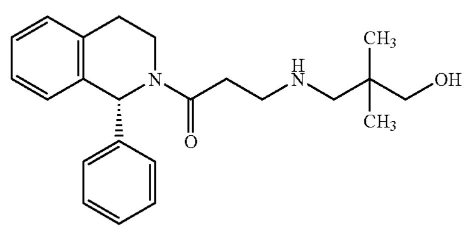 |
| 377 | OX | 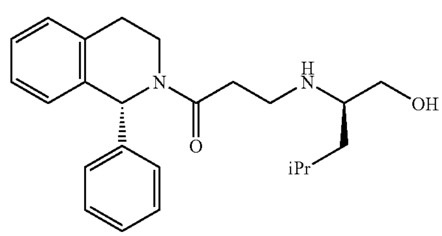 |
| 378 | OX | 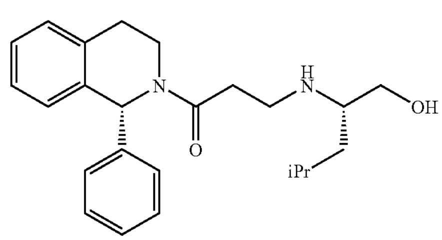 |

TABLE 83-continued
| Ex | salt | STRUCTURE |
|---|---|---|
| 379 | OX | 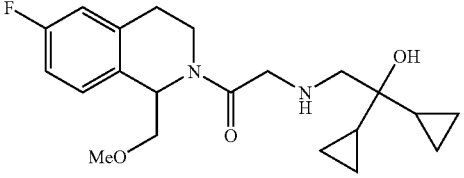 |
| 380 | OX | 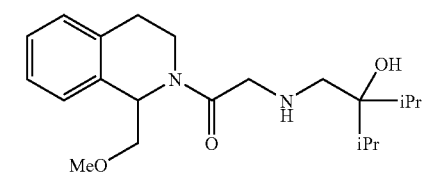 |
TABLE 84
| Ex | salt | STRUCTURE |
|---|---|---|
| 381 | OX | 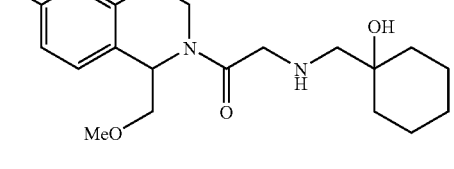 |
| 382 | OX | 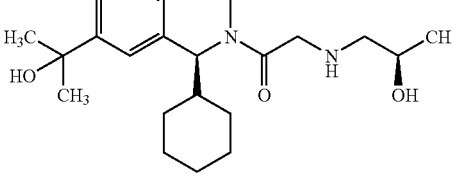 |
| 383 | OX | 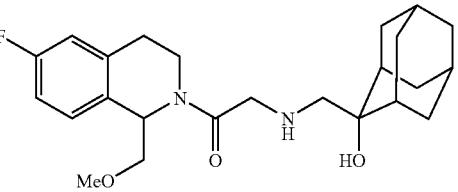 |
| 384 | OX | 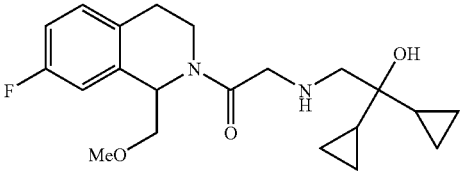 |
| 385 | OX | 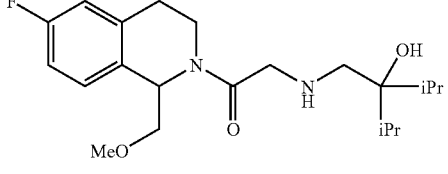 |
TABLE 84-continued
| Ex | salt | STRUCTURE |
|---|---|---|
| 386 | OX | 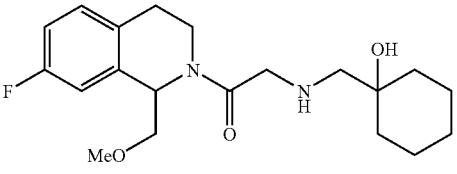 |
| 387 | OX | 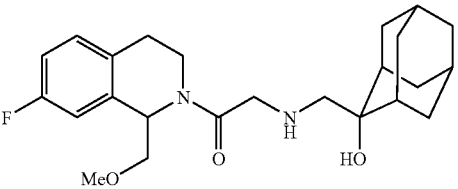 |
| 388 | OX | 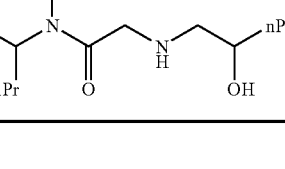 |
TABLE 85
| Ex | salt | STRUCTURE |
|---|---|---|
| 389 | OX | 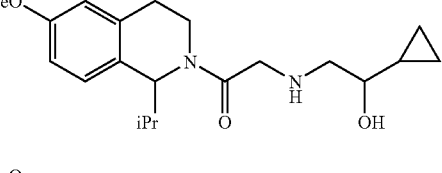 |
| 390 | OX | 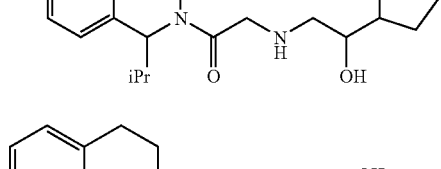 |
| 391 | OX | 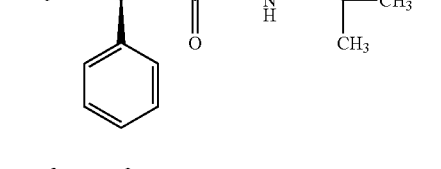 |
| 392 | OX | 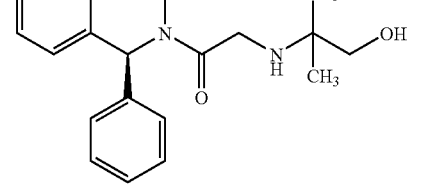 |

TABLE 85-continued

| Ex | salt | STRUCTURE |
|----|------|-----------|
| 393 | OX | 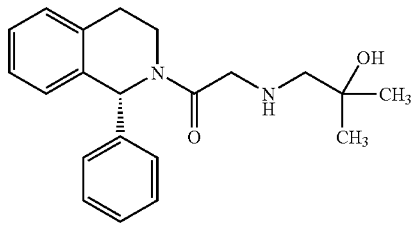 |
| 394 | OX | 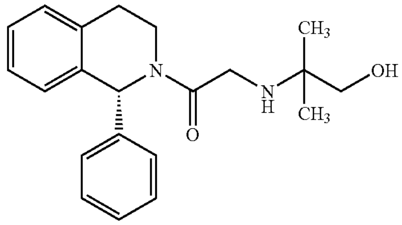 |
| 395 | OX | 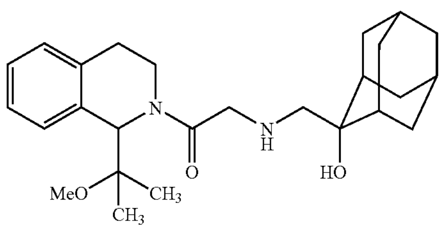 |

TABLE 86

| Ex | salt | STRUCTURE |
|----|------|-----------|
| 396 | OX | |
| 397 | OX | |
| 398 | OX | |
| 399 | OX | 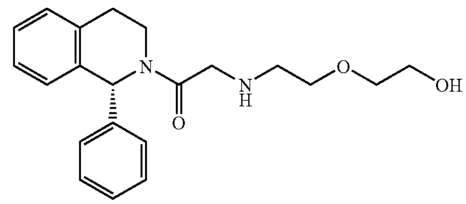 |
| 400 | OX | 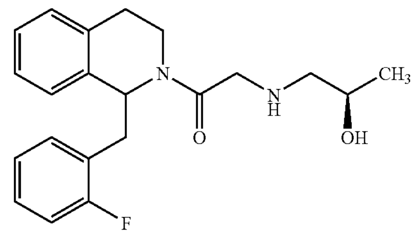 |
| 401 | OX | 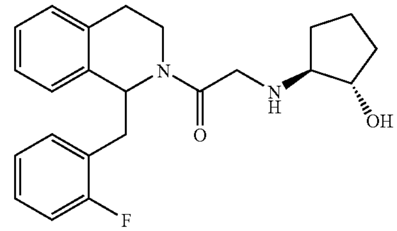 |
| 402 | OX | 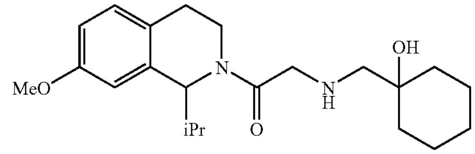 |

TABLE 87

| Ex | salt | STRUCTURE |
|----|------|-----------|
| 403 | OX | 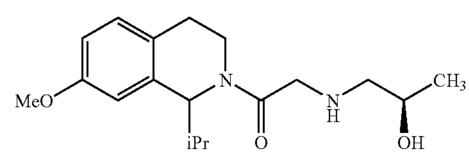 |
| 404 | OX | 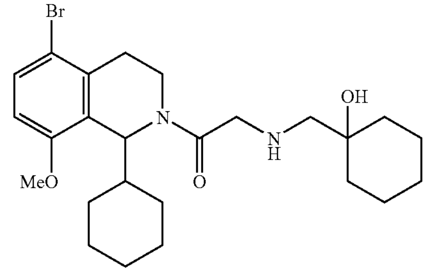 |

TABLE 87-continued

| Ex | salt | STRUCTURE |
|---|---|---|
| 405 | OX | (5-Br, 8-MeO tetrahydroisoquinoline with cyclohexyl at C1, N-CH2-C(O)-NH-CH2-CH(OH)-CH3) |
| 406 | OX | (8-MeO tetrahydroisoquinoline, 1-cyclohexyl, N-CH2-C(O)-NH-CH2-[1-hydroxycyclohexyl]) |
| 407 | OX | (8-MeO tetrahydroisoquinoline, 1-cyclohexyl, N-CH2-C(O)-NH-CH2-CH(OH)-CH3) |
| 408 | OX | (7-(2-hydroxyprop-2-yl) tetrahydroisoquinoline, 1-cyclohexyl, N-CH2-C(O)-NH-(trans-2-hydroxycyclopentyl)) |
| 409 | OX | (7-Et tetrahydroisoquinoline, 1-CH2OMe, N-CH2-C(O)-NH-CH2-[1-hydroxycyclohexyl]) |

TABLE 88

| Ex | salt | STRUCTURE |
|---|---|---|
| 410 | OX | (tetrahydroisoquinoline, 1-(2-methoxybenzyl), N-CH2-C(O)-NH-(trans-2-hydroxycyclopentyl)) |
| 411 | OX | (tetrahydroisoquinoline, 1-(2-methoxybenzyl), N-CH2-C(O)-NH-CH2-CH(OH)-CH3) |
| 412 | OX | (7-(2-hydroxyprop-2-yl) tetrahydroisoquinoline, 1-cyclohexyl (S), N-CH2-C(O)-NH-CH2-CH(OH)-CH3) |
| 413 | OX | (tetrahydroisoquinoline, 1,1-dimethyl, N-CH2-C(O)-NH-CH2-[1-hydroxycyclohexyl]) |
| 414 | OX | (6-MeO tetrahydroisoquinoline, 1-iPr, N-CH2-C(O)-NH-CH2-[1-hydroxycyclohexyl]) |
| 415 | FM | (6-MeO tetrahydroisoquinoline, 1-iPr, N-CH2-C(O)-NH-CH2-[1-hydroxycyclohexyl]) |
| 416 | OX | (7-(2-hydroxyprop-2-yl) tetrahydroisoquinoline, 1-cyclohexyl, N-CH2-C(O)-NH-CH2-(trans-2-hydroxycyclopentyl)) |
| 417 | OX | (7-MeO tetrahydroisoquinoline, 1-cyclohexyl, N-CH2-C(O)-NH-CH2-[1-hydroxycyclopentyl]) |

TABLE 89

| Ex | salt | STRUCTURE |
|---|---|---|
| 418 | OX | 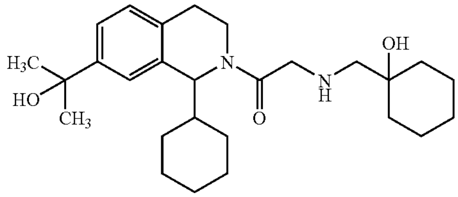 |
| 419 | OX | 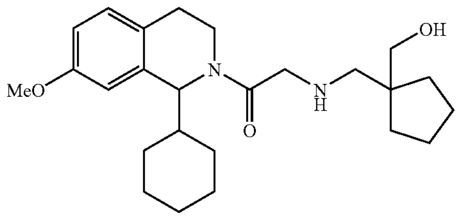 |
| 420 | OX | 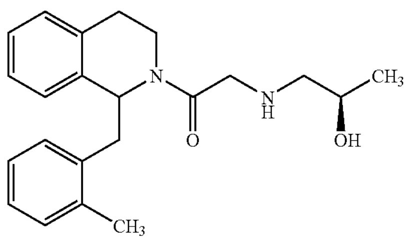 |
| 421 | OX | 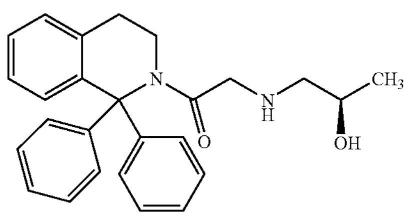 |
| 422 | OX | 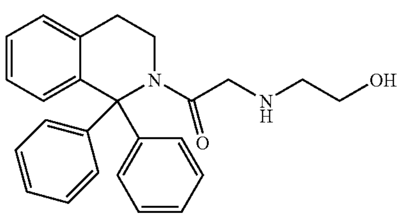 |
| 423 | OX | 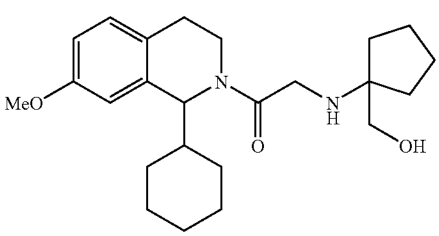 |
| 424 | OX | 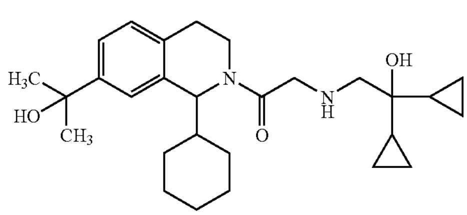 |

TABLE 90

| Ex | salt | STRUCTURE |
|---|---|---|
| 425 | OX | 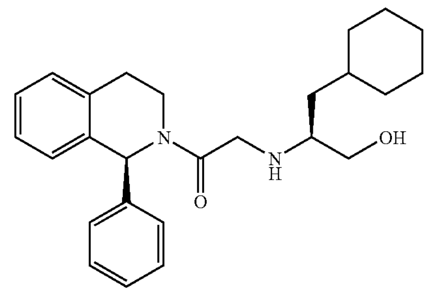 |
| 426 | OX | 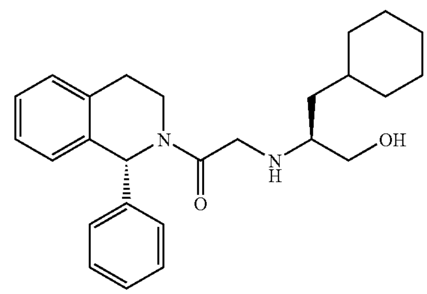 |
| 427 | OX | 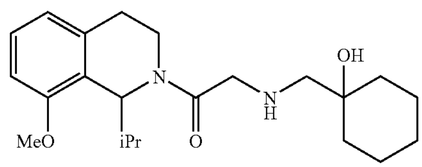 |
| 428 | OX | 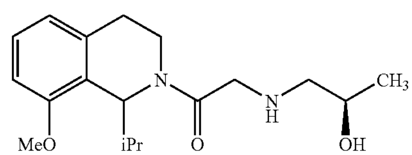 |
| 429 | OX | 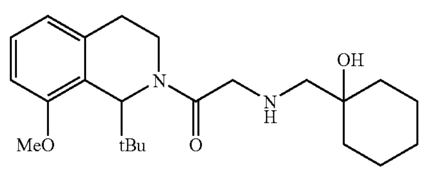 |
| 430 | OX | 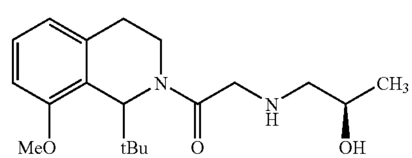 |
| 431 | OX | 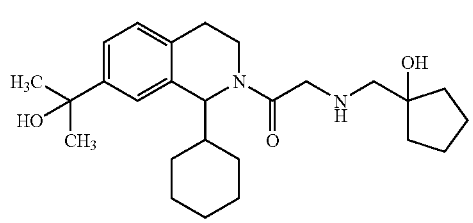 |

TABLE 90-continued
| Ex | salt | STRUCTURE |
|---|---|---|
| 432 | OX | 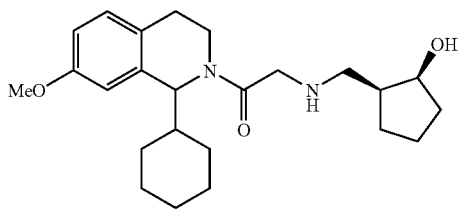 |
TABLE 91
| Ex | salt | STRUCTURE |
|---|---|---|
| 433 | OX | 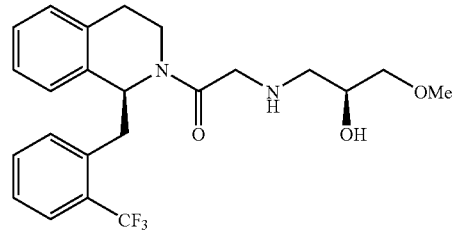 |
| 434 | OX | 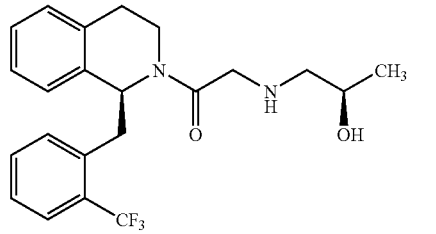 |
| 435 | FM | 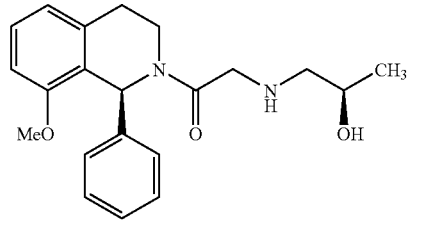 |
| 436 | T2 | 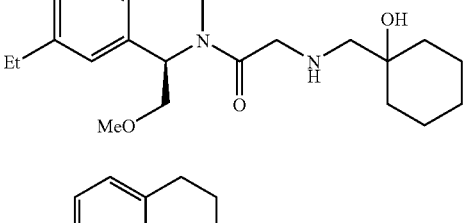 |
| 437 | OX | 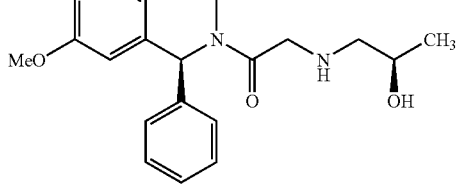 |
TABLE 91-continued
| Ex | salt | STRUCTURE |
|---|---|---|
| 438 | OX | 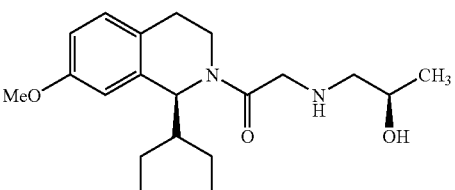 |
| 439 | T1 | 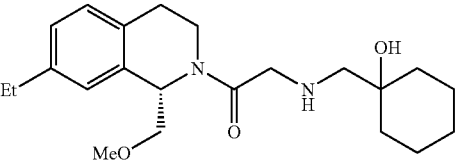 |
TABLE 92
| Ex | salt | STRUCTURE |
|---|---|---|
| 440 | OX | 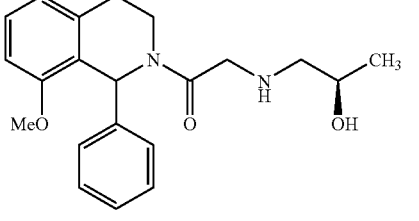 |
| 441 | OX | 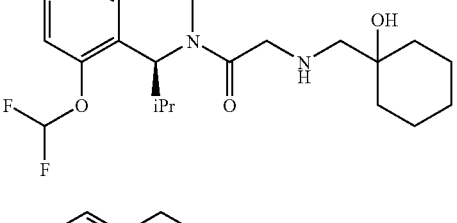 |
| 442 | OX | 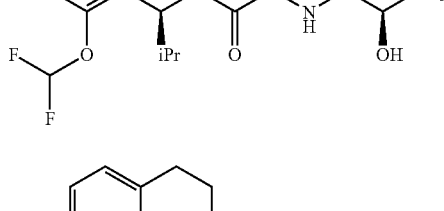 |
| 443 | OX | 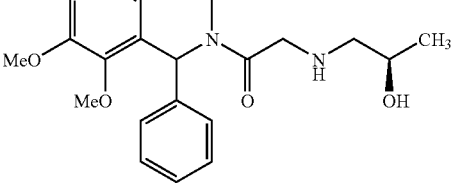 |

TABLE 92-continued

| Ex | salt | STRUCTURE |
|---|---|---|
| 444 | OX | 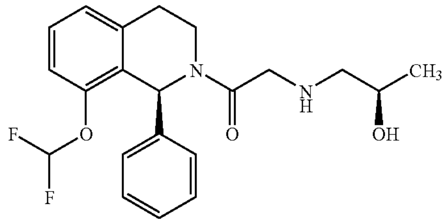 |
| 445 | FM | 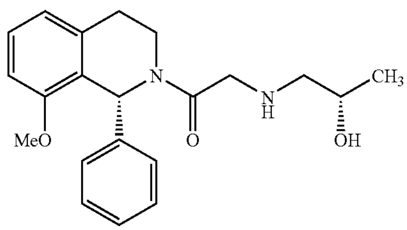 |
| 446 | FM | 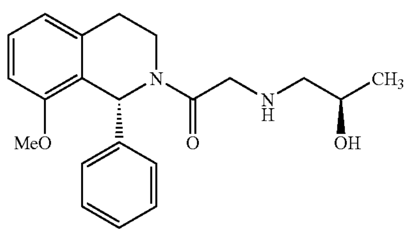 |
| 447 | OX | 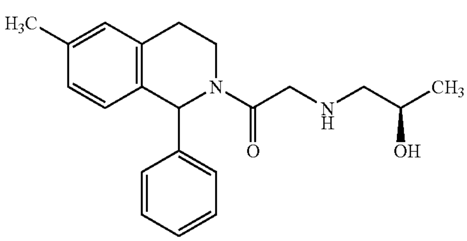 |

TABLE 93

| Ex | salt | STRUCTURE |
|---|---|---|
| 448 | FM | 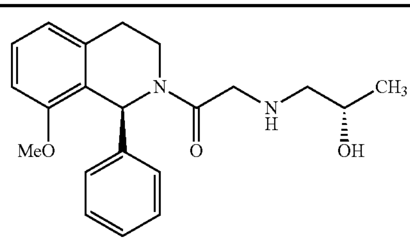 |
| 449 | OX | 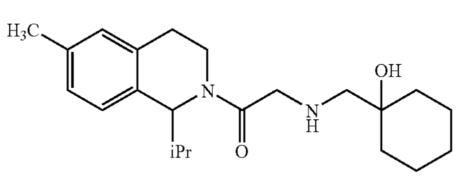 |

TABLE 93-continued

| Ex | salt | STRUCTURE |
|---|---|---|
| 450 | OX | 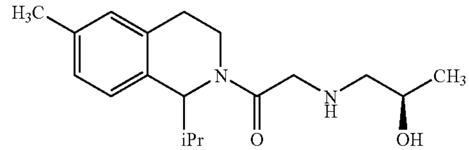 |
| 451 | OX | 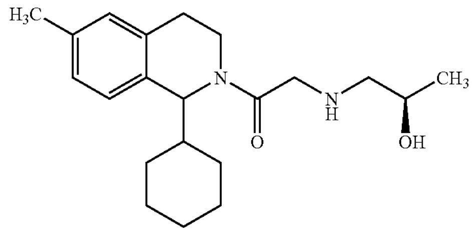 |
| 452 | OX | 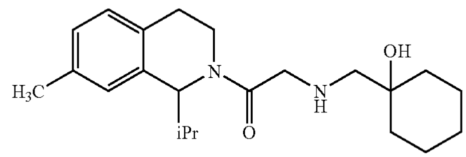 |
| 453 | OX | 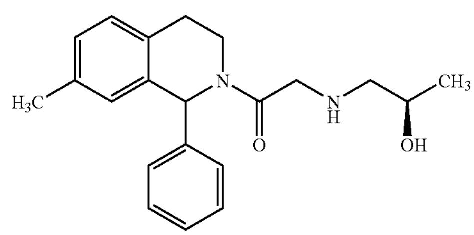 |
| 454 | OX | 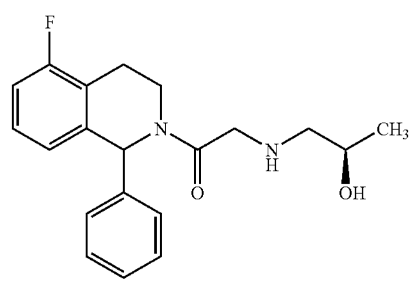 |
| 455 | OX | 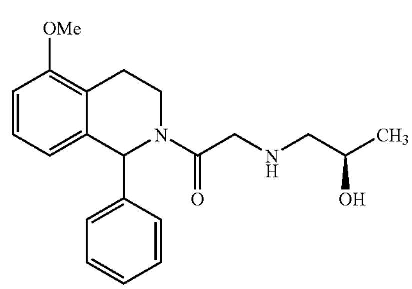 |

TABLE 94

| Ex | salt | STRUCTURE |
|---|---|---|
| 456 | OX | (6-F-1-phenyl-tetrahydroisoquinoline)-N-C(O)-CH2-NH-CH2-CH(OH)-CH3 |
| 457 | OX | (7-F-1-phenyl-tetrahydroisoquinoline)-N-C(O)-CH2-NH-CH2-CH(OH)-CH3 |
| 458 | | (6-MeO-1-(CH2OMe)-tetrahydroisoquinoline)-N-C(O)-CH2-NH-CH2-(1-hydroxycyclohexyl) |
| 459 | OX | (6-MeO-1-(CH2OMe)-tetrahydroisoquinoline)-N-C(O)-CH2-NH-CH2-(1-hydroxycyclohexyl) |
| 460 | | (6-F-1-nPr-tetrahydroisoquinoline)-N-C(O)-CH2-NH-CH2-(1-hydroxycyclohexyl) |
| 461 | OX | (6-F-1-nPr-tetrahydroisoquinoline)-N-C(O)-CH2-NH-CH2-(1-hydroxycyclohexyl) |
| 462 | OX | (5-Me-1-cyclohexyl-tetrahydroisoquinoline)-N-C(O)-CH2-NH-CH2-CH(OH)-CH3 |

TABLE 94-continued

| Ex | salt | STRUCTURE |
|---|---|---|
| 463 | OX | (5-Me-1-iPr-tetrahydroisoquinoline)-N-C(O)-CH2-NH-CH2-(1-hydroxycyclohexyl) |

TABLE 95

| Ex | salt | STRUCTURE |
|---|---|---|
| 464 | OX | (5-Me-1-phenyl-tetrahydroisoquinoline)-N-C(O)-CH2-NH-CH2-CH(OH)-CH3 |
| 465 | FM | (8-MeO-1-phenyl-tetrahydroisoquinoline)-N-C(O)-CH2-NH-CH2-(1-hydroxycyclohexyl) |
| 466 | OX | (5-Me-1-nPr-tetrahydroisoquinoline)-N-C(O)-CH2-NH-CH2-(1-hydroxycyclohexyl) |
| 467 | OX | (5-OMe-1-nPr-tetrahydroisoquinoline)-N-C(O)-CH2-NH-CH2-(1-hydroxycyclohexyl) |
| 468 | | (7-F-1-nPr-tetrahydroisoquinoline)-N-C(O)-CH2-NH-CH2-(1-hydroxycyclohexyl) |

TABLE 95-continued

| Ex | salt | STRUCTURE |
|----|------|-----------|
| 469 | OX | (7-fluoro-1-nPr-tetrahydroisoquinoline)-N-C(O)-CH2-NH-CH2-(1-hydroxycyclohexyl) |
| 470 | OX | (7-methyl-1-nPr-tetrahydroisoquinoline)-N-C(O)-CH2-NH-CH2-(1-hydroxycyclohexyl) |
| 471 | OX | (7-MeO-1-CH2OMe-tetrahydroisoquinoline)-N-C(O)-CH2-NH-CH2-(1-hydroxycyclohexyl) |

TABLE 96

| Ex | salt | STRUCTURE |
|----|------|-----------|
| 472 | OX | (7-MeO-1-nPr-tetrahydroisoquinoline)-N-C(O)-CH2-NH-CH2-(1-hydroxycyclohexyl) |
| 473 | OX | (7-methyl-1-CH2OMe-tetrahydroisoquinoline)-N-C(O)-CH2-NH-CH2-(1-hydroxycyclohexyl) |
| 474 | OX | (5-methyl-1-CH2OMe-tetrahydroisoquinoline)-N-C(O)-CH2-NH-CH2-(1-hydroxycyclohexyl) |
| 475 | OX | (5-OMe-1-CH2OMe-tetrahydroisoquinoline)-N-C(O)-CH2-NH-CH2-(1-hydroxycyclohexyl) |

TABLE 96-continued

| Ex | salt | STRUCTURE |
|----|------|-----------|
| 476 | OX | (5-F-1-nPr-tetrahydroisoquinoline)-N-C(O)-CH2-NH-CH2-(1-hydroxycyclohexyl) |
| 477 | OX | (6-MeO-8-MeO-1-phenyl-tetrahydroisoquinoline)-N-C(O)-CH2-NH-CH2-CH(OH)-CH3 |
| 478 | OX | (5-F-1-CH2OMe-tetrahydroisoquinoline)-N-C(O)-CH2-NH-CH2-(1-hydroxycyclohexyl) |
| 479 | OX | (8-MeO-1-nPr-tetrahydroisoquinoline)-N-C(O)-CH2-NH-CH2-(1-hydroxycyclohexyl) |

TABLE 97

| Ex | salt | STRUCTURE |
|----|------|-----------|
| 480 | OX | (8-MeO-1-CH2OMe-tetrahydroisoquinoline)-N-C(O)-CH2-NH-CH2-(1-hydroxycyclohexyl) |
| 481 | OX | (8-F-1-cyclohexyl-tetrahydroisoquinoline)-N-C(O)-CH2-NH-CH2-(1-hydroxycyclohexyl) |

TABLE 97-continued
| Ex | salt | STRUCTURE |
|---|---|---|
| 482 | OX | 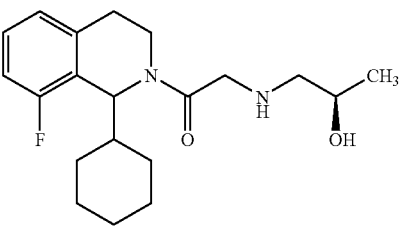 |
| 483 | OX | 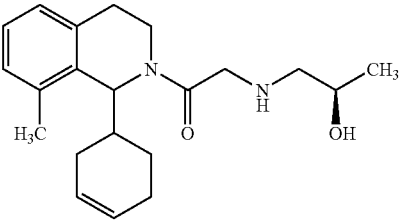 |
| 484 | OX | 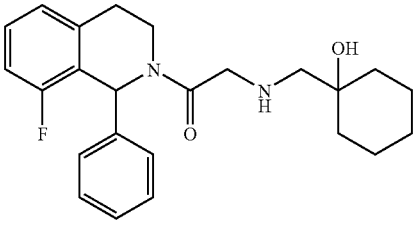 |
| 485 | OX | 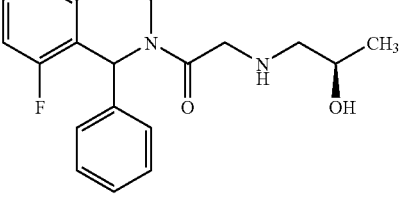 |
| 486 | OX | 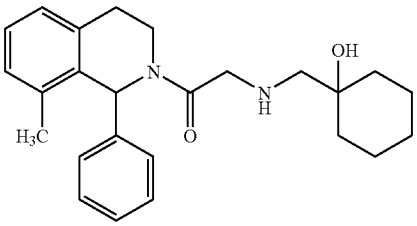 |
| 487 | OX | 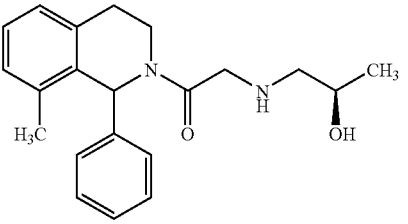 |
TABLE 98
| Ex | salt | STRUCTURE |
|---|---|---|
| 488 | OX | 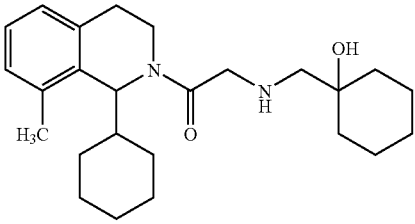 |
| 489 | | 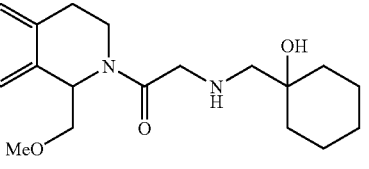 |
| 490 | OX | 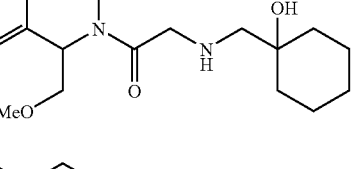 |
| 491 | | 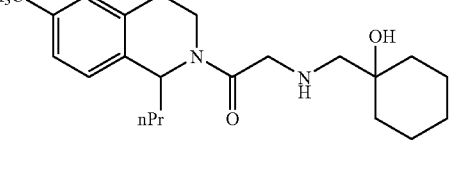 |
| 492 | OX | 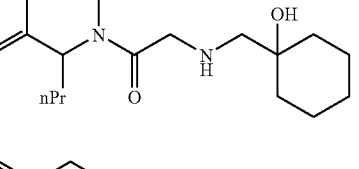 |
| 493 | OX | 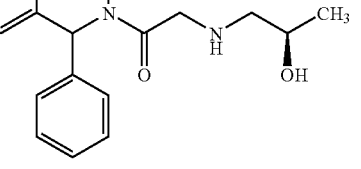 |
| 494 | | 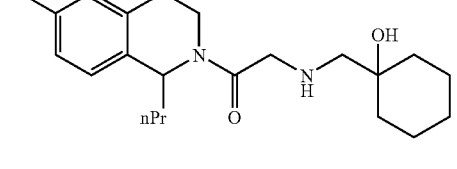 |
| 495 | OX | 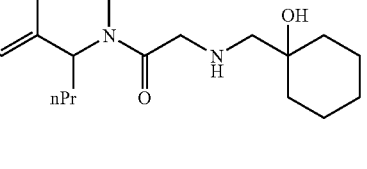 |

TABLE 98-continued

| Ex | salt | STRUCTURE |
|---|---|---|
| 496 | OX | (1-phenyl-3,4-dihydroisoquinolin-2(1H)-yl)acetyl-NH-CH2-CH(iPr)-CH2OH |

TABLE 99

| Ex | salt | STRUCTURE |
|---|---|---|
| 497 | OX | (1-(pyridin-2-yl)-3,4-dihydroisoquinolin-2(1H)-yl)acetyl-NH-CH2-CH(OH)-CH3 |
| 498 | OX | (7-MeO-1-phenyl-3,4-dihydroisoquinolin-2(1H)-yl)acetyl-NH-CH2-CH(OH)-(6-methylpyridin-2-yl) |
| 499 | OX | (7-MeO-1-phenyl-3,4-dihydroisoquinolin-2(1H)-yl)acetyl-NH-CH2-CH(OH)-(6-methoxypyridin-2-yl) |
| 500 | OX | (1-(2-methylphenyl)-3,4-dihydroisoquinolin-2(1H)-yl)acetyl-NH-CH2-CH(OH)-CF3 |
| 501 | OX | (8-MeO-1-(iPr-CH2)-3,4-dihydroisoquinolin-2(1H)-yl)acetyl-NH-CH2-C(OH)(cyclohexyl) |

TABLE 99-continued

| Ex | salt | STRUCTURE |
|---|---|---|
| 502 | OX | (1-(2-MeO-phenyl)-3,4-dihydroisoquinolin-2(1H)-yl)acetyl-NH-CH2-CH(OH)-CF3 |
| 503 | OX | (8-MeO-1-phenyl-3,4-dihydroisoquinolin-2(1H)-yl)acetyl-NH-CH2-CH(OH)-CF3 |

TABLE 100

| Ex | salt | STRUCTURE |
|---|---|---|
| 504 | OX | (7-methyl-1-(EtO-CH2)-3,4-dihydroisoquinolin-2(1H)-yl)acetyl-NH-CH2-C(OH)(cyclohexyl) |
| 505 | OX | (7-MeO-1-(iPr-CH2)-3,4-dihydroisoquinolin-2(1H)-yl)acetyl-NH-CH2-C(OH)(cyclohexyl) |
| 506 | OX | (7-methyl-1-(EtO-CH2)-3,4-dihydroisoquinolin-2(1H)-yl)acetyl-NH-CH2-CH(OH)-CH3 |
| 507 | OX | (7-MeO-1-(iPr-CH2)-3,4-dihydroisoquinolin-2(1H)-yl)acetyl-NH-CH2-CH(OH)-CH3 |
| 508 | OX | (7-MeO-1-cyclohexyl-3,4-dihydroisoquinolin-2(1H)-yl)acetyl-NH-CH2-CH(OH)-CF3 |

TABLE 100-continued

| Ex | salt | STRUCTURE |
|---|---|---|
| 509 | OX | 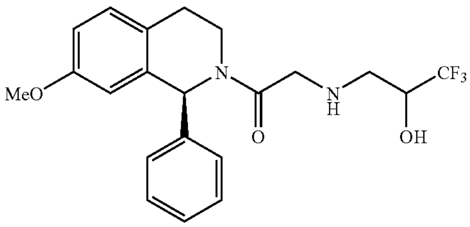 |
| 510 | OX | 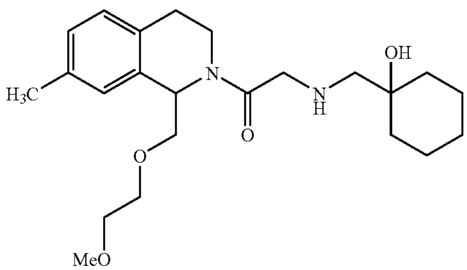 |

TABLE 101

| Ex | salt | STRUCTURE |
|---|---|---|
| 511 | | |
| 512 | | |
| 513 | | |
| 514 | | 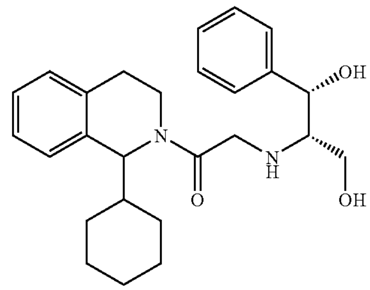 |
| 515 | | 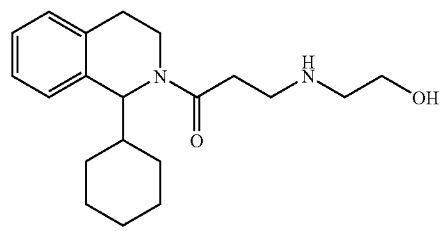 |
| 516 | | 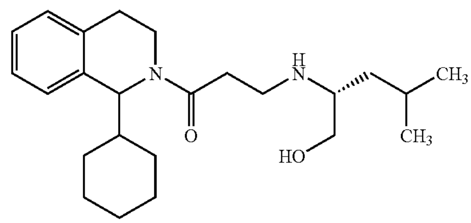 |
| 517 | | 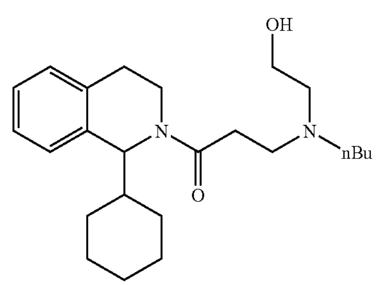 |

TABLE 102

| Ex | salt | STRUCTURE |
|---|---|---|
| 518 | | 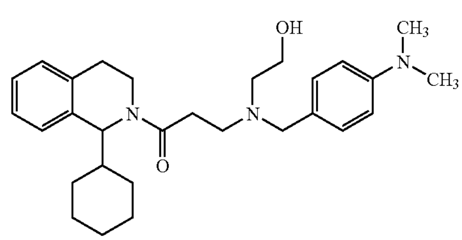 |

TABLE 102-continued

| Ex | salt | STRUCTURE |
|---|---|---|
| 519 | | 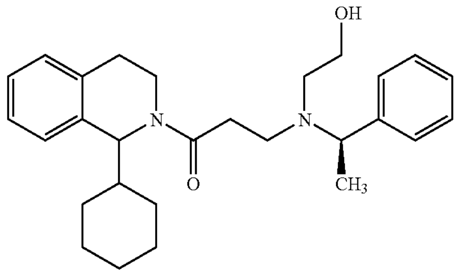 |
| 520 | | 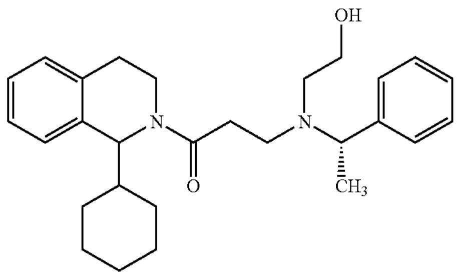 |
| 521 | | 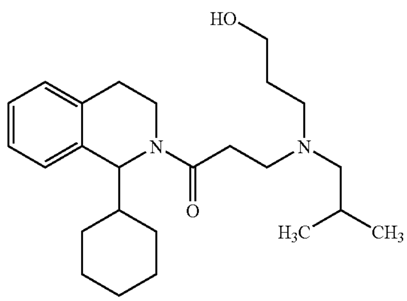 |
| 522 | | 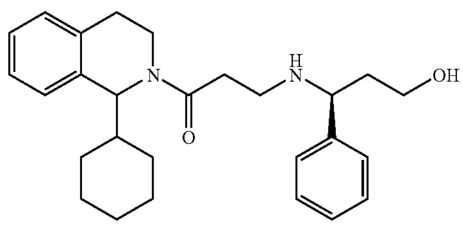 |
| 523 | | 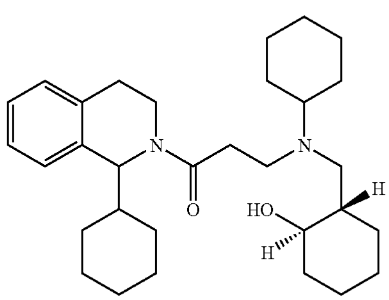 |
| 524 | | 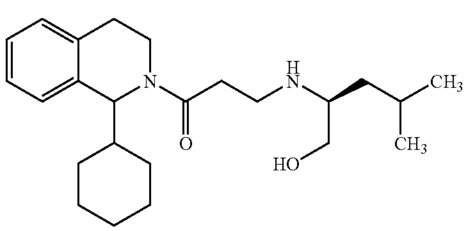 |

TABLE 103

| Ex | salt | STRUCTURE |
|---|---|---|
| 525 | | 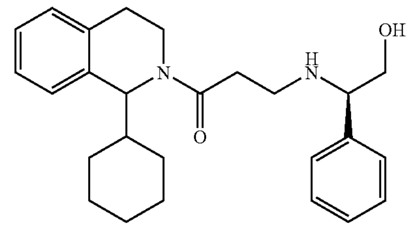 |
| 526 | | 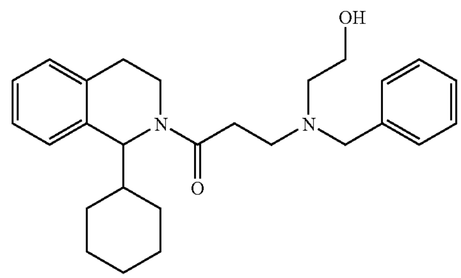 |
| 527 | | 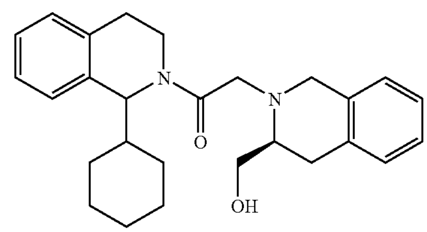 |
| 528 | | 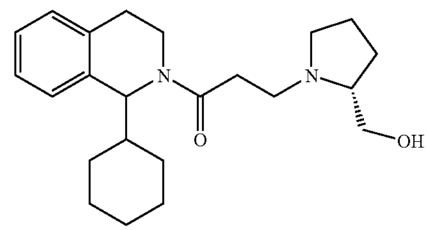 |
| 529 | | 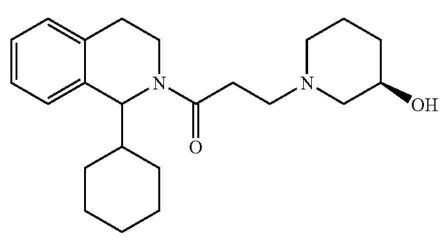 |
| 530 | | 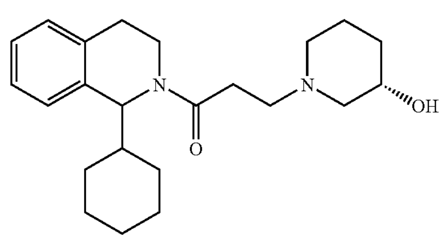 |

TABLE 103-continued
| Ex | salt | STRUCTURE |
|---|---|---|
| 531 | | 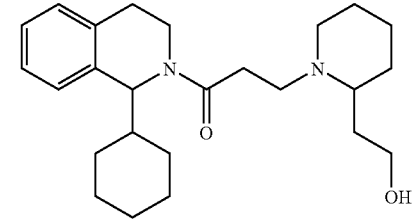 |
TABLE 104
| Ex | salt | STRUCTURE |
|---|---|---|
| 532 | | 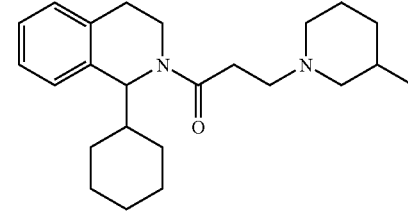 |
| 533 | | 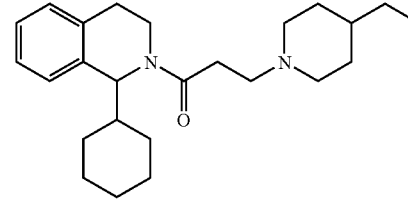 |
| 534 | | 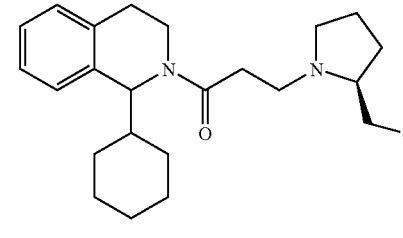 |
| 535 | | 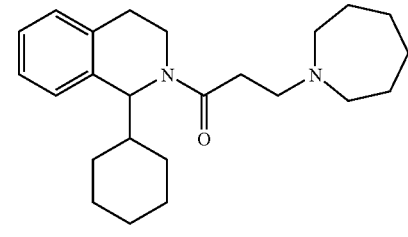 |
| 536 | | 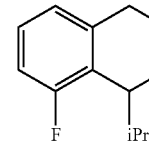 |
TABLE 105
| Ex | salt | STRUCTURE |
|---|---|---|
| 537 | OX | 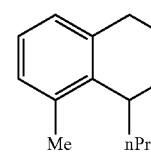 |
| 538 | OX | 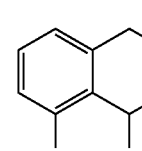 |
| 539 | OX | 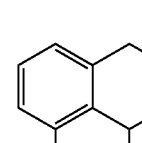 |
| 540 | OX | 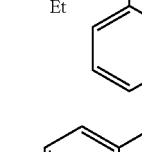 |
| 541 | OX | 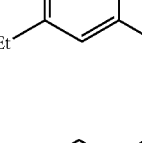 |
| 542 | OX | 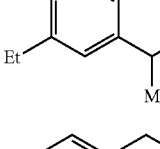 |
| 543 | OX | 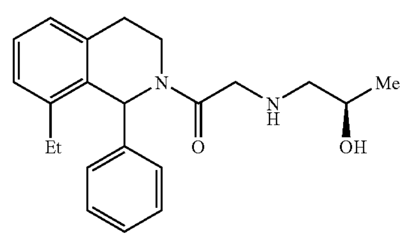 |
| | | |
TABLE 106
| Ex | salt | STRUCTURE |
|---|---|---|
| 544 | OX | 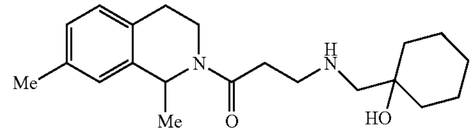 |

TABLE 106-continued
| Ex | salt | STRUCTURE |
|---|---|---|
| 545 | OX | 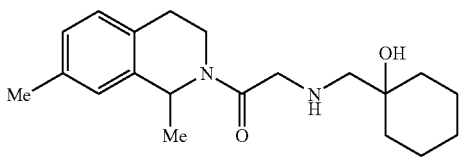 |
| 546 | OX | 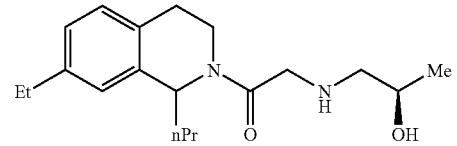 |
| 547 | OX | 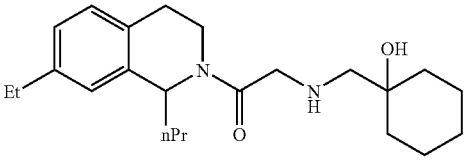 |
| 548 | OX | 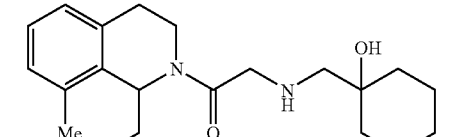 |
| 549 | OX | 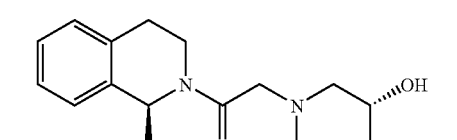 |
| 550 | OX | 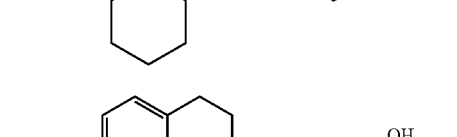 |
TABLE 107
| Ex | salt | STRUCTURE |
|---|---|---|
| 551 | OX | 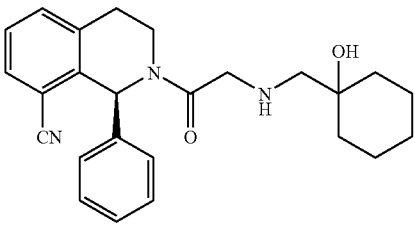 |
| 552 | OX | 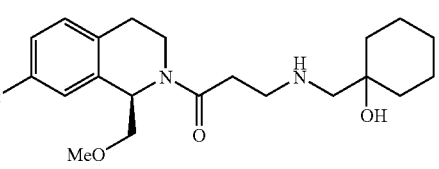 |
TABLE 107-continued
| Ex | salt | STRUCTURE |
|---|---|---|
| 553 | OX | 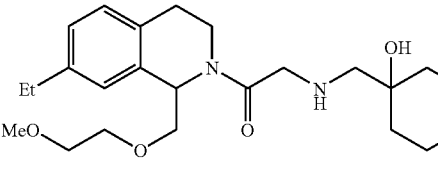 |
| 554 | OX | 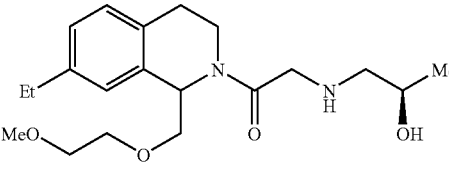 |
| 555 | OX | 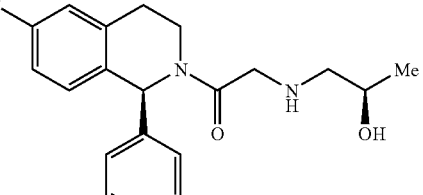 |
| 556 | OX | 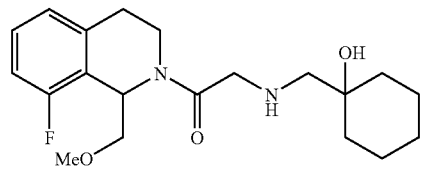 |
| 557 | OX | 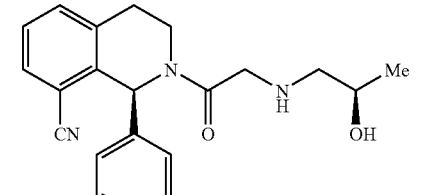 |
TABLE 108
| Ex | salt | STRUCTURE |
|---|---|---|
| 558 | OX | 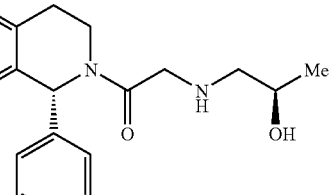 |
| 559 | OX | 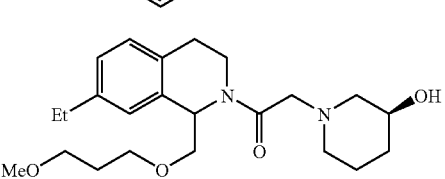 |

TABLE 108-continued

| Ex | salt | STRUCTURE |
|---|---|---|
| 560 | OX | 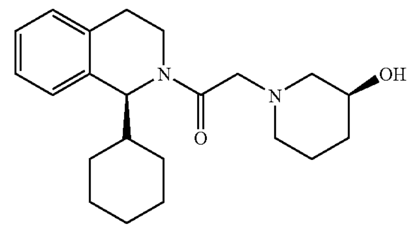 |
| 561*1 | T1 | |
| 562*2 | T2 | |
| 563 | | 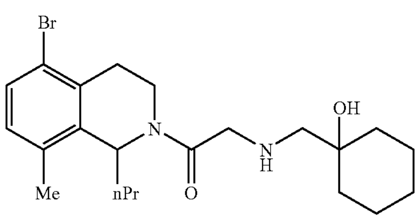 |
| 564 | | 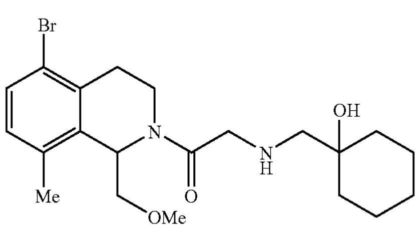 |
| 565 | | 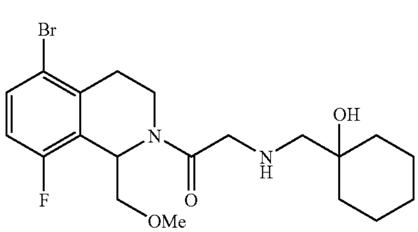 |

TABLE 109

| Ex | salt | STRUCTURE |
|---|---|---|
| 566 | | 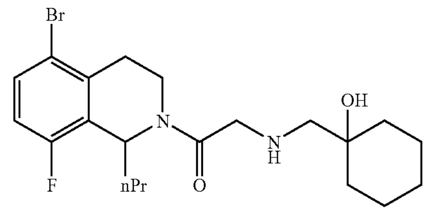 |
| 567 | | 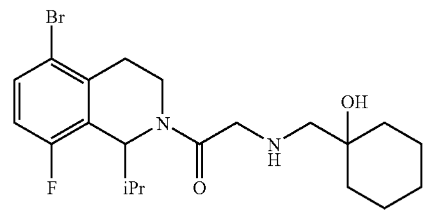 |
| 568 | FM | 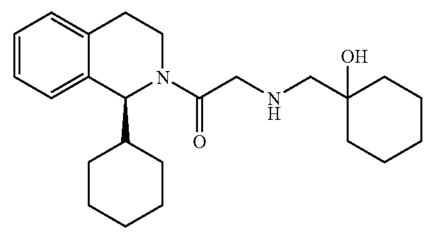 |
| 569 | T2 | 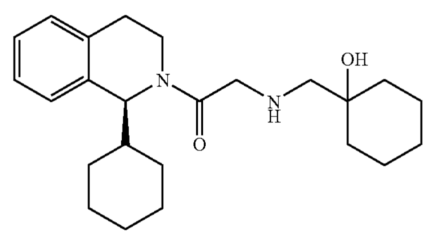 |
| 570 | T1 | 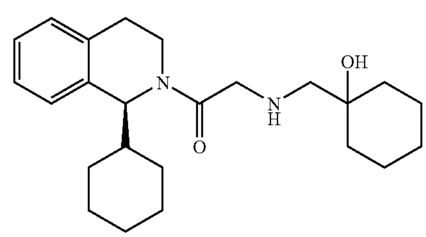 |
| 571 | MB | 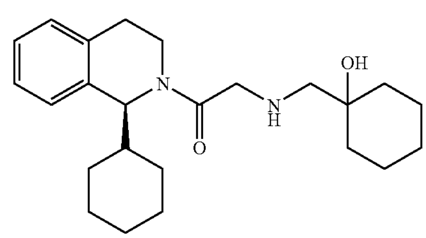 |
| 572 | MA | 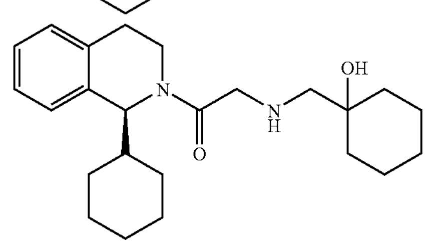 |

TABLE 110
| Ex | salt | STRUCTURE |
|---|---|---|
| 573 | T1 | 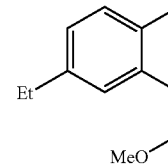 |
| 574 | MA | 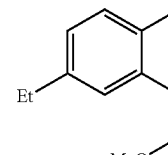 |
| 575 | OX | 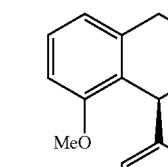 |
| 576 | T2 | 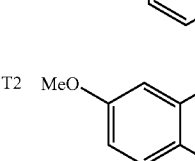 |
| 577 | T1 | 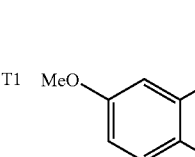 |
| 578 | MB | 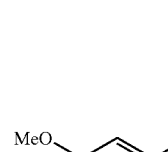 |
| 579 | MA | 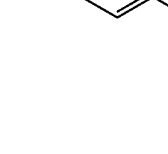 |
TABLE 111
| Ex | Data |
|---|---|
| 1 | FAB: 385 |
| 2 | FAB: 399 |
| 3 | FAB: 389 |
| 4 | FAB: 415 |
| 5 | FAB: 413 |
| 6 | ES: 359 |
| 7 | FAB: 399 |
| 8 | FAB: 429 |
| 9 | FAB: 415 |
| 10 | FAB: 401 |
| 11 | FAB: 428 |
| 12 | FAB: 361 |
| 13 | FAB: 431 |
| 14 | FAB: 426 |
| 15 | FAB: 399 |
| 16 | ES: 413 |
| 17 | ES: 401 |
TABLE 112
| Ex | Syn | Data |
|---|---|---|
| 101 | 1 | FAB: 385 |
| 102 | 1 | FAB: 385 |
| 103 | 1 | FAB: 385 |
| 104 | 1 | FAB: 385 |
| 105 | 1 | FAB: 423 |
| 106 | 1 | FAB: 371 |
| 107 | 1 | FAB: 393 |
| 108 | 1 | FAB: 393 |
| 109 | 1 | FAB: 407 |
| 110 | 1 | FAB: 407 |
| 111 | 1 | FAB: 465 |
| 112 | 1 | FAB: 410 |
| 113 | 1 | FAB: 403 |
| 114 | 1 | FAB: 469 |
| 115 | 1 | FAB: 469 |
| 116 | 1 | FAB: 419 |
| 117 | 1 | FAB: 423 |
| 118 | 1 | FAB: 423 |
| 119 | 1 | FAB: 449 |
| 120 | 1 | FAB: 371 |
| 121 | 7 | FAB: 425 |
| 122 | 1 | FAB: 425 |
| 123 | 1 | FAB: 441 |
| 124 | 1 | FAB: 373 |
| 125 | 1 | FAB: 373 |
| 126 | 1 | FAB: 443 |
| 127 | 1 | FAB: 373 |
| 128 | 7 | FAB: 425 |
| 129 | 5 | FAB: 399 |
| 130 | 7 | FAB: 399 |
| 131 | 1 | FAB: 385 |
| 132 | 1 | FAB: 371 |
| 133 | 1 | FAB: 331 |
| 134 | 1 | FAB: 331 |
| 135 | 1 | FAB: 334 |
| 136 | 1 | FAB: 347 |
| 137 | 1 | FAB: 343 |
| 138 | 7 | FAB: 425 |
| 139 | 7 | FAB: 443 |
| 140 | 1 | FAB: 387 |
| 141 | 7 | FAB: 439 |
| 143 | 1 | FAB: 317.2 |
| 144 | 1 | FAB: 359 |
| 145 | 1 | FAB: 345 |
| 146 | 1 | FAB: 361 |
| 147 | 1 | FAB: 345 |
| 148 | 1 | FAB: 399 |
| 149 | 2 | FAB: 345 |
| 150 | 1 | FAB: 415 |
| 151 | 1 | FAB: 400.5 |
| 152 | 1 | FAB: 345 |
| 153 | 1 | FAB: 331 |
| 154 | 1 | FAB: 413.3 |

TABLE 112-continued

| Ex | Syn | Data |
| --- | --- | --- |
| 155 | 1 | FAB: 359.3 |
| 156 | 7 | FAB: 447 |
| 157 | 1 | FAB: 361 |
| 158 | 1 | FAB: 423 |
| 159 | 1 | FAB: 397 |
| 160 | 1 | FAB: 343 |
| 161 | 1 | FAB: 373 |
| 162 | 7 | FAB: 455 |
| 163 | 1 | FAB: 404 |
| 164 | 1 | FAB: 350 |
| 165 | 1 | FAB: 447 |
| 166 | 1 | FAB: 393 |
| 167 | 1 | FAB: 447 |
| 168 | 1 | FAB: 383.0 |
| 169 | 1 | FAB: 329.1 |
| 170 | 7 | ES: 401 |
| 171 | 1 | FAB: 423 |
| 172 | 1 | FAB: 343 |
| 173 | 1 | FAB: 397 |
| 174 | 1 | FAB: 393 |
| 175 | 1 | FAB: 373 |
| 176 | 1 | FAB: 409 |
| 177 | 1 | FAB: 439 |
| 178 | 1 | FAB: 365 |
| 179 | 1 | FAB: 395 |
| 180 | 1 | FAB: 439 |

TABLE 113

| Ex | Syn | Data |
| --- | --- | --- |
| 181 | 1 | FAB: 409 |
| 182 | 1 | FAB: 411 |
| 183 | 1 | FAB: 439 |
| 184 | 1 | FAB: 415 |
| 185 | 1 | FAB: 391 |
| 186 | 1 | FAB: 419 |
| 187 | 1 | FAB: 365 |
| 188 | 1 | FAB: 395 |
| 189 | 1 | FAB: 419 |
| 190 | 1 | FAB: 361 |
| 191 | 1 | FAB: 391 |
| 192 | 1 | FAB: 415 |
| 193 | 1 | FAB: 365 |
| 194 | 1 | FAB: 395 |
| 195 | 1 | FAB: 391 |
| 196 | 1 | FAB: 421 |
| 197 | 1 | FAB: 367 |
| 198 | 1 | FAB: 397 |
| 199 | 1 | FAB: 345.2 |
| 200 | 1 | FAB: 445.2 |
| 201 | 1 | FAB: 391.2 |
| 202 | 1 | FAB: 371.2 |
| 203 | 1 | FAB: 361 |
| 204 | 1 | FAB: 387 |
| 205 | 1 | FAB: 413 |
| 206 | 1 | FAB: 359 |
| 207 | 1 | FAB: 389 |
| 209 | 1 | FAB: 399.2 |
| 210 | 1 | FAB: 317.1 |
| 212 | 1 | FAB: 397 |
| 213 | 1 | FAB: 361 |
| 214 | 1 | FAB: 415 |
| 215 | 1 | FAB: 349 |
| 216 | 1 | FAB: 379 |
| 217 | 1 | FAB: 403 |
| 218 | 1 | FAB: 349 |
| 219 | 1 | FA1: 378 |
| 220 | 1 | FAB: 413 |
| 221 | 1 | FAB: 359 |
| 222 | 1 | FAB: 373 |
| 223 | 1 | ES: 389 |
| 224 | 1 | ES: 373 |
| 225 | 1 | FAB: 347 |
| 226 | 1 | FAB: 319 |

TABLE 113-continued

| Ex | Syn | Data |
| --- | --- | --- |
| 227 | 1 | ES: 349 |
| 228 | 1 | FAB: 349 |
| 229 | 1 | FAB: 379 |
| 230 | 1 | FAB: 403 |
| 231 | 1 | FAB: 380 |
| 232 | 1 | FAB: 404 |
| 233 | 1 | FAB: 458 |
| 234 | 1 | FAB: 360 |
| 235 | 1 | FAB: 414 |
| 236 | 1 | FAB: 409 |
| 237 | 1 | FAB: 439 |
| 238 | 1 | FAB: 355 |
| 239 | 1 | FAB: 385 |
| 240 | 1 | FAB: 411 |
| 241 | 1 | FAB: 441 |
| 242 | 1 | ES: 369 |
| 243 | 1 | FAB: 399 |
| 244 | 1 | FAB: 414 |
| 245 | 1 | FAB: 360 |
| 246 | 1 | FAB: 353 |
| 247 | 1 | FAB: 383 |
| 249 | 1 | FAB: 386 |
| 250 | 1 | FAB: 356 |
| 252 | 1 | FAB: 371 |
| 253 | 1 | ES: 401 |
| 254 | 1 | FAB: 373 |
| 255 | 1 | FAB: 403 |
| 256 | 1 | FAB: 359 |
| 257 | 1 | FAB: 305 |
| 258 | 1 | FAB: 335 |
| 259 | 1 | FAB: 345 |
| 260 | 1 | FAB: 291 |

TABLE 114

| Ex | Syn | Data |
| --- | --- | --- |
| 261 | 1 | FAB: 321 |
| 262 | 1 | FAB: 403.3 |
| 263 | 1 | FAB: 375.2 |
| 264 | 1 | FAB: 387 |
| 265 | 1 | FAB: 333 |
| 266 | 1 | FAB: 363 |
| 267 | 10 | FAB: 374 |
| 268 | 10 | N/D |
| 269 | 10 | FAB: 404 |
| 270 | 1 | FAB: 416 |
| 271 | 1 | FAB: 356 |
| 272 | 1 | FAB: 386 |
| 273 | 1 | FAB: 345 |
| 274 | 1 | FAB: 375 |
| 275 | 1 | FAB: 407 |
| 276 | 1 | FAB: 437 |
| 277 | 1 | FAB: 414 |
| 278 | 1 | FAB: 349.14 |
| 279 | 1 | FAB: 437 |
| 280 | 1 | FAB: 405.2 |
| 281 | 1 | FAB: 430 |
| 282 | 1 | FAB: 399 |
| 283 | 1 | FAB: 429 |
| 284 | 1 | FAB: 447 |
| 285 | 1 | ES: 393 |
| 286 | 1 | FAB: 423 |
| 287 | 1 | FAB: 431 |
| 288 | 1 | FAB: 377 |
| 289 | 1 | FAB: 407 |
| 290 | 1 | FAB: 355.24 |
| 291 | 1 | FAB: 411.22 |
| 292 | 1 | ES: 359 |
| 293 | 1 | ES: 389 |
| 294 | 1 | FAB: 402 |
| 295 | 1 | ES: 379 |
| 296 | 1 | ES: 325 |
| 297 | 1 | ES: 355 |
| 298 | 1 | FAB: 371 |

TABLE 114-continued

| Ex | Syn | Data |
| --- | --- | --- |
| 299 | 1 | FAB: 317 |
| 300 | 1 | FAB: 347 |
| 301 | 1 | FAB: 383 |
| 302 | 1 | FAB: 456 |
| 303 | 1 | FAB: 430 |
| 304 | 1 | FAB: 407 |
| 305 | 1 | FAB: 437 |
| 306 | 1 | FAB: 385 |
| 307 | 1 | FAB: 385 |
| 308 | 1 | FAB: 389 |
| 309 | 1 | FAB: 373 |
| 310 | 1 | FAB: 399.2 |
| 311 | 1 | FAB: 355 |
| 312 | 1 | FAB: 417 |
| 313 | 1 | FAB: 399 |
| 314 | 1 | FAB: 345 |
| 315 | 1 | FAB: 375 |
| 316 | 1 | FAB: 363 |
| 317 | 1 | FAB: 309 |
| 318 | 1 | FAB: 339 |
| 319 | 1 | FAB: 375 |
| 320 | 1 | FAB: 321 |
| 321 | 1 | FAB: 351 |
| 322 | 1 | FAB: 357 |
| 323 | 1 | FAB: 303 |
| 324 | 1 | FAB: 333 |
| 325 | 1 | FAB: 409 |
| 326 | 1 | FAB: 413 |
| 327 | 2 | ES: 369 |
| 328 | 1 | ES: 417 |
| 329 | 1 | FAB: 255 |
| 330 | 1 | FAB: 381 |
| 331 | 1 | FAB: 381 |
| 332 | 2 | FAB: 355.1 |
| 333 | 2 | FAB: 411.2 |
| 334 | 2 | FAB: 381.2 |
| 335 | 2 | FAB: 381.3 |
| 336 | 2 | FAB: 325.2 |
| 337 | 1 | FAB: 355 |
| 338 | 1 | FAB: 381.31 |
| 339 | 9 | FAB: 445 |
| 340 | 1 | FAB: 373 |

TABLE 115

| Ex | Syn | Data |
| --- | --- | --- |
| 341 | 1 | FAB: 359 |
| 342 | 1 | FAB: 305 |
| 343 | 1 | FAB: 335 |
| 344 | 1 | FAB: 317 |
| 345 | 1 | FAB: 263 |
| 346 | 1 | FAB: 347 |
| 347 | 1 | FAB: 411 |
| 348 | 1 | FAB: 425 |
| 349 | 1 | FAB: 355 |
| 350 | 2 | FAB: 339.1 |
| 351 | 2 | FAB: 367.2 |
| 352 | 1 | FAB: 415 |
| 353 | 9 | FAB: 431 |
| 354 | 1 | ES: 385 |
| 355 | 1 | FAB: 311.2 |
| 356 | 1 | FAB: 325.2 |
| 357 | 1 | FAB: 367.2 |
| 358 | 1 | FAB: 399 |
| 359 | 1 | FAB: 359 |
| 360 | 1 | FAB: 413 |
| 361 | 1 | FAB: 373 |
| 362 | 1 | FAB: 367 |
| 363 | 1 | FAB: 405 |
| 364 | 1 | FAB: 351 |
| 365 | 1 | FAB: 335 |
| 366 | 2 | FAB: 325.2 |
| 367 | 1 | FAB: 363 |
| 368 | 1 | FAB: 309 |

TABLE 115-continued

| Ex | Syn | Data |
| --- | --- | --- |
| 369 | 1 | FAB: 353 |
| 370 | 1 | FAB: 421 |
| 371 | 14 | FAB: 402 |
| 372 | 1 | FAB: 349 |
| 373 | 1 | FAB: 385 |
| 374 | 2 | FAB: 339.4 |
| 375 | 2 | FAB: 339.28 |
| 376 | 2 | FAB: 367.2 |
| 377 | 2 | FAB: 381.2 |
| 378 | 2 | FAB: 381.3 |
| 379 | 1 | FAB: 377 |
| 380 | 1 | FAB: 363 |
| 381 | 1 | FAB: 365 |
| 382 | 1 | FAB: 389 |
| 383 | 1 | FAB: 417 |
| 384 | 1 | FAB: 377 |
| 385 | 1 | FAB: 381 |
| 386 | 1 | FAB: 365 |
| 387 | 1 | FAB: 417 |
| 388 | 1 | FAB: 349 |
| 389 | 1 | FAB: 347 |
| 390 | 1 | FAB: 375 |
| 391 | 1 | FAB: 339.3 |
| 392 | 1 | ES: 339.3 |
| 393 | 1 | ES: 339.3 |
| 394 | 1 | ES: 339.3 |
| 395 | 1 | FAB: 427 |
| 396 | 1 | FAB: 375 |
| 397 | 1 | ES: 347 |
| 398 | 1 | ES: 355.4 |
| 399 | 1 | ES: 355.3 |
| 400 | 1 | ES: 357 |
| 401 | 1 | ES: 383 |
| 402 | 1 | FAB: 375 |
| 403 | 1 | FAB: 321 |
| 404 | 1 | FAB: 495 |
| 405 | 1 | FAB: 441 |
| 406 | 1 | FAB: 415 |
| 407 | 1 | FAB: 361 |
| 408 | 1 | FAB: 415 |
| 409 | 1 | FAB: 375 |
| 410 | 1 | ES: 395 |
| 411 | 1 | FAB: 369 |
| 412 | 1 | FAB: 389 |
| 413 | 1 | FAB: 331 |
| 414 | 1 | FAB: 375 |
| 415 | 1 | ES: 375 |
| 416 | 1 | FAB: 429 |
| 417 | 1 | FAB: 401 |
| 418 | 1 | FAB: 443 |
| 419 | 1 | FAB: 415 |
| 420 | 1 | FAB: 353 |

TABLE 116

| Ex | Syn | Data |
| --- | --- | --- |
| 421 | 1 | FAB: 401 |
| 422 | 1 | FAB: 387 |
| 423 | 1 | FAB: 401 |
| 424 | 1 | FAB: 455 |
| 425 | 1 | FAB: 407.2 |
| 426 | 1 | FAB: 407.2 |
| 427 | 1 | FAB: 375 |
| 428 | 1 | FAB: 321 |
| 429 | 1 | FAB: 389 |
| 430 | 1 | FAB: 335 |
| 431 | 1 | FAB: 429 |
| 432 | 1 | FAB: 401 |
| 433 | 1 | FAB: 407 |
| 434 | 1 | FAB: 427 |
| 435 | 1 | FAB: 355 |
| 436 | 1 | FAB: 375 |
| 437 | 1 | FAB: 355 |
| 438 | 1 | ES: 361 |

TABLE 116-continued

| Ex | Syn | Data |
|---|---|---|
| 439 | 1 | FAB: 375 |
| 440 | 1 | FAB: 385.4 |
| 441 | 1 | FAB: 411 |
| 442 | 1 | FAB: 357 |
| 443 | 1 | FAB: 385.3 |
| 444 | 1 | FAB: 391 |
| 445 | 1 | ES: 355 |
| 446 | 1 | ES: 355 |
| 447 | 1 | FAB: 339 |
| 448 | 1 | FAB: 355 |
| 449 | 1 | FAB: 359 |
| 450 | 1 | ES: 305 |
| 451 | 1 | FAB: 345 |
| 452 | 1 | FAB: 359 |
| 453 | 14 | FAB: 339 |
| 454 | 14 | FAB: 343 |
| 455 | 14 | FAB: 355 |
| 456 | 1 | ES: 343 |
| 457 | 14 | FAB: 343 |
| 458 | 1 | ES: 377.86 |
| 459 | 1 | FAB: 377.2 |
| 460 | 1 | ES: 363.81 |
| 461 | 1 | FAB: 363.2 |
| 462 | 1 | FAB: 345 |
| 463 | 1 | FAB: 359 |
| 464 | 1 | FAB: 339 |
| 465 | 1 | FAB: 409 |
| 466 | 1 | FAB: 359 |
| 467 | 1 | FAB: 375 |
| 468 | 1 | ES: 364.31 |
| 469 | 1 | FAB: 363.2 |
| 470 | 1 | FAB: 359 |
| 471 | 1 | FAB: 377 |
| 472 | 1 | FAB: 375 |
| 473 | 1 | FAB: 361 |
| 474 | 1 | FAB: 361 |
| 475 | 1 | ES: 377 |
| 476 | 1 | ES: 363 |
| 477 | 1 | FAB: 385.4 |
| 478 | 1 | ES: 365 |
| 479 | 1 | ES: 375 |
| 480 | 1 | ES: 377 |
| 481 | 1 | ES: 403 |
| 482 | 1 | ES: 349 |
| 483 | 1 | ES: 345 |
| 484 | 1 | ES: 397 |
| 485 | 1 | ES: 343 |
| 486 | 1 | ES: 393 |
| 487 | 1 | ES: 339 |
| 488 | 1 | ES: 399 |
| 489 | 1 | ES: 362.13 |
| 490 | 1 | FAB: 361.3 |
| 491 | 1 | ES: 360.29 |
| 492 | 1 | FAB: 359.3 |
| 493 | 1 | FAB: 355 |
| 494 | 1 | AP: 375.08 |
| 495 | 1 | FAB: 375.2 |
| 496 | 1 | ES: 367.3 |
| 497 | 1 | FAB: 326 |
| 498 | 1 | FAB: 432 |
| 499 | 1 | ES: 448 |
| 500 | 1 | FAB: 393 |

TABLE 117

| Ex | Syn | Data |
|---|---|---|
| 501 | 1 | ES: 389 |
| 502 | 14 | ES: 409 |
| 503 | 1 | ES: 409 |
| 504 | 1 | ES: 375 |
| 505 | 1 | ES: 389 |
| 506 | 1 | ES: 321 |
| 507 | 1 | ES: 335 |
| 508 | 1 | ES: 415 |

TABLE 117-continued

| Ex | Syn | Data |
|---|---|---|
| 509 | 1 | ES: 409 |
| 510 | 1 | ES: 405 |
| 511 | 16 | ES: 407 |
| 512 | 16 | ES: 399 |
| 513 | 16 | ES: 413 |
| 514 | 16 | ES: 423 |
| 515 | 17 | ES: 331 |
| 516 | 17 | ES: 387 |
| 517 | 17 | ES387 |
| 518 | 17 | ES: 464 |
| 519 | 17 | ES: 435 |
| 520 | 17 | ES: 435 |
| 521 | 17 | ES: 401 |
| 522 | 17 | ES: 421 |
| 523 | 17 | ES: 481 |
| 524 | 17 | ES: 387 |
| 525 | 17 | ES: 407 |
| 526 | 17 | ES: 421 |
| 527 | 16 | ES: 419 |
| 528 | 17 | ES: 371 |
| 529 | 17 | ES: 371 |
| 530 | 17 | ES: 371 |
| 531 | 17 | ES: 385 |
| 532 | 17 | ES: 399 |
| 533 | 17 | ES: 399 |
| 534 | 17 | ES: 399 |
| 535 | 17 | ES: 371 |
| 536 | 17 | ES: 385 |
| 537 | 6 | ES: 363 |
| 538 | 6 | ES: 359 |
| 539 | 6 | ES: 363 |
| 540 | 1 | FAB: 407 |
| 541 | 1 | FAB: 345 |
| 542 | 2 | FAB: 359 |
| 543 | 1 | ES: 353 |
| 544 | 2 | FAB: 345 |
| 545 | 1 | FAB: 331 |
| 546 | 1 | APCI: 319.08 |
| 547 | 1 | ES: 374.08 |
| 548 | 6 | ES: 361 |
| 549 | 1 | ES: 357 |
| 550 | 1 | ES: 433 |
| 551 | 6 | ES: 365 |
| 552 | 1 | ES: 350 |
| 553 | 1 | ES: 404 |
| 554 | 1 | ES: 389 |
| 555 | 1 | FAB: 419.3 |
| 556 | 1 | FAB: 365.2 |
| 557 | 1 | ES: 343 |
| 558 | 1 | ES: 343 |
| 559 | 1 | ES: 405 |
| 560 | 1 | ES: 357 |
| 561 | 1 | ES: 361.3 |
| 562 | 1 | ES: 361.3 |
| 563 | 1 | ES: 437 |
| 564 | 1 | ES: 439 |
| 565 | 1 | ES: 443 |
| 566 | 1 | ES: 441 |
| 567 | 1 | ES: 441 |
| 568 | 1 | ES: 385.3 |
| 569 | 1 | ES: 385.2 |
| 570 | 1 | ES: 385.3 |
| 571 | 1 | ES: 385.3 |
| 572 | 1 | ES: 385.3 |
| 573 | 1 | ES: 375.3 |
| 574 | 1 | FAB: 375.2 |
| 575 | 1 | FAB: 355 |
| 576 | 1 | ES: 375.2 |
| 577 | 1 | ES: 375.2 |
| 578 | 1 | ES: 375.2 |
| 579 | 1 | ES: 375.2 |

TABLE 118

| Ex | Data |
|---|---|
| 14 | NMR: 0.29-0.42(8H, m), 0.85-0.88(2H, m), 2.88-4.41(8H, m), 6.24 and 6.49(1H, s), 7.20-7.74(6H, m), 8.43 and 8.56(1H, m). |
| 15 | NMR: 1.03-2.53(19H, m), 2.93-3.01(4H, m), 3.57-3.72(2H, m), 3.99(1H, d, J = 16.2 Hz), 4.13(1H, d, J = 16.2 Hz), 5.11(1H, d, J = 9.6 Hz), 7.16-7.23(4H, m). |
| 101 | NMR: 1.01-1.73(11H, m), 2.86(2H, m), 3.58(1H, m), 3.67(1H, m), 3.97(1H, m), 4.12(1H, m), 5.11(1H, d, J = 6.9 Hz), 7.14-7.22(4H, m). |
| 102 | NMR: 1.03-1.72(16H, m), 2.79-3.01(4H, m), 3.59(1H, m), 3.68(1H, m), 3.78(1H, m), 4.03(1H, m), 4.16(1H, d, J = 12.0 Hz), 5.10(1H, d, J = 6.9 Hz), 7.16-7.22(4H, m). |
| 103 | NMR: 1.03-1.83(16H, m), 2.81-3.01(4H, m), 3.24(1H, m), 3.60(1H, m), 3.66(1H, m), 3.97-4.19(2H, m), 5.10(1H, d, J = 6.9 Hz), 7.15-7.23(4H, m). |
| 104 | NMR: 0.88-1.72(19H, m), 2.10(1H, m), 2.51-2.99(4H, m), 3.42(1H, m), 3.58(1H, m), 3.66(1H, m), 3.95(1H, d, J = 11.8 Hz), 4.11(1H, s), 4.28(1H, d, J = 11.8 Hz), 5.07(1H, m), 7.15-7.23(4H, m). |
| 105 | NMR: 1.00-1.76(25H, m), 2.22(1H, s, br), 2.98(2H, m), 3.72(2H, m), 3.94(1H, d, J = 12.0 Hz), 4.10(1H, d, J = 12.0 Hz), 5.11(1H, d, J = 6.9 Hz), 7.14-7.23(4H, m). |
| 106 | NMR: 1.00-2.03(19H, m), 2.87-2.99(4H, m), 3.34(1H, m), 3.66(1H, m), 4.04(1H, d, J = 12.1 Hz), 4.19(1H, d, J = 12.1 Hz), 5.10(1H, d, J = 7.5 Hz), 7.14-7.23(4H, m). |
| 107 | NMR: 0.97-1.66(11H, m), 2.85(2H, m), 3.46(2H, m), 3.67-3.77(3H, m), 4.27(2H, m), 5.10(1H, m), 7.13-7.21(4H, M), 7.34-7.43(5H, m). |
| 108 | NMR: 0.97-1.66(11H, m), 2.85(2H, m), 3.46(2H, m), 3.67-3.77(3H, m), 4.27(2H, m), 5.10(1H, m), 7.13-7.21(4H, M), 7.34-7.43(5H, m). |
| 109 | NMR: 1.04-1.70(11H, m), 2.77-4.24(7H, m), 5.12(1H, d, J = 6.9 Hz), 7.17-7.34(9H, m). |
| 110 | NMR: 1.04-1.70(11H, m), 2.77-4.24(7H, m), 5.12(1H, d, J = 6.9 Hz), 7.17-7.34(9H, m). |
| 111 | NMR: 1.02-1.68(21H, m), 2.82(2H, m), 2.98(2H, m), 3.56-3.67(2H, m), 3.97(1H, d, J = 16.4 Hz), 4.11(1H, d, J = 16.0 Hz), 5.11(1H, d, J = 9.2 Hz), 7.13(1H, m), 7.36(1H, m), 7.42(1H, m), 7.47(1H, d, J = 1.6 Hz). |
| 112 | NMR: 1.00-1.68(21H, m), 2.85(2H, m), 3.03(2H, m), 3.64(2H, m), 3.98(1H, d, J = 16.4 Hz), 4.12(1H, d, J = 16.0 Hz), 5.22(1H, d, J = 9.2 Hz), 7.41(1H, d, J = 8.0 Hz), 7.64(1H, m), 7.69(1H, m), 7.74(1H, s). |
| 113 | NMR: 1.02-1.67(21H, m), 2.86(2H, m), 2.98(2H, m), 3.56-3.68(2H, m), 3.98(1H, d, J = 16.0 Hz), 4.10(1H, d, J = 16.0 Hz), 5.12(1H, d, J = 9.6 Hz), 7.01(1H, m), 7.09(1H, m), 7.21(1H, m). |
| 114 | NMR: 1.03-1.64(11H, m), 2.77(2H, m), 3.17(2H, m), 3.20-4.11(2H, m), 4.64-4.70(1H, m), 5.05(1H, m), 5.28-5.34(1H, m), 7.07-7.23(14H, m). |
| 115 | NMR: 1.03-1.64(11H, m), 2.77(2H, m), 3.17(2H, m), 3.20-4.11(2H, m), 4.64-4.70(1H, m), 5.05(1H, m), 5.28-5.34(1H, m), 7.07-7.23(14H, m). |
| 116 | NMR: 0.99-1.68(21H, m), 2.85(2H, m), 2.98(1H, m), 3.56-3.67(1H, m), 3.98(1H, d, J = 16.2 Hz), 4.12(1H, d, J = 16.2 Hz), 5.12(1H, d, J = 9.2 Hz), 7.19-7.33(3H, m). |
| 117 | NMR: 1.01-1.72(11H, m), 2.95(2H, m), 3.26(2H, m), 3.46-3.67(3H, m), 4.03(1H, m), 4.17(1H, m), 4.75(1H, m), 5.12(1H, m), 7.16-7.22(4H, m), 7.32-7.38(5H, m). |

TABLE 119

| Ex | Data |
|---|---|
| 118 | NMR: 1.01-1.72(11H, m), 2.95(2H, m), 3.26(2H, m), 3.46-3.67(3H, m), 4.03(1H, m), 4.17(1H, m), 4.75(1H, m), 5.12(1H, m), 7.16-7.22(4H, m), 7.32-7.38(5H, m). |
| 119 | NMR: 0.98-1.67(17H, m), 1.88(1H, m), 2.05(1H, m), 2.75(1H, m), 2.97(2H, m), 3.49-4.20(5H, m), 5.11(1H, d, J = 9.2 Hz), 7.12(1H, m), 8.4 Hz), 7.36(1H, m), 7.47(1H, s). |
| 120 | NMR: 1.03-1.68(17H, m), 1.88(1H, m), 2.05(1H, m), 2.77(1H, m), 2.97(2H, m), 3.48-4.21(5H, m), 5.11(1H, d, J = 9.2 Hz), 7.16-7.22(4H, m). |
| 121 | NMR: 1.03-4.77(34H, m), 5.14 and 5.18(1H, d, J = 8.8 Hz), 7.16-7.21(4H, m). |

TABLE 119-continued

| Ex | Data |
|---|---|
| 122 | NMR: 1.03-1.68(11H, m), 2.77-4.25(11H, m), 5.14(1H, d, J = 10.0 Hz), 7.01-7.35(8H, m). |
| 123 | NMR: 1.03-1.71(11H, m), 2.78-4.25(11H, m), 5.14(1H, d, J = 9.2 Hz), 7.20-7.34(8H, m). |
| 124 | NMR: 0.97-1.69(20H, m), 2.77-4.29(9H, m), 5.12(1H, d, J = 9.2 Hz), 7.16-7.22(4H, m). |
| 125 | NMR: 0.84-1.70(20H, m), 2.97-4.18(9H, m), 5.12(1H, d, J = 9.2 Hz), 7.16-7.23(4H, m). |
| 126 | NMR: 1.07-1.81(17H, m), 2.86-2.98(4H, m), 3.38-3.70(2H, m), 3.85(4H, s), 4.00(1H, d, J = 16.0 Hz), 4.14(1H, d, J = 16.0 Hz), 5.11(1H, d, J = 9.6 Hz), 7.14-7.23(4H, m). |
| 127 | NMR: 0.85-1.70(20H, m), 2.51-3.04(3H, m), 3.56-4.22(6H, m), 5.12(1H, d, J = 9.2 Hz), 7.16-7.22(4H, m). |
| 128 | NMR: 1.03-4.77(34H, m), 5.14 and 5.18(1H, d, J = 8.8 Hz), 7.16-7.21(4H, m). |
| 129 | NMR: 1.01-1.68(21H, m), 2.68-2.99(7H, m), 3.65(2H, m), 4.10(1H, d, J = 16.2 Hz), 4.22(1H, d, J = 16.2 Hz), 5.11(1H, dmJ = 9.6 Hz), 7.11-7.22(4H, m). |
| 130 | NMR: 1.05-1.73(23H, m), 2.86-2.99(4H, m), 3.55-3.67(2H, m), 4.01(1H, d, J = 16.4 Hz), 4.14(1H, d, J = 16.4 Hz), 5.11(1H, d, J = 9.2 Hz), 7.16-7.23(4H, m). |
| 132 | NMR: 1.01-1.71(19H, m), 2.95-3.10(4H, m), 3.54(1H, m), 3.66(1H, m), 4.00(1H, d, J = 16.0 Hz), 4.14(1H, d, J = 16.0 Hz), 5.11(1H, d, J = 9.2 Hz), 7.14-7.23(4H, m). |
| 133 | NMR: 1.01-1.70(14H, m), 2.74-2.97(4H, m), 3.34-4.19(5H, m), 5.10(1H, d, J = 9.6 Hz), 7.16-7.22(4H, m). |
| 134 | NMR: 1.01-1.70(14H, m), 2.74-2.97(4H, m), 3.34-4.19(5H, m), 5.10(1H, d, J = 9.6 Hz), 7.16-7.22(4H, m). |
| 135 | NMR: 1.01-2.20(15H, m), 2.56-3.81(6H, m), 4.32(1H, d, J = 16.0 Hz), 4.40(1H, m), 4.49(1H, d, J = 16.0 Hz), 5.10(1H, d, J = 9.2 Hz), 7.15-7.23(4H, m). |
| 136 | NMR: 1.02-1.70(11H, m), 2.95-3.77(9H, m), 4.05(1H, d, J = 16.2 Hz), 4.17(1H, d, J = 16.2 Hz), 5.11(1H, d, J = 9.2 Hz), 7.14-7.22(4H, m). |
| 137 | NMR: 1.03-1.60(11H, m), 1.69(1H, m), 1.85(1H, m), 2.96-4.47(11H, m), 5.10(1H, d, J = 9.6 Hz), 7.14-7.22(4H, m). |
| 138 | NMR: 0.31(2H, m), 0.96-1.70(23H, m), 2.49-4.19(9H, m), 5.11(1H, m), 7.12-7.22(4H, m). |
| 139 | NMR: 1.06-1.69(21H, m), 2.83-2.96(5H, m), 3.19(3H, s), 3.49-4.20(.12H, m), 5.11(1H, d, J = 9.2 Hz), 7.14-7.21(4H, m). |
| 140 | NMR: 1.03-1.70(15H, m), 2.86-2.99(4H, m), 3.34-3.72(6H, m), 3.98(1H, d, J = 16.4 Hz), 4.11(1H, d, J = 16.4 Hz), 5.11(1H, d, J = 9.2 Hz)m7.14-7.22(4H, m). |

TABLE 120

| Ex | Data |
|---|---|
| 141 | NMR: 0.99-1.97(25H, m), 2.84-3.89(11H, m), 5.18(1H, d, J = 9.6 Hz), 7.10-7.18(4H, m). |
| 145 | NMR: 1.00-1.67(17H, m), 2.84-2.97(4H, m), 3.24-3.67(6H, m), 5.13(1H, d, J = 9.6 Hz), 7.11-7.18(4H, m). |
| 146 | NMR: 1.03-1.67(11H, m), 2.83-3.97(11H, m), 4.02(1H, d, J = 16.2 Hz), 4.14(1H, d, J = 16.2 Hz), 5.11(1H, d, J = 9.6 Hz), 7.16-7.22(4H, m). |
| 147 | NMR: 0.87(3H, t, J = 7.2 Hz), 1.04-1.70(10H, m), 2.78(1H, m), 2.94-3.00(4H, m), 3.56-4.02(4H, m), 4.04(1H, d, J = 16.0 Hz), 4.17(1H, d, J = 16.0 Hz), 5.11(1H, d, J = 9.6 Hz), 7.16-7.23(4H, m). |
| 152 | NMR: 0.86(3H, t, J = 7.4 Hz), 1.00-1.70(13H, m), 2.50(1H, m), 2.92-3.71(6H, m), 4.01(1H, d, J = 16.0 Hz), 4.15(1H, d, J = 16.0 Hz), 5.11(1H, d, J = 9.2 Hz), 7.14-7.22(4H, m). |
| 153 | NMR: 1.00-1.67(14H, m), 2.50-3.75(9H, m), 5.12(1H, d, J = 9.2 Hz), 6.53(2H, s), 7.14-7.19(4H, m). |
| 156 | NMR: 1.07-1.96(15H, m), 2.85-5.19(13H, m), 7.10-7.47(4H, m). |
| 157 | NMR: 1.03-1.71(11H, m), 2.86-3.05(4H, m), 3.25-3.37(5H, m), 3.57-3.68(2H, m), 4.01(1H, m), 4.08(1H, d, J = 16.0 Hz), 4.19(1H, d, J = 16.0 Hz), 5.10(1H, d, J = 9.2 Hz), 5.58(1H, m), 7.16-7.22(4H, m), 8.75(1H, br). |

TABLE 120-continued

| Ex | Data |
|---|---|
| 158 | NMR: 1.01-1.70(11H, m), 2.68-3.00(4H, m), 3.20(1H, m), 3.40(1H, m), 3.54(1H, m), 3.66(1H, m), 4.05(1H, d, J = 16.2 Hz), 4.22(1H, d, J = 16.2 Hz), 5.12(1H, d, J = 9.2 Hz), 6.69(2H, d, J = 8.0 Hz), 7.03(2H, d, J = 8.4 Hz), 7.16-7.23(4H, m). |
| 159 | NMR: 1.24-1.56(10H, m), 2.78-3.04(4H, m), 3.55(1H, m), 3.64(1H, m), 4.05(1H, d, J = 16.3 Hz), 4.16(1H, d, J = 16.3 Hz), 6.65(1H, s), 7.13-7.28(8H, m). |
| 160 | NMR: 1.09(3H, m), 2.74-2.82(2H, m), 2.90-3.01(2H, m), 3.52(1H, m), 3.65(1H, m), 3.96(1H, m), 4.09(1H, d, J = 16.0 Hz), 4.18(1H, m), 6.65(1H, s), 7.13-7.28(8H, m). |
| 161 | NMR: 2.84(1H, m), 6.98(1H, m), 3.27-3.37(5H, m), 3.98(1H, m), 4.10(1H, d, J = 16.1 Hz), 4.19(1H, m), 6.65(1H, s), 7.13-7.28(4H, m). |
| 163 | NMR: 1.15-1.55(10H, m), 2.67-3.04(4H, m), 3.63(2H, m), 4.04(1H, d, J = 16 Hz), 4.20(1H, d, J = 16 Hz), 6.66(1H, s), 7.26-7.37(4H, m), 7.43(2H, m), 7.80(2H, m). |
| 164 | NMR: 1.10(6H, d, J = 6 Hz), 2.67-3.03(4H, m), 3.62(2H, m), 3.96(1H, m), 4.09(1H, d, J = 16.8 Hz), 4.23(1H, m), 6.66(1H, s), 7.27-7.37(4H, m), 7.41(2H, m), 7.80(2H, m). |
| 165 | NMR: 1.23-1.57(10H, m), 2.72-3.02(4H, m), 3.56(1H, m), 3.69(1H, m), 3.92(1H, d, J = 16.4 Hz), 4.06(1H, d, J = 16.4 Hz), 6.73(1H, s), 7.24-7.31(4H, m), 7.47(1H, m), 7.55-7.58(2H, m), 7.64(1H, m). |
| 166 | NMR: 1.10(6H, m), 2.73-3.03(4H, m), 3.58(1H, m), 3.66(1H, m), 3.97(1H, m), 4.11(1H, d, J16.4 Hz), 4.24(1H, m), 6.72(1H, s), 7.25-7.30(4H, m), 7.48(1H, m), 7.55-7.59(2H, m), 7.65(1H, m). |
| 167 | NMR: 1.22-1.56(10H, m), 2.96-3.12(4H, m), 3.54(1H, m), 3.85(1H, m), 4.06(1H, d, J = 16.6 Hz), 4.13(1H, d, J = 16.6 Hz), 6.82(1H, s), 7.14-7.31(5H, m), 7.50-7.60(2H, m), 7.80(1H, m). |

TABLE 121

| Ex | Data |
|---|---|
| 171 | NMR: 2.80(1H, m), 2.95-2.99(2H, m), 3.07(1H, m), 3.23-3.34(5H, m), 3.55(1H, m), 3.85(1H, m), 3.95(1H, m), 4.05-4.19(2H, m), 6.80(2H, m), 7.14-7.31(4H, m), 7.52(1H, m), 7.58(1H, m), 7.79(1H, d, J = 8 Hz). |
| 172 | NMR: 1.08(6H, d, J = 6.4 Hz), 2.74-4.21(9H, m), 6.73(1H, s), 7.11-7.34(7H, m). |
| 173 | NMR: 1.09-1.57(10H, m), 2.81-3.05(4H, m), 3.67-3.72(2H, m), 4.07(1H, d, J = 16.2 Hz), 4.15(1H, d, J = 16.2 Hz), 6.73(1H, s), 7.11-7.34(7H, m). |
| 174 | NMR: 1.07(6H, d, J = 76.4 Hz), 2.72(1H, m), 2.87(1H, m), 2.96-3.12(2H, m), 3.54(1H, m), 3.84-3.94(2H, m), 4.04-4.19(2H, m), 6.80-6.83(2H, m), 7.14-7.31(4H, m), 7.50-7.60(2H, m), 7.80(1H, d, J = 7.6 Hz). |
| 175 | NMR: 2.83-3.07(4H, m), 3.24-3.38(5H, m), 3.64-3.72(2H, m), 3.96(1H, m), 4.11-4.21(2H, m), 6.74(1H, s), 7.11-7.34(7H, m). |
| 176 | NMR: 0.98-1.70(14H, m), 2.72-2.99(4H, m), 3.61(2H, m), 3.96(1H, m), 4.01(1H, d, J = 16 Hz), 4.13(1H, d, J = 16 Hz), 5.01(1H, d, J = 9.6 Hz), 7.14(1H, d, J = 8.4 Hz), 7.35-7.47(2H, m). |
| 177 | NMR: 1.01-1.70(11H, m), 2.82-3.04(4H, m), 3.24-3.36(5H, m), 3.61(2H, m), 3.98(1H, m), 4.02(1H, d, J = 16 Hz), 4.14(1H, d, J = 16 Hz), 5.11(1H, d, J = 9.2 Hz), 7.14(1H, d, J = 8.4 Hz), 7.35-7.47(2H, m). |
| 180 | NMR: 1.97-1.68(11H, m), 2.86(2H, m), 2.99(2H, m), 3.26-3.41(5H, m), 3.62(1H, m), 3.73(1H, m), 3.98(1H, m), 4.09(1H, d, J = 16.2 Hz), 4.18(1H, d, J = 16.2 Hz), 5.13(1H, d, J = 9.6 Hz), 7.12-7.23(2H, m), 7.54(1H, d, J = 8 Hz). |
| 181 | NMR: 0.99-1.68(14H, m), 2.72-3.00(4H, m), 3.62(1H, m), 3.74(1H, m), 3.95(1H, m), 4.08(1H, d, J = 16 Hz), 4.17(1H, d, J = 16 Hz), 5.13(1H, d, J = 9.6 Hz), 7.12-7.23(2H, m), 7.54(1H, m). |
| 182 | NMR: 0.99-1.67(14H, m), 2.72-2.95(4H, m), 3.61(2H, m), 3.95(1H, m), 4.01(1H, d, J = 16 Hz), 4.13(1H, d, J = 16 Hz), 5.14(1H, d, J = 9.6 Hz), 7.19(1H, m), 7.39-7.43(2H, m). |

TABLE 121-continued

| Ex | Data |
|---|---|
| 183 | NMR: 1.0.95-1.68(11H, m), 2.80-3.04(4H, m), 3.24-3.36(5H, m), 3.61(2H, m), 3.98(1H, m), 4.02(1H, d, J = 16 Hz), 4.14(1H, d, J = 16 Hz), 5.14(1H, d, J = 9.6 Hz), 7.19(1H, m), 7.38-7.42(2H, m). |
| 204 | NMR: 1.03-1.66(15H, m), 2.87-2.95(4H, m), 3.54-3.80(8H, m), 5.13(1H, d, J = 9.2 Hz), 6.56(2H, s), 7.12-7.19(4H, m). |
| 205 | NMR: 1.21-1.54(10H, m), 2.80-3.07(4H, m), 3.59(1H, m), 3.78(1H, m), 4.10(2H, m), 6.76(1H, s), 7.06-7.32(7H, m), 7.49(1H, d, J = 7.2 Hz). |
| 206 | NMR: 1.08(3H, d, J = 6.4 Hz), 2.70-3.07(4H, m), 3.58(1H, m), 3.79(1H, m), 3.94(1H, m), 4.14(2H, m), 6.76(1H, s), 7.04-7.32(7H, m), 7.49(1H, d, J = 7.6 Hz). |
| 207 | NMR: 2.81-3.04(4H, m), 3.24-3.35(5H, m), 3.57(1H, m), 3.78(1H, m), 3.95(1H, m), 4.15(2H, m), 6.76(1H, m), 7.05-7.32(7H, m), 7.49(1H, d, J = 8 Hz). |
| 208 | NMR: 1.23-1.54(10H, m), 2.38 and 2.48(3H, s), 2.81-4.41(8H, m), 6.15 and 6.43(1H, s), 6.83 and 7.10(1H, d, J = 7.6 Hz), 7.18-7.32(5H, m), 7.62-7.68(1H, m). |
| 211 | NMR: 1.10(3H, d, J = 7.2 Hz), 2.74-2.99(4H, m), 3.59-3.64(4H, m), 3.97(1H, m), 4.10(1H, d, J = 16.4 Hz), 4.23(1H, m), 6.63(1H, s), 7.00-7.38(4H, m). |

TABLE 122

| Ex | Data |
|---|---|
| 212 | NMR: 1.240-1.58(10H, m), 2.77-3.02(4H, m), 3.63(2H, m), 4.06(1H, d, J = 16 Hz), 4.22(1H, d, J = 16 Hz), 6.63(1H, s), 7.01-7.38(8H, m). |
| 220 | NMR: 1.24-1.58(10H, m), 2.77-3.05(4H, m), 3.57-3.66(2H, m), 4.06(1H, d, J = 16.2 Hz), 4.22(1H, d, J = 16.2 Hz), 6.63(1H, s), 7.13-7.41(8H, m). |
| 221 | NMR: 1.10(3H, d, J = 6.4 Hz), 2.74-3.04(4H, m), 3.56-3.66(2H, m), 3.97(1H, m), 4.10(1H, d, J = 16.4 Hz), 4.23(1H, m), 6.63(1H, s), 7.11-7.39(8H, m). |
| 222 | NMR: 2.78-3.09(4H, m), 3.27-3.37(7H, m), 3.58-3.63(2H, m), 3.99(1H, m), 4.10(1H, d, J = 16.4 Hz), 4.23(1H, m), 6.63(1H, s), 6.99-7.37(8H, m). |
| 223 | NMR: 2.78-3.09(4H, m), 3.27-3.37(7H, m), 3.56-3.66(2H, m), 3.99(1H, m), 4.11(1H, d, J = 16.4 Hz), 4.24(1H, m), 6.64(1H, s), 7.11-7.39(8H, m). |
| 224 | NMR: 0.79-1.67(21H, m), 2.82-2.99(4H, m), 3.58-3.69(2H, m), 3.99(1H, m), 4.12(1H, d, J = 16.4 Hz), 5.32(1H, d, J = 9.6 Hz), 7.15-7.23(4H, m). |
| 226 | NMR: 0.81-0.89(6H, m), 1.09(3H, m), 1.24-1.41(4H, m), 1.67(1H, m), 2.72-2.99(4H, m), 3.60-3.66(2H, m), 3.95(1H, m), 4.02(1H, d, J = 16.2 Hz), 4.14(1H, d, J = 16.2 Hz), 5.32(1H, d, J = 8.8 Hz), 7.17-7.23(4H, m). |
| 227 | NMR: 0.80-0.88(6H, m), 1.24-1.41(4H, m), 1.66(1H, m), 2.79-3.02(4H, m), 3.24-3.35(7H, m), 3.95(1H, m), 3.99(1H, d, J = 16.4 Hz), 4.10(1H, d, J = 16.4 Hz), 5.32(1H, d, J = 8.8 Hz), 7.15-7.23(4H, m). |
| 231 | NMR: 1.23-1.54(10H, m), 2.81-3.01(4H, m), 3.33-4.46(4H, m), 6.22 and 6.50(1H, s), 7.13-8.58(8H, m). |
| 232 | NMR: 1.07-1.10(3H, m), 2.75-3.02(4H, m), 3.69(1H, m), 3.92-3.98(2H, m), 4.12(1H, d, J = 16 Hz), 4.23(1H, m), 6.43(1H, s), 7.20-7.34(4H, m), 7.52(1H, d, J = 7.6 Hz), 7.60(1H, m), 7.74(1H, m). |
| 233 | NMR: 1.24-1.55(10H, m), 2.79-3.01(4H, m), 3.68(1H, m), 3.94(1H, m), 4.06(1H, d, J = 16.2 Hz), 4.18(1H, d, J = 16.2 Hz), 6.43(1H, s), 7.20-7.34(4H, m), 7.51(1H, d, J = 8 Hz), 7.59(1H, d, J = 7.6 Hz), 7.74(1H, m). |
| 234 | NMR: 1.08-1.11(3H, m), 2.75-3.02(4H, m), 3.69(1H, m), 3.92-3.98(2H, m), 4.12(1H, d, J = 16 Hz), 4.23(1H, m), 6.44(1H, s), 7.20-7.40(4H, m), 7.56(1H, d, J = 7.6 Hz), 7.83-7.87(2H, m). |
| 235 | NMR: 1.23-1.55(10H, m), 2.82-3.02(4H, m), 3.68(1H, m), 3.95(1H, m), 4.09(1H, d, J = 16.6 Hz), 4.22(1H, d, J = 16.6 Hz), 6.45(1H, s), 7.21-7.40(5H, m), 7.57(1H, d, J = 7.2 Hz), 7.85(1H, m). |
| 236 | NMR: 1.08(3H, d, J = 6.4 Hz), 2.73-3.07(4H, m), 3.58(1H, m), 3.73(1H, m), 3.95(1H, m), 4.13(2H, m), 6.82 and 6.83(1H, s), 7.01-7.46(8H, m). |

TABLE 122-continued

| Ex | Data |
|---|---|
| 237 | NMR: 2.81-3.07(4H, m), 3.23-3.35(5H, m), 3.58(1H, m), 3.72(1H, m), 3.97(1H, m), 4.14(2H, m), 6.82 and 6.83(1H, s), 7.00-7.46(8H, m). |
| 238 | NMR: 1.08-1.11(3H, m), 2.76-3.00(4H, m), 3.68-4.35(8H, m), 6.23-7.33(9H, m). |
| 239 | NMR: 2.86-3.10(4H, m), 3.26-3.35(5H, m), 3.35-4.33(8H, m), 6.23-7.32(8H, m). |
| 240 | NMR: 1.09(3H, d, J = 6.4 Hz), 2.68-3.06(4H, m), 3.60(1H, m), 3.87-3.95(2H, m), 4.06-4.21(2H, m), 6.63 and 6.65(1H, s), 6.79(1H, m), 7.02(1H, m), 7.18(1H, m), 7.25-7.39(3H, m), 7.89(1H, m). |

TABLE 123

| Ex | Data |
|---|---|
| 241 | NMR: 2.76-3.06(4H, m), 3.23-3.34(5H, m), 3.59(1H, m), 3.86-3.95(2H, m), 4.09 and 4.11(1H, d, J = 16.2 Hz), 4.19(1H, d, J = 16.8 Hz), 6.63 and 6.66(1H, s), 6.80(1H, m), 7.03(1H, m), 7.18(1H, m), 7.25-7.39(3H, m), 7.89(1H, m). |
| 242 | NMR: 1.08(3H, d, J = 6.4 Hz), 1.29(3H, m), 2.75-4.32(11H, m), 6.70(1H, s), 6.85-7.25(8H, m). |
| 243 | NMR: 1.29(3H, m), 2.85-4.18(16H, m), 6.71(1H, s), 6.85-7.25(8H, m). |
| 244 | NMR: 1.26-1.57(10H, m), 2.86-3.01(4 Hm, m), 3.65(1H, m), 3.99(1H, m), 4.12(1H, d, J = 16.2 Hz), 4.25(1H, d, J = 16.2 Hz), 6.47(1H, s), 7.20-7.43(5H, m), 7.74(1H, m), 8.43(1H, d, J = 5.2 Hz). |
| 245 | NMR: 1.09(3H, d, J = 6.4 Hz), 2.75-3.00(4H, m), 3.66(1H, m), 3.94-3.98(2H, m), 4.12(1H, d, J = 16.2 Hz), 4.22 and 4.24(1H, d, J = 16.2 Hz), 6.47(1H, s), 7.20-7.43(5H, m), 7.72(1H, m), 8.43(1H, d, J = 5.2 Hz). |
| 246 | NMR: 1.08(3H, d, J = 5.6 Hz), 1.25(3H, t, J = 7.4 Hz), 2.72-3.11(6H, m), 3.38(1H, m), 3.71(1H, m), 3.96(1H, m), 4.12(2H, m), 6.66(1H, d, J = 7.6 Hz), 6.84(1H, s), 6.94(1H, d, J = 8 Hz), 7.07(1H, m), 7.16(1H, m), 7.22-7.29(4H, m). |
| 247 | NMR: 1.25(3H, t, J = 7.6 Hz), 2.72-3.11(7H, m), 3.26(3H, s), 3.32-3.37(2H, m), 3.70(1H, m), 3.98(1H, m), 4.13(2H, m), 6.66(1H, d, J = 7.6 Hz), 6.85(1H, s), 6.94(1H, d, J = 7.6 Hz), 7.07(1H, m), 7.16(1H, m), 7.22-7.29(4H, m). |
| 248 | NMR1: 2.93(2H, t, J = 6.8 Hz), 3.72(3H, s), 3.77(2H, m), 6.86(1H, m), 7.1(1H, m), 7.23-7.36(5H, m), 7.92(1H, m). |
| 251 | NMR1: 2.75(2H, t, J = 7 Hz), 3.50(2H, m), 3.56(3H, s), 5.27(1H, br), 7.04(2H, m), 7.20-7.31(5H, m), 7.56(2H, m). |
| 252 | NMR: 1.08(2H, d, J = 6.4 Hz), 5.23(3H, s), 2.62-4.21(9H, m), 6.78(1H, s), 6.91(1H, m), 7.01(1H, m), 7.07(1H, m), 7.14-7.29(4H, m), 7.38(1H, d, J = 8 Hz). |
| 253 | NMR: 2.53(3H, s), 2.62-4.22(14H, m), 6.77 and .78(1H, s), 6.90(1H, m), 7.01(1H, m), 7.07(1H, m), 7.14-7.30(4H, m), 7.38(1H, d, J = 8 Hz). |
| 254 | NMR: 2.73-4.34(15H, m), 6.63 and 6.64(1H, s), 6.92(1H, m), 7.02-7.07(2H, m), 7.14-7.28(4H, m). |
| 255 | NMR: 2.82-4.35(17H, m), 6.63 and 6.4(1H, s), 6.91(1H, m), 7.00-7.28(6H, m). |
| 275 | NMR: 1.04(3H, d, J = 6.4 Hz), 2.49-4.02(11H, m), 5.68(1H, m), 7.18-7.73(8H, m). |
| 276 | NMR: 2.51-4.05(16H, m), 5.68(1H, m), 7.20-7.71(8H, m). |
| 277 | NMR: 1.23-1.56(10H, m), 2.79-3.80(6H, m), 4.11(2H, m), 6.67(1H, s), 7.13(1H, d, J = 8 Hz), 7.19-7.38(4H, m), 7.59(1H, m), 8.33(1H, m). |
| 279 | NMR: 2.57-4.03(16H, m), 5.71(1H, m), 7.04(1H, m), 7.18-7.27(3H, m), 7.34(1H, m), 7.43(1H, m), 7.54(1H, m), 7.68(1H, m). |
| 304 | NMR: 0.99-1.05(3H, m), 2.17-4.46(11H, m), 5.09 and 5.68(1H, m), 7.19-7.71(8H, m). |
| 305 | NMR: 2.26-4.90(16H, m), 5.10 and 5.66(1H, m), 5.18-7.70(8H, m). |
| 306 | NMR: 2.74-4.15(19H, m), 6.26 and 6.75(1H, s), 6.67-7.31(8H, m). |
| 307 | NMR: 2.74-4.15(19H, m), 6.26 and 6.75(1H, s), 6.67-7.31(8H, m). |

TABLE 124

| Ex | Data |
|---|---|
| 311 | NMR: 1.08-1.10(3H, m), 2.73-4.35(12H, m), 6.23 and 6.74(1H, s), 6.64-7.33(8H, m). |
| 312 | NMR: 2.88-4.35(11H, m), 4.93-4.95(1H, m), 6.22 and 6.75(1H, s), 6.64-7.38(13H, m). |
| 325 | NMR: 1.40-1.54(10H, m), 2.84-2.99(3H, m), 3.62-3.76(1H, m), 3.80 and 3.93(3H, s), 4.06-4.35(4H, m), 6.23 and 6.73(1H, s), 6.66-7.33(8H, m). |
| 327 | NMR: 1.03-1.11(3H, m), 2.72-3.21(8H, m), 3.74-4.30(6H, m), 6.33 and 6.76(1H, s), 6.86-7.30(8H, m). |
| 328 | NMR: 2.87-4.35(11H, m), 4.93(1H, m), 6.26 and 6.74(1H, s), 6.64-7.38(13H, m). |
| 329 | NMR: 1.08-1.11(3H, m), 2.74-3.01(4H, m), 3.63-4.34(8H, m), 6.25 and 6.73(1H, s), 6.63-7.32(8H, m). |
| 330 | NMR: 1.47-1.93(6H, m), 2.87-3.79(4H, m), 3.79 and 3.93(3H, s), 4.01-4.36(4H, m), 6.29 and 6.74(1H, s), 6.65-7.33(8H, m). |
| 331 | NMR: 1.45-2.00(6H, m), 2.88-3.76(4H, m), 3.79 and 3.92(3H, s), 3.96-4.35(4H, m), 6.29 and 6.74(1H, s), 6.69-7.32(8H, m). |
| 337 | NMR: 2.80-3.21(4H, m), 3.24 and 3.31(3H, s), 3.54-5.58(8H, m), 7.19-7.37(9H, m). |
| 346 | NMR: 1.23-1.55(10H, m), 2.79-3.22(4H, m), 3.25 and 3.32(3H, s), 3.55-4.52(6H, m), 5.06 and 5.58(1H, m), 7.18-7.32(4H, m). |
| 349 | NMR: 1.08-1.10(3H, m), 2.72-4.35(12H, m), 6.23 and 6.74(1H, s), 6.64-7.33(8H, m). |
| 354 | NMR: 1.35-4.56(24H, m), 5.15 and 5.60(1H, m), 7.20-7.33(4H, m). |
| 358 | NMR: 1.44-1.47(2H, m), 1.64-1.79(10H, m), 2.17-2.20(2H, m), 2.81-4.52(13H, m), 5.06 and 5.58(1H, m), 7.18-7.31(4H, m). |
| 359 | NMR: 0.30-0.43(8H, m), 0.85-0.88(2H, m), 2.82-4.52(13H, m), 5.08 and 5.59(1H, m), 7.19-7.31(4H, m). |
| 360 | NMR: 1.44-2.20(14H, m), 2.79-4.43(15H, m), 4.82 and 5.54(1H, m), 7.16-7.22(4H, m). |
| 361 | NMR: 0.29-0.43(8H, m), 0.85-0.90(2H, m), 1.90-4.42(15H, m), 4.83 and 5.53(1H, m), 7.16-7.22(4H, m). |
| 370 | NMR: 0.28-0.42(8H, m), 0.85-0.88(2H, m), 2.89-3.16(4H, m), 3.63-4.35(7H, m), 6.24 and 6.74(1H, s), 6.69-7.33(8H, m). |
| 371 | NMR: 0.77-0.82(6H, m), 1.41-1.48(4H, m), 2.78-3.01(4H, m), 5.47 and 3.65(1H, m), 3.97-4.39(3H, m), 6.25 and 6.48(1H, s), 7.21-7.73(6H, m), 8.43 and 8.55(1H, m). |
| 372 | NMR: 0.78-0.83(6H, m), 1.44-1.50(4H, m), 1.89-2.06(2H, m), 2.79-4.42(13H, m), 4.83 and 5.53(1H, m), 7.16-7.22(4H, m). |
| 373 | NMR: 1.45-4.85(25H, m), 5.26 and 5.57(1H, m), 7.21-7.32(4H, m). |
| 379 | NMR: 0.30-0.43(8H, m), 0.87-0.90(2H, m), 2.77-4.52(13H, m), 5.07 and 5.58(1H, m), 7.04-7.11(2H, m), 7.34-7.40(1H, m). |
| 380 | NMR: 0.86-0.94(12H, m), 1.84-1.89(2H, m), 2.80-4.52(13H, m), 5.05 and 5.58(1H, m), 7.18-7.32(4H, m). |
| 381 | NMR: 1.24-1.55(10H, m), 2.83-4.51(13H, m), 5.07 and 5.57(1H, m), 7.05-7.08(2H, m), 7.34-7.39(1H, m). |
| 383 | NMR: 1.44-1.77(12H, m), 2.17-2.20(2H, m), 2.78-4.52(13H, m), 5.07 and 5.58(1H, m), 7.05-7.09(2H, m), 7.35-7.38(1H, m). |

TABLE 125

| Ex | Data |
|---|---|
| 384 | NMR: 0.28-0.44(8H, m), 0.87-0.90(2H, m), 2.68-4.53(13H, m), 5.08 and 5.59(1H, m), 7.06-7.25(3H, m). |
| 385 | NMR: 0.85-0.94(12H, m), 1.84-1.89(2H, m), 2.78-4.51(13H, m), 5.06 and 5.58(1H, m), 7.05-7.08(2H, m), 7.35-7.38(1H, m). |
| 386 | NMR: 1.27-1.55(10H, m), 2.68-4.48(13H, m), 5.08 and 5.59(1H, m), 7.04-7.12(2H, m), 7.19-7.25(2H, m). |
| 387 | NMR: 1.44-1.79(12H, m), 2.17-2.20(2H, m), 2.69-4.53(13H, m), 5.07 and 5.59(1H, m), 7.06-7.10(1H, m), 7.20-7.26(2H, m). |
| 395 | NMR: 1.13-1.78(18H, m), 2.18(2H, m), 2.88-3.16(7H, m), 3.65(1H, m), 3.85(1H, m), 4.04(1H, d, J = 16.6 Hz), 4.15(1H, d, J = 16.6 Hz), 5.45(1H, s), 7.14-7.30(4H, m). |
| 396 | NMR: 1.12-1.57(16H, m), 2.81-3.07(7H, m), 3.66(1H, m), 3.84(1H, m), 4.04(1H, d, J = 16.2 Hz), 4.15(1H, d, J = 16.2 Hz), 5.44(1H, s), 7.14-7.30(4H, m). |
| 397 | NMR: 1.13-2.02(12H, m), 2.83-3.16(7H, m), 3.69-4.23(4H, m), 5.44(1H, s), 7.14-7.31(4H, m). |
| 400 | NMR: 1.01-1.07(3H, m), 2.26-4.43(10H, m), 5.00 and 5.69(1H, m), 7.05-7.40(8H, m). |
| 401 | NMR: 1.25-1.94(6H, m), 2.70-4.46(10H, m), 5.02 and 5.67(1H, m), 7.07-7.26(8H, m). |
| 409 | NMR: 1.14-1.57(13H, m), 2.53-4.50(15H, m), 5.06 and 5.55(1H, m), 7.05-7.12(4H, m). |

TABLE 125-continued

| Ex | Data |
|---|---|
| 410 | NMR: 1.25-1.94(6H, m), 2.38-4.47(13H, m), 4.98 and 5.72(1H, m), 6.79-7.29(8H, m). |
| 411 | NMR: 1.02-1.06(3H, m), 2.23-4.38(14H, m), 4.96 and 5.72(1H, m), 6.79-7.29(8H, m). |
| 415 | NMR: 0.86-0.94(6H, m), 1.15-1.62(10H, m), 1.88-2.04(1H, m), 2.60-5.04(12H, m), 6.52(2H, s), 6.72-6.79(2H, m), 7.06-7.12(1H, m). |
| 420 | NMR: 1.00-1.08(3H, m), 2.10-4.51(14H, m), 4.95 and 5.59(1H, m), 6.83-7.28(8H, m). |
| 421 | NMR: 1.03(3H, d, J = 7.2 Hz), 2.58-2.95(4H, m), 3.76-3.88(2H, m), 4.13(1H, d, J = 16 Hz), 4.18(1H, d, J = 16 Hz), 6.61(1H, d, J = 7.2 Hz), 7.06-7.32(13H, m). |
| 422 | NMR: 2.67-2.97(4H, m), 3.38(2H, m), 3.80(2H, m), 4.19(2H, s), 6.61(1H, d, J = 8 Hz), 7.06-7.32(13H, m). |
| 433 | NMR: 0.99-1.11(3H, m), 2.12-4.53(13H, m), 4.94 and 5.72(1H, m), 7.03-7.80(8H, m). |
| 434 | NMR: 0.99-1.11(3H, m), 2.12-4.53(11H, m), 4.94 and 5.71(1H, m), 7.03-7.80(8H, m). |
| 436 | NMR: 1.14-1.55(13H, m), 2.49-4.50(15H, m), 5.08 and 5.56(1H, m), 7.05-7.12(3H, m). |
| 439 | NMR: 1.14-1.56(13H, m), 2.49-4.50(15H, m), 5.07 and 5.56(1H, m), 7.05-7.12(3H, m). |
| 497 | NMR: 1.09-1.10(3H, m), 2.75-3.00(4H, m), 3.37-4.48(4H, m), 6.22 and 6.50(1H, s), 7.12-8.58(8H, m). |

In addition, structures of other compounds of the present invention are shown in Tables 126 and 127. It is possible to easily produce these compounds according to the above-mentioned methods described in production processes and Examples, and methods obvious to a person skilled in the art, or modifications thereof.

Further, in the Tables, No represents a number of the compound.

TABLE 126

| No | Structure |
|---|---|
| 1 | [structure] |
| 2 | [structure] |
| 3 | [structure] |
| 4 | [structure] |
| 5 | [structure] |
| 6 | [structure] |
| 7 | [structure] |
| 8 | [structure] |
| 9 | [structure] |
| 10 | [structure] |
| 11 | [structure] |

TABLE 126-continued

| No | Structure |
|----|-----------|
| 12 | (structure) |
| 13 | (structure) |
| 14 | (structure) |

TABLE 127

| No | Structure |
|----|-----------|
| 15 | (structure) |
| 16 | (structure) |
| 17 | (structure) |
| 18 | (structure) |

TABLE 127-continued

| No | Structure |
|----|-----------|
| 19 | (structure) |
| 20 | (structure) |
| 21 | (structure) |
| 22 | (structure) |
| 23 | (structure) |
| 24 | (structure) |
| 25 | (structure) |

The analysis results of several compounds of Production Examples by chiral column chromatography are shown in Tables 128 and 129

In addition, in the Tables, RT represents a retention time (min) and OP represents an optical purity (% ee).

TABLE 128

| Rex | Condition | RT | OP |
|---|---|---|---|
| 20 | Column: DAICEL CHIRALPAK AD-RH 4.6 × 150 mm<br>Detection: UV: 230 nm<br>Flow rate: 0.5 mL/min<br>Eluent: 20 mM Phosphate buffer(pH 9)/MeCN = 60/40<br>Column temperature: 40° C. | 18.22 | >99.5 |
| 21 | Column: DAICEL CHRALPAK AS-RH 4.6 × 150 mm<br>Detection: UV210 nm<br>Flow rate: 0.8 mL/min<br>Eluent: 20 mM Phosphate buffer(pH 9)/MeCN = 50/50<br>Column temperature: 40° C. | 24.11 | >99.5 |
| 22 | Column: DAICEL CHRALCEL OJ-RH 4.6 × 150 mm<br>Detection: UV210 nm<br>Flow rate: 0.8 mL/min<br>Eluent: 20 mM Phosphate buffer (pH 9)/MeCN = 70/30<br>Column temperature: 40° C. | 9.24 | 99.20 |
| 81 | Column: DAICEL CHRALPAK AS-RH 4.6 × 150 mm<br>Detection: UV210 nm<br>Flow rate: 0.8 mL/min<br>Eluent: 20 mM Phosphate buffer(pH 9)/MeCN = 45/55<br>Column temperature: 40° C. | 15.95 | >99 |
| 82 | Column: DAICEL CHRALCEL OJ-RH 4.6 × 150 mm<br>Detection: UV210 nm<br>Flow rate: 0.8 mL/min<br>Eluent: 20 mM Phosphate buffer(pH 9)/MeCN = 70/30<br>Column temperature: 40° C. | 43.39 | 92 |
| 83 | Column: DAICEL CHRALCEL OD-RH 4.6 × 150 mm<br>Detection: UV210 nm<br>Flow rate: 0.8 mL/min<br>Eluent: 20 mM Phosphate buffer(pH 9)/MeCN = 20/80<br>Column temperature: 40° C. | 52.48 | 98 |
| 513 | Column: DAICEL CHRALCEL OD-RH 4.6 × 150 mm<br>Detection: UV210 nm<br>Flow rate: 0.8 mL/min<br>Eluent: 20 mM Phosphate buffer(pH 9)/MeCN = 20/80<br>Column temperature: 40° C. | 60.99 | 97.40 |
| 547A | Column: DAICEL CHIRALPAK AD-RH 4.6 × 150 mm<br>Detection: UV: 230 nm<br>Flow rate: 0.5 mL/min<br>Eluent: 20 mM Phosphate buffer(pH 9)/MeCN = 60/40<br>Column temperature: 40° C. | 15 | 95 |

TABLE 129

| Rex | Condition | RT | OP |
|---|---|---|---|
| 566 | Column: DAICEL CHRALCEL OJ-RH 4.6 × 150 mm<br>Detection: UV210 nm<br>Flow rate: 0.8 mL/min<br>Eluent: 20 mM Phosphate buffer(pH 9)/MeCN = 70/30<br>Column temperature: 40° C. | 11.28 | 98.30 |
| 567 | Column: DAICEL CHRALCEL OD-RH 4.6 × 150 mm<br>Detection: UV230 nm<br>Flow rate: 0.8 mL/min<br>Eluent: 20 mM Phosphate buffer(pH 9)/MeCN = 45/55<br>Column temperature: 40° C. | 28.60 | >99 |
| 570 | Column: DAICEL CHRALCEL OD-RH 4.6 × 150 mm<br>Detection: UV210 nm<br>Flow rate: 0.8 mL/min<br>Eluent: 20 mM Phosphate buffer(pH 9)/MeCN = 60/40<br>Column temperature: 40° C. | 36.76 | >99 |
| 572 | Column: DAICEL CHRALPAK AS-RH 4.6 × 150 mm<br>Detection: UV210 nm<br>Flow rate: 0.8 mL/min<br>Eluent: 20 mM Phosphate buffer(pH 9)/MeCN = 50/50<br>Column temperature: 40° C. | 20.86 | >99.5 |
| 575 | Column: DAICEL CHRALPAK AS-RH 4.6 × 150 mm<br>Detection: UV210 nm<br>Flow rate: 0.8 mL/min<br>Eluent: 20 mM Phosphate buffer(pH 9)/MeCN = 45/55<br>Column temperature: 40° C. | 17.02 | >99 |
| 576 | Column: DAICEL CHRALCEL OD-RH 4.6 × 150 mm<br>Detection: UV230 nm<br>Flow rate: 0.8 mL/min<br>Eluent: 20 mM Phosphate buffer(pH 9)/MeCN = 45/55<br>Column temperature: 40° C. | 22.72 | >99 |

TABLE 129-continued

| Rex | Condition | RT | OP |
|---|---|---|---|
| 650 | Column: DAICEL CHRALCEL OD-RH 4.6 × 150 mm<br>Detection: UV210 nm<br>Flow rate: 0.8 mL/min<br>Eluent: 20 mM Phosphate buffer(pH 9)/MeCN = 65/35<br>Column temperature: 40° C. | 25.06 | >99 |
| 652 | Column: DAICEL CHRALCEL OD-RH 4.6 × 150 mm<br>Detection: UV210 nm<br>Flow rate: 0.8 mL/min<br>Eluent: 20 mM Phosphate buffer(pH 9)/MeCN = 65/35<br>Column temperature: 40° C. | 26.7 | >99 |

INDUSTRIAL APPLICABILITY

The compound of the present invention can be used as a pharmaceutical composition for preventing and/or treating various pains including neuropathic pain and nociceptive pain, headaches such as migraine and cluster headache, central nervous system diseases such as anxiety, depression, epilepsy, cerebral stroke and restless legs syndrome, abdominal symptoms such as abdominal pain and abdominal distension, stool abnormalities such as diarrhea and constipation, digestive system diseases such as irritable bowel syndrome, urinary system diseases such as overactive bladder and interstitial cystitis, etc.

The invention claimed is:
1. A compound of the formula (I):

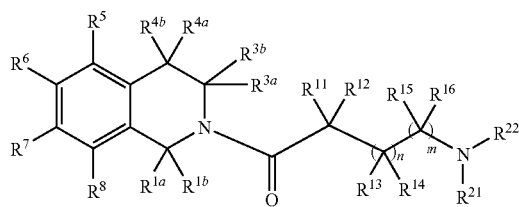

wherein the symbols in the formula have the following meanings:

$R^{1a}$ and $R^{1b}$: are the same or different and may be —H, $C_{1-6}$ alkyl which may be substituted, cycloalkyl which may be substituted, aryl which may be substituted, or an aromatic hetero ring which may be substituted, provided that both of $R^{1a}$ and $R^{1b}$ cannot be —H, and $R^{1a}$ and $R^{1b}$, when taken together with the carbon atom to which they are attached, may represent cycloalkyl which may be substituted, $R^{3a}$, $R^{3b}$, $R^{4a}$ and $R^{4b}$: are the same or different and may be —H, or $C_{1-6}$ alkyl, $R^5$, $R^6$, $R^7$ and $R^8$: are the same or different and may be —H, $C_{1-6}$ alkyl which may be substituted, —O—($C_{1-6}$ alkyl) which may be substituted, cyano, carbamoyl which may be substituted with one or two $C_{1-6}$ alkyl, or halogen, and any two adjacent groups of $R^5$, $R^6$, $R^7$ and $R^8$ when taken together may form —O—$CH_2$—O— or —O—$(CH_2)_2$—O—, $R^{11}$, $R^{12}$, $R^{13}$, $R^{14}$, $R^{15}$ and $R^{16}$: are the same or different and may be —H or $C_{1-6}$ alkyl, $R^{21}$: is —H, $C_{1-6}$ alkyl which may be substituted, or cycloalkyl which may be substituted, $R^{22}$: is
(1) cycloalkyl which is substituted with one or more groups selected from the group consisting of —OH and —$CH_2OH$ and which may be further substituted;
(2) $C_{1-8}$ alkyl substituted with one or two —OH, wherein the $C_{1-8}$ alkyl may further have a substituent, and one or two methylene groups (—$CH_2$—) contained in this alkyl chain may be replaced with —O—; or
(3) $C_{1-6}$ alkyl substituted with cycloalkyl which is substituted with one or more groups selected from the group consisting of —OH and —$CH_2OH$ and which may be further substituted, wherein the $C_{1-6}$ alkyl may be substituted with —OH, and one or two methylene groups (—$CH_2$—) contained in this alkyl chain may be replaced with —O—; and n and m: are the same or different and are 0 or 1,
wherein $R^{12}$ and $R^{21}$ when taken together may form methylene, ethylene, or trimethylene, and in this case, $R^{11}$ may represent —OH, or $R^{21}$ and $R^{22}$, when taken together with the nitrogen atom to which they are attached, may form azetidine, pyrrolidine, piperidine, azepane, azocane, morpholine, tetrahydroisoquinoline or thiomorpholine which are substituted with —OH or $C_{1-6}$ alkyl substituted with —OH; or a pharmaceutically acceptable salt thereof.

2. The compound according to claim 1, wherein m is 0, n is 0, and $R^{1a}$, $R^{3a}$, $R^{3b}$, $R^{4a}$, $R^{4b}$, $R^{11}$, $R^{12}$ and $R^{21}$ are each —H; or a pharmaceutically acceptable salt thereof.

3. The compound according to claim 2, wherein $R^{1b}$ is isopropyl, methoxymethyl, phenyl, 2-(trifluoromethyl)benzyl, or cyclohexyl; or a pharmaceutically acceptable salt thereof.

4. The compound according to claim 2, wherein $R^5$, $R^6$, $R^7$ and $R^8$ are the same or different and are independently selected from the group consisting of —H, methyl, ethyl, methoxy, and fluoro; or a pharmaceutically acceptable salt thereof.

5. The compound according to claim 2, wherein $R^{22}$ is 2-hydroxypropan-1-yl, 2-hydroxy-3-methoxypropan-1-yl, or (1-hydroxycyclohexyl)methyl; or a pharmaceutically acceptable salt thereof.

6. The compound according to claim 1, which is
1-[({2-[(1S)-1-cyclohexyl-3,4-dihydroisoquinolin-2(1H)-yl]-2-oxoethyl}amino)methyl]cyclohexanol,
(2S)-1-({2-[(1S)-1-cyclohexyl-3,4-dihydroisoquinolin-2(1H)-yl]-2-oxoethyl}amino)-3-methoxy propan-2-ol,
1-({[2-(1S)-isopropyl-6-methoxy-3,4-dihydroisoquinolin-2(1H)-yl)-2-oxoethyl]amino}methyl)cyclohexanol,
(2R)-1-({2-[(1S)-8-methoxy-1-phenyl-3,4-dihydroisoquinolin-2(1H)-yl]-2-oxoethyl}amino)propan-2-ol,
1-[({2-[(1R)-7-ethyl-1-(methoxymethyl)-3,4-dihydroisoquinolin-2(1H)-yl]-2-oxoethyl}amino)methyl]cyclohexanol, (2S)-1-methoxy-3-[(2-oxo-2-{1(1S)[2-(trifluoromethyl)
benzyl]-3,4-dihydroisoquinolin-2(1H)-yl}ethyl)amino]
propan-2-ol,
1-({[3-(1-cyclohexyl-3,4-dihydroisoquinolin-2(1H)-yl)-
3-oxo propyl]amino}methyl)cyclohexanol,
(2R)-1-{[2-(1-cyclohexyl-3,4-dihydroisoquinolin-2(1H)-
yl)-2-oxoethyl]amino}propan-2-ol,
(2R)-1-[(2-oxo-2-{1-[2-(trifluoromethyl)phenyl]-3,4-di-
hydroisoquinolin-2(1H)-yl}ethyl)amino]propan-2-ol,
(2S)-1-{[2-(1-cyclohexyl-7-methyl-3,4-dihydroisoquino-
lin-2(1H)-yl)-2-oxoethyl]amino}-3-methoxy propan-2-
ol,
(2R)-1-({2-oxo-2-[(1S)-1-phenyl-3,4-dihydroisoquino-
lin-2(1H)-yl]ethyl}amino)propan-2-ol,
1-[({2-[7-fluoro-1-(methoxymethyl)-3,4-dihydroiso-
quinolin-2(1H)-yl]-2-oxoethyl}amino)methyl]cyclo-
hexanol,
1-[({2-[7-ethyl-1-(methoxymethyl)-3,4-dihydroisoquino-
lin-2(1H)-yl]-2-oxoethyl}amino)methyl]cyclohexanol,
1-({[2-(1-isopropyl-6-methoxy-3,4-dihydroisoquinolin-2
(1H)-yl)-2-oxoethyl]amino}methyl)cyclohexanol,
1-[({2-[5-methoxy-1-(methoxymethyl)-3,4-dihydroiso-
quinolin-2(1H)-yl]-2-oxoethyl}amino)methyl]cyclo-
hexanol,
1-[({2-[1-(methoxymethyl)-6-methyl-3,4-dihydroiso-
quinolin-2(1H)-yl]-2-oxoethyl}amino)methyl]cyclo-
hexanol,
(1S,2S)-2-{[2-(1-cyclohexyl-3,4-dihydroisoquinolin-2
(1H)-yl)-2-oxoethyl]amino}-1-phenyl propane-1,3-
diol,
1-({(2R)-2-[(1-cyclohexyl-3,4-dihydroisoquinolin-2
(1H)-yl)carbonyl]pyrrolidin-1-yl}methyl)cyclohex-
anol,
(2R)-1-{[2-(1-cyclohexyl-1-methyl-3,4-dihydroisoquino-
lin-2(1H)-yl)-2-oxoethyl]amino}propan-2-ol,
1-({[2-(3',4'-dihydro-2'H-spiro[cyclohexane-1,1'-iso-
quinolin]-2'-yl)-2-oxoethyl]amino}methyl)cyclohex-
anol,
(2R)-1-[(2-oxo-2-{1-[2-(trifluoromethoxy)phenyl]-3,4-
dihydroisoquinolin-2(1H)-yl}ethyl)amino]propan-2-
ol,
(2R)-1-{[2-(1-cyclohexyl-7-ethyl-3,4-dihydroisoquino-
lin-2(1H)-yl)-2-oxoethyl]amino}propan-2-ol,
1-({[2-(6-fluoro-1-isopropyl-3,4-dihydroisoquinolin-2
(1H)-yl)-2-oxoethyl]amino}methyl)cyclohexanol,
1,1-dicyclopropyl-2-({2-[6-fluoro-1-(methoxymethyl)-3,
4-dihydroisoquinolin-2(1H)-yl]-2-oxoethyl}amino)
ethanol,
1-({[2-(1-tert-butyl-8-methoxy-3,4-dihydroisoquinolin-2
(1H)-yl)-2-oxoethyl]amino}methyl)cyclohexanol,
1-({[2-(1-isopropyl-6-methyl-3,4-dihydroisoquinolin-2
(1H)-yl)-2-oxoethyl]amino}methyl)cyclohexanol,
1-({[2-(6-fluoro-1-propyl-3,4-dihydroisoquinolin-2(1H)-
yl)-2-oxoethyl]amino}methyl)cyclohexanol,
1-[({2-[1-(methoxymethyl)-7-methyl-3,4-dihydroiso-
quinolin-2(1H)-yl]-2-oxoethyl}amino)methyl]cyclo-
hexanol,
1-({[2-(5-fluoro-1-propyl-3,4-dihydroisoquinolin-2(1H)-
yl)-2-oxoethyl]amino}methyl)cyclohexanol,
1-[({2-[5-fluoro-1-(methoxymethyl)-3,4-dihydroiso-
quinolin-2(1H)-yl]-2-oxoethyl}amino)methyl]cyclo-
hexanol,
1-[({2-[8-methoxy-1-(methoxymethyl)-3,4-dihydroiso-
quinolin-2(1H)-yl]-2-oxoethyl}amino)methyl]cyclo-
hexanol,
1-[({2-[1-(ethoxymethyl)-7-methyl-3,4-dihydroisoquino-
lin-2(1H)-yl]-2-oxoethyl}amino)methyl]cyclohexanol,
or
(1R,2S)-2-({2-[(1R)-1-(2-methoxyphenyl)-3,4-dihy-
droisoquinolin-2(1H)-yl]-2-oxoethyl}amino)cyclopen-
tanol; or a pharmaceutically acceptable salt thereof.

7. The compound according to claim 1, which is

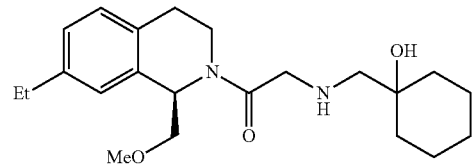

or a pharmaceutically acceptable salt thereof.

8. A pharmaceutical composition comprising a compound of claim 1 or a pharmaceutically acceptable salt thereof and a pharmaceutically acceptable excipient.

9. An N-type $Ca^{2+}$ channel blocker comprising a compound of claim 1 or a pharmaceutically acceptable salt thereof.

10. A pharmaceutical composition for treating pain, neuropathic pain, abdominal symptom, spastic constipation, opioid-induced constipation, irritable bowel syndrome, or constipation-type irritable bowel syndrome, comprising a compound of claim 1 or a pharmaceutically acceptable salt thereof.

11. The pharmaceutical composition according to claim 10, which is a pharmaceutical composition for treating pain.

12. The pharmaceutical composition according to claim 11, which is a pharmaceutical composition for treating neuropathic pain.

13. The pharmaceutical composition according to claim 10, which is a pharmaceutical composition for treating abdominal symptom.

14. The pharmaceutical composition according to claim 10, which is a pharmaceutical composition for treating spastic constipation.

15. The pharmaceutical composition according to claim 14, which is a pharmaceutical composition for treating opioid-induced constipation.

16. The pharmaceutical composition according to claim 10, which is a pharmaceutical composition for treating irritable bowel syndrome.

17. The pharmaceutical composition according to claim 16, which is a pharmaceutical composition for treating constipation-type irritable bowel syndrome.

18. A pharmaceutical composition comprising a compound of claim 1 or a pharmaceutically acceptable salt thereof and an opioid as active ingredients.

19. A pharmaceutical composition comprising a compound of claim 1 or a pharmaceutically acceptable salt thereof as an active ingredient, wherein the composition is used in combination with an opioid.

20. A method for the manufacture of a pharmaceutical composition for treating pain, neuropathic pain, abdominal symptom, spastic constipation, opioid-induced constipation, irritable bowel syndrome, or constipation-type irritable bowel syndrome comprising incorporating into said composition a compound of claim 1 or a pharmaceutically acceptable salt thereof.

21. An active ingredient of a pharmaceutical composition for treating pain, neuropathic pain, abdominal symptom, spastic constipation, opioid-induced constipation, irritable bowel syndrome, or constipation-type irritable bowel syndrome comprising the compound of claim 1.

22. A method for treating pain, neuropathic pain, abdominal symptom, spastic constipation, opioid-induced constipation, irritable bowel syndrome, or constipation-type irritable bowel syndrome, comprising administering to a patient in need thereof an effective amount of a compound of claim 1 or a pharmaceutically acceptable salt thereof.

* * * * *